(12) United States Patent
Calhoun et al.

(10) Patent No.: US 11,820,778 B2
(45) Date of Patent: Nov. 21, 2023

(54) 2-AZASPIRO[3.4]OCTANE DERIVATIVES AS M4 AGONISTS

(71) Applicant: NOVARTIS AG, Basel (CH)

(72) Inventors: Amy Calhoun, Cambridge, MA (US); Xin Chen, Lexington, MA (US); Kevin Matthew Gardinier, Arlington, MA (US); Edward Charles Hall, Boston, MA (US); Keith Jendza, Boston, MA (US); Nancy Labbe-Giguere, Arlington, MA (US); James Neef, Stow, MA (US); Daniel Steven Palacios, Cambridge, MA (US); Ming Qian, Watertown, MA (US); Michael David Shultz, Lexington, MA (US); Christopher G. Thomson, Herts (GB); Kate Yaping Wang, Boxborough, MA (US); Fan Yang, West Roxbury, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 17/818,321

(22) Filed: Aug. 8, 2022

(65) Prior Publication Data
US 2022/0411435 A1    Dec. 29, 2022

Related U.S. Application Data

(62) Division of application No. 17/065,367, filed on Oct. 7, 2020, now Pat. No. 11,485,742.

(60) Provisional application No. 62/912,986, filed on Oct. 9, 2019.

(51) Int. Cl.
  *C07D 491/107*    (2006.01)
  *A61P 25/18*    (2006.01)
  *A61K 45/06*    (2006.01)

(52) U.S. Cl.
  CPC .......... *C07D 491/107* (2013.01); *A61K 45/06* (2013.01); *A61P 25/18* (2018.01)

(58) Field of Classification Search
  CPC ....... C07D 491/107; A61P 25/18; A61P 25/28
  See application file for complete search history.

(56) References Cited

U.S. PATENT DOCUMENTS

2019/0231687 A1    8/2019    Ahmad et al.

FOREIGN PATENT DOCUMENTS

| WO | WO 2004/043955 A1 | 5/2004 |
|---|---|---|
| WO | WO 2005/080376 A1 | 9/2005 |
| WO | WO 2006/006490 A2 | 1/2006 |
| WO | WO 2006/058294 A2 | 6/2006 |
| WO | WO 2008/024497 A1 | 2/2008 |
| WO | WO 2010/049146 A1 | 5/2010 |
| WO | WO 2010/084499 A2 | 7/2010 |
| WO | WO 2012/112743 A1 | 8/2012 |
| WO | WO 2013/013308 A1 | 1/2013 |
| WO | WO 2014/039489 A1 | 3/2014 |
| WO | WO 2014/045031 A1 | 3/2014 |
| WO | WO 2016/067043 A1 | 5/2016 |
| WO | WO 2016/147011 A1 | 9/2016 |
| WO | WO 2017/021728 A1 | 2/2017 |
| WO | WO 2017/021729 A1 | 2/2017 |
| WO | WO 2017/021730 A1 | 2/2017 |
| WO | WO 2017/077292 A1 | 5/2017 |
| WO | WO 2017/214367 A1 | 12/2017 |
| WO | 2018069732 A1 | 4/2018 |
| WO | WO 2017/021732 A1 | 4/2018 |
| WO | WO 2018153312 A1 | 8/2018 |
| WO | WO 2018/175746 A1 | 9/2018 |
| WO | WO 2019/183636 A1 | 9/2019 |
| WO | WO 2019/243850 A1 | 12/2019 |

OTHER PUBLICATIONS

Notification of Transmittal of The International Search Report and the Written Opinion of the International Searching Authority, or the Declaration, dated Nov. 23, 2020, issued in International Patent Appl. No. PCT/IB2020/059430, filed Oct. 7, 2020.
Notification of Transmittal of The International Search Report and the Written Opinion of the International Searching Authority, or the Declaration, dated Nov. 23, 2020, issued in International Patent Appl. No. PCT/IB2020/059431, filed Oct. 7, 2020.
Yang et al., Discovery of Selective M4 Muscarinic Acelylcholine Receptor Agonists with Novel Carbamate Isosteres, ACS Medicinal Chemistry Letters 2019 10 (6), 941-948.

*Primary Examiner* — Sahar Javanmard
(74) *Attorney, Agent, or Firm* — Adil R. Zhugralin

(57) ABSTRACT

Provided herein are compounds according to Formula (I)

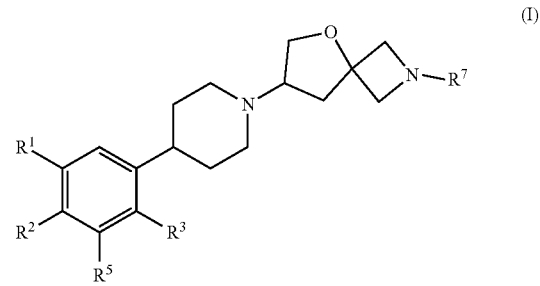

or a pharmaceutically acceptable salt thereof, wherein $R^1$, $R^2$, $R^3$, $R^5$, and $R^7$ are defined herein. Also provided herein are pharmaceutical compositions comprising a compound of Formula (I) as well as the use of such compounds as M4 receptor agonists.

30 Claims, 3 Drawing Sheets

2-AZASPIRO[3.4]OCTANE DERIVATIVES AS M4 AGONISTS

1. CROSS REFERENCE TO RELATED APPLICATIONS

This application is a division of application Ser. No. 17/065,367, filed Oct. 7, 2020, and claims the benefit of U.S. Provisional Application No. 62/912,986, filed Oct. 9, 2019, the disclosures of which are incorporated by reference herein in their entirety.

2. FIELD

Provided herein are novel 2-azaspiro[3.4]octane compounds that act as M4 receptor agonists, as well as pharmaceutical compositions thereof, uses for the treatment of conditions, diseases and disorders related to the M4 receptor, which include, but are not limited to, psychosis, hyperkinetic movement disorders, cognitive dysfunction, and substance use disorders.

3. BACKGROUND

Acetylcholine, a major neurotransmitter in the central and peripheral nervous system, signals by activating its ionotropic (nicotinic) and G-protein coupled (muscarinic) receptors. Five muscarinic receptors (M1-M5) have been identified with differential expression and signaling. The M1, M3 and M5 receptors are coupled to Gq proteins that activate phospholipase C. Phospholipase C hydrolyses membrane phosphoinositides into inositol triphosphate ($IP_3$) and diacylglycerol (DAG), which elevate intracellular calcium and activate a number of signaling pathways. The M2 and M4 receptors are coupled to $G_{i/o}$ proteins which inhibit adenylyl cyclase production and decrease cyclic adenosine monophosphate (cAMP) levels, having an inhibitory effect on cell function. The M1 receptors are predominantly expressed in the forebrain (cortex, hippocampus, striatum and thalamus) and on salivary glands (*Brain Res Mol Brain Res* 2005, 133(1):6-11; *Br. J. Pharmacol* 2006, 148, 565-578; *Pharmacol Ther* 2008, 117: 232-243). The M2 receptors are expressed in the brain, and also highly expressed in the heart where they mediate vagal nerve innervation and can affect the heart rate (*Br. J. Pharmacol* 2006, 148, 565-578; *Pharmacol Ther* 2008, 117: 232-243). The M3 receptors are mostly expressed in the smooth muscles of peripheral tissues, including the gastrointestinal track, bladder, eye, and sweat and salivary glands (*Br. J. Pharmacol* 2006, 148, 565-578). The M4 receptors are enriched in the brain and are mainly expressed in the striatum, a brain area involved in dopamine release and signaling (*J Neurosci* 1994 14(5): 3351-3363; *Proc Natl Acad Sci USA* 1999, 96(18): 10483-10488; *Pharmacol Ther* 2008, 117: 232-243). The M5 receptors are expressed on vasculature, including the cerebral blood vessels (*Proc Natl Acad Sci USA* 2001, 98(24): 14096-14101).

In the central nervous system, muscarinic receptors have been shown to play a central role in cognition and regulation of dopaminergic signaling (*Neuron* 2017, 94(3): 431-446). Of particular interest are M4 receptors that are highly expressed in the striatum. Genetic deletion of M4 receptors causes a hyper-dopaminergic phenotype in rodents. M4 knock-out mice have been shown to have elevated striatal dopamine levels and increased locomotor activity (*Proc Natl Acad Sci USA* 1999, 96(18): 10483-10488.; *FASEB J* 2004, 18(12):1410-1412). Consistent with these observations, pharmacological activation of M4 receptors decreases amphetamine-induced dopamine release and reverses amphetamine hyperlocomotion in mice (*Neuropsychopharm* 2004, 39: 1578-1593). Thus, these results indicate that M4 receptors can act as a negative regulator of dopamine release and signaling in the striatum.

Increased dopamine tone in the striatum is strongly associated with psychotic symptoms in schizophrenia and other disorders, including psychotic depression, bipolar disorder, Huntington's disease and Alzheimer's disease (*Lancet* 1988, 2:119-125; *Schizophr Bull* 2009, 35:549-562). Current antipsychotic drugs act primarily by blocking the action of dopamine at D2 receptors. However, they have limited efficacy and serious side effects, including drug-induced Parkinsonism, tardive dyskinesia, Q-Tc prolongation, weight gain and metabolic syndrome which lead to poor patient compliance (*N Engl J Med* 2005, 353:1209-23).

Activation of muscarinic M4 receptors has been shown to downregulate striatal dopamine signaling and thereby may provide an alternative way to treat psychosis. In support of this notion, the muscarinic agonist xanomeline showed robust antipsychotic efficacy when tested in two clinical trials in Alzheimer disease (*Arch Neurol* 1997, 54(4):465-473) and schizophrenia patients (*Am J Psychiatry* 2008, 165(8):1033-1039). However, its treatment was associated with a number of side effects, including nausea, vomiting, excessive salivation, dyspepsia and chills, which stopped its clinical development. Xanomeline is a pan muscarinic agonist that activates all muscarinic receptor subtypes. Studies suggest that the antipsychotic efficacy of xanomeline is primarily mediated by the activation of M4 receptors. The M4 receptors are highly expressed in the human striatum (*Schizophr Res* 2015, 169: 83-88.) and the antipsychotic-like effects of xanomeline on dopamine-mediated behaviors are eliminated in M4 knock-out mice (*Eur J Pharmacol* 2009, 603: 147-149; *J Neurosci* 2011, 31(16):5905-5908.). In contrast, xanomeline's side effects are most likely due to the activation of M2 and M3 receptors which are expressed in the heart, digestive tract and salivary glands (*CNS Drug Rev* 2003, 9:159-186; *Br. J. Pharmacol* 2006, 148, 565-578). Thus, M4 selective agonists are likely to retain xanomeline's antipsychotic efficacy without causing cholinergic side effects.

Consequently, compounds that act as M4 receptor agonists may be useful for treatment of M4 related conditions.

4. SUMMARY

In one embodiment, provided herein is a compound according to Formula (I)

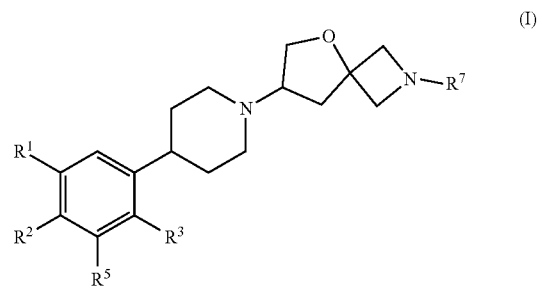

or a pharmaceutically acceptable salt thereof, wherein
$R^1$ is halogen or hydrogen;
$R^2$ is halogen or hydrogen;

R³ is
- optionally substituted $C_{1-3}$ alkyl, said alkyl is optionally substituted with one 4 to 6 membered heterocycloalkyl,
- optionally substituted 5 to 6 membered heteroaryl, said heteroaryl is optionally substituted with one $C_{1-3}$ alkyl, 4 to 6 membered heterocycloalkyl, or —OR⁴;

R⁴ is
- optionally substituted $C_{1-5}$ alkyl, said alkyl is optionally substituted with one or two R⁶,
- optionally substituted 3 to 9 membered heterocycloalkyl, said heterocycloalkyl is optionally substituted with one or two R⁶, or
- optionally substituted 4 to 6 membered cycloalkyl, said cycloalkyl is optionally substituted with one, two, or three R⁶;

R⁵ is halogen or hydrogen;

each R⁶ is independently
- halogen,
- —OH,
- —OCH₃,
- —C(CH₃)₂OH,
- —CH₂OH,
- cyano,
- optionally substituted $C_1$-$C_4$ alkyl, said alkyl is optionally substituted with —OH,
- optionally substituted 4 to 7 membered heterocycloalkyl, said heterocycloalkyl is optionally substituted with one or two substituents independently selected from the group consisting of halogen, —OH, —OCH₃, and $C_{1-3}$ alkyl, or
- optionally substituted 5 to 6 membered heteroaryl, said heteroaryl is optionally substituted with one $C_{1-3}$ alkyl; and R⁷ is 5-membered heteroaryl.

In one embodiment, provided herein is a compound according to Formula (Ia)

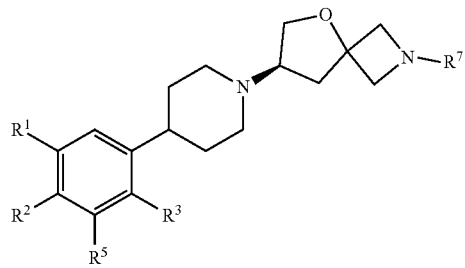

(Ia)

or a pharmaceutically acceptable salt or stereoisomer thereof.

In one embodiment, provided herein is a compound according to Formula (Ib)

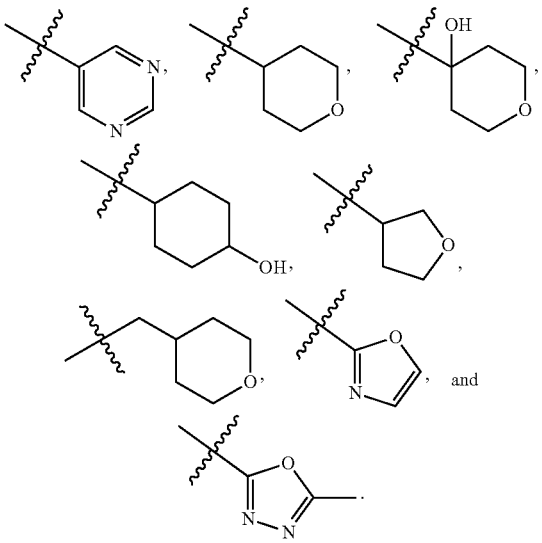

(Ib)

or a pharmaceutically acceptable salt or stereoisomer thereof.

In one embodiment, R¹ is selected from the group consisting of H, chloro, and fluoro. In another embodiment, R¹ is fluoro.

In one embodiment, R² is H or fluoro.
In one embodiment, R⁵ is H or fluoro.
In one embodiment, R¹, R², and R⁵ are H.
In one embodiment, R² and R⁵ are H.
In one embodiment, R³ is selected from the group consisting of:

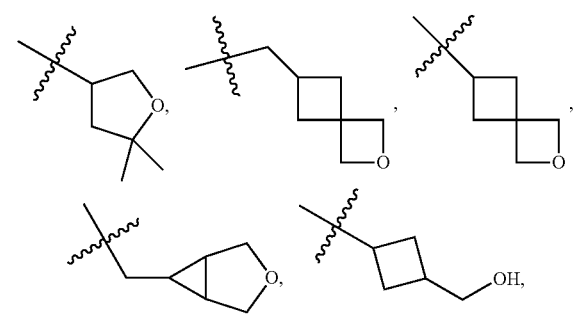

In some embodiments, R³ is —OR⁴.
In one embodiment, R⁴ is selected from the group consisting of CH₃, —CH₂CH₂C(CH₃)₂OH, —CH₂CH₂C(CH₃)₂OCH₃, —CH₂CH₂OCH₃, and —CH₂C(CH₃)₂OH.
In some embodiments, R⁴ is selected from the group consisting of:

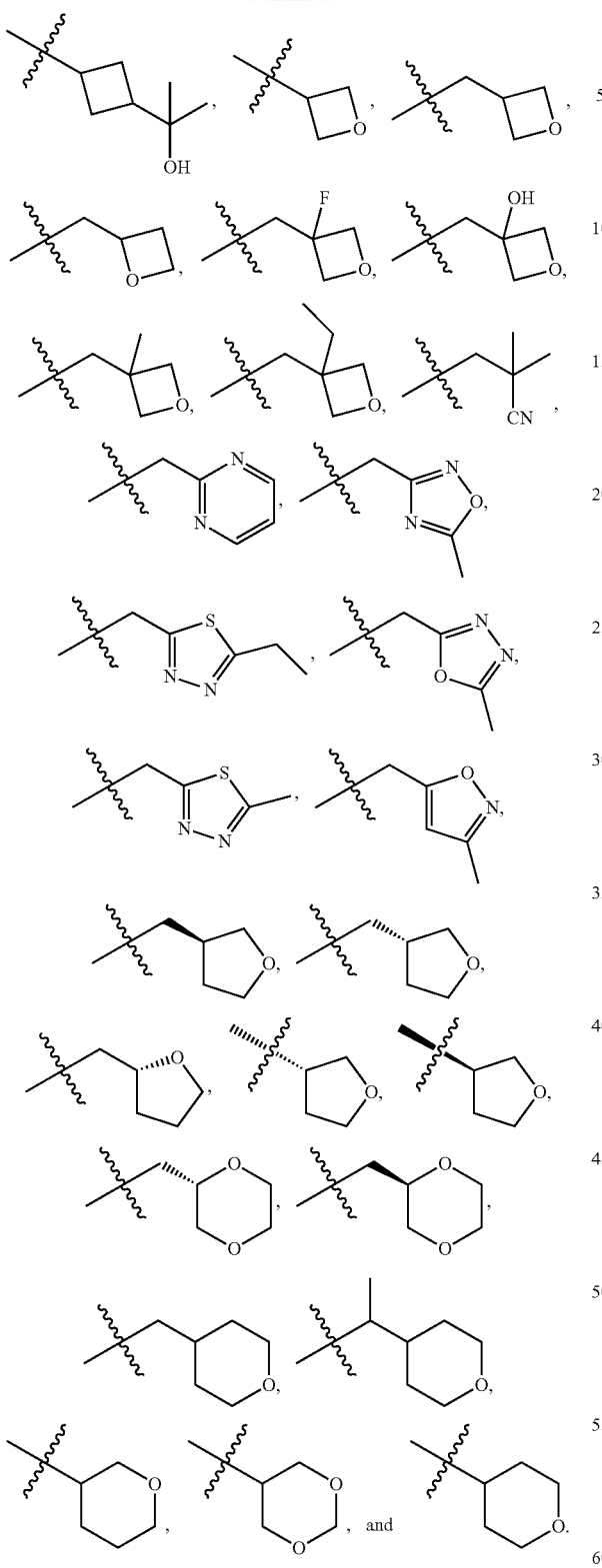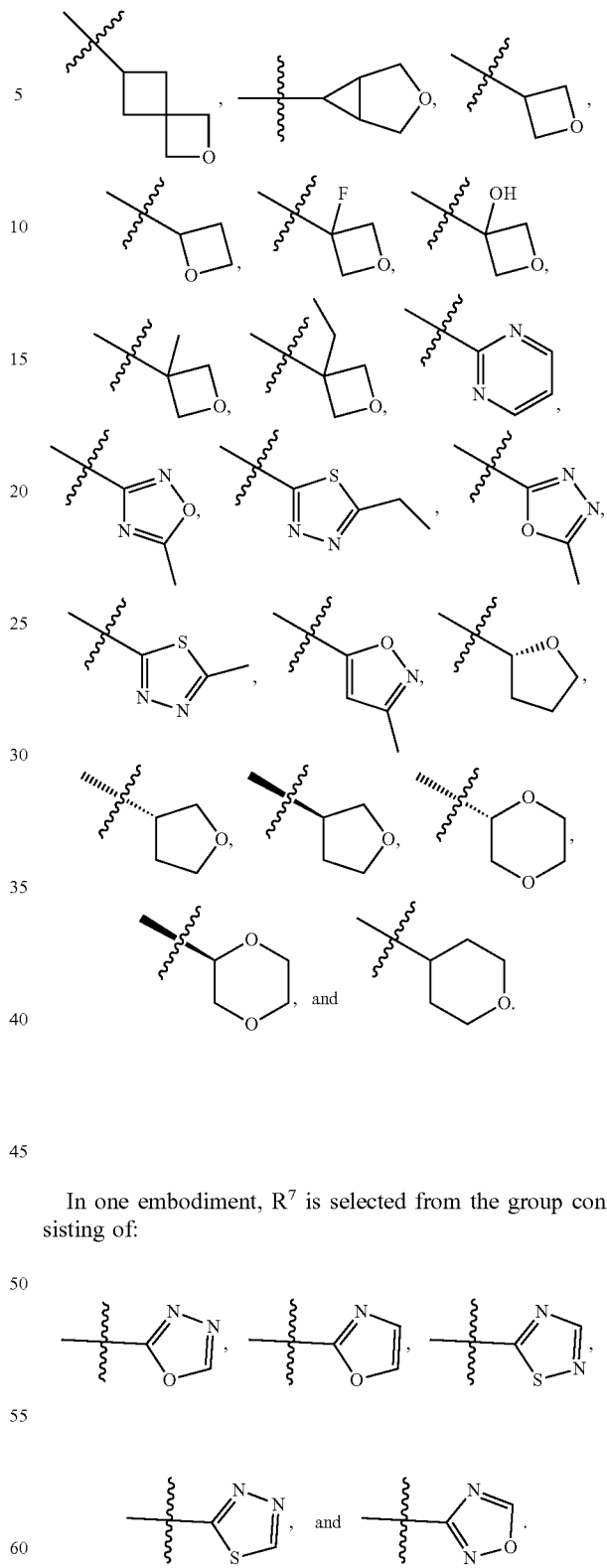
In one embodiment, $R^7$ is selected from the group consisting of:
In another embodiment, $R^4$ is $C_1$-$C_5$ alkyl and $R^6$ is independently cyano, —OH, —OCH$_3$,
In one embodiment, provided herein is a compound according to Formula (I)

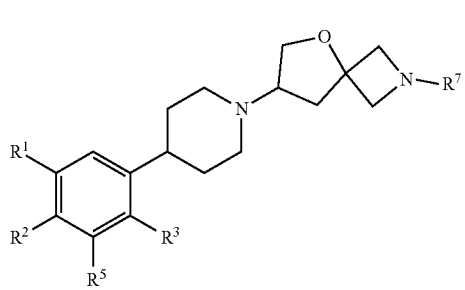

(I)

or a pharmaceutically acceptable salt thereof, wherein
$R^1$ is halogen or hydrogen;
$R^2$ is halogen or hydrogen;
$R^3$ is
- optionally substituted $C_{1-3}$ alkyl, said alkyl is optionally substituted with one 4 to 6 membered heterocycloalkyl,
- optionally substituted 5 to 6 membered heteroaryl, said heteroaryl is optionally substituted with one $C_{1-3}$ alkyl,
- optionally substituted 4 to 6 membered heterocycloalkyl, said heterocycloalkyl is optionally substituted with one —OH,
- optionally substituted 4 to 6 membered cycloalkyl, said cycloalkyl is optionally substituted with one —OH, or
- —OR$^4$;

$R^4$ is
- optionally substituted $C_{1-5}$ alkyl, said alkyl is optionally substituted with one or two $R^6$,
- optionally substituted 3 to 9 membered heterocycloalkyl, said heterocycloalkyl is optionally substituted with one or two $R^6$, or
- optionally substituted 4 to 6 membered cycloalkyl, said cycloalkyl is optionally substituted with one, two, or three $R^6$;

$R^5$ is halogen or hydrogen;
each $R^6$ is independently
- halogen,
- —OH,
- —OCH$_3$,
- —C(CH$_3$)$_2$OH,
- —CH$_2$OH,
- cyano,
- optionally substituted $C_1$-$C_4$ alkyl, said alkyl is optionally substituted with —OH,
- optionally substituted 4 to 7 membered heterocycloalkyl, said heterocycloalkyl is optionally substituted with one or two substituents independently selected from the group consisting of halogen, —OH, —OCH$_3$, and $C_{1-3}$ alkyl, or
- optionally substituted 5 to 6 membered heteroaryl, said heteroaryl is optionally substituted with one $C_{1-3}$ alkyl; and $R^7$ is 5-membered heteroaryl.

In one embodiment, provided herein is a compound according to Formula (Ia)

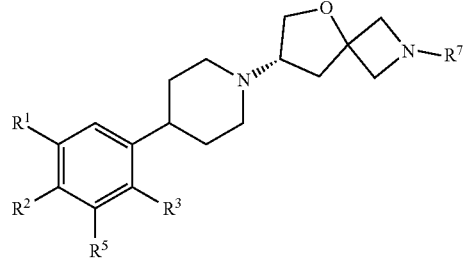

(Ia)

or a pharmaceutically acceptable salt or stereoisomer thereof.

In one embodiment, provided herein is a compound according to Formula (Ib)

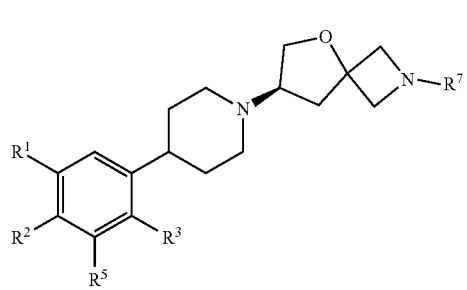

(Ib)

or a pharmaceutically acceptable salt or stereoisomer thereof.

In one embodiment, $R^1$ is selected from the group consisting of H, chloro, and fluoro. In another embodiment, $R^1$ is fluoro.

In one embodiment, $R^2$ is H or fluoro.

In one embodiment, $R^5$ is H or fluoro.

In one embodiment, $R^1$, $R^2$, and $R^5$ are H.

In one embodiment, $R^2$ and $R^5$ are H.

In one embodiment, $R^3$ is selected from the group consisting of:

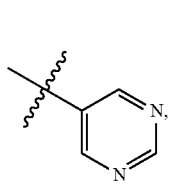 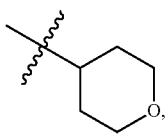

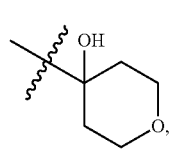 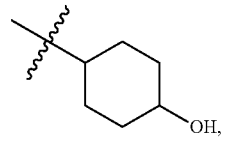

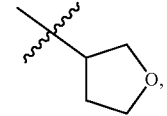 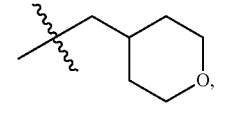

-continued

In some embodiments, $R^3$ is $-OR^4$.

In one embodiment, $R^4$ is selected from the group consisting of $CH_3$, $-CH_2CH_2C(CH_3)_2OH$, $-CH_2CH_2C(CH_3)_2OCH_3$, $-CH_2CH_2OCH_3$, and $-CH_2C(CH_3)_2OH$.

In some embodiments, $R^4$ is selected from the group consisting of:

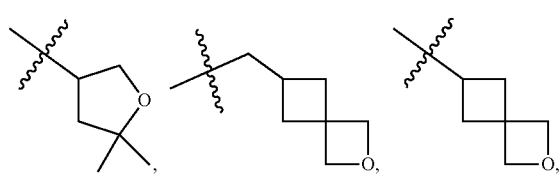

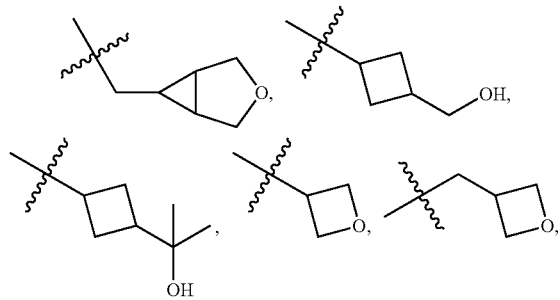

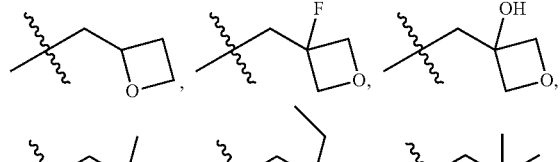

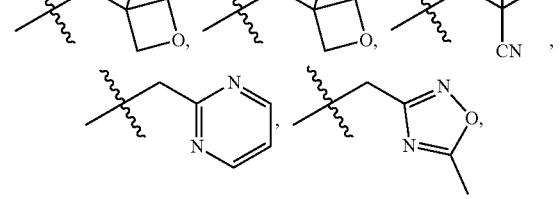

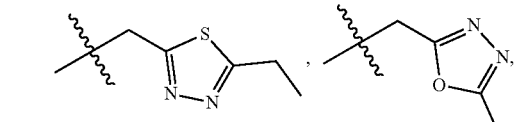

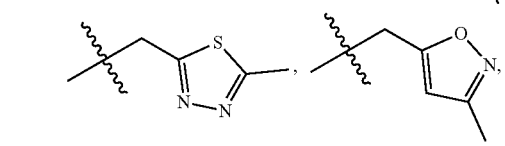

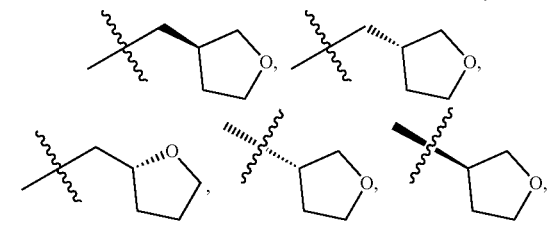

-continued

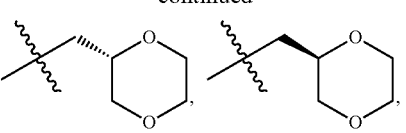

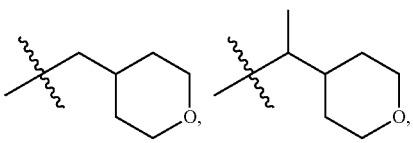

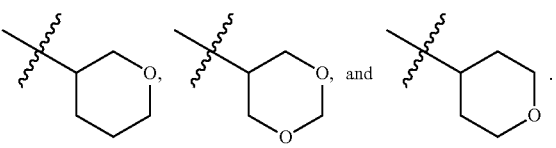

In another embodiment, $R^4$ is $C_1$-$C_5$ alkyl and $R^6$ is independently cyano, $-OH$, $-OCH_3$,

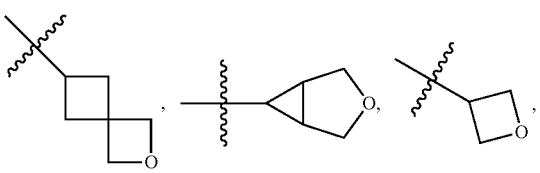

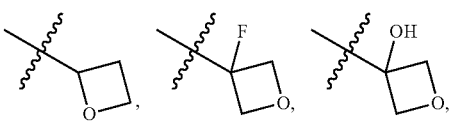

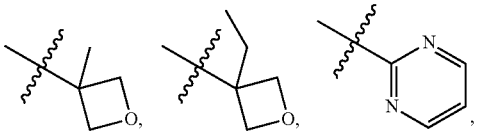

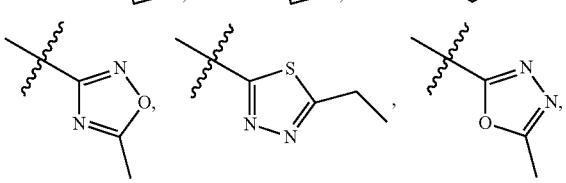

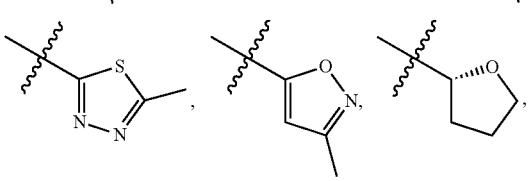

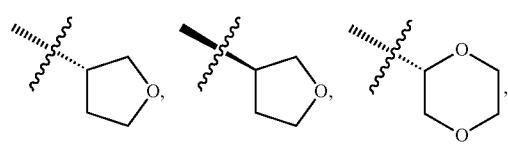

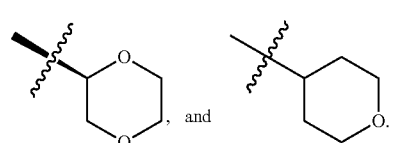

In one embodiment, W is selected from the group consisting of:

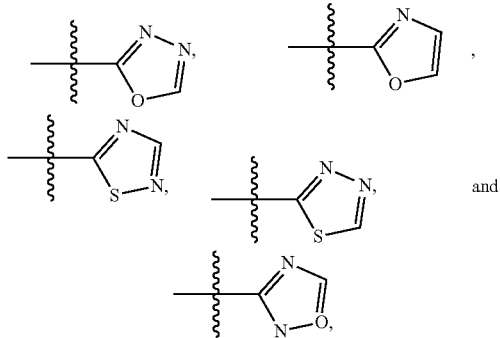

In one embodiment, provided herein is a compound which is selected from the group consisting of:

(S)-7-(4-(5-fluoro-2-(oxetan-3-yloxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydrofuran-3-yl)methoxy)phenyl)piperidin-1-yl)-2-(1,3,4-oxadiazol-2-yl)-5-oxa-2-azaspiro[3.4]octane;

ethyl 5-((S)-7-(4-(2-(((R)-1,4-dioxan-2-yl)methoxy)-5-fluorophenyl)piperidin-1-yl)-5-oxa-2-azaspiro[3.4]octan-2-yl)-1,3,4-oxadiazole-2-carboxylate;

(S)-7-(4-(5-fluoro-2-(((R)-tetrahydrofuran-3-yl)oxy)phenyl)piperidin-1-yl)-2-(1,3,4-oxadiazol-2-yl)-5-oxa-2-azaspiro[3.4]octane;

(S)-3-(2-(1-(2-(1,3,4-oxadiazol-2-yl)-5-oxa-2-azaspiro[3.4]octan-7-yl)piperidin-4-yl)-4-fluorophenoxy)-2,2-dimethylpropanenitrile;

(S)-7-(4-(2-(((S)-1,4-dioxan-2-yl)methoxy)-5-fluorophenyl)piperidin-1-yl)-2-(1,3,4-oxadiazol-2-yl)-5-oxa-2-azaspiro[3.4]octane;

(S)-7-(4-(5-fluoro-2-((tetrahydro-2H-pyran-4-yl)oxy)phenyl)piperidin-1-yl)-2-(1,3,4-oxadiazol-2-yl)-5-oxa-2-azaspiro[3.4]octane;

(S)-7-(4-(5-fluoro-2-(((S)-tetrahydrofuran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((S)-tetrahydrofuran-3-yl)methoxy)phenyl)piperidin-1-yl)-2-(1,3,4-oxadiazol-2-yl)-5-oxa-2-azaspiro[3.4]octane;

(S)-7-(4-(5-fluoro-2-((tetrahydro-2H-pyran-4-yl)methoxy)phenyl)piperidin-1-yl)-2-(1,3,4-oxadiazol-2-yl)-5-oxa-2-azaspiro[3.4]octane;

(S)-7-(4-(5-fluoro-2-(3-methoxy-3-methylbutoxy)phenyl)piperidin-1-yl)-2-(1,3,4-oxadiazol-2-yl)-5-oxa-2-azaspiro[3.4]octane;

(S)-7-(4-(5-fluoro-2-(2-methoxyethoxy)phenyl)piperidin-1-yl)-2-(1,3,4-oxadiazol-2-yl)-5-oxa-2-azaspiro[3.4]octane;

(S)-7-(4-(2-((1,3-dioxan-5-yl)oxy)-5-fluorophenyl)piperidin-1-yl)-2-(1,3,4-oxadiazol-2-yl)-5-oxa-2-azaspiro[3.4]octane;

(S)-4-(2-(1-(2-(1,3,4-oxadiazol-2-yl)-5-oxa-2-azaspiro[3.4]octan-7-yl)piperidin-4-yl)-4-fluorophenoxy)-2-methylbutan-2-ol;

(S)-2-(1,3,4-oxadiazol-2-yl)-7-(4-(2-(((R)-tetrahydrofuran-3-yl)oxy)phenyl)piperidin-1-yl)-5-oxa-2-azaspiro[3.4]octane;

(S)-2-(1,3,4-oxadiazol-2-yl)-7-(4-(2-(oxetan-3-yloxy)phenyl)piperidin-1-yl)-5-oxa-2-azaspiro[3.4]octane;

(S)-7-(4-(2-methoxyphenyl)piperidin-1-yl)-2-(1,3,4-oxadiazol-2-yl)-5-oxa-2-azaspiro[3.4]octane;

(S)-7-(4-(4,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;

(S)-7-(4-(4-fluoro-2-methoxyphenyl)piperidin-1-yl)-2-(1,3,4-oxadiazol-2-yl)-5-oxa-2-azaspiro[3.4]octane;

(S)-4-(2-(1-(2-(1,3,4-oxadiazol-2-yl)-5-oxa-2-azaspiro[3.4]octan-7-yl)piperidin-4-yl)-5-fluorophenoxy)-2-methylbutan-2-ol;

(S)-1-(2-(1-(2-(1,3,4-oxadiazol-2-yl)-5-oxa-2-azaspiro[3.4]octan-7-yl)piperidin-4-yl)-4-fluorophenoxy)-2-methylpropan-2-ol;

(S)-7-(4-(5-fluoro-2-methoxyphenyl)piperidin-1-yl)-2-(1,3,4-oxadiazol-2-yl)-5-oxa-2-azaspiro[3.4]octane;

(S)-2-(1,3,4-oxadiazol-2-yl)-7-(4-(2-(pyrimidin-5-yl)phenyl)piperidin-1-yl)-5-oxa-2-azaspiro[3.4]octane;

(S)-2-(1,3,4-oxadiazol-2-yl)-7-(4-(2-(oxazol-2-yl)phenyl)piperidin-1-yl)-5-oxa-2-azaspiro[3.4]octane;

(S)-7-(4-(2-(5-methyl-1,3,4-oxadiazol-2-yl)phenyl)piperidin-1-yl)-2-(1,3,4-oxadiazol-2-yl)-5-oxa-2-azaspiro[3.4]octane;

(S)-7-(4-(5-fluoro-2-(oxetan-3-ylmethoxy)phenyl)piperidin-1-yl)-2-(1,3,4-thiadiazol-2-yl)-5-oxa-2-azaspiro[3.4]octane;

(S)-7-(4-(5-fluoro-2-((3-methyloxetan-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-((5-methyl-1,3,4-thiadiazol-2-yl)methoxy)phenyl)piperidin-1-yl)-2-(1,3,4-oxadiazol-2-yl)-5-oxa-2-azaspiro[3.4]octane;

(S)-7-(4-(5-fluoro-2-((5-methyl-1,3,4-oxadiazol-2-yl)methoxy)phenyl)piperidin-1-yl)-2-(1,3,4-oxadiazol-2-yl)-5-oxa-2-azaspiro[3.4]octane;

(S)-7-(4-(5-fluoro-2-((3-methylisoxazol-5-yl)methoxy)phenyl)piperidin-1-yl)-2-(1,3,4-oxadiazol-2-yl)-5-oxa-2-azaspiro[3.4]octane;

(S)-7-(4-(5-fluoro-2-(oxetan-3-ylmethoxy)phenyl)piperidin-1-yl)-2-(1,3,4-oxadiazol-2-yl)-5-oxa-2-azaspiro[3.4]octane;

(S)-7-(4-(5-fluoro-2-(pyrimidin-2-ylmethoxy)phenyl)piperidin-1-yl)-2-(1,3,4-oxadiazol-2-yl)-5-oxa-2-azaspiro[3.4]octane;

(S)-7-(4-(5-fluoro-2-((3-fluorooxetan-3-yl)methoxy)phenyl)piperidin-1-yl)-2-(1,3,4-oxadiazol-2-yl)-5-oxa-2-azaspiro[3.4]octane;

(S)-7-(4-(5-fluoro-2-((3-methyloxetan-3-yl)methoxy)phenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane;

(S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane;

(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-((3-ethyloxetan-3-yl)methoxy)-5-fluorophenyl)piperidin-1-yl)-2-(1,3,4-oxadiazol-2-yl)-5-oxa-2-azaspiro[3.4]octane;

(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)methoxy)-5-fluorophenyl)piperidin-1-yl)-2-(1,3,4-oxadiazol-2-yl)-5-oxa-2-azaspiro[3.4]octane;

(S)-7-(4-(2-((5-ethyl-1,3,4-thiadiazol-2-yl)methoxy)-5-fluorophenyl)piperidin-1-yl)-2-(1,3,4-oxadiazol-2-yl)-5-oxa-2-azaspiro[3.4]octane;

(S)-3-((2-(1-(2-(1,3,4-oxadiazol-2-yl)-5-oxa-2-azaspiro[3.4]octan-7-yl)piperidin-4-yl)-4-fluorophenoxy)methyl)oxetan-3-ol;

2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(7S)-7-(4-(2-((3-oxabicyclo[3.1.0]hexan-6-yl)methoxy)-5-fluorophenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)oxy)-3,5-difluorophenyl)piperidin-1-yl)-2-(1,3,4-oxadiazol-2-yl)-5-oxa-2-azaspiro[3.4]octane;

(S)-7-(4-(3,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;

(S)-7-(4-(3,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;

(S)-7-(4-(3,5-difluoro-2-(oxetan-3-ylmethoxy)phenyl)piperidin-1-yl)-2-(1,3,4-oxadiazol-2-yl)-5-oxa-2-azaspiro[3.4]octane;

(S)-7-(4-(3,5-difluoro-2-(oxetan-3-yloxy)phenyl)piperidin-1-yl)-2-(1,3,4-oxadiazol-2-yl)-5-oxa-2-azaspiro[3.4]octane;

(S)-7-(4-(4,5-difluoro-2-(oxetan-3-yloxy)phenyl)piperidin-1-yl)-2-(1,3,4-oxadiazol-2-yl)-5-oxa-2-azaspiro[3.4]octane;

(S)-7-(4-(4,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;

((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;

((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;

((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;

((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;

(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;

(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;

(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;

(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;

(S)-2-(1,3,4-oxadiazol-2-yl)-7-(4-(2-(tetrahydro-2H-pyran-4-yl)phenyl)piperidin-1-yl)-5-oxa-2-azaspiro[3.4]octane;

(S)-7-(4-(5-fluoro-2-(tetrahydro-2H-pyran-4-yl)phenyl)piperidin-1-yl)-2-(1,3,4-oxadiazol-2-yl)-5-oxa-2-azaspiro[3.4]octane;

(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;

(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;

(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;

(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;

(S)-2-(1,3,4-oxadiazol-2-yl)-7-(4-(2-((tetrahydro-2H-pyran-4-yl)methyl)phenyl)piperidin-1-yl)-5-oxa-2-azaspiro[3.4]octane;

(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;

(S)-7-(4-(5-fluoro-2-(oxetan-3-yloxy)phenyl)piperidin-1-yl)-2-(oxazol-2-yl)-5-oxa-2-azaspiro[3.4]octane;

(S)-7-(4-(2-(((R)-1,4-dioxan-2-yl)methoxy)-5-fluorophenyl)piperidin-1-yl)-2-(oxazol-2-yl)-5-oxa-2-azaspiro[3.4]octane;

(S)-2-(oxazol-2-yl)-7-(4-(2-(oxetan-3-yloxy)phenyl)piperidin-1-yl)-5-oxa-2-azaspiro[3.4]octane;

(S)-7-(4-(5-fluoro-2-(((R)-tetrahydrofuran-3-yl)oxy)phenyl)piperidin-1-yl)-2-(oxazol-2-yl)-5-oxa-2-azaspiro[3.4]octane;

(S)-7-(4-(5-fluoro-2-((tetrahydro-2H-pyran-4-yl)oxy)phenyl)piperidin-1-yl)-2-(oxazol-2-yl)-5-oxa-2-azaspiro[3.4]octane;

(S)-2-(oxazol-2-yl)-7-(4-(2-(((R)-tetrahydrofuran-3-yl)oxy)phenyl)piperidin-1-yl)-5-oxa-2-azaspiro[3.4]octane;

(S)-7-(4-(2-((2-oxaspiro[3.3]heptan-6-yl)oxy)-5-fluorophenyl)piperidin-1-yl)-2-(oxazol-2-yl)-5-oxa-2-azaspiro[3.4]octane;

(S)-2-(oxazol-2-yl)-7-(4-(2-(((S)-tetrahydrofuran-3-yl)oxy)phenyl)piperidin-1-yl)-5-oxa-2-azaspiro[3.4]octane;

(S)-7-(4-(5-fluoro-2-methoxyphenyl)piperidin-1-yl)-2-(oxazol-2-yl)-5-oxa-2-azaspiro[3.4]octane;

(S)-2-(oxazol-2-yl)-7-(4-(2-((tetrahydro-2H-pyran-4-yl)oxy)phenyl)piperidin-1-yl)-5-oxa-2-azaspiro[3.4]octane;

(S)-1-(4-fluoro-2-(1-(2-(oxazol-2-yl)-5-oxa-2-azaspiro[3.4]octan-7-yl)piperidin-4-yl)phenoxy)-2-methylpropan-2-ol;

(S)-7-(4-(5-fluoro-2-(2-methoxyethoxy)phenyl)piperidin-1-yl)-2-(oxazol-2-yl)-5-oxa-2-azaspiro[3.4]octane;

(S)-7-(4-(2-((2-oxaspiro[3.3]heptan-6-yl)oxy)phenyl)piperidin-1-yl)-2-(oxazol-2-yl)-5-oxa-2-azaspiro[3.4]octane;

(S)-7-(4-(2-methoxyphenyl)piperidin-1-yl)-2-(oxazol-2-yl)-5-oxa-2-azaspiro[3.4]octane;

(S)-7-(4-(4,5-difluoro-2-(oxetan-3-ylmethoxy)phenyl)piperidin-1-yl)-2-(oxazol-2-yl)-5-oxa-2-azaspiro[3.4]octane;

(S)-7-(4-(4,5-difluoro-2-((3-fluorooxetan-3-yl)methoxy)phenyl)piperidin-1-yl)-2-(oxazol-2-yl)-5-oxa-2-azaspiro[3.4]octane;

(S)-7-(4-(4,5-difluoro-2-(oxetan-3-yloxy)phenyl)piperidin-1-yl)-2-(oxazol-2-yl)-5-oxa-2-azaspiro[3.4]octane;

(S)-2-(oxazol-2-yl)-7-(4-(2-(pyrimidin-5-yl)phenyl)piperidin-1-yl)-5-oxa-2-azaspiro[3.4]octane;

(S)-7-(4-(4-fluoro-2-(oxetan-3-yloxy)phenyl)piperidin-1-yl)-2-(oxazol-2-yl)-5-oxa-2-azaspiro[3.4]octane;

2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

(S)-2-(oxazol-2-yl)-7-(4-(2-(tetrahydro-2H-pyran-4-yl)phenyl)piperidin-1-yl)-5-oxa-2-azaspiro[3.4]octane;

(S)-7-(4-(5-fluoro-2-(tetrahydro-2H-pyran-4-yl)phenyl)piperidin-1-yl)-2-(oxazol-2-yl)-5-oxa-2-azaspiro[3.4]octane;

(S)-7-(4-(5-chloro-2-methoxyphenyl)piperidin-1-yl)-2-(1,2,4-thiadiazol-5-yl)-5-oxa-2-azaspiro[3.4]octane;

(S)-7-(4-(2-methoxyphenyl)piperidin-1-yl)-2-(1,2,4-thiadiazol-5-yl)-5-oxa-2-azaspiro[3.4]octane;

(S)-1-(2-(1-(2-(1,2,4-thiadiazol-5-yl)-5-oxa-2-azaspiro[3.4]octan-7-yl)piperidin-4-yl)-4-fluorophenoxy)-2-methylpropan-2-ol;

(S)-7-(4-(5-fluoro-2-(2-methoxyethoxy)phenyl)piperidin-1-yl)-2-(1,2,4-thiadiazol-5-yl)-5-oxa-2-azaspiro[3.4]octane;

(S)-7-(4-(4-fluoro-2-methoxyphenyl)piperidin-1-yl)-2-(1,2,4-thiadiazol-5-yl)-5-oxa-2-azaspiro[3.4]octane;

(S)-7-(4-(2-((5-methyl-1,2,4-oxadiazol-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-(oxetan-3-yloxy)phenyl)piperidin-1-yl)-2-(1,3,4-thiadiazol-2-yl)-5-oxa-2-azaspiro[3.4]octane;

(S)-7-(4-(5-fluoro-2-(((R)-tetrahydrofuran-3-yl)oxy)phenyl)piperidin-1-yl)-2-(1,3,4-thiadiazol-2-yl)-5-oxa-2-azaspiro[3.4]octane;

(S)-7-(4-(5-fluoro-2-(((R)-tetrahydrofuran-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-((tetrahydro-2H-pyran-4-yl)oxy)phenyl)piperidin-1-yl)-2-(1,3,4-thiadiazol-2-yl)-5-oxa-2-azaspiro[3.4]octane;

(S)-7-(4-(2-(((R)-1,4-dioxan-2-yl)methoxy)-5-fluorophenyl)piperidin-1-yl)-2-(1,3,4-thiadiazol-2-yl)-5-oxa-2-azaspiro[3.4]octane;

(S)-7-(4-(2-(((S)-1,4-dioxan-2-yl)methoxy)-5-fluorophenyl)piperidin-1-yl)-2-(1,3,4-thiadiazol-2-yl)-5-oxa-2-azaspiro[3.4]octane;

(S)-7-(4-(4,5-difluoro-2-(((R)-tetrahydrofuran-3-yl)oxy)phenyl)piperidin-1-yl)-2-(1,3,4-thiadiazol-2-yl)-5-oxa-2-azaspiro[3.4]octane;

(S)-7-(4-(5-fluoro-2-(3-methoxy-3-methylbutoxy)phenyl)piperidin-1-yl)-2-(1,3,4-thiadiazol-2-yl)-5-oxa-2-azaspiro[3.4]octane;

(S)-7-(4-(5-fluoro-2-(((S)-tetrahydrofuran-3-yl)oxy)phenyl)piperidin-1-yl)-2-(1,3,4-thiadiazol-2-yl)-5-oxa-2-azaspiro[3.4]octane;

(S)-4-(2-(1-(2-(1,3,4-thiadiazol-2-yl)-5-oxa-2-azaspiro[3.4]octan-7-yl)piperidin-4-yl)-4-fluorophenoxy)-2-methylbutan-2-ol;

(S)-7-(4-(2-(oxetan-3-yloxy)phenyl)piperidin-1-yl)-2-(1,3,4-thiadiazol-2-yl)-5-oxa-2-azaspiro[3.4]octane formate salt;

(S)-7-(4-(2-methoxyphenyl)piperidin-1-yl)-2-(1,3,4-thiadiazol-2-yl)-5-oxa-2-azaspiro[3.4]octane;

(S)-7-(4-(5-fluoro-2-(2-methoxyethoxy)phenyl)piperidin-1-yl)-2-(1,3,4-thiadiazol-2-yl)-5-oxa-2-azaspiro[3.4]octane;

(S)-7-(4-(4-fluoro-2-methoxyphenyl)piperidin-1-yl)-2-(1,3,4-thiadiazol-2-yl)-5-oxa-2-azaspiro[3.4]octane;

(S)-1-(2-(1-(2-(1,3,4-thiadiazol-2-yl)-5-oxa-2-azaspiro[3.4]octan-7-yl)piperidin-4-yl)-4-fluorophenoxy)-2-methylpropan-2-ol;

(S)-4-(2-(1-(2-(1,3,4-thiadiazol-2-yl)-5-oxa-2-azaspiro[3.4]
  octan-7-yl)piperidin-4-yl)-5-fluorophenoxy)-2-methylbu-
  tan-2-ol;
(S)-7-(4-(2-((2-oxaspiro[3.3]heptan-6-yl)oxy)-5-fluorophe-
  nyl)piperidin-1-yl)-2-(1,3,4-thiadiazol-2-yl)-5-oxa-2-
  azaspiro[3.4]octane;
(S)-7-(4-(5-fluoro-2-(((S)-tetrahydrofuran-3-yl)methoxy)
  phenyl)piperidin-1-yl)-2-(1,3,4-thiadiazol-2-yl)-5-oxa-2-
  azaspiro[3.4]octane;
(S)-1-(2-(1-(2-(1,2,4-thiadiazol-5-yl)-5-oxa-2-azaspiro[3.4]
  octan-7-yl)piperidin-4-yl)phenoxy)-2-methylpropan-2-
  ol;
(S)-7-(4-(5-fluoro-2-((tetrahydro-2H-pyran-4-yl)oxy)phe-
  nyl)piperidin-1-yl)-2-(1,2,4-oxadiazol-3-yl)-5-oxa-2-
  azaspiro[3.4]octane;
(S)-7-(4-(5-fluoro-2-(oxetan-3-yloxy)phenyl)piperidin-1-
  yl)-2-(1,2,4-oxadiazol-3-yl)-5-oxa-2-azaspiro[3.4]oc-
  tane; and
(S)-7-(4-(2-((2-oxaspiro[3.3]heptan-6-yl)oxy)-5-fluorophe-
  nyl)piperidin-1-yl)-2-(1,2,4-oxadiazol-3-yl)-5-oxa-2-
  azaspiro[3.4]octane, or a pharmaceutically acceptable salt
  thereof.

In one embodiment, the compound is selected from the group consisting of:
(S)-7-(4-(2-((2-oxaspiro[3.3]heptan-6-yl)oxy)-5-fluorophe-
  nyl)piperidin-1-yl)-2-(1,3,4-oxadiazol-2-yl)-5-oxa-2-
  azaspiro[3.4]octane, having the following structure:

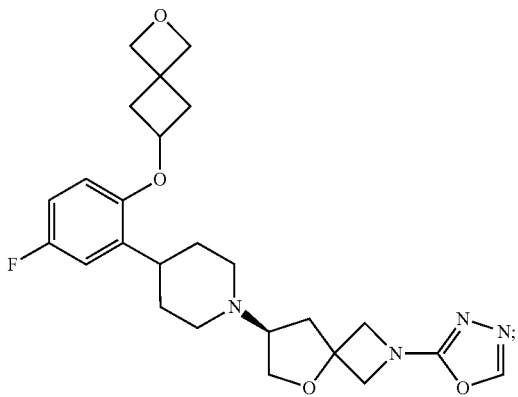 [SMILES: Fc1ccc(OC2CC3(COC3)C2)c(C2CCN([C@@H]3COC4(C3)CN(c3nnco3)C4)CC2)c1]

(R)-7-(4-(2-((2-oxaspiro[3.3]heptan-6-yl)oxy)-5-fluorophe-
  nyl)piperidin-1-yl)-2-(1,3,4-oxadiazol-2-yl)-5-oxa-2-
  azaspiro[3.4]octane, having the following structure:

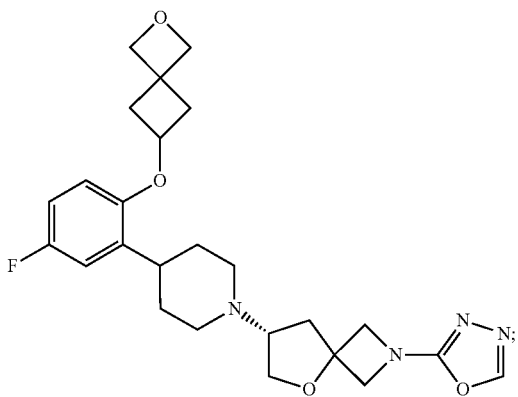 [SMILES: Fc1ccc(OC2CC3(COC3)C2)c(C2CCN([C@H]3COC4(C3)CN(c3nnco3)C4)CC2)c1]

(S)-7-(4-(5-fluoro-2-(oxetan-3-yloxy)phenyl)piperidin-1-
  yl)-2-(1,3,4-oxadiazol-2-yl)-5-oxa-2-azaspiro[3.4]octane,
  having the following structure:

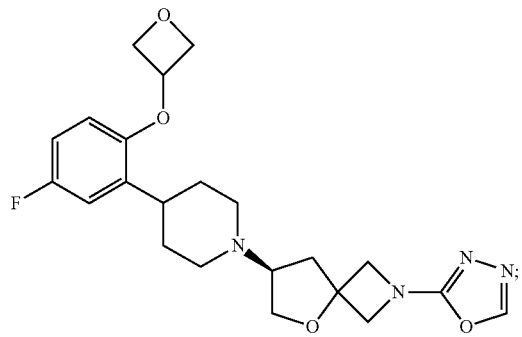 [SMILES: Fc1ccc(OC2COC2)c(C2CCN([C@@H]3COC4(C3)CN(c3nnco3)C4)CC2)c1]

and
(S)-2-(oxazol-2-yl)-7-(4-(2-(tetrahydro-2H-pyran-4-yl)phe-
  nyl)piperidin-1-yl)-5-oxa-2-azaspiro[3.4]octane, having
  the following structure:

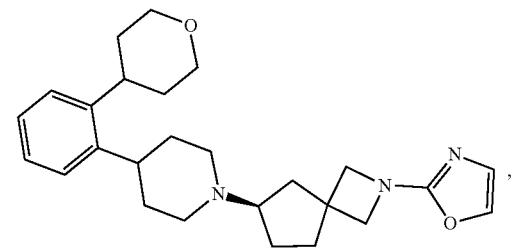 [SMILES: c1ccc(C2CCN([C@@H]3CCC4(C3)CN(c3ncco3)C4)CC2)c(C2CCOCC2)c1]

or a pharmaceutically acceptable salt thereof.

In certain embodiments, the compound is (S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

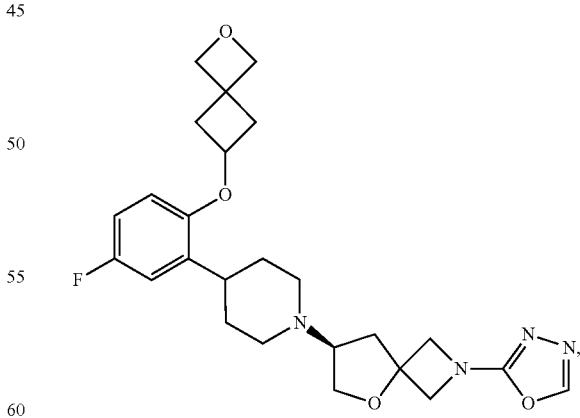

or a pharmaceutically acceptable salt thereof.

In certain embodiments, the compound is (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

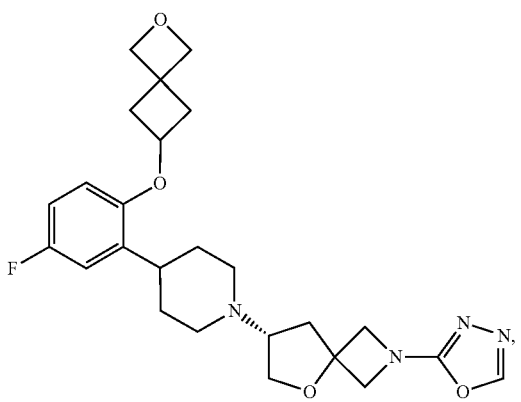 [SMILES: Fc1ccc(OC2CC3(COC3)C2)c(C2CCN([C@H]3COC4(C3)CN(c3nnco3)C4)CC2)c1]

or a pharmaceutically acceptable salt thereof.

In certain embodiments, the compound is (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane, having the following structure:

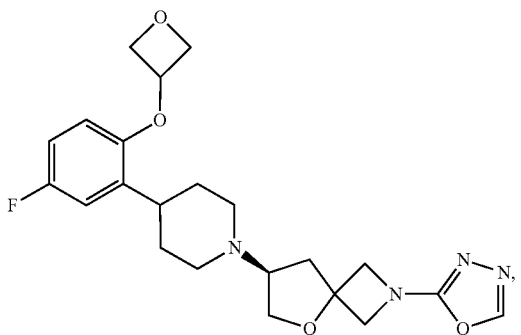 [SMILES: Fc1ccc(OC2COC2)c(C2CCN([C@@H]3COC4(C3)CN(c3nnco3)C4)CC2)c1]

or a pharmaceutically acceptable salt thereof.

In certain embodiments, the compound is (S)-2-(oxazol-2-yl)-7-(4-(2-(tetrahydro-2H-pyran-4-yl)phenyl)piperidin-1-yl)-5-oxa-2-azaspiro[3.4]octane, having the following structure:

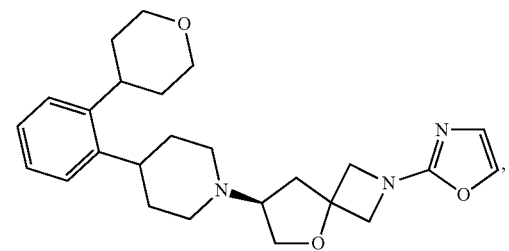 [SMILES: c1ccc(C2CCN([C@@H]3COC4(C3)CN(c3ncco3)C4)CC2)c(C2CCOCC2)c1]

or a pharmaceutically acceptable salt thereof.

In one embodiment, provided herein is a pharmaceutical composition comprising a compound provided herein or a pharmaceutically acceptable salt thereof.

In one embodiment, provided herein is a method for the treatment of a M4 related a condition, disease or disorder comprising administration of a therapeutically effective amount of a compound provided herein or a pharmaceutically acceptable salt thereof to a patient in need of treatment thereof.

In one embodiment, provided herein is a method for the treatment of psychosis comprising administration of a therapeutically effective amount of a compound provided herein or a pharmaceutically acceptable salt thereof to a patient in need of treatment thereof. In some embodiments, the psychosis is associated with schizophrenia, schizoaffective disorder, psychotic depression, bipolar disorder with psychotic features, Alzheimer's disease, or frontotemporal dementia. In another embodiment, the psychosis is associated with Alzheimer's disease.

In one embodiment, provided herein is a method for the treatment of cognitive dysfunction comprising administration of a therapeutically effective amount of a compound provided herein or a pharmaceutically acceptable salt thereof to a subject in need of treatment thereof. In some embodiments, the cognitive dysfunction is associated with schizophrenia, schizoaffective disorder, psychotic depression, bipolar disorder with psychotic features, Alzheimer's disease, or frontotemporal dementia. In another embodiment, the cognitive dysfunction is associated with Alzheimer's disease.

In one embodiment, provided herein is a method for the treatment of a hyperkinetic movement disorder comprising administration of a therapeutically effective amount of a compound provided herein or a pharmaceutically acceptable salt thereof to a subject in need of treatment thereof. In some embodiments, the hyperkinetic movement disorder is associated with schizophrenia, schizoaffective disorder, psychotic depression, bipolar disorder with psychotic features, Alzheimer's disease, or frontotemporal dementia. In another embodiment, the hyperkinetic movement disorder is associated with Alzheimer's disease. In some embodiments, the hyperkinetic movement disorder is Tourette's syndrome, chorea or tardive dyskinesia.

In one embodiment, provided herein is a method for treatment of substance use disorders comprising administration of a therapeutically effective amount of a compound provided herein or a pharmaceutically acceptable salt thereof to a subject in need of treatment thereof.

In one embodiment, provided herein is a method of treating a condition, disease or disorder which is treated with a M4 receptor agonist comprising administration of a therapeutically effective amount of a compound provided herein or a pharmaceutically acceptable salt thereof and an antidepressant to a subject in need of treatment thereof.

In one embodiment, provided herein is a method for the treatment of a condition, disease or disorder which is treated with a M4 receptor agonist comprising administration of a therapeutically effective amount of a compound provided herein or a pharmaceutically acceptable salt thereof in conjunction with computer-assisted psychosocial or behavioral therapy.

In one embodiment, provided herein is the use of a compound of Formula (I) or a pharmaceutically acceptable salt thereof in a therapy. In a further embodiment, the therapy is selected from a condition, disease or disorder which is treated by a M4 receptor agonist.

In another embodiment, provided herein is the use of a compound of Formula (I) or a pharmaceutically acceptable salt thereof in a M4 related a condition, disease or disorder.

In another embodiment, provided herein is the use of a compound of Formula (I) or a pharmaceutically acceptable salt thereof in psychosis. In some embodiments, the psychosis is associated with schizophrenia, schizoaffective disorder, psychotic depression, bipolar disorder with psychotic features, Alzheimer's disease, or frontotemporal dementia. In another embodiment, the psychosis is associated with Alzheimer's disease.

In one embodiment, provided herein is the use of a compound of Formula (I) or a pharmaceutically acceptable salt thereof in cognitive dysfunction. In some embodiments, the cognitive dysfunction is associated with schizophrenia, schizoaffective disorder, psychotic depression, bipolar disorder with psychotic features, Alzheimer's disease, or frontotemporal dementia. In another embodiment, the cognitive dysfunction is associated with Alzheimer's disease.

In one embodiment, provided herein is the use of a compound of Formula (I) or a pharmaceutically acceptable salt thereof in hyperkinetic movement disorder. In some embodiments, the hyperkinetic movement disorder is associated with schizophrenia, schizoaffective disorder, psychotic depression, bipolar disorder with psychotic features, Alzheimer's disease, or frontotemporal dementia. In another embodiment, the hyperkinetic movement disorder is associated with Alzheimer's disease. In some embodiments, the hyperkinetic movement disorder is Tourette's syndrome, chorea or tardive dyskinesia.

In one embodiment, provided herein is the use of a compound of Formula (I) or a pharmaceutically acceptable salt thereof in substance use disorders.

In one embodiment, provided herein is the use of a compound of Formula (I) or a pharmaceutically acceptable salt thereof in a condition, disease or disorder which is treated by a M4 receptor agonist. In certain embodiments, the use is in conjunction with computer-assisted psychosocial or behavioral therapy.

In one embodiment, provided herein is the use of a compound of Formula (I) or a pharmaceutically acceptable salt thereof for the manufacture of a medicament. In a further embodiment, the medicament is for treatment of a condition, disease or disorder which is treated by a M4 receptor agonist. In another embodiment, the condition, disease or disorder is psychosis, including but not limited to, psychosis associated with schizophrenia, schizoaffective disorder, psychotic depression, bipolar disorder with psychotic features, Alzheimer's disease, and frontotemporal dementia.

In one embodiment, provided herein is the use of a compound of Formula (I) or a pharmaceutically acceptable salt thereof for the manufacture of a medicament for the treatment of hyperkinetic movement disorder. In some embodiments, the hyperkinetic movement disorder is associated with schizophrenia, schizoaffective disorder, psychotic depression, bipolar disorder with psychotic features, Alzheimer's disease, or frontotemporal dementia. In another embodiment, the hyperkinetic movement disorder is associated with Alzheimer's disease.

In one embodiment, provided herein is the use of a compound of Formula (I) or a pharmaceutically acceptable salt thereof for the manufacture of a medicament for the treatment of cognitive dysfunction. In some embodiments, the cognitive dysfunction is associated with schizophrenia, schizoaffective disorder, psychotic depression, bipolar disorder with psychotic features, Alzheimer's disease, or frontotemporal dementia. In another embodiment, the cognitive dysfunction is associated with Alzheimer's disease.

In one embodiment, provided herein is the use of a compound of Formula (I) or a pharmaceutically acceptable salt thereof for the manufacture of a medicament for the treatment of substance use disorders.

5. BRIEF DESCRIPTION OF THE DRAWINGS

6. DETAILED DESCRIPTION

1. Definitions

Figure 1:
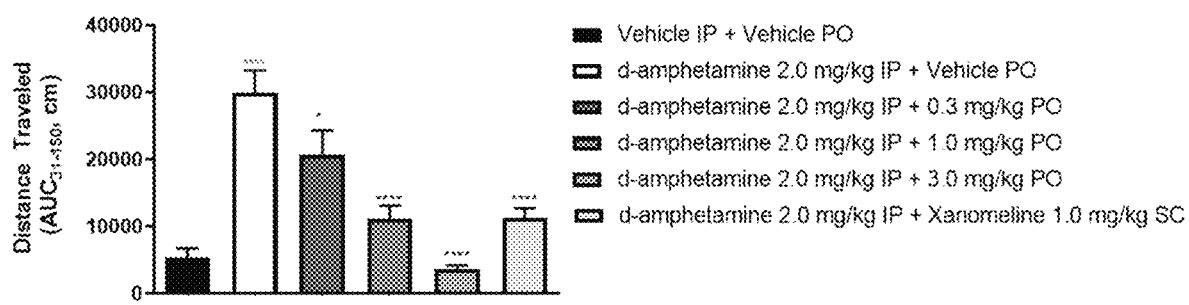
FIG. 1 illustrates the effect of Example 1A and Example 2L on the hyperactivity in mice induced by the stimulant d-amphetamine using a mouse amphetamine induced hyperlocomotion assay.
Figure 1:
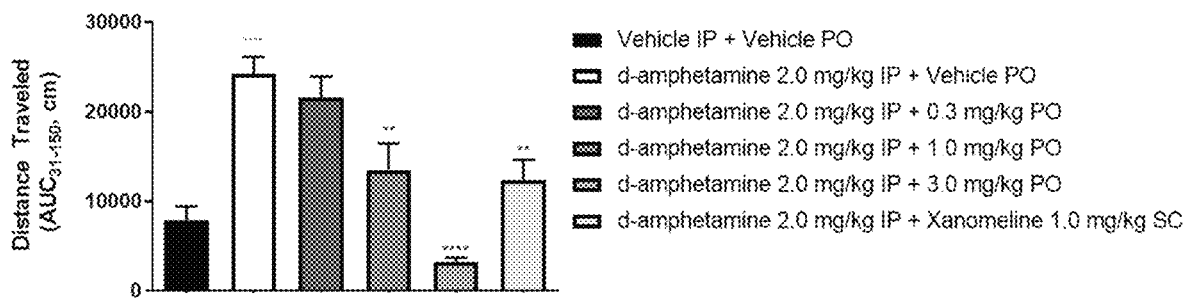

"Alkyl" as used herein refers to a monovalent saturated hydrocarbon chain having the specified number of carbon atoms. For example, $C_{1-3}$ alkyl refers to an alkyl group having from 1 to 3 carbon atoms. Alkyl groups may be optionally substituted with one or more substituents as defined in Formula (I). Alkyl groups may be straight or branched. Representative branched alkyl groups have one, two, or three branches. Examples of alkyl groups include, but are not limited to, methyl, ethyl, propyl (n-propyl and isopropyl), butyl (n-butyl, isobutyl, sec-butyl, and t-butyl), pentyl (n-pentyl, isopentyl, and neopentyl), and hexyl.

"Cycloalkyl" as used herein refers to a saturated hydrocarbon ring system having the specified number of carbon atoms. Cycloalkyl groups are monocyclic or bicyclic ring systems. For example, $C_{3-7}$ cycloalkyl refers to a cycloalkyl group having from 3 to 7 carbon atoms. Cycloalkyl groups may be optionally substituted with one or more substituents as defined in Formula (I). Examples of cycloalkyl groups include, but are not limited to, cyclopropyl, cyclobutyl, cyclopentyl and cyclohexyl.

"Halo" or "halogen" as used herein refers to a fluoro, chloro, or bromo group.

"Haloalkyl" as used herein refers to an alkyl group, having the specified number of carbon atoms, wherein at least one hydrogen atom attached to a carbon atom within the alkyl group is replaced with halo. The number of halo substituents includes, but is not limited to, 1, 2, 3, 4, 5, or 6 substituents. Haloalkyl includes, but is not limited to, monofluoromethyl, difluoroethyl, and trifluoromethyl.

"Heteroaryl" as used herein refers to an aromatic ring system containing one or more heteroatoms. Heteroaryl groups containing more than one heteroatom may contain different heteroatoms. Heteroaryl groups may be optionally substituted with one or more substituents as defined in Formula (I). Heteroaryl groups may be monocyclic ring systems or fused bicyclic ring systems. Monocyclic heteroaryl rings have from 5 to 6 ring atoms. Bicyclic heteroaryl rings have from 8 to 10 member atoms. Bicyclic heteroaryl rings include those ring systems wherein a heteroaryl ring is fused to a phenyl ring. Heteroaryl includes, but is not limited to, pyrrolyl, pyrazolyl, imidazolyl, oxazolyl, isoxazolyl, oxadiazolyl (including 1,3,4-oxadiazolyl and 1,2,4-oxadiazolyl), thiazolyl, isothiazolyl, thiadiazolyl (including 1,3,4-thiadiazolyl), furanyl, furanzanyl, thienyl, triazolyl, pyridinyl (including 2-, 3-, and 4-pyridinyl), pyrimidinyl, pyridazinyl, pyrazinyl, trazinyl, tetrazinyl, tetrazolyl, indonyl, isoindolyl, indolizinyl, indazolyl, purinyl, quinolinyl, isoquinolinyl, quinoxalinyl, quinazolinyl, benzimidazolyl, benzopyranyl, benzopyranyl, benzoxazolyl, benzoisoxazolyl, benzofuranyl, benzothiazolyl, benzothienyl, naphthyridinyl, 1H-pyrrolo[2,3-b]pyridinyl, tetrazolo[1,5-a]pyridinyl, imidazo[2,1-b][1,3,4]thiadiazolyl and the like.

"5-6 membered heteroaryl" as used herein refers to a heteroaryl group defined above, having 5 or 6 ring atoms and containing 1 to 4 heteroatoms. Examples of a 5-6 membered heteroaryl include, but are not limited to, thiazole, oxazole, isoxazole, 1,3,4-thiadiazole, 1,2,4-oxadiazole, 1,2,4-oxadiazole, 1,3,4-oxadiazole, 1,2,5-thiadiazole, 1H-imidazole, 1H-pyrazole, pyridine, pyrimidine, 1,3,5-triazine and the like.

"Heteroatom" as used herein refers to a nitrogen, oxygen, or sulfur atom.

"Heterocyclic" or "heterocycloalkyl" as used herein refers to a saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic includes ring systems wherein a sulfur atom is oxidized to form SO or $SO_2$. Heterocyclic groups may be optionally substituted with one or more substituents as defined in Formula (I). Heterocyclic groups are monocyclic, bicyclic, spiro, or fused or bridged bicyclic ring systems. Monocyclic heterocyclic rings have 3 to 7 ring atoms. Examples of monocyclic heterocyclic groups include pyranyl, tetrahydropyranyl, oxetanyl, tetrahydrofuranyl, dihydrofuranyl, 1,4-dioxanyl, morpholinyl, 1,4-dithianyl, piperazinyl, piperidinyl, 1,3-dioxolanyl, imidazolidinyl, imidazolinyl, pyrrolinyl, pyrrolidinyl, tetrahydropyranyl, dihydropyranyl, oxathiolanyl, dithiolanyl, 1,3-dioxanyl, 1,4-dioxanyl, 1,3-dithianyl, oxathianyl, thiomorpholinyl, tetrahydro-thiopyran1,1-dioxide, 1,4-diazepanyl, and the like. Examples of bicyclic heterocyclic groups include 3-oxabicyclo[3.1.0]hexane and the like. Examples of bridged heterocyclic groups include 2-azabicyclo[2.2.1]heptanyl and the like. Examples of spiro heterocyclic groups include 2-oxaspiro[3.3]heptanyl and the like.

"4 to 6 membered heterocyclic" or "4 to 6 membered heterocycloaryl" as used herein refers to a heterocyclic group as defined above, having from 4 to 6 ring atoms and containing from 1 to 3 heteroatoms. Examples of 4 to 6 membered heterocyclic include but are not limited to, oxetanyl, pyrrolidinyl, morpholinyl, piperazinyl, piperidinyl, 1,4-diazepanyl, 3-oxabicyclo[3.1.0]hexanyl and the like.

"5 to 6 membered heterocyclic" or "5 to 6 membered heterocycloaryl" as used herein refers to a heterocyclic group as defined above, having from 5 to 6 ring atoms and containing from 1 to 3 heteroatoms. Examples of 5 to 6 membered heterocyclic include but are not limited to, pyrrolidinyl, morpholinyl, piperazinyl, piperidinyl, 1,4-diazepanyl, 3-oxabicyclo[3.1.0]hexanyl and the like.

"3 to 9 membered heterocyclic" or "3 to 9 membered heterocycloaryl" as used herein refers to a heterocyclic group as defined above, having from 3 to 9 ring atoms and containing from 1 to 3 heteroatoms. Examples of 3-9 membered heterocyclic include but are not limited to, pyrrolidinyl, morpholinyl, piperazinyl, piperidinyl, 1,4-diazepanyl, 2-oxaspiro[3.3]heptanyl, 3-oxabicyclo[3.1.0]hexanyl and the like.

"Optionally substituted" as used herein indicates that a group, such as an alkyl, heteroaryl and heterocyclic, may be unsubstituted or the group may be substituted with one or more substituents as defined in Formula (I).

"Salt" or "salts" as used herein refers to an acid addition or base addition salt of a compound provided herein. "Salts" include in particular "pharmaceutically acceptable salts". "Pharmaceutically acceptable salts" as used herein refers to salts that retain the biological effectiveness and properties of the compounds according to Formula (I) and, which typically are not biologically or otherwise undesirable. In many cases, the compounds according to Formula (I) are capable of forming acid and/or base salts by virtue of the presence of amino and/or carboxyl groups or groups similar thereto. The skilled artisan will appreciate that salts, including pharmaceutically acceptable salts, of the compounds according to Formula (I) may be prepared. These salts may be prepared in situ during the final isolation and purification of the compound, or by separately reacting the purified compound in its free acid or free base form with a suitable base or acid, respectively.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases, such as carboxylate, sulfonate and phosphate salts.

In certain embodiments, provided herein are compounds according to Formula (I) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, formate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form. In certain embodiments, provided herein are compounds according to Formula (I) in formate or citrate salt form.

"Isomers" refers to different compounds according to Formula (I) that have the same molecular formula but differ in arrangement and configuration of the atoms.

"Optical isomer" or "stereoisomer" refers to any of the various stereo isomeric configurations which may exist for a given compound provided herein and includes geometric isomers. It is understood that a substituent may be attached at a chiral center of a carbon atom. Therefore, compounds provided herein include enantiomers, diastereomers or racemates of the compound.

Depending on the choice of the starting materials and procedures, the compounds according to Formula (I) can be present in the form of one of the possible stereoisomers or as mixtures thereof, for example as pure optical isomers, or as stereoisomer mixtures, such as racemates and diastereoisomer mixtures, depending on the number of asymmetric carbon atoms. The compounds according to Formula (I) provided herein are meant to include all such possible stereoisomers, including racemic mixtures, diastereomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compounds according to Formula (I) can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, a compound provided herein can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of the compounds according to Formula (I) or of intermediates thereof can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds according to Formula (I) into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds according to Formula (I) or racemic intermediates can also be resolved by chiral chromatography, e.g., high pressure liquid chromatography (HPLC) using a chiral adsorbent.

Any formula given herein is also intended to represent unlabeled forms as well as isotopically labeled forms of the compounds. Isotopically labeled compounds have structures depicted by the formulae given herein except that one or more atoms are replaced by an atom having a selected atomic mass or mass number. Isotopes that can be incorporated into compounds according to Formula (I) include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound provided herein. The concentration of deuterium, may be defined by the isotopic enrichment factor. "Isotopic enrichment factor" as used herein means the ratio between the isotopic abundance and the natural abundance of a specified isotope. If a substituent in a compound provided herein is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

For example, Formula (I) may be deuterated as shown in Formula (Ic):

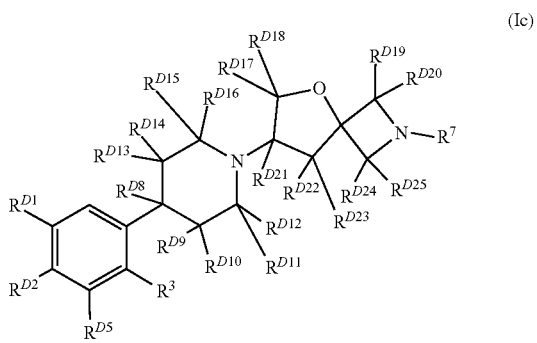

(Ic)

or a pharmaceutically acceptable salt thereof, wherein $R^3$ and $R^7$ are as defined in Formula (I); and $R^{D1}$, $R^{D2}$, $R^{D5}$, and $R^{D8}$-$R^{D27}$ are each independently D or halogen.

Other examples of isotopes that can be incorporated into compounds according to Formula (I) include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. Accordingly it should be understood that compounds according to Formula (I) includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds according to Formula (I) can generally be prepared by conventional techniques known to those skilled in the art or by processes analogous to those described in the accompanying Examples and preparations using an appropriate isotopically-labeled reagents in place of the non-labeled reagent previously employed.

"Administration" and "administering" and "administer" as used herein refer to the manner in which a compound provided herein (e.g., a compound according to Formula (I)) is presented to a subject.

"Subject" or "patient" as used herein refers to a living organism suffering from one or more of the diseases or disorders described here that can be treated by administration of a pharmaceutical composition described herein. Examples of subjects include mammals (e.g., humans and animals such as dogs, cows, horses, monkeys, pigs, guinea pigs, sheep, goats, cats, mice, rabbits, rats, and transgenic non-human animals). In certain embodiments, the subject is a primate. In certain embodiments, the subject is a human, e.g., a human suffering from, at risk of suffering from, or potentially capable of suffering from a disease described herein. In particular embodiments, the subject is an adult human at least about 18 years of age. In particular embodiments, the subject is an adult human from about 18 to about 75 years of age. In some embodiments, the subject is a human child up to about 18 years of age.

"Treat", "treating" or "treatment" of any disease or disorder as used herein refers to relieve, alleviate, delay, reduce, reverse, or improve at least one symptom of a condition in a subject. The term "treating" may also mean to arrest, delay the onset (i.e., the period prior to clinical manifestation of a disease) and/or reduce the risk of developing or worsening a condition. In certain embodiments, the term "treating" refers to relieving, alleviating, delaying of progression, reducing, reversing, or improving at least one symptom of a condition selected from psychosis, including psychosis associated with schizophrenia, schizoaffective disorder, psychotic depression, bipolar disorder with psychotic features, Alzheimer's Disease, Parkinson's Disease, post-traumatic stress disorder, and frontotemporal dementia, hyperkinetic movement disorders, including but not limited to Tourette's Syndrome, chorea and tardive dyskinesia, cognitive dysfunction, including but not limited to cognitive dysfunction associated with schizophrenia, Alzheimer's Disease, frontotemporal dementia, schizoaffective disorder, and depression; and/or substance use disorders.

"Prevent", "preventing" or "prevention" of any disease or disorder as used herein refers to the prophylactic treatment of the disease or disorder; or delaying the onset or progression of the disease or disorder.

"Pharmaceutical composition" as used herein refers to a compound provided herein, or a pharmaceutically acceptable salt thereof, together with at least one pharmaceutically acceptable carrier, in a form suitable for oral or parenteral administration.

"Pharmaceutically acceptable carrier" as used herein refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

A "therapeutically effective amount" of a compound provided herein as used herein refers to an amount of the compound that will elicit the biological or medical response of a subject, for example, increase enzyme or a protein activity, or ameliorate symptoms, alleviate conditions, slow or delay disease progression, or prevent a disease, etc. In one embodiment, the term "a therapeutically effective amount" refers to the amount of the compound provided herein that, when administered to a subject, is effective to (1) at least partially alleviate, prevent and/or ameliorate a condition, or a disorder or a disease (i) mediated by M4, or (ii) associated with M4 activity, or (iii) characterized by activity (normal or abnormal) of M4; or (2) increase the activity of M4. In another embodiment, the term "a therapeutically effective amount" refers to the amount of the compound provided herein that, when administered to a cell, or a tissue, or a non-cellular biological material, or a medium, is effective to increase the activity of M4.

"Inhibit", "inhibition" or "inhibiting" as used herein refers to the reduction or suppression of a given condition, symptom, or disorder, or disease, or a significant decrease in the baseline activity of a biological activity or process.

A subject is "in need of" a treatment if such subject would benefit biologically, medically or in quality of life from such treatment.

"Substance use disorder" or "SUD" as used herein is defined with reference to DSM-5 criteria (i.e., according to the Diagnostic and Statistical Manual of Mental Disorders. $5^{th}$ Edition, Washington, DC: American Psychiatric Association, 2013; hereinafter "DSM-5"), the entire contents of which are incorporated herein by reference. The term "substance use disorder" as used herein is defined as when the recurrent use of alcohol and/or drugs causes clinically and functionally significant impairment, such as health problems, disability, and failure to meet major responsibilities at work, school, or home. According to the DSM-5, a diagnosis of substance use disorder is based on evidence of impaired control, social impairment, risky use, and pharmacological criteria. Substance use disorder includes, for example, alcohol use disorder, tobacco use disorder, cannabis use disorder, stimulant use disorder, hallucinogen use disorder and opioid use disorder.

"Psychosocial or behavioral therapy" as used herein refers to, but not limited to, cognitive behavioral therapy (e.g., as described in *Arch. Gen. Psychiatry* 1999; 56:493-502), interpersonal therapy (e.g., as described in *Psychol Addict Behav* 2009; 23(1): 168-174), contingency management based therapy e.g., as described in *Psychol Addict Behav* 2009; 23(1): 168-174; in *J. Consul. Clin. Psychol.* 2005; 73(2): 354-59; or in *Case Reports in Psychiatry*, Vol. 2012, Article ID 731638), community reinforcement approach based therapy (e.g., as described in *Drug Alcohol Depend* 2004; 74:1-13), motivational interviewing based therapy (e.g., as described in *J. Consul. Clin. Psychol.* 2001; 69(5): 858-62), motivational enhancement based therapy (e.g., as described in *Drug Alcohol Depend* 2007, 91:97-101) or meditation based therapy, such as transcendental meditation based therapy (e.g., as described in Addiction 2004; 99(7): 862-874 or *J. Consul. Clin. Psychol.* 2000; 68(3): 515-52); in particular contingency management based therapy.

"Standardized psychological treatment" or "standardized psychological support" as used herein refers to standard counselling sessions, for example once a week, in particular counselling focused on cocaine consumption.

"Computer-assisted" or "computer-assistance" as used herein refers to psychosocial or behavioral therapy comprising the use of electronic or digital tools such as online tools, smartphones, laptops, tablets, wireless devices or health Apps.

Unless specified otherwise, "a compound provided herein" or "compounds provided herein" refers to compounds of Formula (I) and subformulae thereof, including Formula (Ia), (Ib), and (Ic), and any exemplified compounds and salts thereof, as well as all stereoisomers (including diastereoisomers and enantiomers), rotamers, tautomers and isotopically labeled compounds (including deuterium substitutions), as well as inherently formed moieties.

"A," "an," "the" and similar terms as used herein (especially in the context of the claims) are to be construed to cover both the singular and plural unless otherwise indicated herein or clearly contradicted by the context.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps.

If there is a discrepancy between a depicted structure and a chemical name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure of portion of the structure.

All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed.

2. Compounds

In one embodiment, provided herein is a compound according to Formula (I)

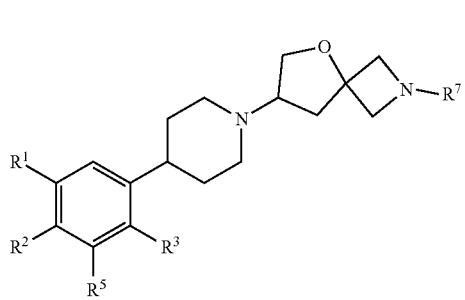

(I)

or a pharmaceutically acceptable salt thereof, wherein
$R^1$ is halogen or hydrogen;
$R^2$ is halogen or hydrogen;
$R^3$ is
  optionally substituted $C_{1-3}$ alkyl, said alkyl is optionally substituted with one 4 to 6 membered heterocycloalkyl,
  optionally substituted 5 to 6 membered heteroaryl, said heteroaryl is optionally substituted with one $C_{1-3}$ alkyl,
  optionally substituted 4 to 6 membered heterocycloalkyl, said heterocycloalkyl is optionally substituted with one —OH,
  optionally substituted 4 to 6 membered cycloalkyl, said cycloalkyl is optionally substituted with one —OH, or
  —$OR^4$;
$R^4$ is
  optionally substituted $C_{1-5}$ alkyl, said alkyl is optionally substituted with one or two $R^6$,
  optionally substituted 3 to 9 membered heterocycloalkyl, said heterocycloalkyl is optionally substituted with one or two $R^6$, or
  optionally substituted 4 to 6 membered cycloalkyl, said cycloalkyl is optionally substituted with one, two, or three $R^6$;
$R^5$ is halogen or hydrogen;
each $R^6$ is independently
  halogen,
  —OH,
  —$OCH_3$,
  —$C(CH_3)_2OH$,
  —$CH_2OH$,
  cyano,
  optionally substituted $C_1$-$C_4$ alkyl, said alkyl is optionally substituted with —OH,
  optionally substituted 4 to 7 membered heterocycloalkyl, said heterocycloalkyl is optionally substituted with one or two substituents independently selected from the group consisting of halogen, —OH, —$OCH_3$, and $C_{1-3}$ alkyl, or
  optionally substituted 5 to 6 membered heteroaryl, said heteroaryl is optionally substituted with one $C_{1-3}$ alkyl; and
$R^7$ is 5-membered heteroaryl.

In one embodiment, provided herein is a compound according to Formula (Ia)

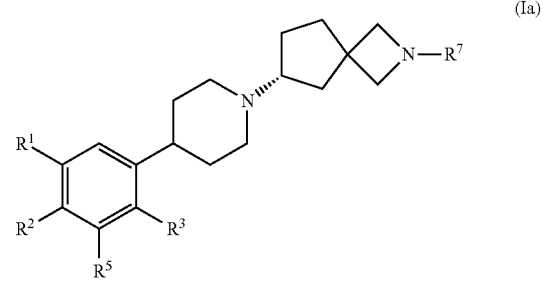

(Ia)

or a pharmaceutically acceptable salt or stereoisomer thereof.

In one embodiment, provided herein is a compound according to Formula (Ib)

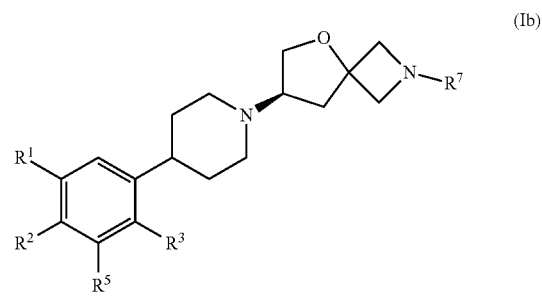

(Ib)

or a pharmaceutically acceptable salt or stereoisomer thereof.

In one embodiment, $R^1$ is selected from the group consisting of H, chloro, and fluoro. In another embodiment, $R^1$ is fluoro.

In one embodiment, $R^2$ is H or fluoro.

In one embodiment, $R^5$ is H or fluoro.

In one embodiment, $R^1$, $R^2$, and $R^5$ are H.

In one embodiment, $R^2$ and $R^5$ are H.

In one embodiment, $R^3$ is selected from the group consisting of:

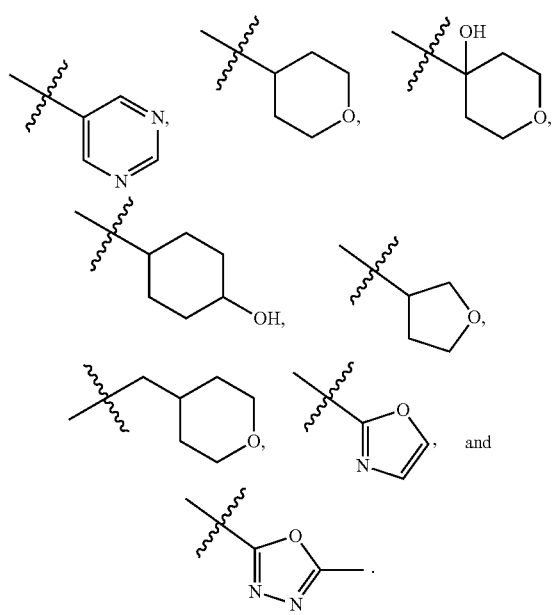
In some embodiments, $R^3$ is —$OR^4$.
In one embodiment, $R^4$ is selected from the group consisting of $CH_3$, —$CH_2CH_2C(CH_3)_2OH$, —$CH_2CH_2C(CH_3)_2OCH_3$, —$CH_2CH_2OCH_3$, and —$CH_2C(CH_3)_2OH$. In some embodiments, $R^4$ is selected from the group consisting of:
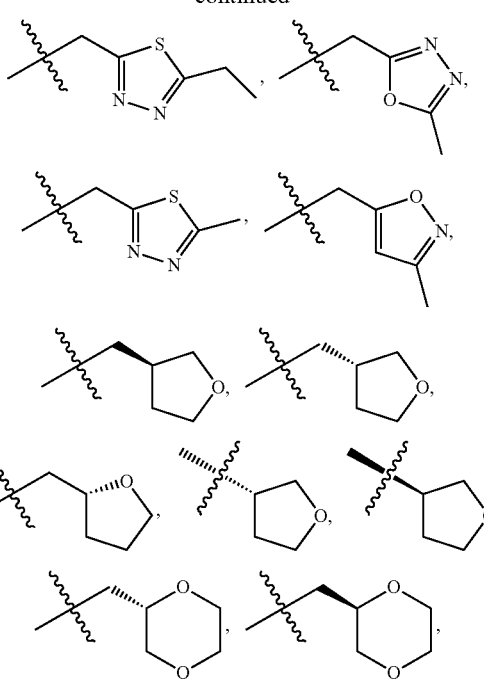
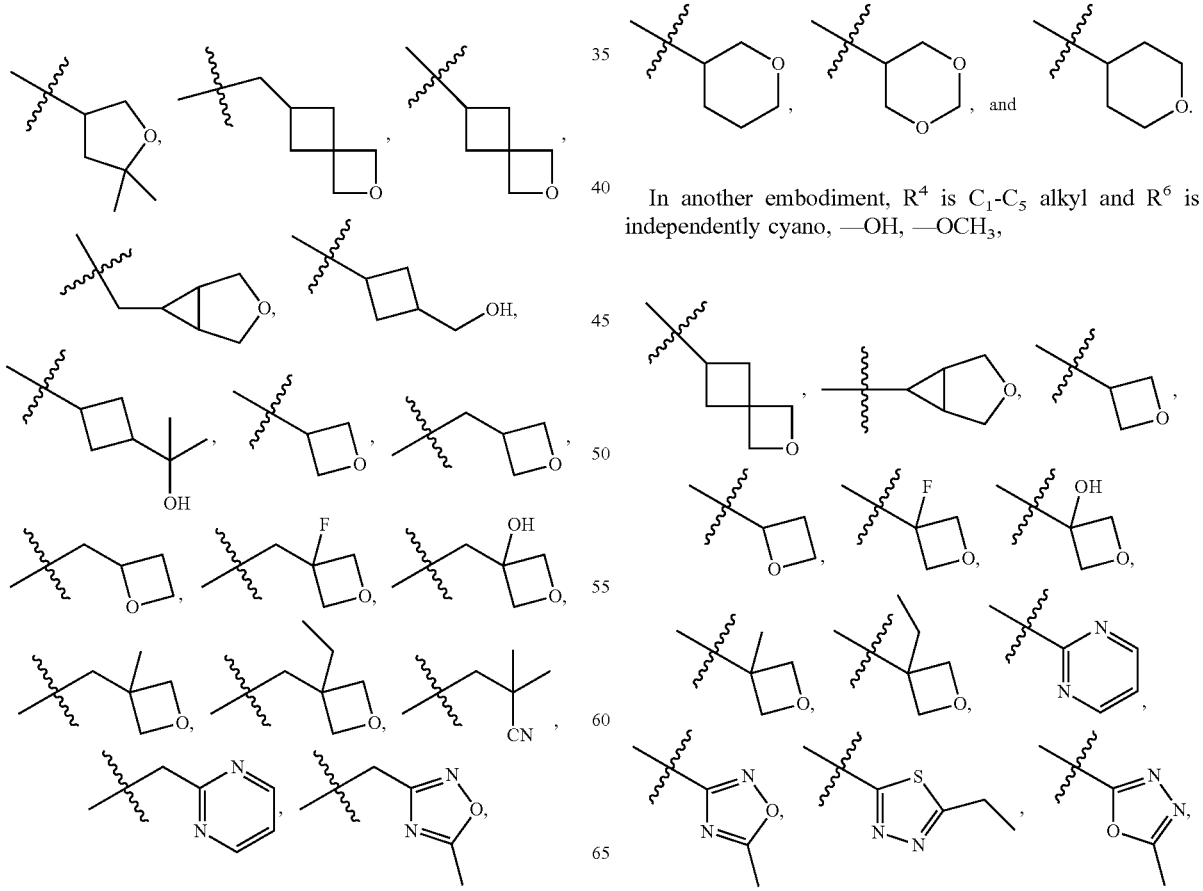
In another embodiment, $R^4$ is $C_1$-$C_5$ alkyl and $R^6$ is independently cyano, —OH, —$OCH_3$, -continued

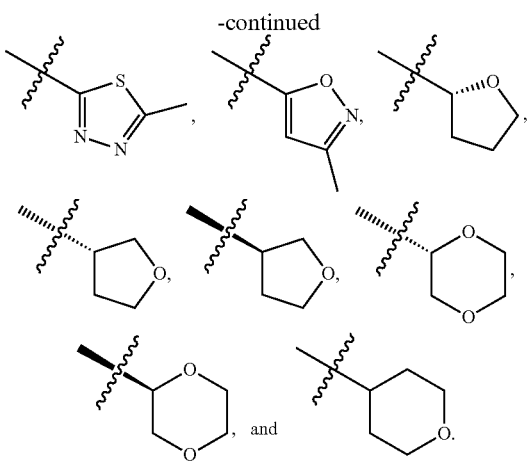

In one embodiment, R⁷ is selected from the group consisting of:

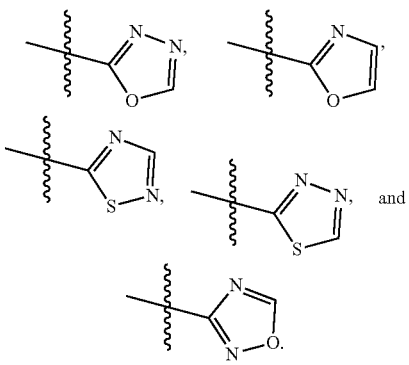

In one embodiment, provided herein is a compound which is selected from the group consisting of:
(S)-7-(4-(5-fluoro-2-(oxetan-3-yloxy)phenyl)piperidin-1-yl)-2-(1,3,4-oxadiazol-2-yl)-5-oxa-2-azaspiro[3.4]octane;
(S)-7-(4-(5-fluoro-2-(((R)-tetrahydrofuran-3-yl)methoxy)phenyl)piperidin-1-yl)-2-(1,3,4-oxadiazol-2-yl)-5-oxa-2-azaspiro[3.4]octane;
ethyl 5-((S)-7-(4-(2-(((R)-1,4-dioxan-2-yl)methoxy)-5-fluorophenyl)piperidin-1-yl)-5-oxa-2-azaspiro[3.4]octan-2-yl)-1,3,4-oxadiazole-2-carboxylate;
(S)-7-(4-(5-fluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
(S)-3-(2-(1-(2-(1,3,4-oxadiazol-2-yl)-5-oxa-2-azaspiro[3.4]octan-7-yl)piperidin-4-yl)-4-fluorophenoxy)-2,2-dimethylpropanenitrile;
(S)-7-(4-(2-(((S)-1,4-dioxan-2-yl)methoxy)-5-fluorophenyl)piperidin-1-yl)-2-(1,3,4-oxadiazol-2-yl)-5-oxa-2-azaspiro[3.4]octane;
(S)-7-(4-(5-fluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
(S)-7-(4-(5-fluoro-2-(((S)-tetrahydrofuran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((S)-tetrahydrofuran-3-yl)methoxy)phenyl)piperidin-1-yl)-2-(1,3,4-oxadiazol-2-yl)-5-oxa-2-azaspiro[3.4]octane;
(S)-7-(4-(5-fluoro-2-((tetrahydro-2H-pyran-4-yl)methoxy)phenyl)piperidin-1-yl)-2-(1,3,4-oxadiazol-2-yl)-5-oxa-2-azaspiro[3.4]octane;
(S)-7-(4-(5-fluoro-2-(3-methoxy-3-methylbutoxy)phenyl)piperidin-1-yl)-2-(1,3,4-oxadiazol-2-yl)-5-oxa-2-azaspiro[3.4]octane;
(S)-7-(4-(5-fluoro-2-(2-methoxyethoxy)phenyl)piperidin-1-yl)-2-(1,3,4-oxadiazol-2-yl)-5-oxa-2-azaspiro[3.4]octane;
(S)-7-(4-(2-((1,3-dioxan-5-yl)oxy)-5-fluorophenyl)piperidin-1-yl)-2-(1,3,4-oxadiazol-2-yl)-5-oxa-2-azaspiro[3.4]octane;
(S)-4-(2-(1-(2-(1,3,4-oxadiazol-2-yl)-5-oxa-2-azaspiro[3.4]octan-7-yl)piperidin-4-yl)-4-fluorophenoxy)-2-methylbutan-2-ol;
(S)-2-(1,3,4-oxadiazol-2-yl)-7-(4-(2-(((R)-tetrahydrofuran-3-yl)oxy)phenyl)piperidin-1-yl)-5-oxa-2-azaspiro[3.4]octane;
(S)-2-(1,3,4-oxadiazol-2-yl)-7-(4-(2-(oxetan-3-yloxy)phenyl)piperidin-1-yl)-5-oxa-2-azaspiro[3.4]octane;
(S)-7-(4-(2-methoxyphenyl)piperidin-1-yl)-2-(1,3,4-oxadiazol-2-yl)-5-oxa-2-azaspiro[3.4]octane;
(S)-7-(4-(4,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
(S)-7-(4-(4-fluoro-2-methoxyphenyl)piperidin-1-yl)-2-(1,3,4-oxadiazol-2-yl)-5-oxa-2-azaspiro[3.4]octane;
(S)-4-(2-(1-(2-(1,3,4-oxadiazol-2-yl)-5-oxa-2-azaspiro[3.4]octan-7-yl)piperidin-4-yl)-5-fluorophenoxy)-2-methylbutan-2-ol;
(S)-1-(2-(1-(2-(1,3,4-oxadiazol-2-yl)-5-oxa-2-azaspiro[3.4]octan-7-yl)piperidin-4-yl)-4-fluorophenoxy)-2-methylpropan-2-ol;
(S)-7-(4-(5-fluoro-2-methoxyphenyl)piperidin-1-yl)-2-(1,3,4-oxadiazol-2-yl)-5-oxa-2-azaspiro[3.4]octane;
(S)-2-(1,3,4-oxadiazol-2-yl)-7-(4-(2-(pyrimidin-5-yl)phenyl)piperidin-1-yl)-5-oxa-2-azaspiro[3.4]octane;
(S)-2-(1,3,4-oxadiazol-2-yl)-7-(4-(2-(oxazol-2-yl)phenyl)piperidin-1-yl)-5-oxa-2-azaspiro[3.4]octane;
(S)-7-(4-(2-(5-methyl-1,3,4-oxadiazol-2-yl)phenyl)piperidin-1-yl)-2-(1,3,4-oxadiazol-2-yl)-5-oxa-2-azaspiro[3.4]octane;
(S)-7-(4-(5-fluoro-2-(oxetan-3-ylmethoxy)phenyl)piperidin-1-yl)-2-(1,3,4-thiadiazol-2-yl)-5-oxa-2-azaspiro[3.4]octane;
(S)-7-(4-(5-fluoro-2-((3-methyloxetan-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-((5-methyl-1,3,4-thiadiazol-2-yl)methoxy)phenyl)piperidin-1-yl)-2-(1,3,4-oxadiazol-2-yl)-5-oxa-2-azaspiro[3.4]octane;
(S)-7-(4-(5-fluoro-2-((5-methyl-1,3,4-oxadiazol-2-yl)methoxy)phenyl)piperidin-1-yl)-2-(1,3,4-oxadiazol-2-yl)-5-oxa-2-azaspiro[3.4]octane;

(S)-7-(4-(5-fluoro-2-((3-methylisoxazol-5-yl)methoxy)phenyl)piperidin-1-yl)-2-(1,3,4-oxadiazol-2-yl)-5-oxa-2-azaspiro[3.4]octane;
(S)-7-(4-(5-fluoro-2-(oxetan-3-ylmethoxy)phenyl)piperidin-1-yl)-2-(1,3,4-oxadiazol-2-yl)-5-oxa-2-azaspiro[3.4]octane;
(S)-7-(4-(5-fluoro-2-(pyrimidin-2-ylmethoxy)phenyl)piperidin-1-yl)-2-(1,3,4-oxadiazol-2-yl)-5-oxa-2-azaspiro[3.4]octane;
(S)-7-(4-(5-fluoro-2-((3-fluorooxetan-3-yl)methoxy)phenyl)piperidin-1-yl)-2-(1,3,4-oxadiazol-2-yl)-5-oxa-2-azaspiro[3.4]octane;
(S)-7-(4-(5-fluoro-2-((3-methyloxetan-3-yl)methoxy)phenyl)piperidin-1-yl)-2-(1,3,4-oxadiazol-2-yl)-5-oxa-2-azaspiro[3.4]octane;
(S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane;
(S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane;
(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-((3-ethyloxetan-3-yl)methoxy)-5-fluorophenyl)piperidin-1-yl)-2-(1,3,4-oxadiazol-2-yl)-5-oxa-2-azaspiro[3.4]octane;
(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(2-((2-oxaspiro[3.3]heptan-6-yl)methoxy)-5-fluorophenyl)piperidin-1-yl)-2-(1,3,4-oxadiazol-2-yl)-5-oxa-2-azaspiro[3.4]octane;
(S)-7-(4-(2-((5-ethyl-1,3,4-thiadiazol-2-yl)methoxy)-5-fluorophenyl)piperidin-1-yl)-2-(1,3,4-oxadiazol-2-yl)-5-oxa-2-azaspiro[3.4]octane;
(S)-3-((2-(1-(2-(1,3,4-oxadiazol-2-yl)-5-oxa-2-azaspiro[3.4]octan-7-yl)piperidin-4-yl)-4-fluorophenoxy)methyl)oxetan-3-ol;
2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(7S)-7-(4-(2-((3-oxabicyclo[3.1.0]hexan-6-yl)methoxy)-5-fluorophenyl)piperidin-1-yl)-2-(1,3,4-oxadiazol-2-yl)-5-oxa-2-azaspiro[3.4]octane;
(S)-7-(4-(2-((2-oxaspiro[3.3]heptan-6-yl)oxy)-3,5-difluorophenyl)piperidin-1-yl)-2-(1,3,4-oxadiazol-2-yl)-5-oxa-2-azaspiro[3.4]octane;
(S)-7-(4-(3,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
(S)-7-(4-(3,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
(S)-7-(4-(3,5-difluoro-2-(oxetan-3-ylmethoxy)phenyl)piperidin-1-yl)-2-(1,3,4-oxadiazol-2-yl)-5-oxa-2-azaspiro[3.4]octane;
(S)-7-(4-(3,5-difluoro-2-(oxetan-3-yloxy)phenyl)piperidin-1-yl)-2-(1,3,4-oxadiazol-2-yl)-5-oxa-2-azaspiro[3.4]octane;
(S)-7-(4-(4,5-difluoro-2-(oxetan-3-yloxy)phenyl)piperidin-1-yl)-2-(1,3,4-oxadiazol-2-yl)-5-oxa-2-azaspiro[3.4]octane;
(S)-7-(4-(4,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;
(S)-2-(1,3,4-oxadiazol-2-yl)-7-(4-(2-(tetrahydro-2H-pyran-4-yl)phenyl)piperidin-1-yl)-5-oxa-2-azaspiro[3.4]octane;
(S)-7-(4-(5-fluoro-2-(tetrahydro-2H-pyran-4-yl)phenyl)piperidin-1-yl)-2-(1,3,4-oxadiazol-2-yl)-5-oxa-2-azaspiro[3.4]octane;
(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;

(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;
(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;
(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;
(S)-2-(1,3,4-oxadiazol-2-yl)-7-(4-(2-((tetrahydro-2H-pyran-4-yl)methyl)phenyl)piperidin-1-yl)-5-oxa-2-azaspiro[3.4]octane;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(S)-7-(4-(5-fluoro-2-(oxetan-3-yloxy)phenyl)piperidin-1-yl)-2-(oxazol-2-yl)-5-oxa-2-azaspiro[3.4]octane;
(S)-7-(4-(2-(((R)-1,4-dioxan-2-yl)methoxy)-5-fluorophenyl)piperidin-1-yl)-2-(oxazol-2-yl)-5-oxa-2-azaspiro[3.4]octane;
(S)-2-(oxazol-2-yl)-7-(4-(2-(oxetan-3-yloxy)phenyl)piperidin-1-yl)-5-oxa-2-azaspiro[3.4]octane;
(S)-7-(4-(5-fluoro-2-(((R)-tetrahydrofuran-3-yl)oxy)phenyl)piperidin-1-yl)-2-(oxazol-2-yl)-5-oxa-2-azaspiro[3.4]octane;
(S)-7-(4-(5-fluoro-2-((tetrahydro-2H-pyran-4-yl)oxy)phenyl)piperidin-1-yl)-2-(oxazol-2-yl)-5-oxa-2-azaspiro[3.4]octane;
(S)-2-(oxazol-2-yl)-7-(4-(2-(((R)-tetrahydrofuran-3-yl)oxy)phenyl)piperidin-1-yl)-5-oxa-2-azaspiro[3.4]octane;
(S)-7-(4-(2-((2-oxaspiro[3.3]heptan-6-yl)oxy)-5-fluorophenyl)piperidin-1-yl)-2-(oxazol-2-yl)-5-oxa-2-azaspiro[3.4]octane;
(S)-2-(oxazol-2-yl)-7-(4-(2-(((S)-tetrahydrofuran-3-yl)oxy)phenyl)piperidin-1-yl)-5-oxa-2-azaspiro[3.4]octane;
(S)-7-(4-(5-fluoro-2-methoxyphenyl)piperidin-1-yl)-2-(oxazol-2-yl)-5-oxa-2-azaspiro[3.4]octane;
(S)-2-(oxazol-2-yl)-7-(4-(2-((tetrahydro-2H-pyran-4-yl)oxy)phenyl)piperidin-1-yl)-5-oxa-2-azaspiro[3.4]octane;
(S)-1-(4-fluoro-2-(1-(2-(oxazol-2-yl)-5-oxa-2-azaspiro[3.4]octan-7-yl)piperidin-4-yl)phenoxy)-2-methylpropan-2-ol;
(S)-7-(4-(5-fluoro-2-(2-methoxyethoxy)phenyl)piperidin-1-yl)-2-(oxazol-2-yl)-5-oxa-2-azaspiro[3.4]octane;
(S)-7-(4-(2-((2-oxaspiro[3.3]heptan-6-yl)oxy)phenyl)piperidin-1-yl)-2-(oxazol-2-yl)-5-oxa-2-azaspiro[3.4]octane;
(S)-7-(4-(2-methoxyphenyl)piperidin-1-yl)-2-(oxazol-2-yl)-5-oxa-2-azaspiro[3.4]octane;
(S)-7-(4-(4,5-difluoro-2-(oxetan-3-ylmethoxy)phenyl)piperidin-1-yl)-2-(oxazol-2-yl)-5-oxa-2-azaspiro[3.4]octane;
(S)-7-(4-(4,5-difluoro-2-((3-fluorooxetan-3-yl)methoxy)phenyl)piperidin-1-yl)-2-(oxazol-2-yl)-5-oxa-2-azaspiro[3.4]octane;
(S)-7-(4-(4,5-difluoro-2-(oxetan-3-yloxy)phenyl)piperidin-1-yl)-2-(oxazol-2-yl)-5-oxa-2-azaspiro[3.4]octane;
(S)-2-(oxazol-2-yl)-7-(4-(2-(pyrimidin-5-yl)phenyl)piperidin-1-yl)-5-oxa-2-azaspiro[3.4]octane;
(S)-7-(4-(4-fluoro-2-(oxetan-3-yloxy)phenyl)piperidin-1-yl)-2-(oxazol-2-yl)-5-oxa-2-azaspiro[3.4]octane;
2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
(S)-2-(oxazol-2-yl)-7-(4-(2-(tetrahydro-2H-pyran-4-yl)phenyl)piperidin-1-yl)-5-oxa-2-azaspiro[3.4]octane;
(S)-7-(4-(5-fluoro-2-(tetrahydro-2H-pyran-4-yl)phenyl)piperidin-1-yl)-2-(oxazol-2-yl)-5-oxa-2-azaspiro[3.4]octane;
(S)-7-(4-(5-chloro-2-methoxyphenyl)piperidin-1-yl)-2-(1,2,4-thiadiazol-5-yl)-5-oxa-2-azaspiro[3.4]octane;
(S)-7-(4-(2-methoxyphenyl)piperidin-1-yl)-2-(1,2,4-thiadiazol-5-yl)-5-oxa-2-azaspiro[3.4]octane;
(S)-1-(2-(1-(2-(1,2,4-thiadiazol-5-yl)-5-oxa-2-azaspiro[3.4]octan-7-yl)piperidin-4-yl)-4-fluorophenoxy)-2-methylpropan-2-ol;
(S)-7-(4-(5-fluoro-2-(2-methoxyethoxy)phenyl)piperidin-1-yl)-2-(1,2,4-thiadiazol-5-yl)-5-oxa-2-azaspiro[3.4]octane;
(S)-7-(4-(4-fluoro-2-methoxyphenyl)piperidin-1-yl)-2-(1,2,4-thiadiazol-5-yl)-5-oxa-2-azaspiro[3.4]octane;
(S)-7-(4-(2-((5-methyl-1,2,4-oxadiazol-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-(oxetan-3-yloxy)phenyl)piperidin-1-yl)-2-(1,3,4-thiadiazol-2-yl)-5-oxa-2-azaspiro[3.4]octane;
(S)-7-(4-(5-fluoro-2-(((R)-tetrahydrofuran-3-yl)oxy)phenyl)piperidin-1-yl)-2-(1,3,4-thiadiazol-2-yl)-5-oxa-2-azaspiro[3.4]octane;
(S)-7-(4-(5-fluoro-2-(((R)-tetrahydrofuran-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-((tetrahydro-2H-pyran-4-yl)oxy)phenyl)piperidin-1-yl)-2-(1,3,4-thiadiazol-2-yl)-5-oxa-2-azaspiro[3.4]octane;
(S)-7-(4-(2-(((R)-1,4-dioxan-2-yl)methoxy)-5-fluorophenyl)piperidin-1-yl)-2-(1,3,4-thiadiazol-2-yl)-5-oxa-2-azaspiro[3.4]octane;
(S)-7-(4-(2-(((S)-1,4-dioxan-2-yl)methoxy)-5-fluorophenyl)piperidin-1-yl)-2-(1,3,4-thiadiazol-2-yl)-5-oxa-2-azaspiro[3.4]octane;
(S)-7-(4-(4,5-difluoro-2-(((R)-tetrahydrofuran-3-yl)oxy)phenyl)piperidin-1-yl)-2-(1,3,4-thiadiazol-2-yl)-5-oxa-2-azaspiro[3.4]octane;
(S)-7-(4-(5-fluoro-2-(3-methoxy-3-methylbutoxy)phenyl)piperidin-1-yl)-2-(1,3,4-thiadiazol-2-yl)-5-oxa-2-azaspiro[3.4]octane;

(S)-7-(4-(5-fluoro-2-(((S)-tetrahydrofuran-3-yl)oxy)phenyl)
piperidin-1-yl)-2-(1,3,4-thiadiazol-2-yl)-5-oxa-2-
azaspiro[3.4]octane;
(S)-4-(2-(1-(2-(1,3,4-thiadiazol-2-yl)-5-oxa-2-azaspiro[3.4]
octan-7-yl)piperidin-4-yl)-4-fluorophenoxy)-2-methylbu-
tan-2-ol;
(S)-7-(4-(2-(oxetan-3-yloxy)phenyl)piperidin-1-yl)-2-(1,3,
4-thiadiazol-2-yl)-5-oxa-2-azaspiro[3.4]octane formate
salt;
(S)-7-(4-(2-methoxyphenyl)piperidin-1-yl)-2-(1,3,4-thiadi-
azol-2-yl)-5-oxa-2-azaspiro[3.4]octane;
(S)-7-(4-(5-fluoro-2-(2-methoxyethoxy)phenyl)piperidin-1-
yl)-2-(1,3,4-thiadiazol-2-yl)-5-oxa-2-azaspiro[3.4]oc-
tane;
(S)-7-(4-(4-fluoro-2-methoxyphenyl)piperidin-1-yl)-2-(1,3,
4-thiadiazol-2-yl)-5-oxa-2-azaspiro[3.4]octane;
(S)-1-(2-(1-(2-(1,3,4-thiadiazol-2-yl)-5-oxa-2-azaspiro[3.4]
octan-7-yl)piperidin-4-yl)-4-fluorophenoxy)-2-methyl-
propan-2-ol;
(S)-4-(2-(1-(2-(1,3,4-thiadiazol-2-yl)-5-oxa-2-azaspiro[3.4]
octan-7-yl)piperidin-4-yl)-5-fluorophenoxy)-2-methylbu-
tan-2-ol;
(S)-7-(4-(2-((2-oxaspiro[3.3]heptan-6-yl)oxy)-5-fluorophe-
nyl)piperidin-1-yl)-2-(1,3,4-thiadiazol-2-yl)-5-oxa-2-
azaspiro[3.4]octane;
(S)-7-(4-(5-fluoro-2-(((S)-tetrahydrofuran-3-yl)methoxy)
phenyl)piperidin-1-yl)-2-(1,3,4-thiadiazol-2-yl)-5-oxa-2-
azaspiro[3.4]octane;
(S)-1-(2-(1-(2-(1,2,4-thiadiazol-5-yl)-5-oxa-2-azaspiro[3.4]
octan-7-yl)piperidin-4-yl)phenoxy)-2-methylpropan-2-
ol;
(S)-7-(4-(5-fluoro-2-((tetrahydro-2H-pyran-4-yl)oxy)phe-
nyl)piperidin-1-yl)-2-(1,2,4-oxadiazol-3-yl)-5-oxa-2-
azaspiro[3.4]octane;
(S)-7-(4-(5-fluoro-2-(oxetan-3-yloxy)phenyl)piperidin-1-
yl)-2-(1,2,4-oxadiazol-3-yl)-5-oxa-2-azaspiro[3.4]oc-
tane; and
(S)-7-(4-(2-((2-oxaspiro[3.3]heptan-6-yl)oxy)-5-fluorophe-
nyl)piperidin-1-yl)-2-(1,2,4-oxadiazol-3-yl)-5-oxa-2-
azaspiro[3.4]octane, or a pharmaceutically acceptable salt
thereof.

In one embodiment, the compound is selected from the
group consisting of:
(S)-7-(4-(2-((2-oxaspiro[3.3]heptan-6-yl)oxy)-5-fluorophe-
nyl)piperidin-1-yl)-2-(1,3,4-oxadiazol-2-yl)-5-oxa-2-
azaspiro[3.4]octane, having the following structure:

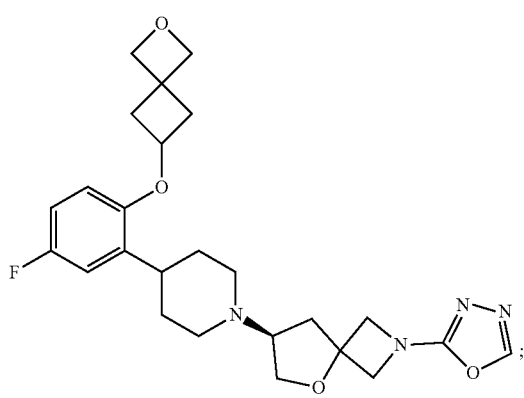 [SMILES: Fc1ccc(OC2CC3(COC3)C2)c(C2CCN([C@@H]3COC4(C3)CN(c3nnco3)C4)CC2)c1]

(R)-7-(4-(2-((2-oxaspiro[3.3]heptan-6-yl)oxy)-5-fluorophe-
nyl)piperidin-1-yl)-2-(1,3,4-oxadiazol-2-yl)-5-oxa-2-
azaspiro[3.4]octane, having the following structure:

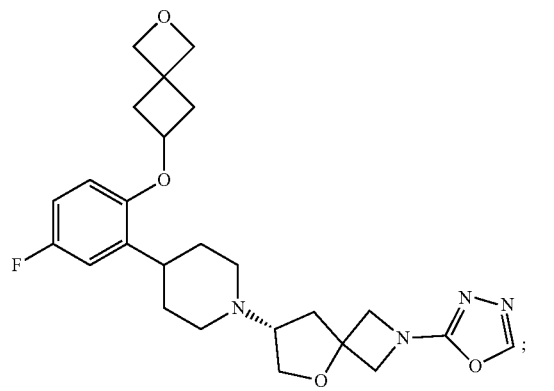 [SMILES: Fc1ccc(OC2CC3(COC3)C2)c(C2CCN([C@H]3COC4(C3)CN(c3nnco3)C4)CC2)c1]

(S)-7-(4-(5-fluoro-2-(oxetan-3-yloxy)phenyl)piperidin-1-
yl)-2-(1,3,4-oxadiazol-2-yl)-5-oxa-2-azaspiro[3.4]octane,
having the following structure:

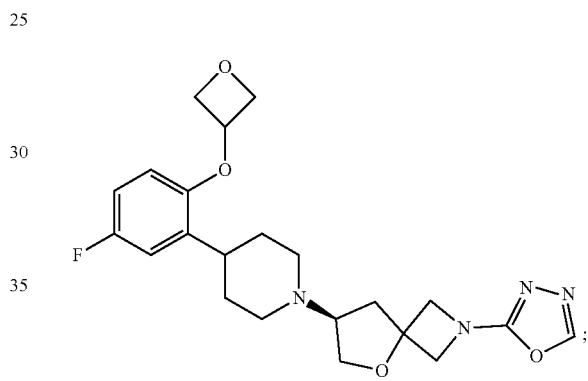

and
(S)-2-(oxazol-2-yl)-7-(4-(2-(tetrahydro-2H-pyran-4-yl)phe-
nyl)piperidin-1-yl)-5-oxa-2-azaspiro[3.4]octane, having
the following structure:

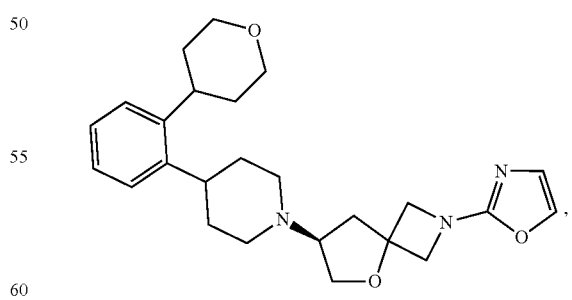

or a pharmaceutically acceptable salt thereof.

In certain embodiments, the compound is (S)-7-(4-(2-((2-
oxaspiro[3.3]heptan-6-yl)oxy)-5-fluorophenyl)piperidin-1-
yl)-2-(1,3,4-oxadiazol-2-yl)-5-oxa-2-azaspiro[3.4]octane,
having the following structure:

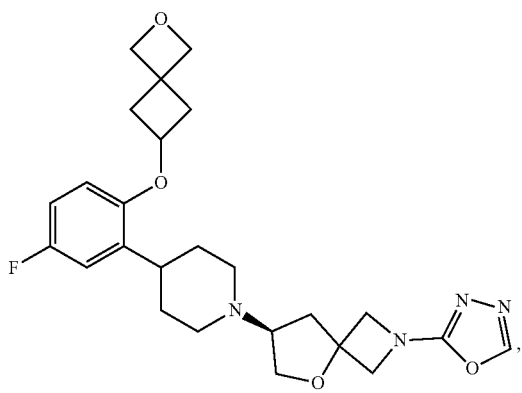

or a pharmaceutically acceptable salt thereof.

In certain embodiments, the compound is (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

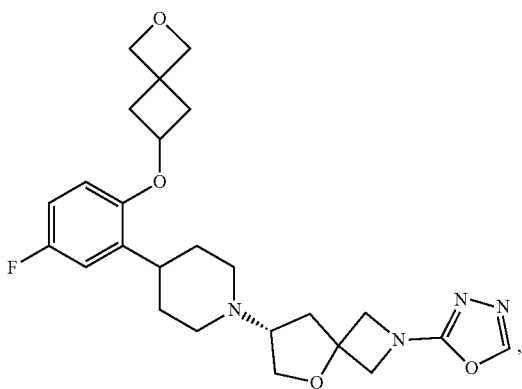 [SMILES: Fc1ccc(OC2CC3(COC3)C2)c(C2CCN([C@H]3COC4(C3)CN(c3nnco3)C4)CC2)c1]

or a pharmaceutically acceptable salt thereof.

In certain embodiments, the compound is (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane, having the following structure:

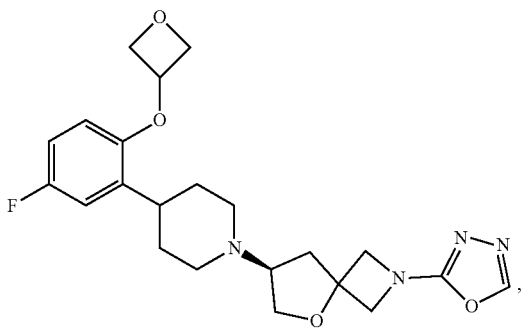 [SMILES: Fc1ccc(OC2COC2)c(C2CCN([C@@H]3COC4(C3)CN(c3nnco3)C4)CC2)c1]

or a pharmaceutically acceptable salt thereof.

In certain embodiments, the compound is (S)-2-(oxazol-2-yl)-7-(4-(2-(tetrahydro-2H-pyran-4-yl)phenyl)piperidin-1-yl)-5-oxa-2-azaspiro[3.4]octane, having the following structure:

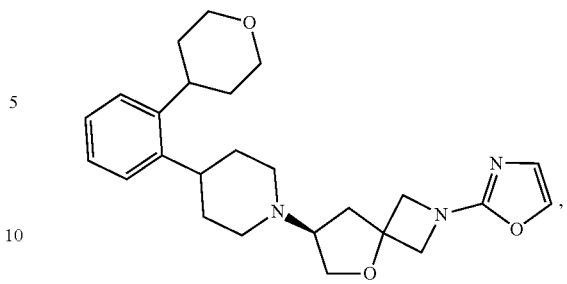

or a pharmaceutically acceptable salt thereof.

In one embodiment, provided herein is a pharmaceutical composition comprising a compound provided herein or a pharmaceutically acceptable salt thereof.

3. Pharmaceutical Compositions

In one embodiment, provided herein is a pharmaceutical composition comprising a compound provided herein, or a pharmaceutically acceptable salt thereof, and a pharmaceutically acceptable carrier. In another embodiment, provided herein is a pharmaceutical composition comprising a therapeutically effective amount of a compound of Formula (I), or a pharmaceutically acceptable salt thereof, and a pharmaceutically acceptable carrier. In another embodiment, provided herein is a pharmaceutical composition comprising a compound of Formula (I), or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g., by injection, infusion, transdermal or topical administration), and rectal administration. Topical administration may also pertain to inhalation or intranasal application. The pharmaceutical compositions provided herein can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of the following:

a) diluents, e.g., lactose, dextrose, sucrose, mannitol, sorbitol, cellulose and/or glycine;
    b) lubricants, e.g., silica, talcum, stearic acid, its magnesium or calcium salt and/or polyethylene glycol; for tablets also
    c) binders, e.g., magnesium aluminum silicate, starch paste, gelatin, tragacanth, methylcellulose, sodium carboxymethylcellulose and/or polyvinylpyrrolidone; if desired
    d) disintegrants, e.g., starches, agar, alginic acid or its sodium salt, or effervescent mixtures; and
    e) absorbents, colorants, flavors and sweeteners.

The pharmaceutical compositions provided herein can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound or the pharmaceutical composition thereof is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds provided herein can be applied in vitro in the form of solutions, e.g., aqueous solutions, and in vivo either enterally, parenterally, advantageously intravenously, e.g., as a suspension or in aqueous solution. The dosage in vitro may range between about $10^3$ molar and $10^9$ molar concentrations. A therapeutically effective amount in vivo may range depending on the route of administration, between about 0.1-500 mg/kg, or between about 1-100 mg/kg.

4. Methods of Use

In one embodiment, the compounds provided herein are in free form or in pharmaceutically acceptable salt form and have activity as muscarinic M4 receptor agonists. In a specific embodiment, provided herein are compounds according to Formula (I) in free form or in pharmaceutically acceptable salt form having activity as muscarinic M4 receptor agonists. A significant advantage of the compounds provided herein is that they are highly selective for the M4 receptor, relative to the M1, M2, and M3 receptor subtypes and thus are thought to retain their desired activity in the brain but not produce unwanted cholinergic side effects. The muscarinic activity of the compounds provided herein can be determined using the CHRM4 $Ca^{++}$ Flux Assay described in Section 8.2 below.

By virtue of their M4 receptor agonist activity, the compounds provided herein may be useful in the treatment of:
Psychosis, including psychosis associated with schizophrenia, schizoaffective disorder, psychotic depression, bipolar disorder with psychotic features, Alzheimer's Disease, Parkinson's Disease, post-traumatic stress disorder, and frontotemporal dementia;
Hyperkinetic Movement Disorders, including but not limited to Tourette's Syndrome, chorea and tardive dyskinesia;
Cognitive dysfunction, including but not limited to cognitive dysfunction associated with schizophrenia, Alzheimer's Disease, frontotemporal dementia, schizoaffective disorder, and depression; and/or
Substance Use Disorders.

In one embodiment, provided herein is a method of treating a condition, disease or disorder which is treated by a M4 receptor agonist comprising administration of a therapeutically effective amount of a compound according to Formula (I) or a pharmaceutically acceptable salt thereof to a subject in need of treatment thereof. In a further embodiment, the condition, disease or disorder is psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia. In a specific embodiment, the psychosis is associated with Alzheimer's disease In another embodiment, provided herein is a method of treating a hyperkinetic movement disorder, such as Tourette's syndrome, chorea or tardive dyskinesia, comprising administration of a therapeutically effective amount of a compound according to Formula (I) or a pharmaceutically acceptable salt thereof to a subject in need of treatment thereof. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is a method of treating cognitive dysfunction, such as cognitive dysfunction associated with schizophrenia, Alzheimer's disease, frontotemporal dementia, schizoaffective disorder, or depression, comprising administration of a therapeutically effective amount of a compound according to Formula (I) or a pharmaceutically acceptable salt thereof to a subject in need of treatment thereof. In a specific embodiment, the cognitive dysfunction is associated with Alzheimer's disease.

In another embodiment, provided herein is a method of treating substance use disorders comprising administration of a therapeutically effective amount of a compound according to Formula (I) or a pharmaceutically acceptable salt thereof to a subject in need of treatment thereof.

In one embodiment, provided herein is the use of a compound according to Formula (I) or a pharmaceutically acceptable salt thereof in therapy. In a further embodiment, the therapy is selected from a condition, disease or disorder which is treated by a M4 receptor agonist. In another embodiment, the condition, disease or disorder is selected from the afore-mentioned list, suitably psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia.

In another embodiment, provided herein is the use of a compound according to Formula (I) or a pharmaceutically acceptable salt thereof in a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is the use of a compound according to Formula (I) or a pharmaceutically acceptable salt thereof in cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is the use of a compound according to Formula (I) or a pharmaceutically acceptable salt thereof in substance use disorders.

In another embodiment, provided herein is the use of a compound according to Formula (I) or a pharmaceutically acceptable salt thereof for the manufacture of a medicament. In a further embodiment, the medicament is for treatment of a condition, disease or disorder which is treated by a M4 receptor agonist. In another embodiment, the condition, disease or disorder is psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia.

In another embodiment, provided herein is the use of a compound according to Formula (I) or a pharmaceutically acceptable salt thereof for the manufacture of a medicament for the treatment of a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is the use of a compound according to Formula (I) or a pharmaceutically acceptable salt thereof for the manufacture of a medicament for the treatment of cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is the use of a compound according to Formula (I) or a pharmaceutically acceptable salt thereof for the manufacture of a medicament for the treatment of substance use disorders.

In another embodiment, provided herein is a compound according to Formula (I) or a pharmaceutically acceptable salt thereof for use in the treatment of a condition, disease or disorder which is treated by a M4 receptor agonist. In a further embodiment, the condition, disease or disorder is selected from the afore-mentioned list, suitably psychosis, including but not limited to, psychosis associated with schizophrenia, schizoaffective disorder, psychotic depression, bipolar disorder with psychotic features, Alzheimer's disease, Parkinson's Disease, post-traumatic stress disorder, and frontotemporal dementia. In a specific embodiment, the psychosis is associated with Alzheimer's disease.

In another embodiment, provided herein is a compound according to Formula (I) or a pharmaceutically acceptable salt thereof for use in the treatment of a hyperkinetic movement disorder, such as Tourette's syndrome, chorea or tardive dyskinesia. In some embodiments, the hyperkinetic movement disorder is associated with schizophrenia, schizoaffective disorder, psychotic depression, bipolar disorder with psychotic features, Alzheimer's disease, or frontotemporal dementia. In specific embodiment, the hyperkinetic movement disorder is associated with Alzheimer's disease.

In another embodiment, provided herein is a compound of Formula (I) or a pharmaceutically acceptable salt thereof for use in the treatment of cognitive dysfunction, for example cognitive dysfunction associated with schizophrenia, Alzheimer's disease, frontotemporal dementia, schizoaffective disorder, or depression. In a specific embodiment, the cognitive dysfunction is associated with Alzheimer's disease.

In another embodiment, provided herein is a compound of Formula (I) or a pharmaceutically acceptable salt thereof for use in the treatment of substance use disorders.

A compound according to Formula (I) or a pharmaceutically acceptable salt thereof may be administered either simultaneously with, or before or after, one or more other therapeutic agents. The compounds according to Formula (I) may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a subject in combination with a compound provided herein.

In the combination therapies provided herein, a compound according to Formula (I) and the other therapeutic agent may be manufactured and/or formulated by the same or different manufacturers. Moreover, the compounds provided herein and the other therapeutic may be brought together into a combination therapy: (i) prior to release of the combination product to physicians (e.g., in the case of a kit comprising a compound provided herein and the other therapeutic agent); (ii) by the physician themselves (or under the guidance of the physician) shortly before administration; (iii) in the patient themselves, e.g., during sequential administration of a compound provided herein and the other therapeutic agent.

A compound according to Formula (I) or a pharmaceutically acceptable salt thereof may be administered with an antipsychotic, suitably a first-generation antipsychotic such as chlorpromazine (thorazine), haloperidol, mesoridazine, thioridazine, thiothixene, pimozide, fluphenazine or perphenazine, a second-generation antipsychotic such as clozapine, olanzapine, risperidone, quetiapine, aripiprazole, asenapine, brexpiprazole, cariprazine, iloperidone, ziprasidone, lurasidone, pimavanserin or paliperidone. In certain embodiments, a compound according to Formula (I) or a pharmaceutically acceptable salt thereof may be administered with an antipsychotic and a cholinesterase inhibitor, such as donepizil, rivastigmine tartrate, galantamine, tacrine or memantine. In certain embodiments, a compound according to Formula (I) or a pharmaceutically acceptable salt thereof may be administered with an antipsychotic and a mood stabilizer, such as lithium, divalproex sodium, carbamazepine or lamotrigine.

A compound according to Formula (I) or a pharmaceutically acceptable salt thereof may be administered with an antidepressant, suitably a selective serotonin reuptake inhibitor such as sertraline, fluoxetine, fluvoxamine, escitalopram, paroxetine or citalopram, a serotonin-norepinephrine reuptake inhibitor such as vortioxetine, venlafaxine, desvenlafaxine, milnacipran, duloxetine or levomilnacipran, a phenylpiperazine antidepressant such as nefazodone, vilazodone or trazodone, reversible monoamine oxidase inhibitors such as moclobemide, melatonin agonists such as agomelatine, serotonin agonists such as mirtazapine, N-methyl-D-aspartate receptor antagonists such as esketamine and ketamine, and monoamine oxidase inhibitors such as tranylcypromine, phenelzine, transdermal selegiline or isocarboxazid.

A compound according to Formula (I) or a pharmaceutically acceptable salt thereof may be administered in conjunction with standardize psychological treatment, for example at individual or group therapy. In another embodiment, a compound according to Formula (I) or a pharmaceutically acceptable salt thereof may be administered in conjunction with psychosocial or behavioral therapy either through standardized psychological treatment or through computer-assistance. In certain embodiment, the computer-assistance is by means of a digital or electronic device such as online tools, smartphones, laptops, tablets, wireless devices or health Apps.

In a further embodiment, provided herein is a method of treatment of a condition, disease or disorder which is treated with a M4 receptor agonist comprising administration of a therapeutically effective amount of a compound according to Formula (I) or a pharmaceutically acceptable salt thereof and an antipsychotic to a subject in need of treatment thereof. In certain embodiments, provided herein is a method of treatment of a condition, disease or disorder which is treated with a M4 receptor agonist comprising administration of a therapeutically effective amount of a compound according to Formula (I) or a pharmaceutically acceptable salt thereof, an antipsychotic, and a cholinesterase inhibitor to a subject in need of treatment thereof. In certain embodiments, provided herein is a method of treatment of a condition, disease or disorder which is treated with a M4 receptor agonist comprising administration of a therapeutically effective amount of a compound according to Formula (I) or a pharmaceutically acceptable salt thereof, an antipsychotic, and a mood stabilizer to a subject in need of treatment thereof.

In a further embodiment, provided herein is a method of treatment of a condition, disease or disorder which is treated with a M4 receptor agonist comprising administration of a therapeutically effective amount of a compound according to Formula (I) or a pharmaceutically acceptable salt thereof and an antidepressant to a subject in need of treatment thereof.

In a further embodiment, provided herein is the use of a compound according to Formula (I) or a pharmaceutically acceptable salt thereof in a condition, disease or disorder which is treated with a M4 receptor agonist, wherein the use is combined with an antipsychotic. In certain embodiments, provided herein is the use of a compound according to Formula (I) or a pharmaceutically acceptable salt thereof in a condition, disease or disorder which is treated with a M4 receptor agonist, wherein the use is combined with an antipsychotic and a cholinesterase inhibitor. In certain embodiments, provided herein is the use of a compound according to Formula (I) or a pharmaceutically acceptable salt thereof in a condition, disease or disorder which is treated with a M4 receptor agonist, wherein the use is combined with an antipsychotic and a mood stabilizer.

In a further embodiment, provided herein is the use of a compound according to Formula (I) or a pharmaceutically acceptable salt thereof in a condition, disease or disorder which is treated with a M4 receptor agonist, wherein the use is combined with an antidepressant.

In a further embodiment, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic. In certain embodiments, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic and a cholinesterase inhibitor. In certain embodiments, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antipsychotic and a mood stabilizer.

In a further embodiment, provided herein is the use of a compound according to Formula (I) or a pharmaceutically acceptable salt thereof for the manufacture of a medicament for treatment of a condition, disease or disorder which is treated with a M4 receptor agonist wherein the use is combined with an antidepressant.

In a further embodiment, provided herein is the use of a compound according to Formula (I) or a pharmaceutically acceptable salt thereof in a condition, disease or disorder which is treated with a M4 receptor agonist, wherein the use is combined with computer-assisted psychosocial or behavioral therapy.

In a further embodiment, provided herein is a method for the treatment of a condition, disease or disorder which is treated with a M4 receptor agonist comprising administration of a therapeutically effective amount of a compound according to Formula (I) or a pharmaceutically acceptable salt thereof in conjunction with computer-assisted psychosocial or behavioral therapy.

In a further embodiment, provided herein is the use of a compound according to Formula (I) or a pharmaceutically acceptable salt thereof for the manufacture of a medicament for treatment of a condition, disease or disorder which is treated by a M4 receptor agonist wherein the use is combined computer-assisted psychosocial or behavioral therapy.

5. Methods of Making

The compounds provided herein may be made by a variety of methods, including standard chemistry. Suitable synthetic routes are depicted in the schemes below.

The compounds provided herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (see T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds provided herein.

Those skilled in the art will recognize if a stereocenter exists in the compounds provided herein. Accordingly, the compounds provided herein include both possible stereoisomers and includes not only racemic compounds but the individual enantiomers and/or diastereomers as well. When a compound provided herein is desired as a single enantiomer or diastereomer, it may be obtained by stereospecific synthesis or by resolution of the final product or any convenient intermediate. Resolution of the final product, an intermediate, or a starting material may be effected by any suitable method known in the art. See, for example, "Stereochemistry of Organic Compounds" by E. L. Eliel, S. H. Wilen, and L. N. Mander (Wiley-Interscience, 1994).

The compounds provided herein can be prepared according to the sequence shown in Scheme 1 below.

Scheme 1
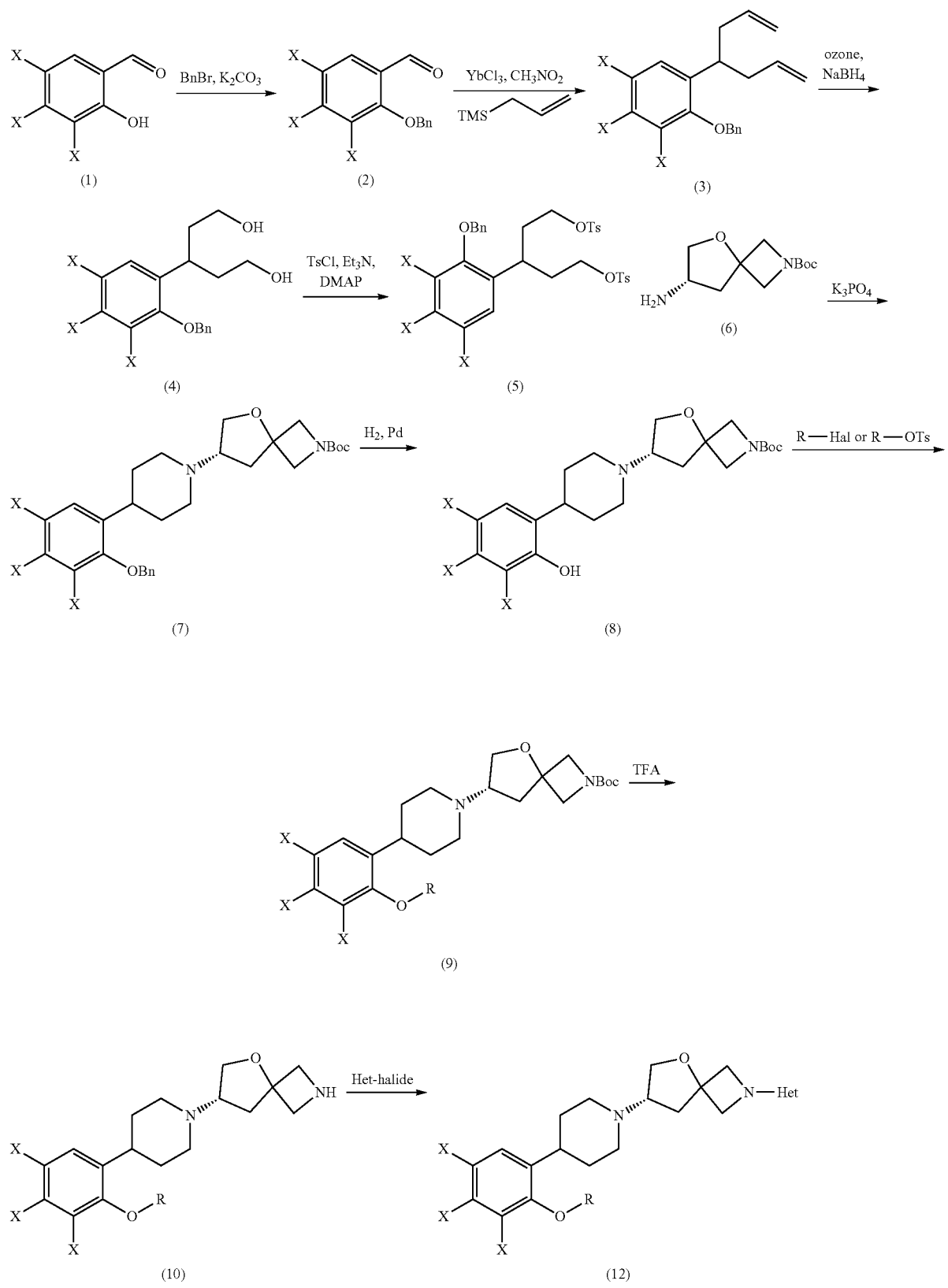

-continued

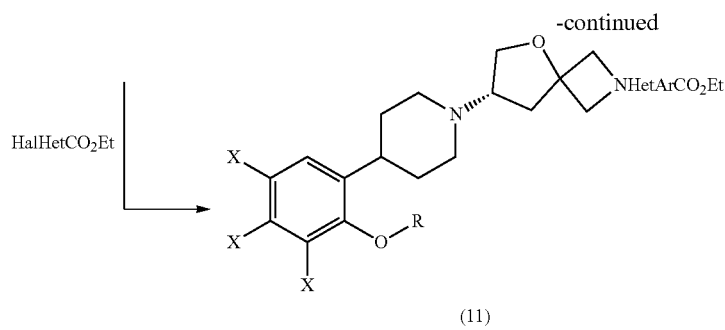

(11)

X = H or halide

In Scheme 1, the phenols such as 1 can be protected as benzyl ether and to give protected phenols such as 2. The aldehyde can then be doubly allylated with allyltrimethylsilane in the presence of an activating Lewis acid, such as ytterbium chloride. The resulting bis-olefins such as 3 can then be oxidized by ozone gas followed by a reducing agent such as sodium borohydride to give diols such as 4. The alcohols can then be activated as para-toluene sulfonic esters to give activated diols such as 5 which can be displace by an amine such as 6 to give tertiary amines such as 7. The benzyl protecting group can be removed through palladium catalysis in the presence of hydrogen to give free phenols such as 8 that can then be alkylated by an aliphatic halide or tosylate in the presence of a base such as cesium carbonate to give substituted phenols such as 9. The amine can then be deprotected with an acid such as TFA to give free amines which can react with heteroaromatic halides under Buchwald Hartwig or nucleophilic aromatic substitution conditions to give examples such as 12. Alternatively, amines such as 10 can react with heteroaromatic halides that contain an ester to yield heteroaromatics such as 11. The ester can then be hydrolyzed with an aqueous base such as lithium hydroxide and the resulting acid can be decarboxylated with an aqueous acid such as HCl to give examples such as 12.

Scheme 2

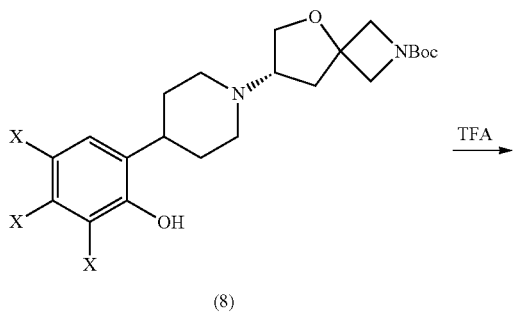

(8)

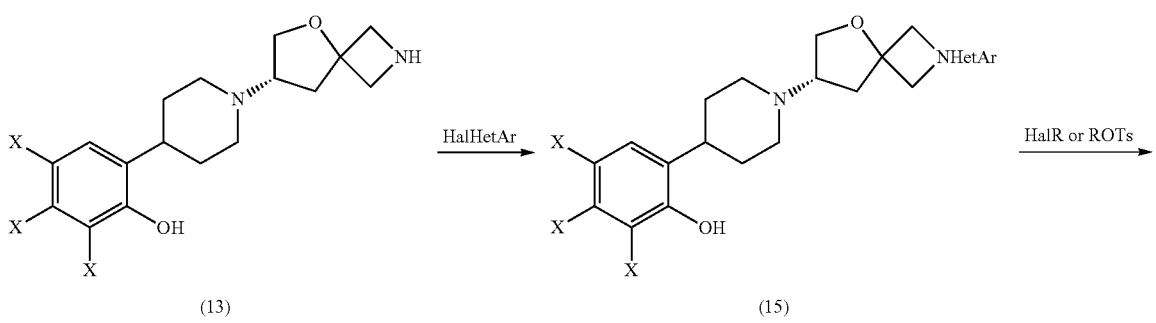

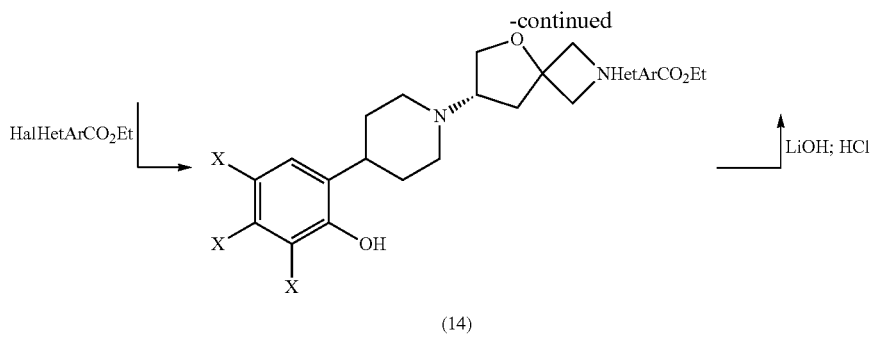

(14)

X = H or halide

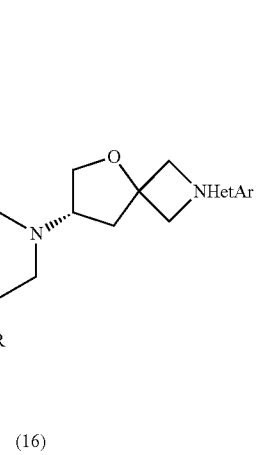

(16)

In Scheme 2, phenols such as 9 can be deprotected with an acid such as TFA and the resulting amine can react with a heteroaromatic halide under Buchwald Hartwig or nucleophilic aromatic substitution conditions to give heteroaromatics such as 15. Alternatively, the amine can react with a heteroaromatic halide that contains an ethyl ester to give esters such as 14. The ester can then be hydrolyzed with an aqueous base such as lithium hydroxide and the resulting acid can be decarboxylated with an acid such as HCl to give heteroaromatic halides such as 15. Alternatively, compounds provided herein can be prepared as shown in Scheme 3.

Scheme 3

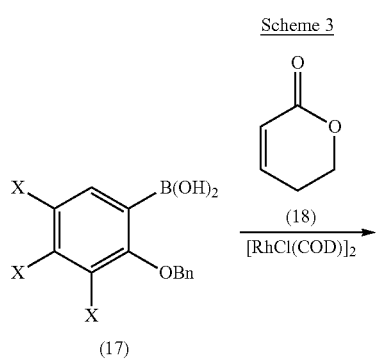

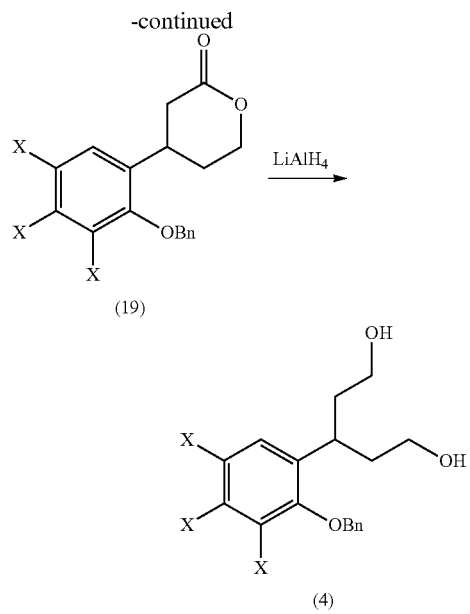

In Scheme 3, aryl boronic acids such as 17 can react with unsaturated lactones such as 18 under rhodium catalysis to give saturated lactones such as 19. The lactone can then be reduced with a reducing agent such as lithium aluminum hydride to give diols such as 4. These diols can then be further elaborated as depicted in Scheme 1 or Scheme 2. Alternatively, compounds provided herein can be prepared as shown in Scheme 4 below.

Scheme 4
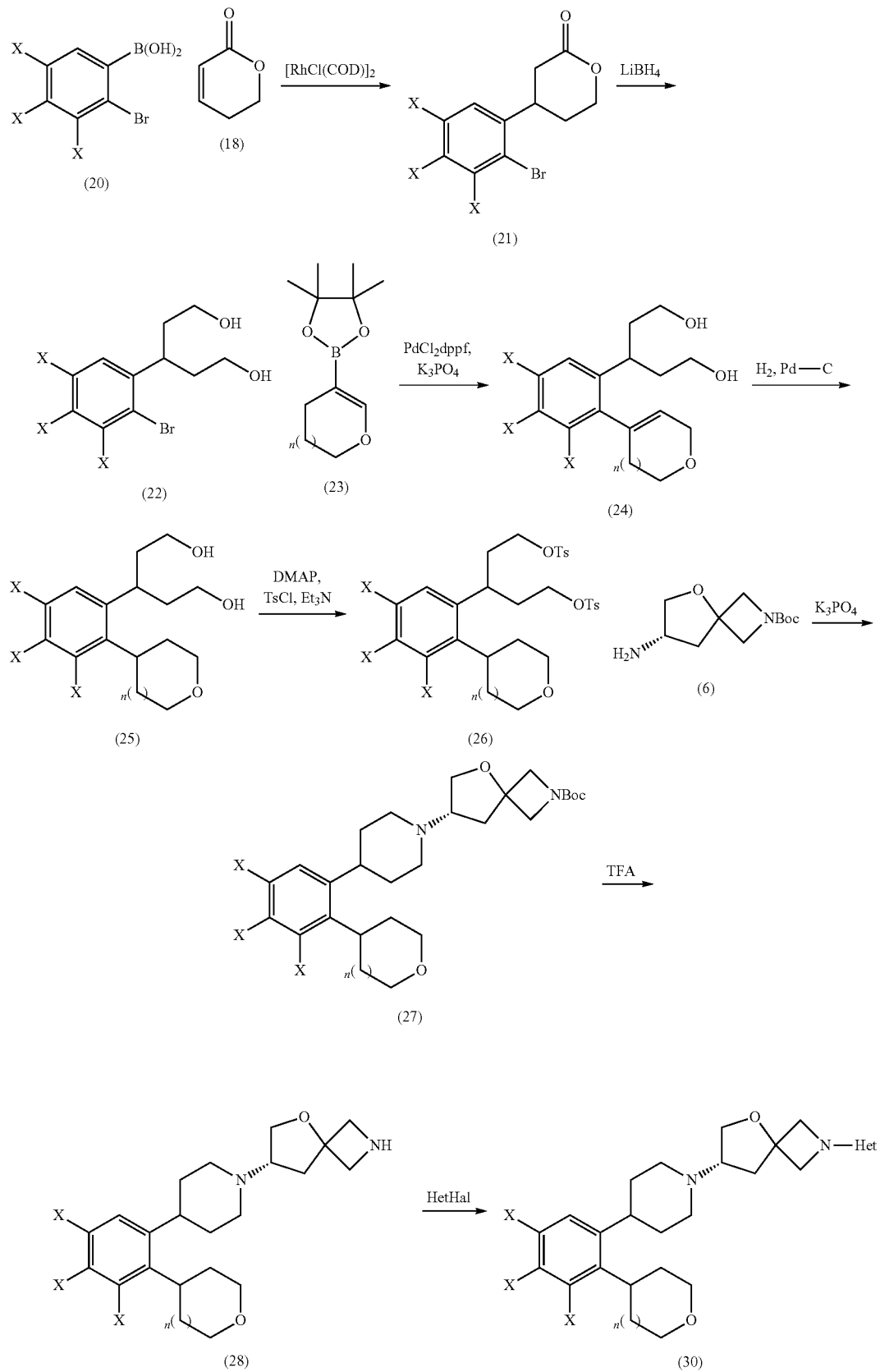

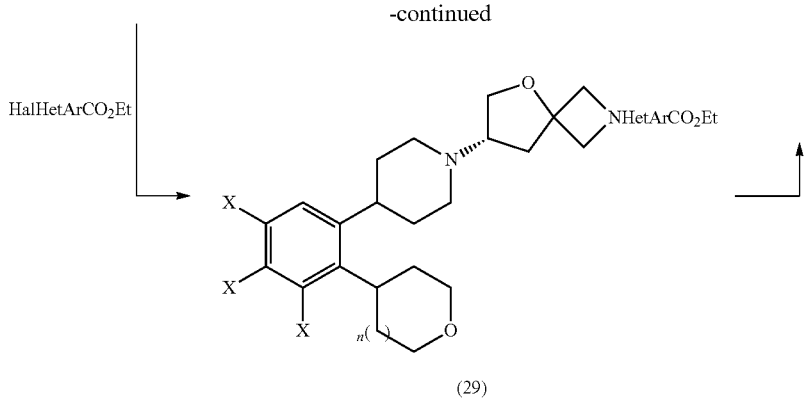

(29)

X = H or Hal

In Scheme 4, aryl boronic acids such as 20 can react with an unsaturated lactone such as 19 under rhodium catalysis and the resulting saturated lactone 21 can be reduced with a reducing agent such as lithium borohydride to give diols such as 22. The resulting diol can then be reacted with a boronic ester such as 23 under Suzuki-Miyaura conditions to give an unsaturated ring such as 24. The olefin can then be reduced with palladium catalysis in the presence of hydrogen to give saturated rings such as 25 and the hydroxyl groups can then be activated with tosyl chloride to give activated diols such as 26. The tosyl groups can then be displaced with an amine such as 6 in the presence of a base such as potassium phosphate to give a tertiary amine such as 27. The amine can be deprotected with an acid such as TFA and the resulting amine 28 can react with a heteroaromatic halide under Buchwald Hartwig or nucleophilic aromatic substitution conditions to give examples such as 30. Alternatively, the amine can react with a heteroaromatic halide that contains an ester to give ethyl esters such as 29 and the ester can be hydrolyzed with an aqueous acid such as lithium hydroxide and the resulting acid can be decarboxylated with an aqueous acid such as HCl to give examples such as 30. Alternatively, compounds provided herein can be prepared as shown in Scheme 5 shown below.

Scheme 5

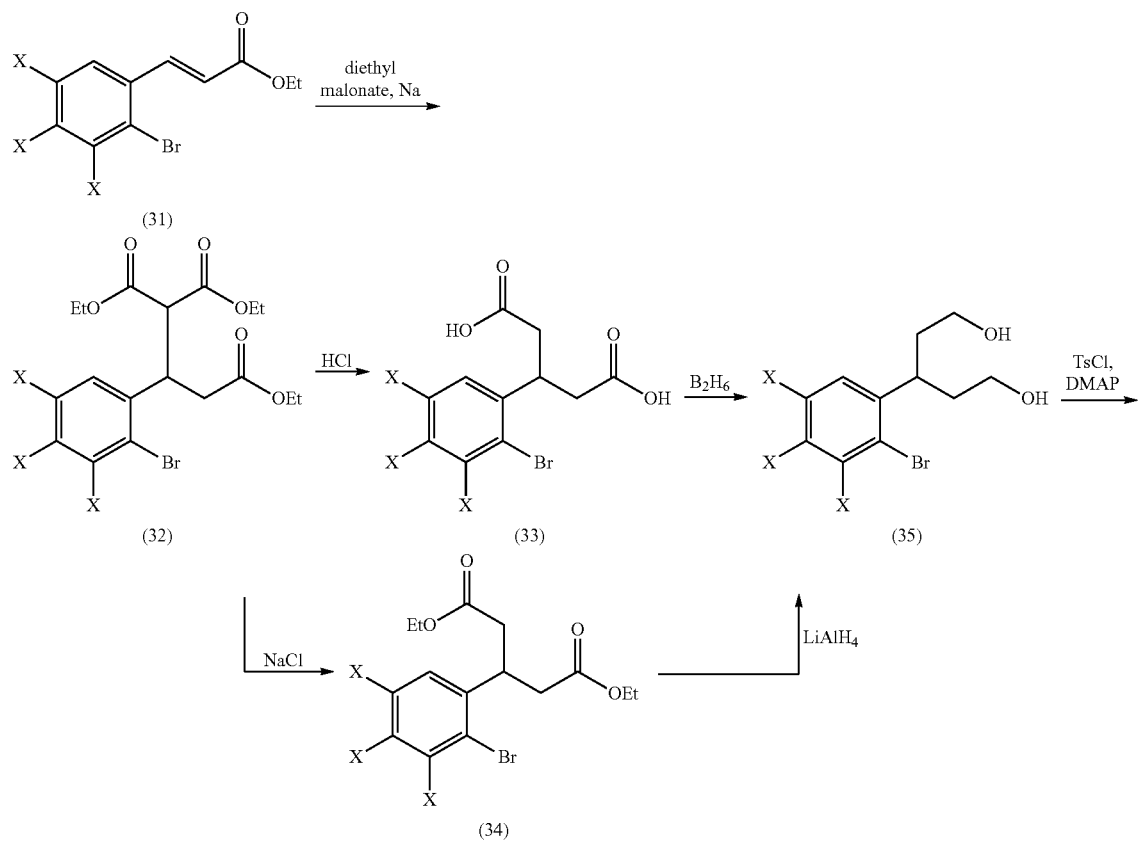

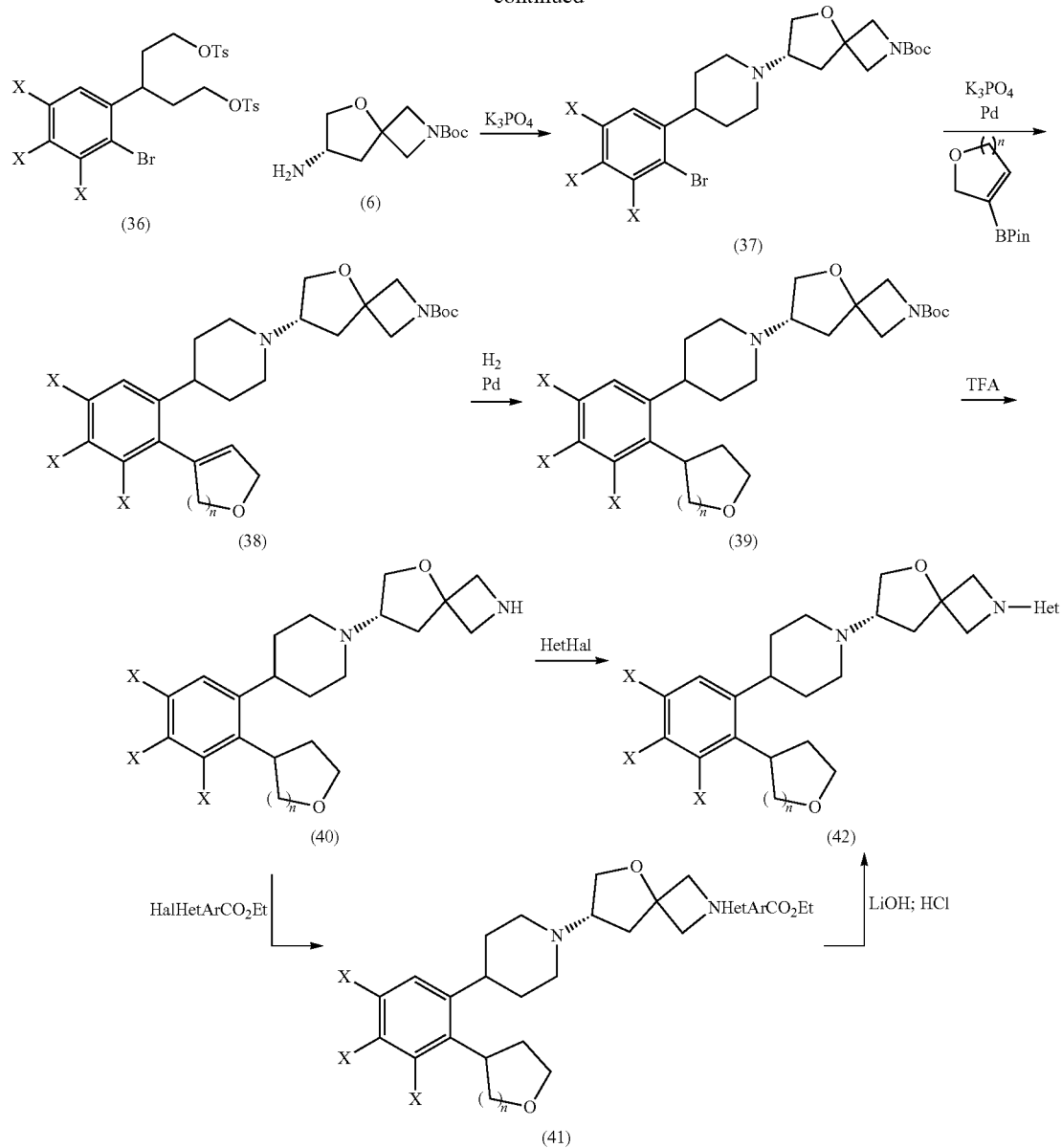

X = H or halide

In Scheme 5, the unsaturated esters such as 31 can be reacted with diethyl malonate in the presence of a reducing metal such as sodium to give the tri-esters such as 32. The ester can then be hydrolyzed and decarboxylated with an acid such as HCl to give di-acids such as 33. The acids can then be reduced with borane to give diols such as 35. Alternatively, the ester can be decarboxylated to give di-esters such as 34 and the esters can be reduced with a reducing agent such as lithium borohydride to give diols such as 35. Diols such as 35 can then be activated as tosylates with tosyl chloride and the activated diols 36 can react with an amine such as 6 to give tertiary amines such as 37. Bromides such as 37 can then react with pinacol boronic esters to give unsaturated rings such as 38. The olefin can then be reduced with hydrogen and palladium catalysis to give saturated rings such as 39 and the amine can then be deprotected with an acid such as TFA. Free amines such as 40 can then react with a heteroaromatic halide under Buchwald Hartwig or nucleophilic aromatic substitution conditions to give examples such as 42. Alternatively, the free amine can react with a heteroaromatic halide that contains an ethyl ester. Esters such as 41 can then be hydrolyzed with an aqueous acid such as lithium hydroxide to give an acid with can then be decarboxylated with an acid such as HCl to generate examples such as 42. Alternatively, compounds provided herein can be prepared as described in Scheme 6 below.

Scheme 6
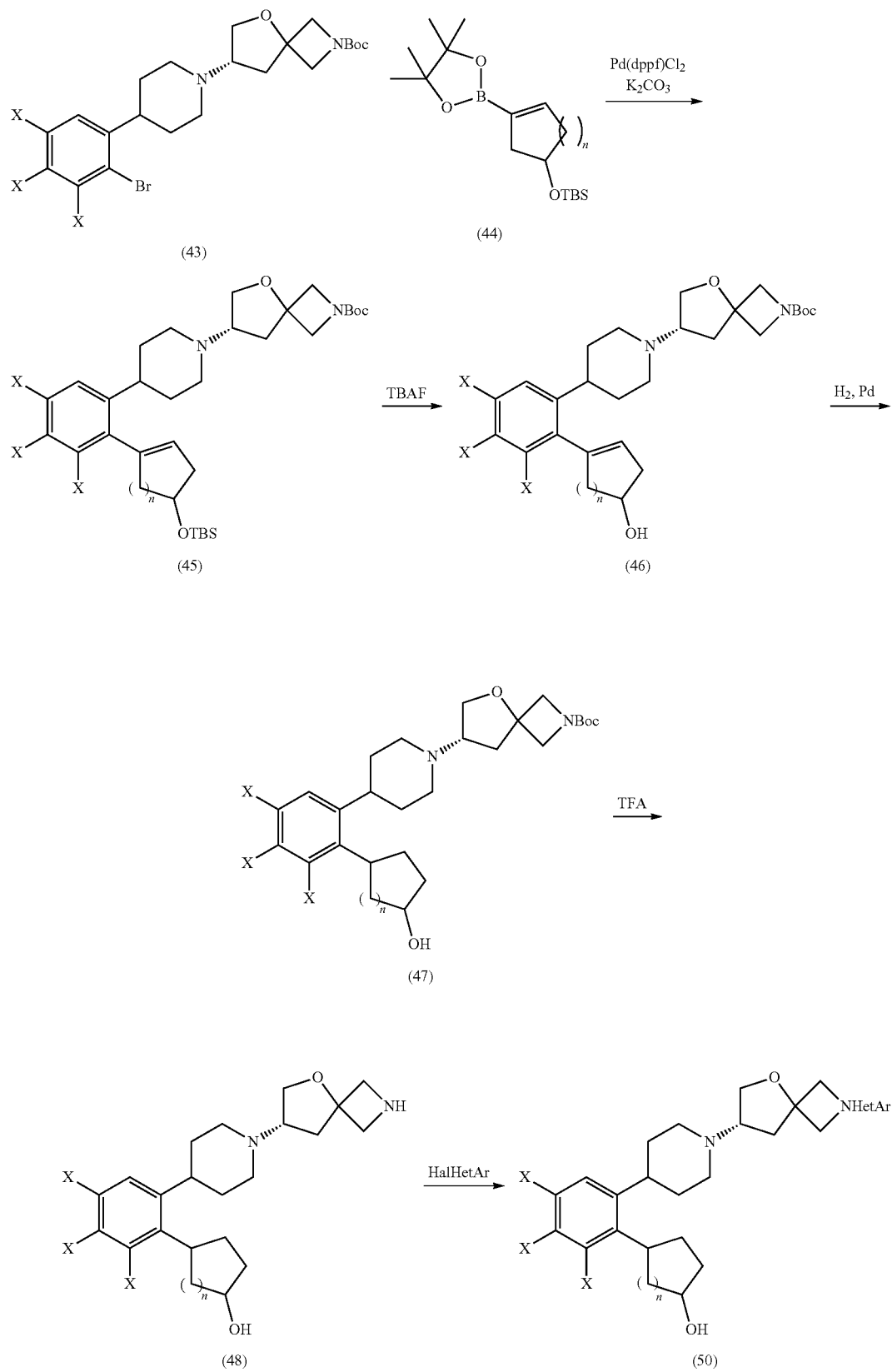

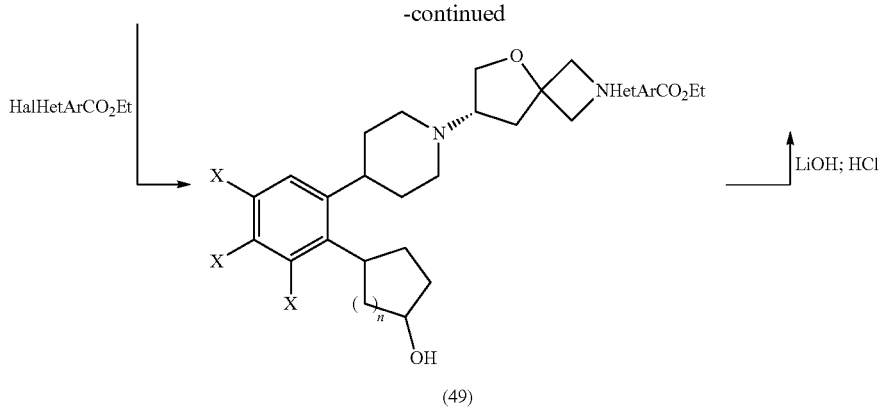

(49)

X = H or halide

In Scheme 6, aryl bromides such as 43 can be combined with pinacol boronic esters such as 44 under Suzuki-Miyaura cross coupling conditions to yield unsaturated rings such as 45. The alcohol can then be deprotected with a fluoride source such as TBAF to give free alcohols such as 46 and the olefin can then be reduced with hydrogen and palladium catalysis to produce saturated rings such as 47. The amine can then be deprotected with an acid such as TFA and the free amine can then react with a heteroaromatic halide under Buchwald Hartwig or nucleophilic aromatic substitution conditions to give examples such as 50. Alternatively, free amines such as 48 can react with heteroaromatic halides that contain an ethyl ester to give esters such as 49. The ester can then be hydrolyzed with an aqueous base such as lithium hydroxide and the resulting acid can then be decarboxylated with an aqueous acid such as HCl to give examples such as 50. Alternatively, compounds provided herein can be prepared as described in Scheme 7 below.

Scheme 7

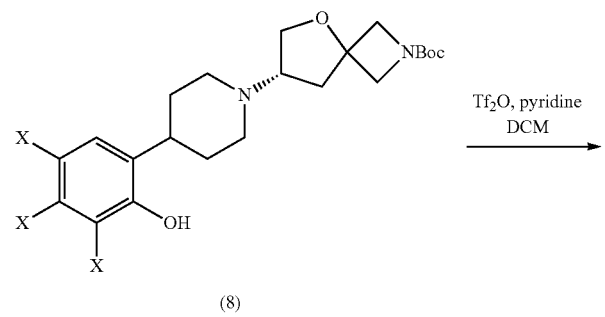

(8)

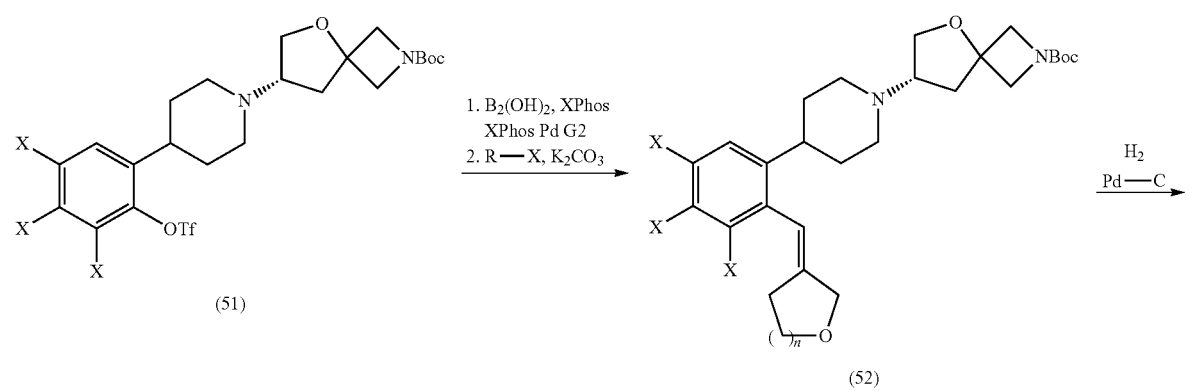

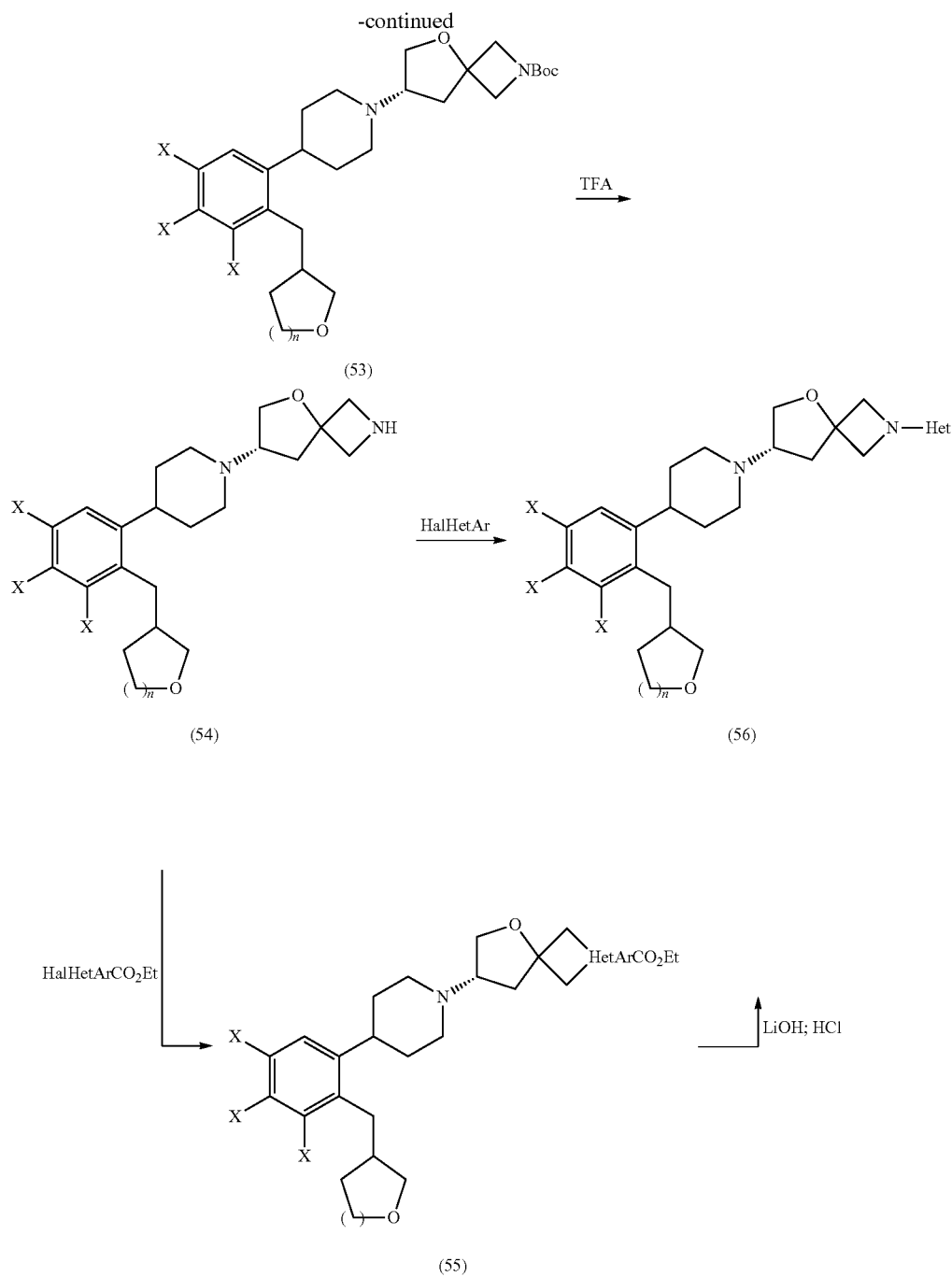

In Scheme 7, phenols such as 8 can be activated such as with trifluoromethanesulfonic anhydride in the presence of a base such as pyridine to generate sulfonylester such as 51. The trifluoromethylsulfonyl ester can then be transformed into a boronic acid with tetrahydroxydiboron in the presence of a palladium catalyst and the corresponding boronic acid can be reacted with a halide in the presence of a base to generate an olefin such as 52. Subsequently, the compound can be reduced with hydrogen in the presence of palladium catalysis to give saturated compounds such as 53 and the compound can be subsequently deprotected with an acid such as TFA to give an amines such as 54. The amine can react with an aryl halide under Buchwald-Hartwig or nucleophilic aromatic substitution conditions to generate examples such as 56. Alternatively, amines such as 51 can react with a heteroaromatic halide containing an ethyl ester to give esters such as 55. The ester can then be hydrolyzed with an aqueous base such as lithium hydroxide and the resulting acid can be decarboxylated with an aqueous acid such as HCl to generate examples such as 56. Alternatively, compounds provided herein can be prepared as shown in Scheme 8 below.

Scheme 8

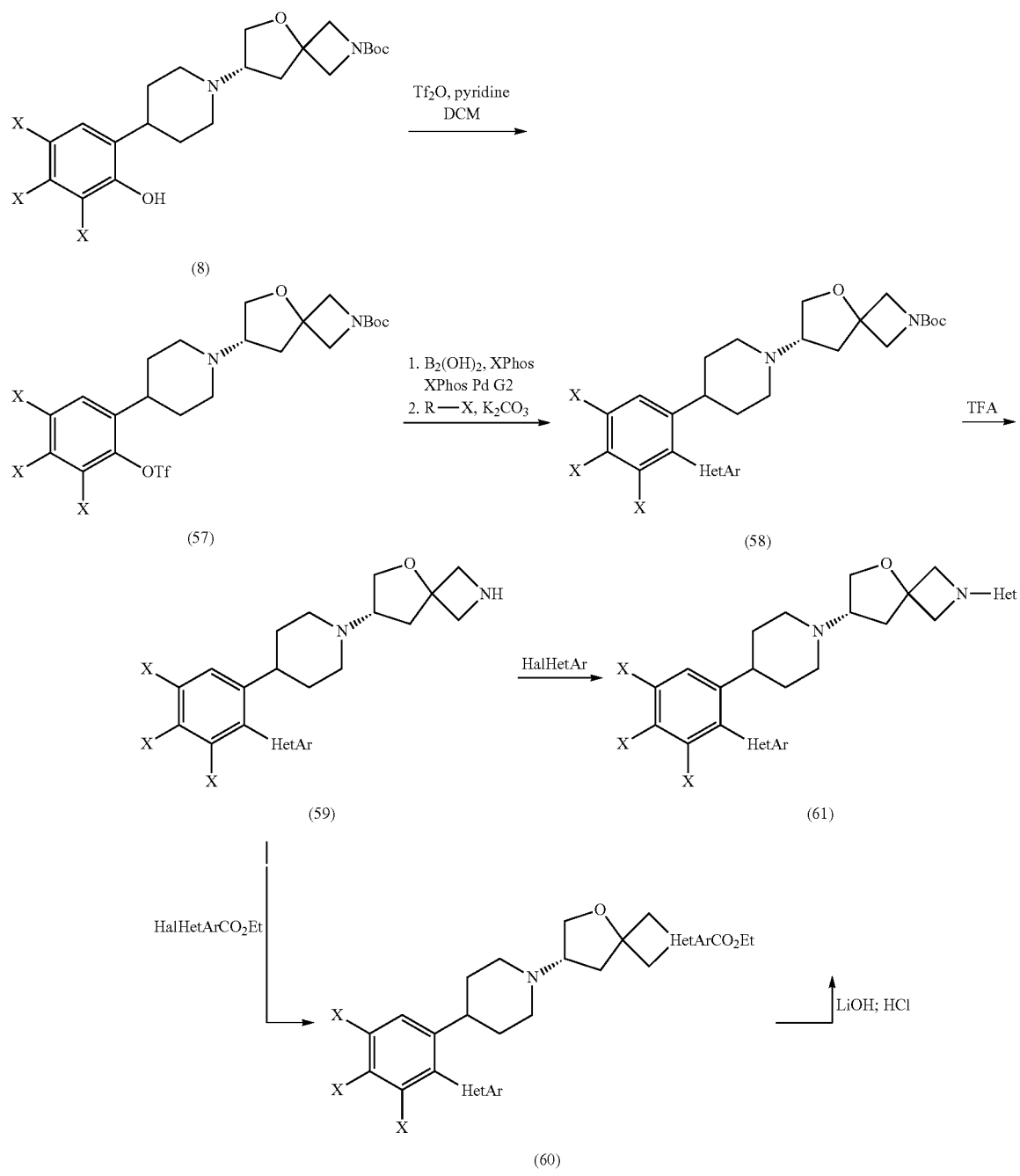

X = H or halide

In Scheme 8, phenols such as 8 can be activated as trifluoromethylsulfonyl esters such as 57 using triflic anhydride. The resulting activated ester can then be converted into a boronic acid using tetrahydroxydiboron in the presence of palladium and the resulting boronic acid can react under Suzuki-Miyaura conditions with a heteroaromatic halide to generate heteroaromatics such as 58. The amine can then be deprotected with an acid such as TFA and resulting free amines such as 59 can react with a heteroaromatic halide such under Buchwald Hartwig or nucleophilic aromatic substitution conditions to generate heteroaromatics such as 61. Alternatively, amines such as 59 can react with heteroaromatic halides containing an ethyl ester to give esters such as 60. The ester can then be hydrolyzed with an aqueous base such as lithium hydroxide and the resulting acid can then be decarboxylated with an aqueous acid such as HCl to generate heteroaromatics such as 61. Alternatively, compounds provided herein can be prepared as shown in Scheme 9 below.

Scheme 9

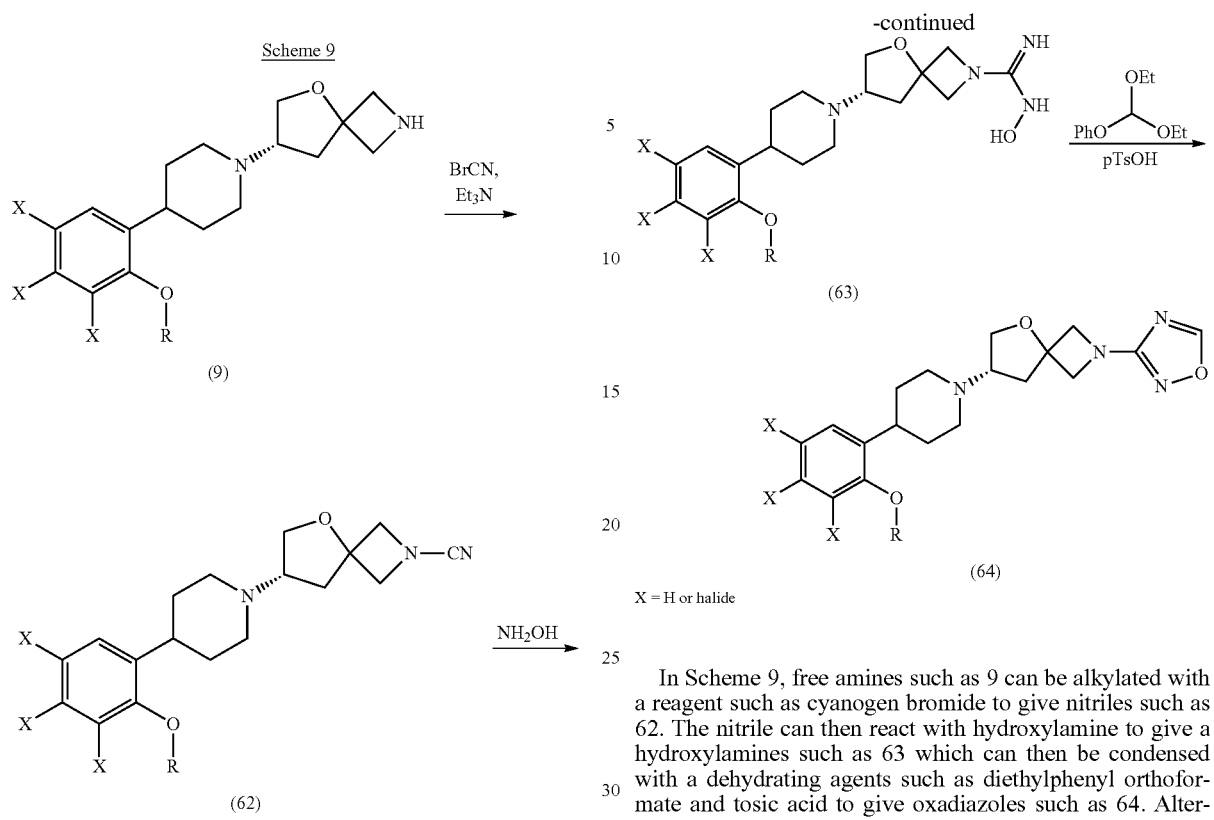

X = H or halide

In Scheme 9, free amines such as 9 can be alkylated with a reagent such as cyanogen bromide to give nitriles such as 62. The nitrile can then react with hydroxylamine to give a hydroxylamines such as 63 which can then be condensed with a dehydrating agents such as diethylphenyl orthoformate and tosic acid to give oxadiazoles such as 64. Alternatively, compounds can be prepared as show in in Scheme 10 below.

Scheme 10

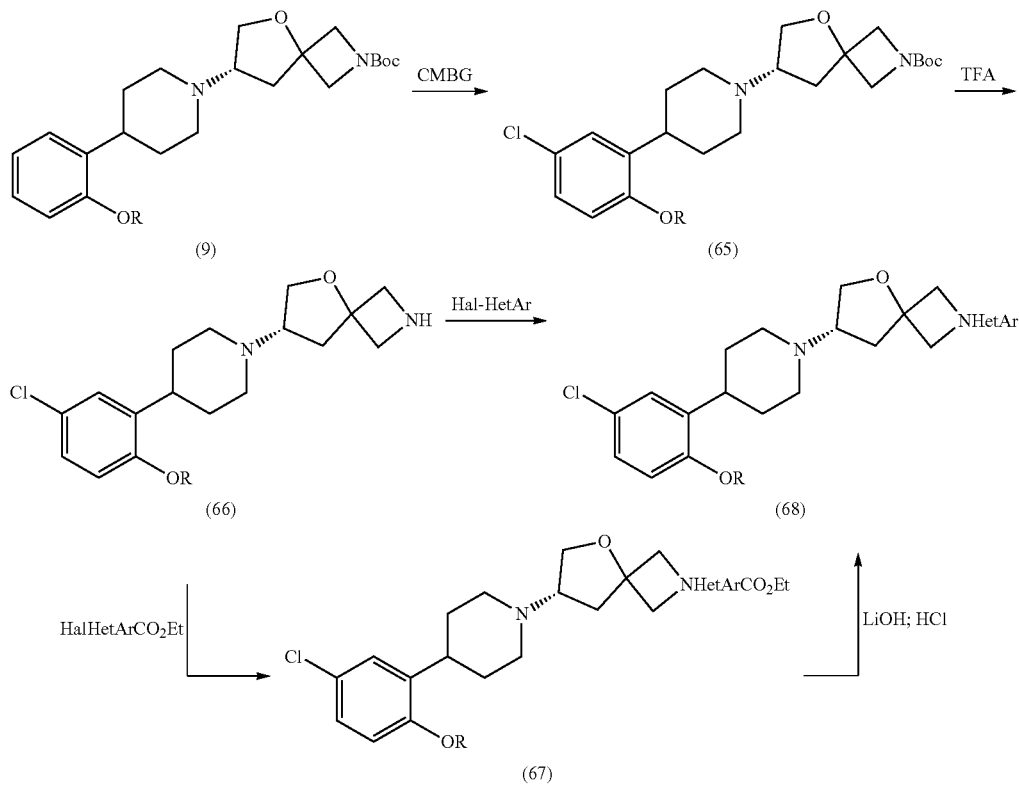

In Scheme 10, substituted phenols such as 9 can be chlorinated with a chlorinating agent such as 2-chloro-1,3-bis(methoxycarbonyl)guanidine to give an aryl chloride such as 65. The Boc group can then be removed with an acid such as TFA to generate free amines such as 56 which can then further react with a heteroaryl halide under nucleophilic aromatic substitution or Buchwald-Hartwig conditions to generate compounds such as 68. Alternatively, the amine can react with a heteroaromatic halide that contains an ethyl ester to give an ester such as 67. The ester can be hydrolyzed with an aqueous base such as lithium hydroxide and the resulting acid can be decarboxylated with an acid such as HCl to give examples such as 68. Alternatively, compounds provided herein can be prepared as shown in Scheme 11 below.

Scheme 11

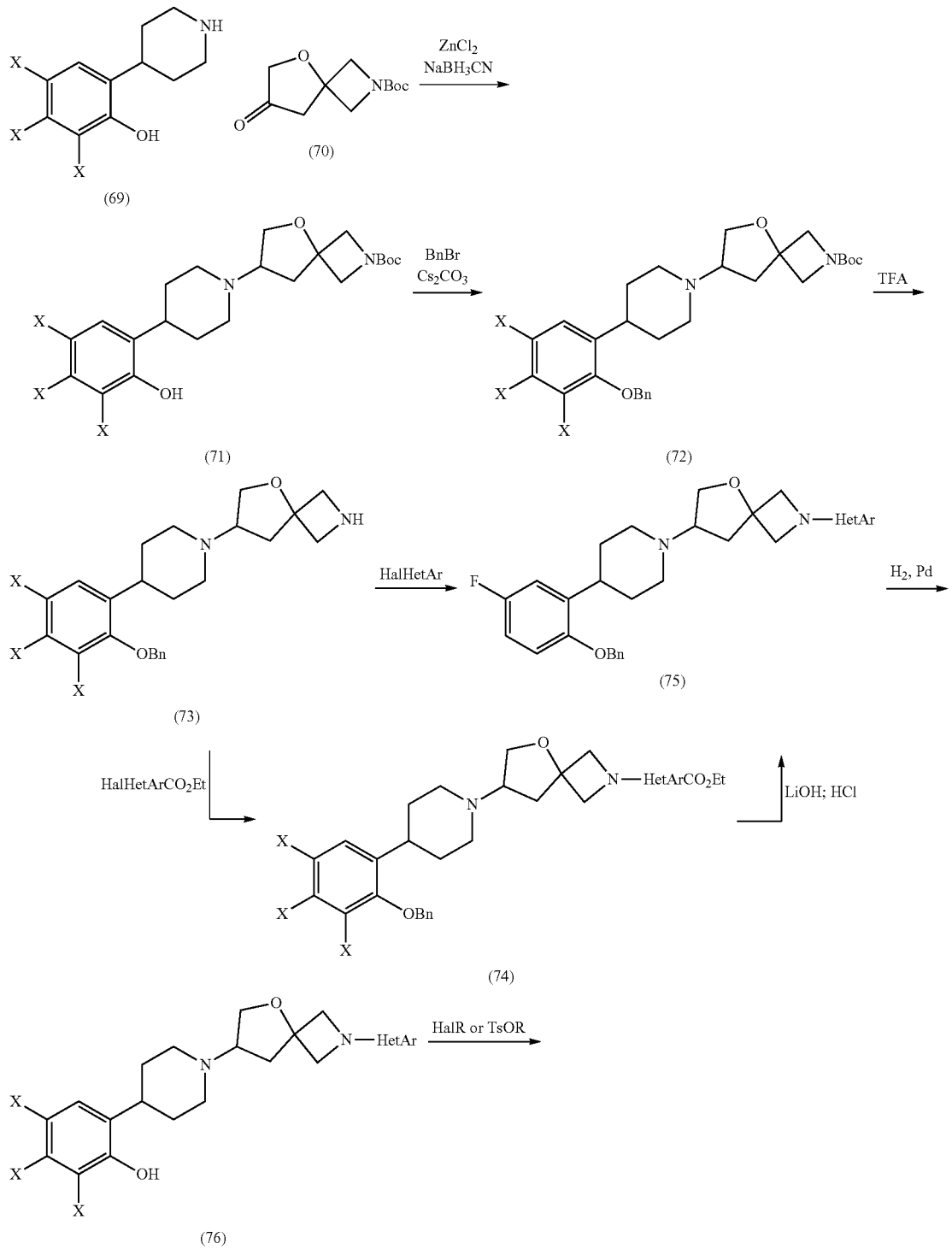

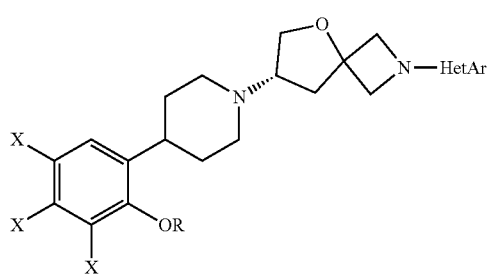
(77)

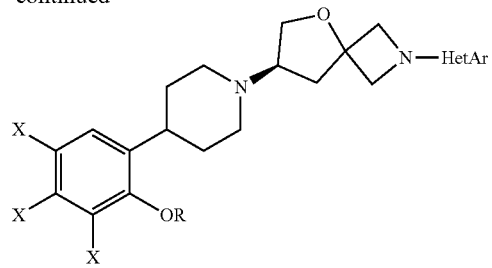
(78)

X = Halide or H

In Scheme 11, piperidines such as 69 can be reacted with ketones such as 70 under reductive amination conditions such as zinc chloride and sodium cyanoborohyride to generate carbon nitrogen bonds such as found in 71. The phenol can then be protected as a benzyl group with benzyl bromide and a base such as cesium carbonate and the amine can then be deprotected with an acid such as TFA. Free amines such as 73 can then react with heteroaromatic halides under nucleophilic aromatic substitution conditions or Buchwald-Hartwig conditions. Alternatively, free amines such as 73 can react with ester containing heteroaromatic halides to generate esters such as 74. The ester can then be hydrolyzed with an aqueous base such as lithium hydroxide and the resulting acid can be decarboxylated with an acid such as HCl to give heteroaromatic such as 75. The benzyl group can then be removed by hydrogenation with palladium catalysis and the resulting phenol 76 can react with a halide or tosylate in the presence of a base such as cesium carbonate. The racemic mixture can then be separated with, for example, chiral chromatography to generate single enantiomers 77 and 78.

7. Incorporation by Reference

The entire disclosure of each of the patent documents and scientific articles cited herein are incorporated by reference for all purposes.

8. EXAMPLES

The present disclosure is further illustrated by the following examples, which are intended to be illustrative only and not limiting in any way. It is to be understood that resort may be had to various other embodiments, modifications, and equivalents thereof which may suggest themselves to those skilled in the art without departing from the spirit of the present disclosure and/or scope of the appended claims.

1. Synthesis of Intermediates and Examples

Abbreviations used are those conventional in the art or the following:
Å angstrom(s)
AcOH acetic acid
aq aqueous
ATP adenosine triphosphate
AUC area under curve
BOC tert-Butyloxycarbonyl
tBu tert-butyl
C Celsius
CDI carbonyldiimidazole
CMBG 2-Chloro-1,3-bis(methoxycarbonyl)guanidine
DCE 1,2 dichloroethane
DCM dichloromethane
DIPEA N,N-Diisopropylethylamine
DME 1,4-dimethoxyethane
DMEM Dulbecco's Modified Eagle Medium
DMF N,N-dimethylformamide
DMSO dimethylsulfoxide
DPBS Dulbecco's Phosphate Buffered Saline
EtOAc Ethyl acetate
EtOH Ethyl alcohol
FBS Fetal Bovine Serum
FCC flash column chromatography
g gram(s)
hr hour(s)
HATU 1-[Bis(dimethylamino)methylene]-1H-1,2,3-triazolo[4,5-b]pyridinium 3-oxide hexafluorophosphate
HBSS Hanks' balanced salt solution
HBTU 1-[bis(dimethylamino)methylene]-1H-benzotriazoliumhexafluorophosphate(1-) 3-oxide
Hz Hertz
HOBt 1-hydroxy-7-azabenzotriazole
HPLC high pressure liquid chromatography
IP intraperitoneal
IPA isopropyl alcohol
J coupling constant
kg kilogram(s)
L liter(s)
LCMS liquid chromatography and mass spectrometry
LED light emitting diode
Me Methyl
MHz Megahertz
mM millimolar
MTBE methyl tert-butyl ether
MS mass spectrometry
min minute(s)
mg milligram(s)
mL milliliter(s)
mmol millimole(s)
m/z mass to charge ratio
nm nanometer(s)
nM nanomolar
NMR nuclear magnetic resonance
Pd/C, Pd—C palladium on carbon
Pd(dba)$_2$ bis(dibenzylideneacetone)palladium(O)
Pd$_2$(dba)$_3$ tris(dibenzylideneacetone)dipalladium(O)
Pd(dppf)Cl$_2$ dichloro[1,1'-bis(diphenylphosphino)ferrocene]palladium(II)
PO per os (oral administration)
psi pounds per square inch pTSCl para-toluene sulfonyl chloride
rac racemic
RB round bottom
rpm revolutions per minute
RT room temperature
Rt retention time
SFC Supercritical fluid chromatography
SC subcutaneous
TBTU 2-(1H-Benzotriazole-1-yl)-1,1,3,3-tetramethylaminium tetrafluoroborate
TC tissue culture
TEA triethylamine
TFA trifluoroacetic acid
THF tetrahydrofuran
TPGS-750-M DL-α-Tocopherol methoxypolyethylene glycol succinate solution
TTMSS tris(trimethylsilyl)silane
μL microliter(s)
μM micromolar
UPLC ultra performance liquid chromatography
UV ultraviolet
Xantphos 4,5-Bis(diphenylphosphino)-9,9-dimethylxanthene
XPhosPd G2 Chloro(2-dicyclohexylphosphino-2',4',6'-triisopropyl-1,1'-biphenyl)[2-(2'-amino-1,1'-biphenyl)]palladium(II)

General Procedures:

Where no preparative route is described the material is commercially available. Commercial reagents were used without additional purification unless otherwise stated. Room temperature (RT) is approximately 20-25° C. $^1$H NMR were recorded at 400 MHz on a Bruker instrument and processed with mNOVA. Chemical shifts are reported as parts per million (ppm) relative to tetramethylsilane and coupling constants (J) are reported in Hertz. Abbreviations for multiplicity are: s=singlet, d=doublet, t=triplet, q=quartet, dd=doublet of doublet, dt=doublet of triplets, br=broad.

LCMS Method 1:
Instrument: Waters Acquity UPLC, photodiode array detector; Column: AcQuity UPLC BEH $C_{18}$ 1.7 μm, 21×30 mm; 2 min run time, 2% solvent B from 0 to 0.1 min, 2→98% solvent B:solvent A from 0.1 to 1.8 min, 98% solvent B for 0.2 min. Solvents: Solvent A=0.1% formic acid in water (v/v), solvent B=0.1% formic acid in acetonitrile (v/v). Injection volume 2-5 uL; UV detection array 210-400, Mass detection 120-1250 (electrospray ionization); column at 50° C.; flow rate 1.0 mL/min.

LCMS Method 2:
Instrument: Waters Acquity UPLC, photodiode array detector; Column: AcQuity UPLC BEH $C_{18}$ 1.7 μm 21×50 mm; 2 min run time, 2% solvent B from 0 to 0.1 min, 2→98% solvent B:solvent A from 0.1 to 1.8 min, 98% solvent B for 0.2 min. Solvents: Solvent A=5 mM ammonium hydroxide in water, solvent B=5 mM ammonium hydroxide in acetonitrile. Injection volume 2-5 uL; UV detection array 210-400, Mass detection 120-1250 (electrospray ionization); column at 50° C.; flow rate 1.0 mL/min.

LCMS Method 3:
Instrument: Waters Acquity UPLC, photodiode array detector; Column AcQuity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=0.1% formic acid in water (v/v), solvent B=0.1% formic acid in acetonitrile (v/v). Injection volume 2-5 uL; UV detection array 210-400, Mass detection 120-1600; column at 50° C., flow rate 1.0 mL/min.

LCMS Method 4:
Instrument: Waters Acquity UPLC, photodiode array detector; Column AcQuity UPLC BEH $C_{18}$ 1.7 μm 21×30 mm; 5.2 min run time, 2→98% solvent B:solvent A from 0 to 5.15 min, 98% solvent B from 5.15 to 5.20 min. Solvents: Solvent A=5 mM ammonium hydroxide in water, solvent B=5 mM ammonium hydroxide in acetonitrile). Injection volume 2-5 uL; UV detection array 210-400, Mass detection 120-1600; column at 50° C., flow rate 1.0 mL/min.

Intermediate 1A: 3-(2-(benzyloxy)phenyl)pentane-1,5-diyl bis(4-methylbenzenesulfonate)

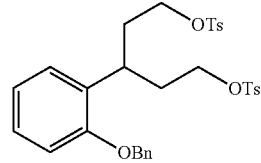 [SMILES: Cc1ccc(S(=O)(=O)OCCC(CCOS(=O)(=O)c2ccc(C)cc2)c2ccccc2OCc2ccccc2)cc1]

Step 1:
4-(2-(benzyloxy)phenyl)tetrahydro-2H-pyran-2-one

Potassium hydroxide (3.95 g, 70.3 mmol) in water (17.50 mL) was added dropwise to a solution of [RhCl(COD)]$_2$ (0.347 g, 0.703 mmol), (2-(benzyloxy)phenyl)boronic acid (commercially available, 22.46 g, 98 mmol) and 5,6-dihydro-2H-pyran-2-one (commercially available, 6.06 mL, 70.3 mmol) in 1,4-dioxane (175 mL) at 0° C. over a period of 2 mins. The temperature of reaction was then raised to 35° C. and stirred for 16 h. The reaction was diluted with EtOAc and 2M HCl. The aqueous solution was separated and back extracted with EtOAc. The combined organic layers were dried over MgSO$_4$ and the solvent was removed under reduced pressure. The crude mixture was then purified by FCC (0→60% EtOAc/heptanes) to yield the title compound (19.49 g, 68.3 mmol).

LCMS: Rt=1.03 min (LCMS Method 1); MS m/z 281.3 [M+H]$^+$.

$^1$H NMR (400 MHz, CD$_3$OD) δ 7.49-7.27 (m, 5H), 7.20 (ddd, J=14.8, 7.5, 1.8 Hz, 2H), 7.05 (dd, J=8.1, 1.2 Hz, 1H), 6.99-6.89 (m, 1H), 5.13 (s, 2H), 4.49-4.27 (m, 2H), 3.71-3.50 (m, 1H), 2.85 (dd, J=17.2, 6.4 Hz, 1H), 2.68 (dd, J=17.2, 9.8 Hz, 1H), 2.10 (m, 2H).

Step 2: 3-(2-(benzyloxy)phenyl)pentane-1,5-diol

Lithium aluminum hydride (76 mL, 76 mmol, 1M in THF) was added to a stirred solution of 4-(2-(benzyloxy)phenyl)tetrahydro-2H-pyran-2-one (19.49 g, 69.0 mmol) in anhydrous THF (400 mL) at 0° C. and then the reaction mixture was stirred for 2 h at 0° C. The reaction was quenched by water at −5° C. until gas production ceased and then a solution of NaOH (25 g) in water (25 mL) was portion-wise added to the mixture at 0° C. Na$_2$SO$_4$ (300 g) was next added to the reaction mixture and was stirred for 60 min. The mixture was filtered and the solvent was removed under reduced pressure. The crude product was purified by FCC (0-10% MeOH/DCM) to yield the title compound (19.3 g, 64.1 mmol).

LCMS: Rt=0.85 min (LCMS Method 1); MS m/z 287.3 [M+H]$^+$.

¹H NMR (400 MHz, CDCl₃) δ 7.51-7.31 (m, 5H), 7.26-7.16 (m, 2H), 7.07-6.95 (m, 2H), 5.11 (s, 2H), 3.61-3.35 (m, 5H), 1.92 (m, 4H), 1.66 (s, 2H).

Step 3: 3-(2-(benzyloxy)phenyl)pentane-1,5-diyl bis(4-methylbenzenesulfonate)

To the solution of 3-(2-(benzyloxy)phenyl)pentane-1,5-diol (19.31 g, 67.4 mmol) and triethylamine (41.4 mL, 297 mmol) in MeCN (40 mL) at −5° C. was added pTsCl (28.3 g, 148 mmol) and DMAP (0.824 g, 6.74 mmol). After addition, the reaction was stirred at RT overnight. The solvent was removed under reduced pressure. The crude product was dissolved in DCM and washed with water and brine then dried over Na₂SO₄ and filtered. The DCM was removed under reduced pressure and the crude was purified by FCC (0→50% EtOAc/heptanes) to yield the title compound.

LCMS: Rt=1.37 min
¹H NMR (400 MHz, CDCl₃) δ 7.74-7.63 (m, 4H), 7.46-7.33 (m, 5H), 7.30 (s, 4H), 7.20-7.13 (m, 1H), 6.99-6.72 (m, 3H), 5.00 (s, 2H), 4.01-3.61 (m, 4H), 3.15 (m, 1H), 2.45 (s, 6H), 2.03 (m, 2H), 1.89 (m, 2H).

Intermediate 1B: 3-(2-(benzyloxy)-5-fluorophenyl)pentane-1,5-diyl bis(4-methylbenzenesulfonate)

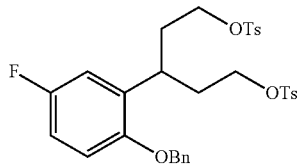 [SMILES: Cc1ccc(S(=O)(=O)OCCC(CCOS(=O)(=O)c2ccc(C)cc2)c2cc(F)ccc2OCc2ccccc2)cc1]

Step 1: 4-(2-(benzyloxy)-5-fluorophenyl)tetrahydro-2H-pyran-2-one (5-(benzyloxy)-2-fluorophenyl)boronic acid (commercially available, 24 g, 98 mmol), 5,6-dihydro-2H-pyran-2-one (commercially available, 6.06 mL, 70.3 mmol) and [RhCl(COD)]₂ (0.5 g, 1.014 mmol), were dissolved in dioxane (180 mL) and cooled to −10° C. Then, potassium hydroxide (4.38 g, 78 mmol) was dissolved in water (17.8 mL) and added to the dioxane solution dropwise over 10 min. The reaction was then warmed to 35° C. and stirred for 2 hours. The reaction was neutralized with 1M HCl (to pH 3), then concentrated under vacuum to remove the dioxane. The residue was then diluted with water and extracted with EtOAc the organics were combined and concentrated under vacuum. The crude was purified by FCC (0→100% EtOAc/heptanes) to yield the title compound (19.65 g, 78 mmol).

LCMS: RT=1.07 min (LCMS Method 2); MS m/z 301.4 [M+H]⁺.

Step 2: 3-(2-(benzyloxy)-5-fluorophenyl)pentane-1,5-diol

Lithium aluminum hydride (31.2 mL, 71.8 mmol) was added to a stirred solution of 4-(2-(benzyloxy)-5-fluorophenyl)tetrahydro-2H-pyran-2-one (19.6 g, 65.3 mmol) in dry THF (384 mL) at 0° C. The reaction mixture was stirred for 2 h at −5° C. under N₂. The reaction was quenched by H₂O (10 mL) at −5° C. until gas production ceased and then a solution of NaOH (25 g) in water (25 mL) was portion-wise added to the mixture at 0° C. Na₂SO₄ (300 g) was added to the reaction mixture and was stirred for 60 min. The mixture was filtered and the solvent was removed under reduced pressure. The crude product was purified by FCC (0-10% MeOH/DCM) to yield the title compound (17.8 g, 55.6 mmol).

LCMS: Rt=0.90 min (LCMS Method 2); MS m/z 304.4 [M+H]⁺.
¹H NMR (400 MHz, CDCl₃) δ 7.47-7.33 (m, 5H), 6.97-6.84 (m, 3H), 5.06 (s, 2H), 3.60-3.47 (m, 2H), 3.41 (m, 2H), 2.06-1.91 (m, 3H), 1.77 (m, 2H).

Step 3: 3-(2-(benzyloxy)-5-fluorophenyl)pentane-1,5-diyl bis(4-methylbenzenesulfonate)

3-(2-(benzyloxy)-5-fluorophenyl)pentane-1,5-diol (17.8 g, 58.5 mmol) and TEA (35.9 mL, 257 mmol) were dissolved in MeCN (200 mL) and cooled to −5° C. pTsCl (24.53 g, 129 mmol) and DMAP (0.714 g, 5.85 mmol) were added and the reaction was warmed to RT and stirred overnight. The solvent was removed under reduced pressure. The crude product was dissolved in DCM and washed with water and brine, dried over Na₂SO₄, filtered and concentrated. The crude product was purified by FCC (0→50% EtOAc/heptanes) to yield the title compound (22.8 g, 37.2 mmol).

LCMS Rt=1.37 min (LCMS Method 2); MS m/z 630.4 [M+NH₄]⁺.

Intermediate 1C: 3-(2-(benzyloxy)-4-fluorophenyl)pentane-1,5-diyl bis(4-methylbenzenesulfonate)

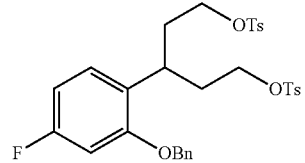 [SMILES: Cc1ccc(S(=O)(=O)OCCC(CCOS(=O)(=O)c2ccc(C)cc2)c2ccc(F)cc2OCc2ccccc2)cc1]

Step 1: 2-(benzyloxy)-4-fluoro-1-(hepta-1,6-dien-4-yl)benzene

A 250 mL round bottom flask was charged with 2-(benzyloxy)-4-fluorobenzaldehyde (commercially available, 23.90 g, 104 mmol) followed by nitromethane (250 mL). Then, ytterbium(III) chloride (7.25 g, 26.0 mmol) was added to the reaction and the mixture was stirred for 15 min at RT. After 15 min of stirring, allyltrimethylsilane (41.2 mL, 260 mmol) was slowly added over 5 min. The mixture was stirred overnight at RT. The reaction was concentrated and the crude product was purified by FCC (0→30% EtOAc/heptanes) to yield the title compound as a clear, colorless oil (22.64 g, 72.6 mmol).

LCMS: Rt=1.43 min (LCMS Method 1).
¹H NMR (400 MHz, CDCl₃) δ 7.38-7.19 (m, 5H), 6.97 (dd, 1H), 6.61-6.47 (m, 2H), 5.57 (m, 2H), 4.95 (s, 2H), 4.90-4.78 (m, 4H), 3.19 (t, 1H), 2.29 (m, 4H).

Step 2: 3-(2-(benzyloxy)-4-fluorophenyl)pentane-1,5-diol 2-(benzyloxy)-4-fluoro-1-(hepta-1,6-dien-4-yl)benzene (22.64 g, 76 mmol) was dissolved in MeOH (450 mL) and cooled to −78° C. Next, ozone was bubbled through the reaction mixture for 120 min over which time the reaction turned a pale purple color. Nitrogen was then bubbled through the reaction for 20 min and it was then warmed to 0° C. and NaBH₄ (28.9 g, 764 mmol) was added to the reaction portion wise over 4 h and the reaction was then stirred for 16 hours at RT. The reaction was then poured into DCM and sat NH₄Cl was added and the mixture was stirred at RT for 1 h. The organic layer was separated and washed with water and brine then dried over Na₂SO₄ and filtered. The solvent was removed under reduced pressure. The resulting product (15.22 g, 50.0 mmol) was taken forward without further purification.

LCMS: Rt=0.90 min (LCMS Method 1); MS m/z 305.2 [M+H]⁺.

¹H NMR (400 MHz, CDCl₃) δ 7.36-7.22 (m, 6H), 7.03 (m, 1H), 6.64-6.57 (m, 2H), 4.95 (s, 2H), 3.42 (m, 2H), 3.31 (m, 2H), 1.92-1.81 (m, 2H), 1.79-1.64 (m, 2H).

Step 3: 3-(2-(benzyloxy)-4-fluorophenyl)pentane-1, 5-diyl bis(4-methylbenzenesulfonate)

3-(2-(benzyloxy)-4-fluorophenyl)pentane-1,5-diol (6.96 g, 22.87 mmol) was dissolved in MeCN (150 mL) and TEA (13.63 mL, 98 mmol) was added and the reaction was cooled to 0° C. The reaction was incubated for 10 min and then pTsCl (9.59 g, 50.3 mmol) and DMAP (0.559 g, 4.57 mmol) were added. The reaction was slowly warmed to RT and stirred overnight. The reaction was then diluted with water and extracted with DCM. The combined organic layers were dried over magnesium sulfate, filtered and concentrated. The residue was then purified by FCC (0→60% EtOAc/heptanes) to yield the title compound (8.91 g, 14.54 mmol).

LCMS: Rt=1.35 min (LCMS Method 1); MS m/z 630.3 [M+NH₄]⁺.

¹H NMR (400 MHz, CDCl₃) δ 7.68-7.61 (m, 4H), 7.42-7.32 (m, 5H), 7.27 (m, 4H), 6.57 (dd, J=10.9, 2.4 Hz, 1H), 6.46 (td, J=8.3, 2.4 Hz, 1H), 4.93 (s, 2H), 3.90-3.80 (m, 2H), 3.74 (m, 2H), 3.08 (m, 1H), 2.43 (s, 6H), 1.98 (m, 3H), 1.92-1.80 (m, 2H).

Intermediate 1D: 3-(2-(benzyloxy)-4,5-difluorophenyl)pentane-1,5-diyl bis(4-methylbenzenesulfonate)

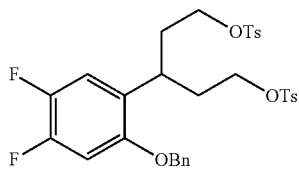 [SMILES: Cc1ccc(S(=O)(=O)OCCC(CCOS(=O)(=O)c2ccc(C)cc2)c2cc(F)c(F)cc2OCc2ccccc2)cc1]

Step 1: 4,5-difluoro-2-(hepta-1,6-dien-4-yl)phenol

A 1 L three-neck flask was charged with YbCl₃·6H₂O (20 g, 51 mmol) which was dehydrated by heating under vacuum. Then 4,5-difluoro-2-hydroxybenzaldehyde (20 g, 126 mmol) in nitromethane (200 mL) was added to the flask at 25° C. After 30 min of stirring, allyltrimethylsilane (51 g, 443 mmol) was added drop-wised at 25° C. The mixture was then warmed to 60° C. and stirred for 16 h. Next, the reaction was cooled to 25° C., filtered and concentrated. Then MeCN (200 mL) and 2N HCl (200 mL) were added to the crude reaction and the resulting solution was stirred for 30 min at 25° C. The MeCN was removed in vacuo and the remaining aqueous phase was extracted with EtOAc, dried by Na₂SO₄, filtered and concentrated. The crude was purified by FCC (0-10% EtOAc/petroleum ether) to yield the title compound as a yellow liquid (14.5 g, 64.66 mmol).

¹H NMR (400 MHz, CDCl₃) δ 6.90 (dd, J=8.9, 11.6 Hz, 1H), 6.62 (dd, J=6.8, 11.2 Hz, 1H), 5.68 (m, 2H), 5.56 (br s, 1H), 5.07-4.92 (m, 4H), 3.16-3.03 (m, 1H), 2.48-2.24 (m, 4H).

Step 2: 3-(4,5-difluoro-2-hydroxyphenyl)pentane-1,5-diol

To a stirring solution of 4,5-difluoro-2-(hepta-1,6-dien-4-yl)phenol (14.5 g, 64.66 mmol) in MeOH (150 mL) at −78° C., ozone was bubbled through the reaction mixture for 3 h until the starting material was consumed and the reaction turned pale purple. The ozone bubbling was stopped and excess ozone in the reaction mixture was removed by bubbling N₂ through the reaction mixture for 10 min. The reaction was then warmed to −20° C. and NaBH₄ (14.68 g, 387.96 mmol) was added in portions and the reaction was warmed to 0° C. and stirred for 2 h. The reaction was quenched with saturated aqueous NH₄Cl, and the MeOH was removed under reduced pressure. The aqueous layer was then extracted with EtOAc, and the combined organic layers were dried over Na₂SO₄, filtered and concentrated. The residue was purified by FCC (0-75% EtOAc/petroleum ether). The isolated material was then further purified (0-5% MeOH/DCM) to yield the title compound (3.1 g, 13.35 mmol) as a yellow solid.

¹H NMR (400 MHz, DMSO-d₆) δ 9.58 (s, 1H), 7.09 (dd, J=9.5, 12.1 Hz, 1H), 6.70 (dd, J=7.3, 12.4 Hz, 1H), 4.28 (t, J=5.1 Hz, 2H), 3.27-3.18 (m, 3H), 3.07 (m, 1H), 1.76-1.64 (m, 3H).

Step 3: 3-(2-(benzyloxy)-4,5-difluorophenyl)pentane-1,5-diol 3-(4,5-difluoro-2-hydroxyphenyl)pentane-1,5-diol (3.46 g, 14.90 mmol) was added to a 250 mL round bottom flask and dissolved in acetone (100 mL). K₂CO₃ (3.09 g, 22.35 mmol) and benzyl bromide (1.86 mL, 15.64 mmol) were added and the reaction was refluxed for 3 h. The reaction was then cooled to RT, and the acetone was evaporated under reduced pressure. The residue was dissolved in DCM and washed with water and then the aqueous layer was back extracted with DCM. The combined organic layers were washed with brine, dried over magnesium sulfate, filtered, and concentrated. The crude was then purified by FCC (0-10% MeOH/DCM) to yield the title compound (4.75 g, 14.74 mmol).

LCMS: Rt=0.89 min (LCMS Method 2); MS m/z 321.2 [M−H]⁻.

Step 4: 3-(2-(benzyloxy)-4,5-difluorophenyl)pentane-1,5-diyl bis(4-methylbenzenesulfonate)

3-(2-(benzyloxy)-4,5-difluorophenyl)pentane-1,5-diol (4.72 g, 14.64 mmol) and pTsCl (6.42 g, 33.7 mmol) were dissolved in MeCN (70 mL) at room temperature. DMAP (0.179 g, 1.464 mmol) and triethylamine (8.16 mL, 58.6 mmol) were then added to the solution and the reaction was stirred at room temperature for 16 h. The MeCN was evaporated, and the residue was diluted with water, and extracted with DCM. The organic extracts were combined, washed with brine, dried over MgSO₄, filtered and concentrated. The crude was purified by FCC (0-10% MeOH/DCM) to yield the title compound (7.47 g, 11.8 mmol).

LCMS: Rt=1.36 min (LCMS Method 1); MS m/z 648.6 [M+NH$_4$]$^+$.

Intermediate 1E: 3-(2-(tetrahydro-2H-pyran-4-yl)phenyl)pentane-1,5-diyl bis(4-methylbenzenesulfonate)

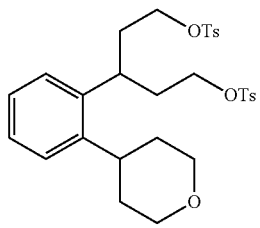 [SMILES: Cc1ccc(S(=O)(=O)OCCC(CCOS(=O)(=O)c2ccc(C)cc2)c2ccccc2C2CCOCC2)cc1]

Step 1:
4-(2-bromophenyl)tetrahydro-2H-pyran-2-one

A solution of potassium hydroxide (5.15 g, 92 mmol) in water (10 mL) was added dropwise to a solution of [RhCl(COD)]$_2$ (0.452 g, 0.917 mmol), (2-bromophenyl)boronic acid (27.6 g, 138 mmol) and 5,6-dihydro-2H-pyran-2-one (8.78 mL, 92 mmol) in 1,4-dioxane (200 mL) at 0° C. over a period of 10 min. The temperature of reaction was then raised to 35° C. and the reaction was stirred for 16 hours. The reaction was diluted with EtOAc and 3M HCl. The aqueous solution was separated and back extracted with EtOAc. The combined organic layers were dried over MgSO$_4$ and the solvent was removed under reduced pressure. The residue was purified by FCC (0-60% EtOAc/heptanes) to yield the title compound (12.9 g, 50.4 mmol).

LCMS: Rt=0.85 min (LCMS Method 2); MS m/z 255.3 [M+H]$^+$.

$^1$H NMR (400 MHz, CDCl$_3$) δ 7.53 (t, J=6.9 Hz, 1H), 7.34-7.21 (m, 1H), 7.17 (dd, J=7.8, 2.2 Hz, 1H), 7.09 (q, J=6.9 Hz, 1H), 4.39 (m, 2H), 3.66 (m, 1H), 2.93 (m, 1H), 2.57-2.47 (m, 1H), 2.16 (m, 1H), 1.98 (m, 1H).

Step 2: 3-(2-bromophenyl)pentane-1,5-diol

A solution of lithium borohydride (16.66 mL, 33.3 mmol, 2M in THF) was added to a stirred solution of 4-(2-bromophenyl)tetrahydro-2H-pyran-2-one (5.00 g, 19.60 mmol) in a mixture of THF (50 mL) and MeOH (0.50 mL) at 0° C. The reaction mixture was slowly warmed to RT and stirred for 18 h. The THF was then removed under reduced pressure and the reaction mixture was diluted with EtOAc and water. The pH of the aqueous phase was adjusted to 7 with acetic acid and was then extracted with EtOAc. The combined organic layers were then dried over MgSO$_4$, filtered and concentrated. The crude product was purified by FCC (0-10% MeOH/DCM) to yield the title intermediate (4.70 g, 18.1 mmol).

LCMS: Rt=1.27 min (LCMS Method 3); MS m/z 241.2 [M-H$_2$O]$^+$.

$^1$H NMR (400 MHz, DMSO-d$_6$) δ 7.55 (d, J=7.7 Hz, 1H), 7.39-7.31 (m, 2H), 7.11 (dt, J=8.6, 4.4 Hz, 1H), 4.35 (t, J=4.9 Hz, 2H), 3.34-3.14 (m, 5H), 1.85-1.66 (m, 4H).

Step 3: 3-(2-(3,6-dihydro-2H-pyran-4-yl)phenyl)pentane-1,5-diol

To 3-(2-bromophenyl)pentane-1,5-diol (14.0 g, 54.0 mmol), 2-(3,6-dihydro-2H-pyran-4-yl)-4,4,5,5-tetramethyl-1,3,2-dioxaborolane (17.02 g, 81 mmol), [1,1'-Bis(di-tert-butylphosphino)ferrocene] dichloropalladium(II) (1.761 g, 2.70 mmol) and potassium phosphate tribasic (20.64 g, 97 mmol) were suspended in degassed 1,4-dioxane (150 mL), and water (15.00 mL) and the reaction was stirred at RT for 16 h. The reaction was next diluted with water and extracted with EtOAc. The organic layer was dried over MgSO$_4$, filtered and concentrated. The crude was purified by FCC (0-10% MeOH/DCM) and further purified by recrystallization from EtOAc/heptanes (1:1) to yield the title compound as a white solid (9.85 g, 37.5 mmol).

LCMS: Rt=0.70 min (LCMS Method 2); MS m/z 261.3 [M-H]$^-$.

$^1$H NMR (400 MHz, DMSO-d$_6$) δ 7.25 (d, J=7.6 Hz, 2H), 7.12 (t, J=7.5 Hz, 1H), 7.02 (d, J=7.7 Hz, 1H), 5.51 (s, 1H), 4.27 (t, J=5.0 Hz, 2H), 4.15 (q, J=2.9 Hz, 2H), 3.79 (t, J=5.3 Hz, 2H), 3.19 (m, 4H), 3.04 (m, 1H), 2.24 (m, 2H), 1.71 (m, 4H).

Step 4: 3-(2-(tetrahydro-2H-pyran-4-yl)phenyl)pentane-1,5-diol 3-(2-(3,6-dihydro-2H-pyran-4-yl)phenyl)pentane-1,5-diol (7.60 g, 29.0 mmol) was dissolved in MeOH (75 mL) and 10% palladium on carbon (3.08 g, 2.90 mmol) was added. The flask was purged with 3 balloons of hydrogen and then the reaction was stirred under a balloon of hydrogen for 18 h. The reaction was filtered through a pad of celite and concentrated to obtain the crude product as white solid. This material was combined with a parallel reaction of starting 3-(2-(3,6-dihydro-2H-pyran-4-yl)phenyl)pentane-1,5-diol (3.30 g, 12.6 mmol) for recrystallization.

The combined solids were recrystallized from EtOH/heptanes to yield the title compound (9.95 g, 37.6 mmol) as a white solid.

LCMS: 1.29 min (LCMS Method 3); MS m/z 265.3 [M+H]$^+$.

$^1$H NMR (400 MHz, CDCl$_3$) δ 7.26-7.18 (m, 2H), 7.14 (m, 2H), 3.93 (dd, J=11.1, 3.6 Hz, 2H), 3.43 (t, J=11.6, 3H), 3.31 (bs, 1H), 3.30-3.20 (m, 3H), 3.15 (m, 3H), 1.79 (m, 2H), 1.68 (m, 4H), 1.56 (m, 2H).

Step 4: 3-(2-(tetrahydro-2H-pyran-4-yl)phenyl)pentane-1,5-diyl bis(4-methylbenzenesulfonate)

3-(2-(tetrahydro-2H-pyran-4-yl)phenyl)pentane-1,5-diol (7050 mg, 26.7 mmol) was suspended in MeCN (70 mL) and THF (70 mL) and cooled to 0° C. Next, DMAP (326 mg, 2.67 mmol) and TEA (16.4 mL 117 mmol) were added. The reaction was cooled to 0° C. and stirred for 15 minutes and then tosyl anhydride (19.19 g, 58.7 mmol) was added in four portions and the heterogeneous tan reaction was slowly warmed to RT and stirred for 16 h. Next, additional tosyl anhydride (4.5 g, 13.8 mmol) was added and the reaction was stirred for another hour. The reaction was then concentrated and the residue was dissolved in EtOAc and the organic phase was washed with water and brine. The combined aqueous washings were back extracted with EtOAc and the combined organic layers were dried over sodium sulfate, filtered and concentrated onto celite. The crude was then purified by FCC (0-60% EtOAc/heptanes) to give the title intermediate as a pale yellow solid (10336 mg, 18.05 mmol).

LCMS: Rt=2.96 min (LCMS Method 3); MS m/z 573.3 [M+H]⁺.

¹H NMR (400 MHz, DMSO-d₆) δ 7.73-7.65 (m, 4H), 7.44 (d, J=8.3 Hz, 4H), 7.23 (d, J=7.4 Hz, 1H), 7.21-7.07 (m, 3H), 3.86 (m, 4H), 3.69 (m, 2H), 3.35 (d, J=10.3 Hz, 5H), 3.23 (s, 1H), 2.97 (t, J=11.6 Hz, 1H), 2.41 (s, 6H), 1.91 (m, 2H), 1.86-1.73 (m, 2H), 1.62 (m, 2H), 1.41 (d, J=12.1 Hz, 2H).

Intermediate 1F: 3-(2-(benzyloxy)-3,5-difluorophenyl)pentane-1,5-diyl bis(4-methylbenzenesulfonate)

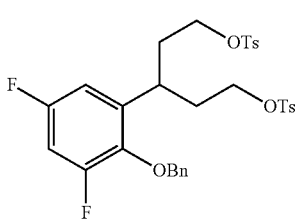 [SMILES: Cc1ccc(S(=O)(=O)OCCC(CCOS(=O)(=O)c2ccc(C)cc2)c2cc(F)cc(F)c2OCc2ccccc2)cc1]

Step 1: 4-(2-(benzyloxy)-3,5-difluorophenyl)tetrahydro-2H-pyran-2-one

In a round bottom flask, a solution of 5,6-dihydro-2H-pyran-2-one (0.298 mL, 3.47 mmol), (3,5-difluoro-2-methoxyphenyl)boronic acid (0.915 g, 3.47 mmol) and [RhCl(COD)]₂ (0.034 g, 0.069 mmol) in 1,4-dioxane (8.6 mL) was cooled to 0° C., and a solution of potassium hydroxide (0.194 g, 3.47 mmol) in water (0.9 mL) was added dropwise. The reaction was then warmed to 35° C. and stirred for 15 minutes. The reaction was then diluted with EtOAc and 1M HCl. The layers were separated and the aq. phase was extracted with EtOAc (2×50 mL). The combined organic layers were dried with MgSO₄, filtered and concentrated and the crude was purified by FCC (0-100% EtOAc/Heptanes) to yield the title intermediate as a clear, colorless oil (784 mg, 2.46 mmol).

LCMS: Rt: 1.07 min (LCMS Method 1); MS m/z 319.2 [M+H]⁺.

Step 2: 3-(2-(benzyloxy)-3,5-difluorophenyl)pentane-1,5-diol

In a round bottom flask, to a solution of 4-(2-(benzyloxy)-3,5-difluorophenyl)tetrahydro-2H-pyran-2-one (0.533 g, 1.674 mmol) in THF (10 mL) at −5° C. under nitrogen was added LiAlH₄ (1.0M in THF, 1.84 mL, 1.842 mmol) dropwise over ~2 minutes. After stirring for 35 minutes, the reaction was quenched with water (0.25 mL) at −5° C. until gas production stopped, then a solution of NaOH (614 mg) in water (0.614 mL) was added dropwise followed by Na₂SO₄ (7.38 g). The reaction was stirred for 1 hour and it was then filtered through celite, rinsing with THF, and the filtrate was concentrated. The crude was purified by FCC (0-20% MeOH (10% NH₄OH)/DCM) to yield the title intermediate as a clear, colorless oil (501 mg, 1.55 mmol).

LCMS: Rt: 0.90 min (LCMS Method 1); MS m/z 323.5 [M+H]⁺.

Step 3: 3-(2-(benzyloxy)-3,5-difluorophenyl)pentane-1,5-diyl bis(4-methylbenzenesulfonate)

In a round bottom flask, to a solution of 3-(2-(benzyloxy)-3,5-difluorophenyl)pentane-1,5-diol (0.501 g, 1.554 mmol) in acetonitrile (9.0 mL) was added triethylamine (1.08 mL, 7.77 mmol) and pTsCl (0.741 g, 3.89 mmol) and DMAP (0.019 g, 0.155 mmol). The reaction was stirred for 16 hours and then the reaction was concentrated and the residue was dissolved in DCM (50 mL) and washed with water (2×10 mL) and brine (1×10 mL), dried with MgSO₄, filtered and concentrated. The residue was purified by FCC (0-80% EtOAc/Heptanes) to yield the title compound as a yellow oil (772 mg, 1.22 mmol).

LCMS: Rt: 1.38 min (LCMS Method 1); MS m/z 648.5 [M+NH₄]⁺.

¹H NMR (400 MHz, CD₃OD) δ 7.71-7.60 (m, 4H), 7.47-7.32 (m, 9H), 6.88 (m, 1H), 6.58 (dt, J=9.3, 2.5 Hz, 1H), 3.83 (m, 2H), 3.69 (m, 2H), 3.22 (m, 1H), 2.45 (s, 6H), 1.92-1.66 (m, 4H). Two protons are obscured by the solvent.

Intermediate 1G: 3-(2-bromo-5-fluorophenyl)pentane-1,5-diyl bis(4-methylbenzenesulfonate)

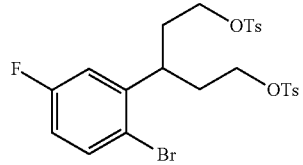 [SMILES: Cc1ccc(S(=O)(=O)OCCC(CCOS(=O)(=O)c2ccc(C)cc2)c2cc(F)ccc2Br)cc1]

Step 1: triethyl 2-(2-bromo-5-fluorophenyl)propane-1,1,3-tricarboxylate

Sodium metal (25.25 g, 1.10 mol) was added to EtOH (1.5 L) in several batches under N₂ gas flow and the reaction mixture was stirred at 25° C. until the solid dissolved. Next, diethyl malonate (176 g, 1.10 mol) was added to the mixture and stirred at 25° C. for 30 minutes, ethyl (E)-3-(2-bromo-5-fluorophenyl)acrylate (150 g, 0.55 mol; Preparation in Org. Biomol. Chem. 2012, 10, 3655-3661) was added to the reaction mixture and the reaction was stirred for 16 hours at 80° C. The reaction mixture was then concentrated and the residue was purified by FCC (2-10% EtOAc/petroleum ether) to the title intermediate (140 g, 323 mmol) as a colorless oil.

¹H NMR (400 MHz, CDCl₃) δ 7.51 (dd, J=5.5, 8.8 Hz, 1H), 7.02 (dd, J=3.1, 9.8 Hz, 1H), 6.83 (m, 1H), 4.38 (q, J=7.4 Hz, 1H), 4.24-4.18 (m, 2H), 4.10-3.97 (m, 4H), 3.92 (m, 1H), 2.91 (d, J=7.1 Hz, 2H), 1.23 (t, J=7.2 Hz, 3H), 1.13 (t, J=7.2 Hz, 6H).

Step 2: 3-(2-bromo-5-fluorophenyl)pentanedioic acid

Triethyl 2-(2-bromo-5-fluorophenyl)propane-1,1,3-tricarboxylate (140 g, 323 mmol) was dissolved in HCl (36.5%, 1 L) and was stirred at 100° C. for 48 hr. The solution was concentrated to give the title intermediate (109 g, 358 mmol, crude) as light yellow solid that was used without further purification.

¹H NMR (400 MHz, DMSO-d₆) δ 7.61 (m, 1H), 7.47-7.28 (m, 1H), 7.20-6.98 (m, 1H), 3.91-3.80 (m, 1H), 2.61 (m, 4H).

Step 3: 3-(2-bromo-5-fluorophenyl)pentane-1,5-diol

To a solution of 3-(2-bromo-5-fluorophenyl)pentanedioic acid (105 g, crude) in THF (1000 mL) was dropwise added B₂H₆ (172 mL, 17.2 mmol, 10M in dimethyl sulfide) at 0° C. The solution was then warmed to RT and stirred for 2 hours. The reaction was cooled to 0° C. and quenched with MeOH (500 mL) and HCl (250 mL, 4M in EtOAc), and the solution was then concentrated. The residue was purified by FCC (5-100% EtOAc: DCM (3:1)/petroleum ether) to give the title intermediate (43.3 g, 156 mmol) as a white solid.

¹H NMR (400 MHz, CD₃OD) δ 7.58-7.54 (m, 1H), 7.12 (m, 1H), 6.89 (m, 1H), 3.55-3.38 (m, 5H), 2.00-1.79 (m, 4H).

Step 4: 3-(2-bromo-5-fluorophenyl)pentane-1,5-diyl bis(4-methylbenzenesulfonate)

3-(2-bromo-5-fluorophenyl)pentane-1,5-diol (5000 mg, 18.04 mmol) to a 250 mL RB flask and it was dissolved in MeCN (100 mL). Next, TEA (11.1 mL 79 mmol) and DMAP (220 mg, 1.804 mmol) were added and the reaction and the reaction was cooled to 0° C. The reaction was stirred for 10 minutes at 0° C. and then tosyl anhydride (13000 mg, 39.8 mmol) was added and the reaction was slowly warmed to RT and the reaction was stirred overnight. The material was next concentrated onto celite for purification by FCC (0-60% EtOAc/heptanes) to yield the title intermediate as a light brown oil (9700 mg, 16.57 mmol).

LCMS: Rt: 3.00 min (LCMS Method 1); MS m/z 604.1 [M+H]⁺.

¹H NMR (400 MHz, CDCl₃) δ 7.75-7.67 (m, 4H), 7.42 (dd, J=8.8, 5.5 Hz, 1H), 7.31 (d, J=8.0 Hz, 4H), 6.78 (m, 1H), 6.73-6.62 (m, 1H), 3.88 (m, 2H), 3.80 (dt, J=10.1, 6.9 Hz, 2H), 3.34 (s, 1H), 2.44 (s, 6H), 2.05-1.93 (m, 2H), 1.89 (bs, 2H).

Intermediate 111:
3-(2-bromophenyl)pentane-1,5-diyl bis(4-methylbenzenesulfonate)

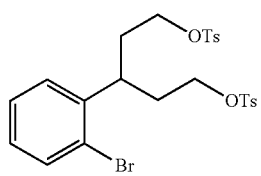 [SMILES: Cc1ccc(S(=O)(=O)OCCC(CCOS(=O)(=O)c2ccc(C)cc2)c2ccccc2Br)cc1]

Step 1: triethyl 2-(2-bromophenyl)propane-1,1,3-tricarboxylate

Na (27.04 g, 1180 mmol) was added into EtOH (1.5 L) for several batches under N₂ gas flow and the reaction mixture was stirred at 25° C. until the solid disappeared. Then diethyl malonate (188 g, 1180 mmol) was added and the reaction was stirred at 25° C. for 30 min. Next, ethyl (E)-3-(2-bromophenyl)acrylate (150 g, 588 mmol) was added to the mixture. The mixture was then stirred for 16 hours at 80° C. The reaction mixture was then concentrated and the residue was purified by FCC (afford the residue which was purified by column chromatography (2-20% EtOAc/petroleum ether) to yield the title compound (133 g, 320 mmol,) as a colorless oil.

¹H NMR (400 MHz, CDCl₃) δ 7.57-7.48 (m, 1H), 7.30-7.18 (m, 2H), 7.11-7.00 (m, 1H), 4.48-4.36 (m, 1H), 4.24-4.13 (m, 2H), 4.07-3.90 (m, 5H), 3.00-2.84 (m, 2H), 1.26-1.20 (m, 3H), 1.13-0.99 (m, 6H).

Step 2: diethyl 3-(2-bromophenyl)pentanedioate

To a solution of triethyl 2-(2-bromophenyl)propane-1,1,3-tricarboxylate (133 g, 320 mmol) in DMSO (500 mL) was added NaCl (56 g, 960 mmol) and H₂O (17 g, 960 mmol). The mixture was stirred at 160° C. for 6 hours. The reaction mixture was then quenched with H₂O (500 mL) and extracted with MTBE (3×500 mL) and the combined organic phases were washed with brine (500 mL), then dried over sodium sulfate, filtered and concentrated to give the title compound as a yellow oil that was used without further purification (105 g, 305 mmol).

¹H NMR (400 MHz, CDCl₃) δ 7.58-7.55 (m, 1H), 7.28-7.25 (m, 2H), 7.10-7.08 (m, 1H), 4.20-4.15 (m, 1H), 4.09-4.04 (m, 4H), 2.79-2.70 (m, 4H), 1.19-1.15 (m, 6H).

Step 3: 3-(2-bromophenyl)pentane-1,5-diol

To a suspension of lithium aluminum hydride (29 g, 765 mmol) in THF (800 mL) was added dropwise a solution of diethyl 3-(2-bromophenyl)pentanedioate (105 g, 305 mmol) in THF (200 mL) at 0° C. The reaction mixture was stirred at 25° C. for 2 hours and then the reaction mixture was added dropwise to a solution of 2N HCl (2 L) and then extracted with EtOAc (3×500 mL). The combined organic phases were washed with brine (500 mL), dried over sodium sulfate, filtered and concentrated. The residue was purified FCC (10-100% EtOAc/DCM (3:1)/petroleum ether) to give a white solid. The solid was then triturated with EtOAc (100 mL) and filtered, the filter cake was washed with cold EtOAc (2×50 mL) to afford the title compound as a white solid (47.2 g, 182 mmol).

¹H NMR (400 MHz, CD₃OD) δ 7.55-7.53 (m, 1H), 7.33-7.32 (m, 2H), 7.10-7.06 (m, 1H), 3.47-3.39 (m, 5H), 1.96-1.86 (m, 4H).

Step 4: 3-(2-bromophenyl)pentane-1,5-diyl bis(4-methylbenzenesulfonate)

3-(2-bromophenyl)pentane-1,5-diol (10 g, 38.6 mmol) and DMAP (0.471 g, 3.86 mmol) were added to a 500 mL RB flask and dissolved in MeCN (200 mL). The reaction was cooled to 0° C. and TEA (32.1 ml, 232 mmol) was added and the reaction was stirred for 10 minutes and then pTsCl (16.92 g, 89 mmol) was added. The reaction was then slowly warmed to RT and stirred overnight. The reaction was concentrated and the residue was dissolved in DCM and washed with 1N HCl (4×50 mL) and the combined aq layers were back extracted 1×50 mL DCM (1×50 mL). The combine organic layers were washed brine (1×10 mL), dried over sodium sulfate and concentrated. The crude was then purified by FCC (0-50% EtOAc/heptanes) to yield the title compound (19.52 g, 34.4 mmol) as a yellow oil.

¹H NMR (400 MHz, DMSO-d₆) δ 7.70-7.62 (m, 4H), 7.49 (dd, J=8.2, 1.4 Hz, 1H), 7.41 (d, J=8.2 Hz, 4H), 7.25 (m, 1H), 7.20-7.13 (m, 1H), 7.13-7.07 (m, 1H), 3.83 (dt,

J=9.8, 5.9 Hz, 2H), 3.70 (dt, J=9.9, 6.6 Hz, 2H), 3.20 (dd, J=14.0, 7.0 Hz, 1H), 2.40 (s, 6H), 1.97-1.77 (m, 4H).

Intermediate 2A: tert-butyl (S)-7-amino-5-oxa-2-azaspiro[3.4]octane-2-carboxylate hydrochloride

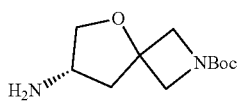

tert-butyl 7-oxo-5-oxa-2-azaspiro[3.4]octane-2-carboxylate (commercially available, 200 g, 0.88 mol), isopropylamine hydrochloride (845 g, 8.89 mol) and pyridoxal 5'-phosphate hydrate (10 g, 0.04 mol) were dissolved in DMSO (800 mL) and 0.1M borate buffer (6200 mL, pH 9.0). The reaction was then warmed to 40° C. and a solution of ATA412 (Codexis, 20 g) in 0.1M borate buffer (400 mL, pH 9.0) was added. N$_2$ was bubbled through the solution and the reaction was stirred until complete conversion was achieved. The reaction was then cooled to 26° C. and citric acid was added until the pH reached 4.88. DCM (1500 mL) was added and the DCM layer was filtered through micro crystalline cellulose to remove the enzyme. The aqueous layer was treated with NaCl (1200 mg, 20.5 mol) and the pH was adjusted to 9.9 with 32% NaOH solution. The aqueous layer was extracted with DCM (3×2000 mL). The DCM extracts and filtrate were combined and concentrated under reduced pressure and the residue was taken up in EtOAc (1500 mL) and washed with brine (2×100 mL). The EtOAc was then concentrated to dryness and the residue was suspended in EtOAc (1000 mL) and filtered to remove NaCl and enzyme. The EtOAc was concentrated to obtain the free base of the title compound (146.9 g, 0.643 mol). The free base was dissolved in EtOAc (870 mL) and HCl in EtOAc (2M, 390 mL) was added over an hour. The reaction was stirred for 2 hours, then filtered and the filter cake was washed with EtOAc (100 mL).

The filter cake was then dried to give the title intermediate (169 g, 0.639 mmol).

$[\alpha]_D^{25}$=−0.478 0 (c=1.0330 w/v %, CH$_3$OH).

$^1$H NMR (400 MHz, CD$_3$OD) δ 4.11 (d, J=4.8 Hz, 2H), 4.01-3.89 (m, 5H), 2.71 (m, 1H), 2.27-2.17 (m, 1H), 1.46 (s, 9H).

Intermediate 3A: tert-butyl (S)-7-(4-(2-(benzyloxy)-5-fluorophenyl)piperidin-1-yl)-5-oxa-2-azaspiro[3.4]octane-2-carboxylate

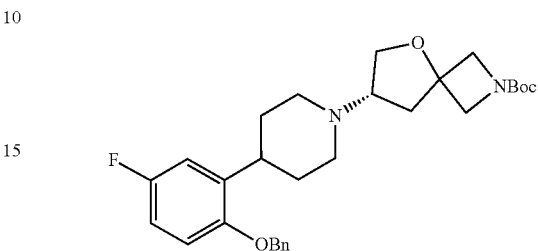

3-(2-(benzyloxy)-5-fluorophenyl)pentane-1,5-diyl bis(4-methylbenzenesulfonate) (Intermediate 1B, 35.41 g, 54.8 mmol) and tert-butyl (S)-7-amino-5-oxa-2-azaspiro[3.4]octane-2-carboxylate hydrochloride (Intermediate 2, 14.50 g, 54.8 mmol) were suspended in MeCN (500 mL) and potassium phosphate tribasic (34.9 g, 164 mmol) was added to the solution. The reaction was stirred at 90° C. for 72 hours. Next, the solvent was removed in vacuo and the solid residue was suspended in EtOAc. The slurry was filtered and the filtrate was concentrated to obtain the crude product as an orange oil. The crude product was purified by FCC (0-10% MeOH (1% NH$_4$OH)/DCM to yield the title compound (17.09 g, 33.9 mmol).

LCMS: Rt=1.33 min (LCMS Method 2); MS m/z 497.2 [M+H]$^+$.

$^1$H NMR (400 MHz, CD$_3$OD) δ 7.47-7.26 (m, 5H), 7.23-7.09 (m, 2H), 7.04-6.84 (m, 1H), 5.09 (s, 2H), 4.11-3.78 (m, 5H), 3.70 (dd, J=8.7, 7.4 Hz, 2H), 3.05 (m, 3H), 2.96-2.72 (m, 1H), 2.42 (dd, J=12.9, 7.5 Hz, 1H), 2.18 (m, 2H), 2.03 (dd, J=12.9, 8.5 Hz, 1H), 1.91-1.60 (m, 4H), 1.43 (s, 9H).

The following compounds in Table 1 were prepared using a similar procedure and the relevant starting materials:

TABLE 1

| Intermediate | Structure | Retention time (min) and Method | Expected Mass | Observed Mass |
|---|---|---|---|---|
| Intermediates 3B to 3H | | | | |
| 3B | 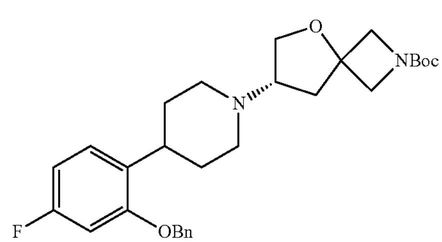 [SMILES: CC(C)(C)OC(=O)N1CC2(C[C@H](N3CCC(c4ccc(F)cc4OCc4ccccc4)CC3)CO2)C1] | 1.33 LCMS Method 2 | 497.3 [M + H]$^+$ | 497.4 [M + H]$^+$ |

TABLE 1-continued

Intermediates 3B to 3H

| Intermediate | Structure | Retention time (min) and Method | Expected Mass | Observed Mass |
|---|---|---|---|---|
| 3C | 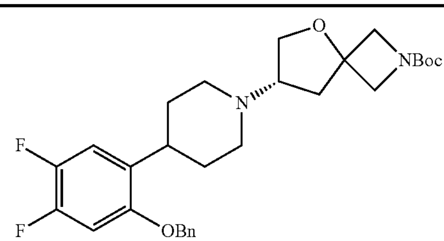 | 1.31 LCMS Method 2 | 515.3 [M + H]+ | 515.4 [M + H]+ |
| 3D | 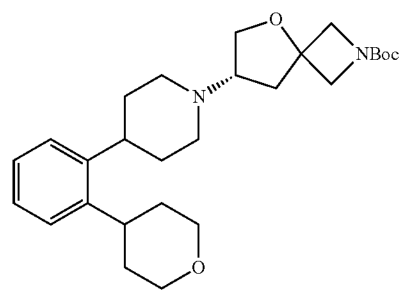 [SMILES: CC(C)(C)OC(=O)N1CC2(C[C@H](N3CCC(c4ccccc4C4CCOCC4)CC3)CO2)C1] | 2.61 LCMS Method 4 | 457.3 [M + H]+ | 457.8 [M + H]+ |
| 3E | 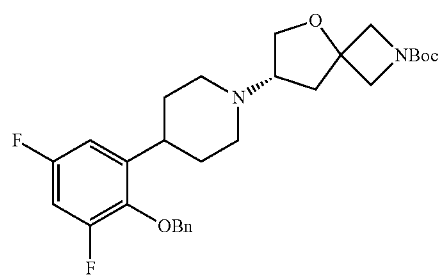 [SMILES: CC(C)(C)OC(=O)N1CC2(C[C@H](N3CCC(c4cc(F)cc(F)c4OCc4ccccc4)CC3)CO2)C1] | 1.35 LCMS Method 2 | 515.3 [M + H]+ | 515.3 [M + H]+ |
| 3F | 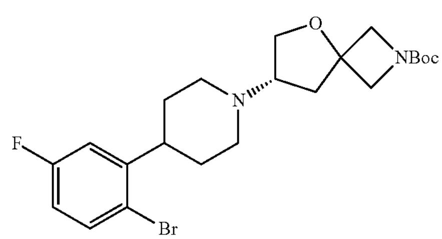 [SMILES: CC(C)(C)OC(=O)N1CC2(C[C@H](N3CCC(c4cc(F)ccc4Br)CC3)CO2)C1] | 2.96 LCMS Method 4 | 469.2 [M + H]+ | 469.5 [M + H]+ |
| 3G | 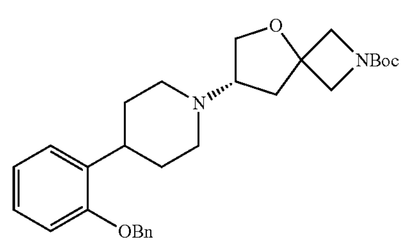 [SMILES: CC(C)(C)OC(=O)N1CC2(C[C@H](N3CCC(c4ccccc4OCc4ccccc4)CC3)CO2)C1] | 1.33 min LCMS Method 2 | 479.3 [M + H]+ | 479.2 [M + H]+ |
| 3H | 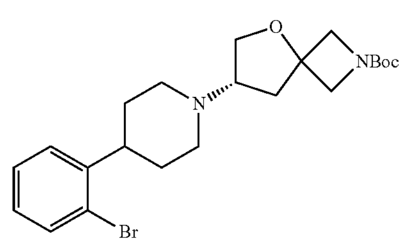 [SMILES: CC(C)(C)OC(=O)N1CC2(C[C@H](N3CCC(c4ccccc4Br)CC3)CO2)C1] | 0.76 min LCMS Method 1 | 451.2 [M + H]+ | 451.3 [M + H]+ |

Intermediate 4A: tert-butyl (S)-7-(4-(5-fluoro-2-hydroxyphenyl)piperidin-1-yl)-5-oxa-2-azaspiro[3.4]octane-2-carboxylate

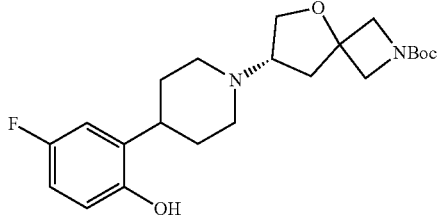 [SMILES: CC(C)(C)OC(=O)N1CC2(C[C@H](N3CCC(c4cc(F)ccc4O)CC3)CO2)C1]

To a stirring solution of tert-butyl (S)-7-(4-(2-(benzyloxy)-5-fluorophenyl)piperidin-1-yl)-5-oxa-2-azaspiro[3.4]octane-2-carboxylate (Intermediate 3A, 7.67 g, 15.44 mmol) in ethanol (150 mL), 10% palladium on carbon (213 mg, 0.201 mmol) was added. The reaction was then stirred under a balloon of hydrogen for 5 hr. The reaction was then filtered through a pad of celite and the solvent was removed under reduced pressure to give a clear oil. Diethyl ether (100 mL) was added and the solvent was removed in vacuo. This was repeated two more times to give the title compound as a white solid (5.48 g, 13.48 mmol).

LCMS: Rt=2.24 min (LCMS Method 4); MS m/z 407.2 [M+H]$^+$.

$^1$H NMR (400 MHz, CD$_3$OD) δ 6.90-6.80 (m, 1H), 6.79-6.66 (m, 2H), 4.15-3.81 (m, 5H), 3.74 (dd, J=8.7, 7.4 Hz, 1H), 3.16-2.81 (m, 4H), 2.45 (dd, J=12.9, 7.5 Hz, 1H), 2.23 (m, 2H), 2.07 (dd, J=12.9, 8.5 Hz, 1H), 1.93-1.61 (m, 4H), 1.46 (s, 9H).

The following compounds in Table 2 were prepared using a similar procedure and the relevant starting materials:

TABLE 2

Intermediates 4B to 4E

| Intermediate | Structure | Retention time (min) and Method | Expected Mass | Observed Mass |
|---|---|---|---|---|
| 4B | 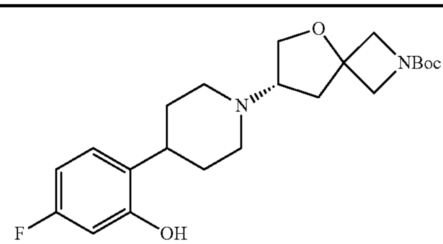 | 1.18 LCMS Method 1 | 407.4 [M + H]$^+$ | 407.2 [M + H]$^+$ |
| 4C | 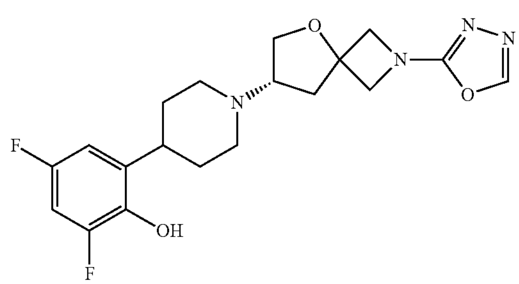 [SMILES: Oc1c(F)cc(F)cc1C1CCN([C@@H]2COC3(C2)CN(c2nnco2)C3)CC1] | 0.52 LCMS Method 1 | 393.4 [M + H]$^+$ | 393.2 [M + H]$^+$ |
| 4D | 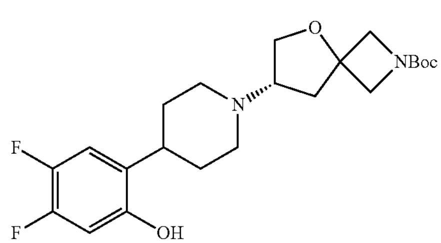 [SMILES: CC(C)(C)OC(=O)N1CC2(C[C@H](N3CCC(c4cc(F)c(F)cc4O)CC3)CO2)C1] | 1.02 LCMS Method 2 | 425.2 [M + H]$^+$ | 425.2 [M + H]$^+$ |
| 4E | 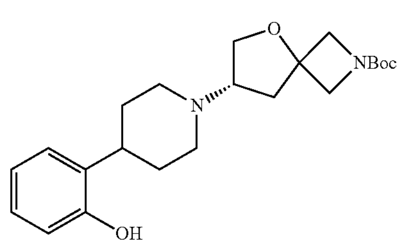 [SMILES: CC(C)(C)OC(=O)N1CC2(C[C@H](N3CCC(c4ccccc4O)CC3)CO2)C1] | 0.97 LCMS Method 2 | 389.2 [M + H]$^+$ | 389.3 [M + H]$^+$ |

Intermediate 4F: (S)-2-(1-(2-(1,3,4-oxadiazol-2-yl)-5-oxa-2-azaspiro[3.4]octan-7-yl)piperidin-4-yl)-4-fluorophenol

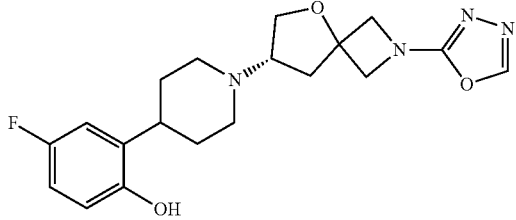 [SMILES: Oc1ccc(F)cc1C1CCN([C@@H]2COC3(C2)CN(c2nnco2)C3)CC1]

(S)-7-(4-(2-(benzyloxy)-5-fluorophenyl)piperidin-1-yl)-2-(1,3,4-oxadiazol-2-yl)-5-oxa-2-azaspiro[3.4]octane (Intermediate 8B, 1680 mg, 3.62 mmol) was dissolved in ethanol (200 mL) and 10% Pd/C (43 mg, 0.362 mmol) was added. The flask was then stirred under hydrogen filled balloon for six hours. The slurry was then filtered through a pad of celite and the cake was rinsed with DCM. The filtrate was concentrated under reduced pressure to yield the title intermediate (1300 mg, 3.47 mmol).

LCMS: Rt: 0.75 min (LCMS Method 2); MS m/z 375.3 [M+H]$^+$.

Intermediate 5A: (2-oxaspiro[3.3]heptan-6-yl)methyl 4-methylbenzenesulfonate

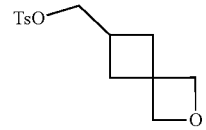

To the solution of (2-oxaspiro[3.3]heptan-6-yl)MeOH (50 mg, 0.390 mmol), DMAP (4.77 mg, 0.039 mmol) and triethylamine (0.136 mL, 0.975 mmol) in DCM (5 mL), pTsCl (78 mg, 0.410 mmol) was added. The reaction was stirred at RT overnight and then diluted with DCM and washed with 1N HCl solution, sat. NaHCO$_3$ solution, water and brine then dried over Na$_2$SO$_4$. The solvent was removed under reduced pressure and the crude product was purified by FCC EtOAc/heptanes) to yield the title compound (71 mg, 0.226 mmol).

LCMS: Rt: 0.92 min (LCMS Method 1).

$^1$H NMR (400 MHz, CD$_3$OD) δ 7.80 (d, J=8.5 Hz, 2H), 7.47 (d, J=8.4 Hz, 2H), 4.66 (s, 2H), 4.54 (s, 2H), 3.95 (d, J=5.9 Hz, 2H), 2.48 (s, 3H), 2.46-2.27 (m, 3H), 2.01-1.89 (m, 2H).

The following compounds in Table 3 were prepared using a similar procedure and the relevant starting materials:

TABLE 3

Intermediates 5B to 5T

| Intermediate | Structure | Retention time (min) and Method | Expected Mass | Observed Mass |
|---|---|---|---|---|
| 5B | Ts-O-[1,4-dioxane-2-yl-methyl] | 0.82 LCMS Method 2 | 273.1 [M + H]$^+$ | 273.0 (M + H) |
| 5C | TsO-[tetrahydrofuran-3-yl] | 0.84 LCMS Method 1 | 243.1 [M + H]$^+$ | 243.1 (M + H) |
| 5D | TsO-CMe$_2$-CN | 0.91 LCMS Method 1 | 254.1 [M + H]$^+$ | 254.2 (M + H) |
| 5E | TsO-[1,4-dioxane-2-yl-methyl] | 0.82 LCMS Method 1 | 273.1 [M + H]$^+$ | 273.0 (M + H) |
| 5F | TsO-[tetrahydrofuran-3-yl] | 0.83 LCMS Method 2 | 260.1 [M + NH$_4$]$^+$ | 260.3 [M + NH$_4$]$^+$ |
| 5G | TsO-[tetrahydrofuran-3-yl-methyl] | 0.86 LCMS Method 1 | 257.1 [M + H]$^+$ | 257.2 [M + H]$^+$ |
| 5H | TsO-[tetrahydropyran-4-yl-methyl] | 0.90 LCMS Method 2 | 269.1 [M − H]$^-$ | 269.2 [M − H]$^-$ |

TABLE 3-continued

| | Intermediates 5B to 5T | | | |
|---|---|---|---|---|
| Intermediate | Structure | Retention time (min) and Method | Expected Mass | Observed Mass |
| 5I | TsO—CH2—(tetrahydrofuran-3-yl) | 0.87 LCMS Method 1 | 257.1 [M + H]⁺ | 257.2 [M + H]⁺ |
| 5J | TsO—CH2—(3-hydroxyoxetan-3-yl) | 0.70 LCMS Method 1 | 259.1 [M + H]⁺ | 259.3 [M + H]⁺ |
| 5K | TsO—CH2—(3-oxabicyclo[3.1.0]hexane) | 0.99 LCMS Method 1 | 286.1 [M + NH4]⁺ | 286.0 [M + NH4]⁺ |
| 5L | tetrahydropyran-3-yl OTs | 0.92 LCMS Method 1 | 257.1 [M + H]⁺ | 257.2 [M + H]⁺ |
| 5M | TsO—(2-oxaspiro[3.3]heptan-6-yl) | 0.87 LCMS Method 2 | 269.1 [M + H]⁺ | 269.3 [M + H]⁺ |
| 5N | 2,2-dimethyl-tetrahydrofuran-4-yl OTs | 0.96 LCMS Method 1 | 288.1 [M + NH4]⁺ | 288.1 [M + NH4]⁺ |
| 5O | TsO—CH2—(3-ethyloxetan-3-yl) | 0.93 LCMS Method 1 | 271.1 [M + H]⁺ | 271.2 [M + H]⁺ |
| 5P | TsO—CH2CH2—C(Me)2—OMe | 1.02 LCMS Method 2 | 273.1 [M + H]⁺ | 273.2 [M + H]⁺ |
| 5Q | TsO—CH2—(3-fluorooxetan-3-yl) | 0.84 LCMS Method 1 | 278.1 [M + NH4]⁺ | 278.1 [M + NH4]⁺ |
| 5S | TsO—(3-(methoxycarbonyl)cyclobutyl) | 0.95 LCMS Method 1 | 285.2 [M + H]⁺ | 257.2 [M + H]⁺ |

TABLE 3-continued

Intermediates 5B to 5T

| Intermediate | Structure | Retention time (min) and Method | Expected Mass | Observed Mass |
|---|---|---|---|---|
| 5T | Me, TsO, tetrahydropyran structure | 0.97 LCMS Method 2 | 302.2 [M + NH₄]⁺ | 302.1 [M + NH₄]⁺ |

Intermediate 6A: tert-butyl (S)-7-(4-(5-fluoro-2-(oxetan-3-yloxy)phenyl)piperidin-1-yl)-5-oxa-2-azaspiro[3.4]octane-2-carboxylate

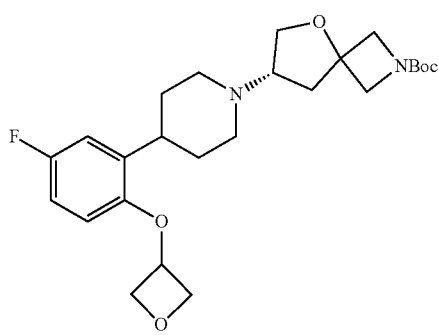 [SMILES: CC(C)(C)OC(=O)N1CC2(C[C@H](N3CCC(c4cc(F)ccc4OC4COC4)CC3)CO2)C1]

tert-butyl (S)-7-(4-(5-fluoro-2-hydroxyphenyl)piperidin-1-yl)-5-oxa-2-azaspiro[3.4]octane-2-carboxylate (Intermediate 4A, 549 mg, 1.35 mmol), cesium carbonate (1.32 g, 4.05 mmol) and oxetan-3-yl 4-methylbenzenesulfonate (commercially available, 308 mg, 1.35 mmol) were dissolved in DMF (5.6 mL) and the reaction was stirred at 80° C. overnight. The mixture was diluted with EtOAc, and washed with water, dried over MgSO₄ and concentrated in vacuo. The residue was purified by FCC (0-10% MeOH/DCM) to afford the title intermediate (412 mg, 0.891 mmol).

LCMS: Rt: 1.08 min (LCMS Method 2); MS m/z 463.3 [M+H]⁺.

The following compounds in Table 4 were prepared using a similar procedure and the relevant starting materials:

TABLE 4

Intermediates 6B to 6AA

| Intermediate | Structure | Retention time (min) and Method | Expected Mass | Observed Mass |
|---|---|---|---|---|
| 6B | (structure) | 1.18 LCMS Method 2 | 491.3 [M + H]⁺ | 491.2 [M + H]⁺ |

TABLE 4-continued

Intermediates 6B to 6AA

| Intermediate | Structure | Retention time (min) and Method | Expected Mass | Observed Mass |
|---|---|---|---|---|
| 6C | 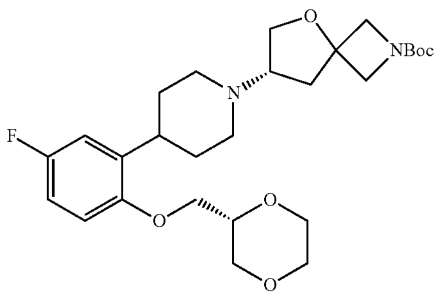 [SMILES: CC(C)(C)OC(=O)N1CC2(C[C@H](N3CCC(c4cc(F)ccc4OC[C@H]4COCCO4)CC3)CO2)C1] | 0.82 LCMS Method 1 | 507.3 [M + H]⁺ | 507.3 [M + H]⁺ |
| 6D | 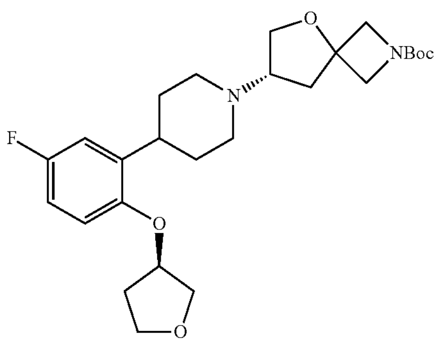 [SMILES: CC(C)(C)OC(=O)N1CC2(C[C@H](N3CCC(c4cc(F)ccc4O[C@@H]4CCOC4)CC3)CO2)C1] | 0.83 LCMS Method 1 | 477.3 [M + H]⁺ | 477.4 [M + H]⁺ |
| 6E | 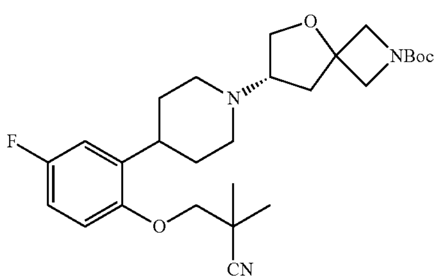 [SMILES: CC(C)(C#N)COc1ccc(F)cc1C1CCN([C@@H]2COC3(C2)CN(C(=O)OC(C)(C)C)C3)CC1] | 1.15 LCMS Method 2 | 488.3 [M + H]⁺ | 488.3 [M + H]⁺ |
| 6F | 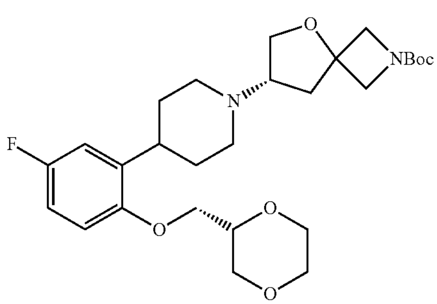 | 1.11 LCMS Method 2 | 507.3 [M + H]⁺ | 507.4 [M + H]⁺ |

TABLE 4-continued

| | Intermediates 6B to 6AA | | | |
|---|---|---|---|---|
| Intermediate | Structure | Retention time (min) and Method | Expected Mass | Observed Mass |
| 6G | | 1.16 LCMS Method 2 | 491.1 [M + H]⁺ | 491.3 [M + H]⁺ |
| 6H | | 1.13 LCMS Method 2 | 477.3 [M + H]⁺ | 477.4 [M + H]⁺ |
| 6I | | 0.98 LCMS Method 2 | 491.3 [M + H]⁺ | 491.4 [M + H]⁺ |
| 6J | | 1.18 LCMS Method 2 | 505.3 [M + H]⁺ | 505.3 [M + H]⁺ |

TABLE 4-continued

Intermediates 6B to 6AA

| Intermediate | Structure | Retention time (min) and Method | Expected Mass | Observed Mass |
|---|---|---|---|---|
| 6K | 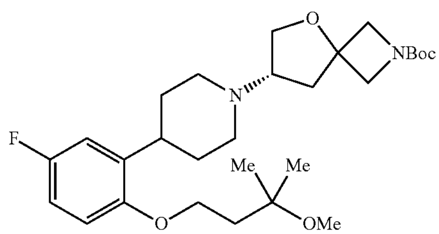 [SMILES: COC(C)(C)CCOc1ccc(F)cc1C1CCN([C@@H]2COC3(C2)CN(C(=O)OC(C)(C)C)C3)CC1] | 1.28 LCMS Method 2 | 507.3 [M + H]+ | 507.4 [M + H]+ |
| 6L | 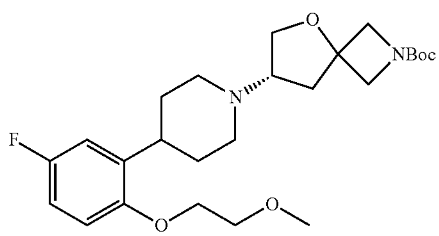 [SMILES: COCCOc1ccc(F)cc1C1CCN([C@@H]2COC3(C2)CN(C(=O)OC(C)(C)C)C3)CC1] | 1.13 LCMS Method 2 | 465.3 [M + H]+ | 465.4 [M + H]+ |
| 6M | 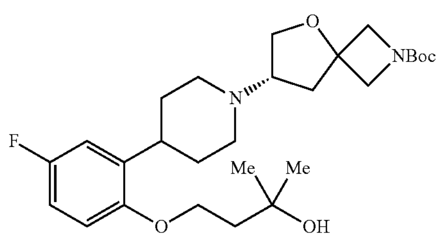 [SMILES: CC(C)(O)CCOc1ccc(F)cc1C1CCN([C@@H]2COC3(C2)CN(C(=O)OC(C)(C)C)C3)CC1] | 1.27 LCMS Method 2 | 499.3 [M + H]+ | 499.2 [M + H]+ |
| 6N | 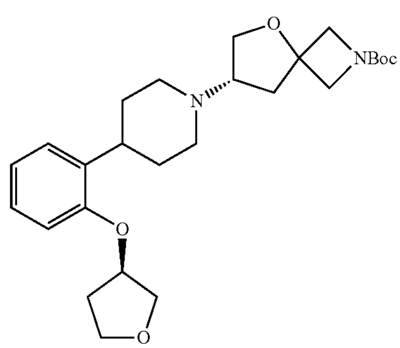 [SMILES: CC(C)(C)OC(=O)N1CC2(C[C@H](N3CCC(c4ccccc4O[C@@H]4CCOC4)CC3)CO2)C1] | 1.11 LCMS Method 2 | 459.3 [M + H]+ | 459.2 [M + H]+ |
| 6O | 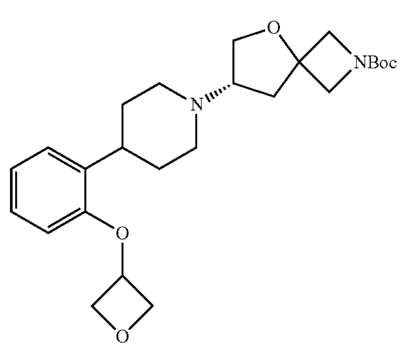 [SMILES: CC(C)(C)OC(=O)N1CC2(C[C@H](N3CCC(c4ccccc4OC4COC4)CC3)CO2)C1] | 0.75 LCMS Method 1 | 445.3 [M + H]+ | 445.2 [M + H]+ |

TABLE 4-continued

Intermediates 6B to 6AA

| Intermediate | Structure | Retention time (min) and Method | Expected Mass | Observed Mass |
|---|---|---|---|---|
| 6P | 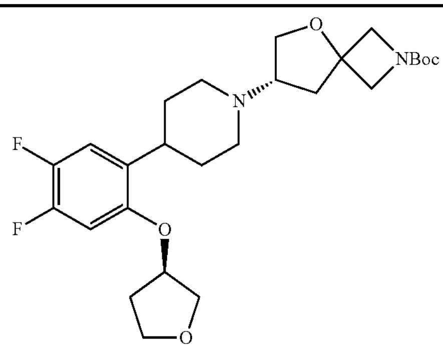 | 1.16 LCMS Method 2 | 495.3 [M + H]⁺ | 495.3 [M + H]⁺ |
| 6Q | 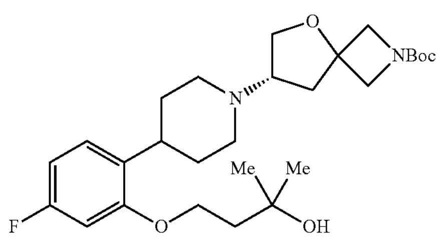 [SMILES: CC(C)(O)CCOc1cc(F)ccc1C1CCN([C@@H]2COC3(C2)CN(C(=O)OC(C)(C)C)C3)CC1] | 0.75 LCMS Method 1 | 493.3 [M + H]⁺ | 492.9 [M + H]⁺ |
| 6R | 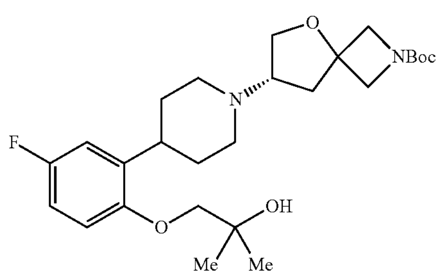 [SMILES: CC(C)(O)COc1ccc(F)cc1C1CCN([C@@H]2COC3(C2)CN(C(=O)OC(C)(C)C)C3)CC1] | 1.08 LCMS Method 4 | 479.3 [M + H]⁺ | 479.7 [M + H]⁺ |
| 6S | 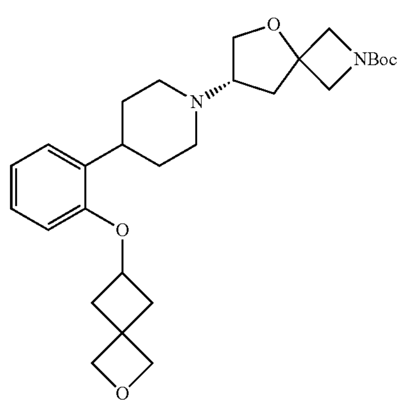 [SMILES: CC(C)(C)OC(=O)N1CC2(C[C@H](N3CCC(c4ccccc4OC4CC5(COC5)C4)CC3)CO2)C1] | 1.13 LCMS Method 2 | 485.3 [M + H]⁺ | 485.2 [M + H]⁺ |
| 6T | 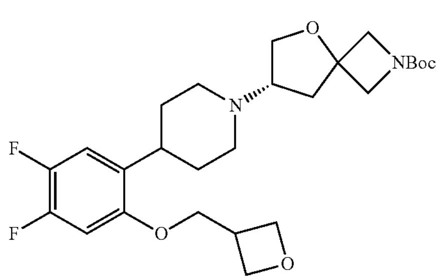 [SMILES: CC(C)(C)OC(=O)N1CC2(C[C@H](N3CCC(c4cc(F)c(F)cc4OCC4COC4)CC3)CO2)C1] | 1.11 LCMS Method 2 | 495.2 [M + H]⁺ | 495.2 [M + H]⁺ |

TABLE 4-continued

Intermediates 6B to 6AA

| Intermediate | Structure | Retention time (min) and Method | Expected Mass | Observed Mass |
|---|---|---|---|---|
| 6U | 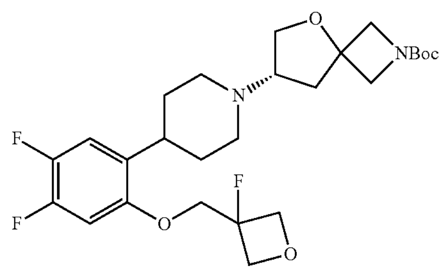 [SMILES: CC(C)(C)OC(=O)N1CC2(C[C@H](N3CCC(c4cc(F)c(F)cc4OCC4(F)COC4)CC3)CO2)C1] | 1.12 LCMS Method 2 | 513.3 [M + H]+ | 513.6 [M + H]+ |
| 6V | 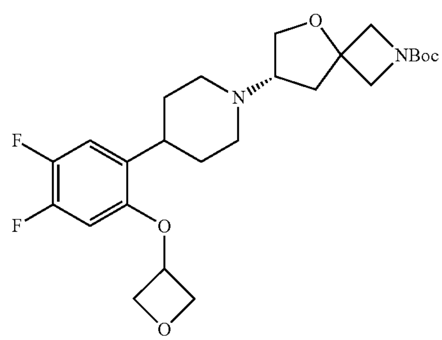 [SMILES: CC(C)(C)OC(=O)N1CC2(C[C@H](N3CCC(c4cc(F)c(F)cc4OC4COC4)CC3)CO2)C1] | 1.09 LCMS Method 2 | 481.2 [M + H]+ | 481.5 [M + H]+ |
| 6W | 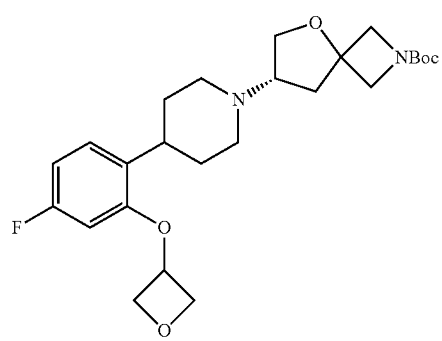 [SMILES: CC(C)(C)OC(=O)N1CC2(C[C@H](N3CCC(c4ccc(F)cc4OC4COC4)CC3)CO2)C1] | 1.09 LCMS Method 2 | 463.3 [M + H]+ | 463.4 [M + H]+ |
| 6X | 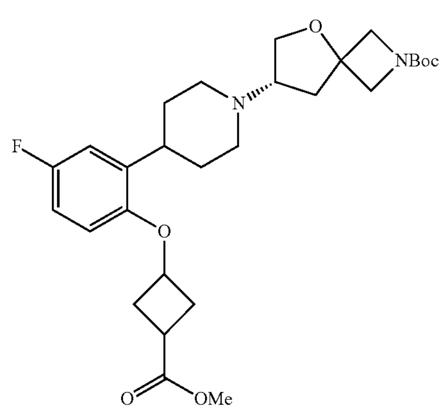 [SMILES: COC(=O)C1CC(Oc2ccc(F)cc2C2CCN([C@@H]3COC4(C3)CN(C(=O)OC(C)(C)C)C4)CC2)C1] | 1.22 LCMS Method 2 | 519.3 [M + H]+ | 519.2 [M + H]+ |

TABLE 4-continued

Intermediates 6B to 6AA

| Intermediate | Structure | Retention time (min) and Method | Expected Mass | Observed Mass |
|---|---|---|---|---|
| 6Y | 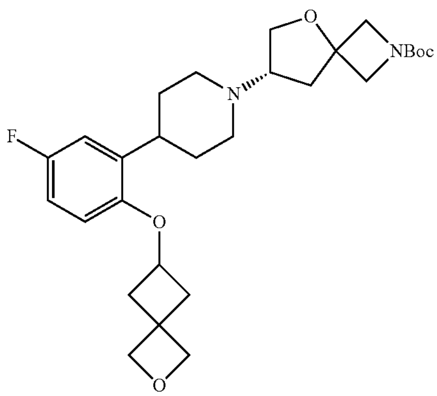 [SMILES: CC(C)(C)OC(=O)N1CC2(C[C@H](N3CCC(c4cc(F)ccc4OC4CC5(COC5)C4)CC3)CO2)C1] | 1.13 LCMS Method 1 | 503.3 [M + H]⁺ | 503.2 [M + H]⁺ |
| 6Z | 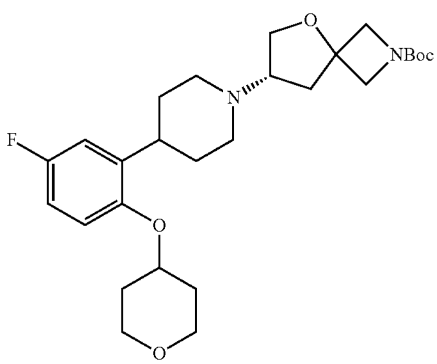 [SMILES: CC(C)(C)OC(=O)N1CC2(C[C@H](N3CCC(c4cc(F)ccc4OC4CCOCC4)CC3)CO2)C1] | 0.81 LCMS Method 1 | 473.6 [M + H]⁺ | 473.6 [M + H]⁺ |
| 6AA | 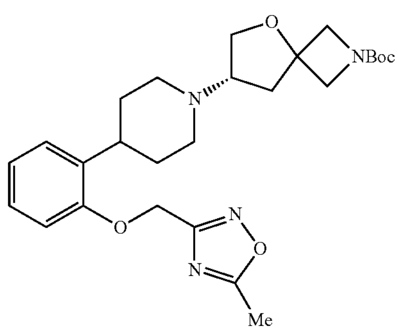 [SMILES: Cc1nc(COc2ccccc2C2CCN([C@@H]3COC4(C3)CN(C(=O)OC(C)(C)C)C4)CC2)no1] | 1.08 LCMS Method 2 | 485.3 [M + H]⁺ | 485.4 [M + H]⁺ |

Intermediate 6Z: tert-butyl (S)-7-(4-(5-fluoro-2-methoxyphenyl)piperidin-1-yl)-5-oxa-2-azaspiro[3.4]octane-2-carboxylate

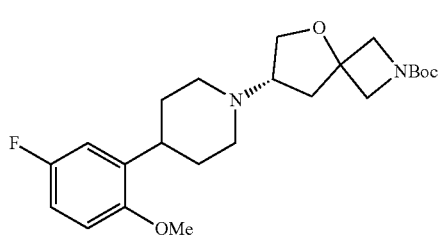 [SMILES: COc1ccc(F)cc1C1CCN([C@@H]2COC3(C2)CN(C(=O)OC(C)(C)C)C3)CC1]

(S)-tert-butyl 7-(4-(5-fluoro-2-hydroxyphenyl)piperidin-1-yl)-5-oxa-2-azaspiro[3.4]octane-2-carboxylate (Intermediate 4A, 200 mg, 0.49 mmol) was dissolved in THF (4.9 mL), and anhydrous MeOH (975 µL, 24.1 mmol) was added followed by triphenylphosphine resin (3 mmol/g, 821 mg, 2.46 mmol), and di-tert-butyl azodicarboxylate (566 mg, 2.460 mmol). The reaction was stirred at room temperature for 3 days, filtered, and rinsed with EtOAc. The filtrated was concentrated and purified by FCC (0-10% MeOH/DCM) to afford the title intermediate (216 mg, 0.49 mmol).

LCMS: Rt: 1.18 mL (LCMS Method 2); MS m/z 421.2 [M+H]⁺.

The following compounds in Table 5 were prepared in a similar fashion using the relevant starting materials:

TABLE 5

Intermediates 6BB to 6DD

| Intermediate | Structure | Retention time (min) and Method | Expected Mass | Observed Mass |
|---|---|---|---|---|
| 6BB | 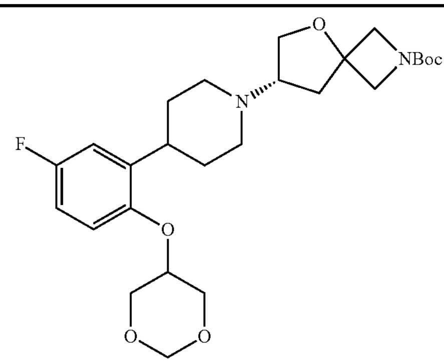 | 1.15 LCMS Method 2 | 493.3 [M + H]+ | 493.3 [M + H]+ |
| 6CC | 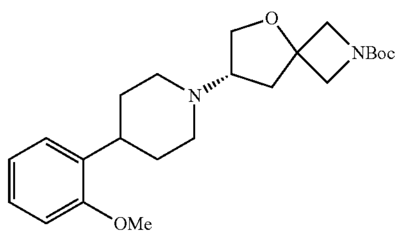 | 1.17 LCMS Method 2 | 403.3 [M + H]+ | 403.3 [M + H]+ |
| 6DD | 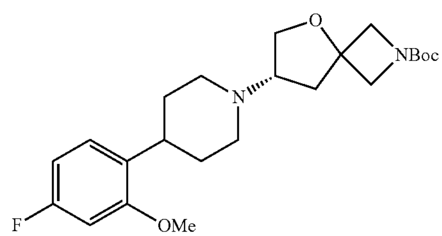 | 1.17 LCMS Method 2 | 421.2 [M + H]+ | 421.6 [M + H]+ |

Intermediate 7A: (S)-7-(4-(5-fluoro-2-(oxetan-3-yloxy)phenyl)piperidin-1-yl)-5-oxa-2-azaspiro[3.4]octane

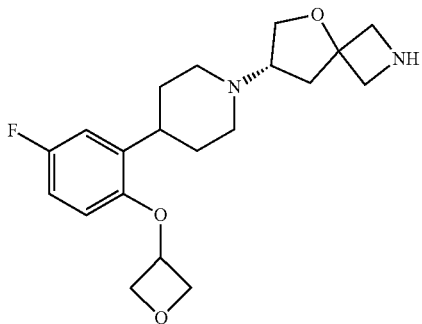 [SMILES: Fc1ccc(OC2COC2)c(C2CCN([C@@H]3COC4(CNC4)C3)CC2)c1]

tert-butyl (S)-7-(4-(5-fluoro-2-(oxetan-3-yloxy)phenyl)piperidin-1-yl)-5-oxa-2-azaspiro[3.4]octane-2-carboxylate (Intermediate 6A, 825 mg, 1.78 mmol) was dissolved in DCM (18 mL), cooled to 0° C. and TFA (1.3 mL, 17 mmol) was added. The mixture was stirred at room temperature overnight, concentrated in vacuo and the residue was dissolved in DCM, washed with 1N NaOH and brine, dried over MgSO₄, filtered and concentrated to afford the title intermediate (582 mg, 1.61 mmol).

LCMS: Rt: 0.44 min (LCMS Method 1); MS m/z 363.3 [M+H]+.

Intermediate 7B: (S)-7-(4-(2-(benzyloxy)-5-fluorophenyl)piperidin-1-yl)-5-oxa-2-azaspiro[3.4]octane

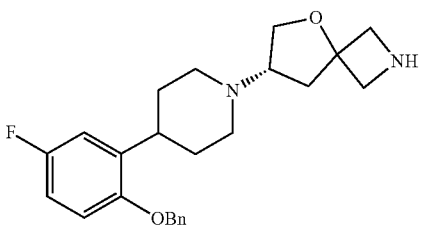 [SMILES: Fc1ccc(OCc2ccccc2)c(C2CCN([C@@H]3COC4(CNC4)C3)CC2)c1]

To a stirring solution of tert-butyl (S)-7-(4-(2-(benzyloxy)-5-fluorophenyl)piperidin-1-yl)-5-oxa-2-azaspiro[3.4]octane-2-carboxylate (Intermediate 3A, 2000 mg, 4.03 mmol) in DCM (5 mL), TFA (6.2 mL) was added. The reaction was stirred at RT for 3 hours and then the solvent was removed under reduced pressure. The residues was diluted in EtOAc and water and the pH of the aq phase was adjusted to 8-9 with 4N NaOH. The layers were separated and the aq phase was extracted with EtOAc and the combined organic layers were dried over magnesium sulfate, filtered and concentrated. The resulting brown foam was used without further purification (1500 mg, 3.78 mmol).

LCMS: Rt: 0.61 min (LCMS Method 1); MS m/z 397.4 [M+H]$^+$.

The following compounds in Table 6 were prepared in a similar manner using the relevant starting materials:

TABLE 6

Intermediates 7C to 7QQ

| Intermediate | Structure | Retention time (min) and Method | Expected Mass | Observed Mass |
|---|---|---|---|---|
| 7C | 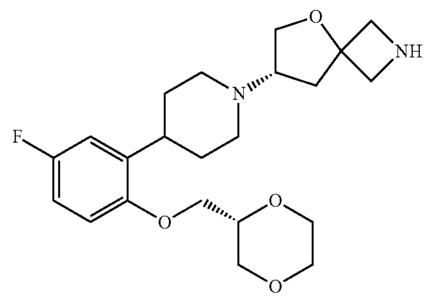 [SMILES: Fc1ccc(OC[C@H]2COCCO2)c(C2CCN([C@@H]3COC4(CNC4)C3)CC2)c1] | 0.50 LCMS Method 1 | 407.2 [M + H]$^+$ | 407.4 [M + H]$^+$ |
| 7D | 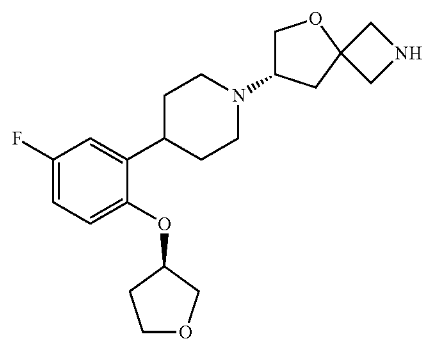 [SMILES: Fc1ccc(O[C@@H]2CCOC2)c(C2CCN([C@@H]3COC4(CNC4)C3)CC2)c1] | 0.88 LCMS Method 2 | 377.2 [M + H]$^+$ | 377.2 [M + H]$^+$ |
| 7E | 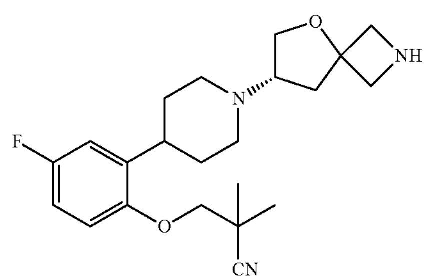 [SMILES: CC(C)(C#N)COc1ccc(F)cc1C1CCN([C@@H]2COC3(CNC3)C2)CC1] | 0.54 LCMS Method 1 | 388.2 [M + H]$^+$ | 388.3 [M + H]$^+$ |
| 7F | 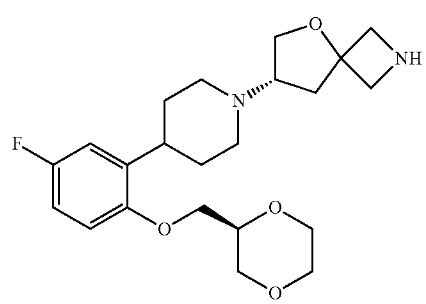 [SMILES: Fc1ccc(OC[C@@H]2COCCO2)c(C2CCN([C@@H]3COC4(CNC4)C3)CC2)c1] | 0.50 LCMS Method 1 | 407.2 [M + H]$^+$ | 407.4 [M + H]$^+$ |

TABLE 6-continued

Intermediates 7C to 7QQ

| Intermediate | Structure | Retention time (min) and Method | Expected Mass | Observed Mass |
|---|---|---|---|---|
| 7G | 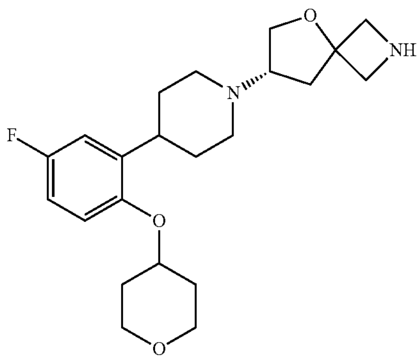 [SMILES: Fc1ccc(OC2CCOCC2)c(C2CCN([C@@H]3COC4(CNC4)C3)CC2)c1] | 0.94 LCMS Method 2 | 391.2 [M + H]+ | 391.2 [M + H]+ |
| 7H | 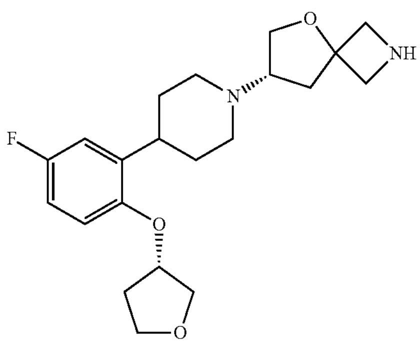 [SMILES: Fc1ccc(O[C@H]2CCOC2)c(C2CCN([C@@H]3COC4(CNC4)C3)CC2)c1] | 0.45 LCMS Method 1 | 377.2 [M + H]+ | 377.5 [M + H]+ |
| 7I | 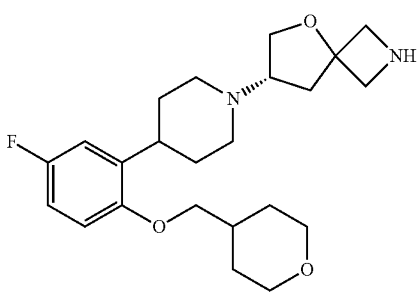 [SMILES: Fc1ccc(OCC2CCOCC2)c(C2CCN([C@@H]3COC4(CNC4)C3)CC2)c1] | 0.52 LCMS Method 1 | 405.3 [M + H]+ | 405.3 [M + H]+ |
| 7J | 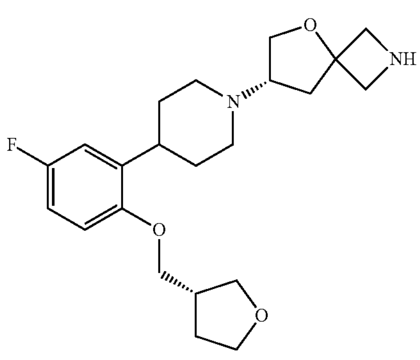 [SMILES: Fc1ccc(OC[C@H]2CCOC2)c(C2CCN([C@@H]3COC4(CNC4)C3)CC2)c1] | 0.94 LCMS Method 2 | 391.2 [M + H]+ | 391.2 [M + H]+ |

TABLE 6-continued

| Intermediates 7C to 7QQ | | | | |
|---|---|---|---|---|
| Intermediate | Structure | Retention time (min) and Method | Expected Mass | Observed Mass |
| 7K | | 0.60 LCMS Method 1 | 379.2 [M + H]⁺ | 379.4 [M + H]⁺ |
| 7L | | 0.47 LCMS Method 1 | 357.3 [M + H]⁺ | 357.4 [M + H]⁺ |
| 7M | | 0.99 LCMS Method 2 | 407.3 [M + H]⁺ | 407.2 [M + H]⁺ |
| 7N | | 0.92 LCMS Method 2 | 365.2 [M + H]⁺ | 365.1 [M + H]⁺ |
| 7O | | 0.50 LCMS Method 1 | 393.3 [M + H]⁺ | 393.0 [M + H]⁺ |

TABLE 6-continued

Intermediates 7C to 7QQ

| Intermediate | Structure | Retention time (min) and Method | Expected Mass | Observed Mass |
|---|---|---|---|---|
| 7P | 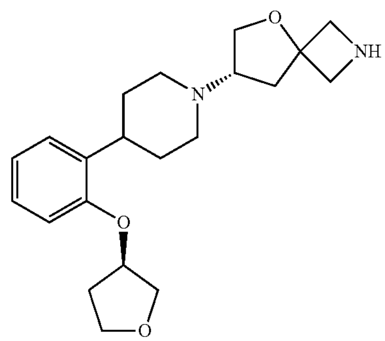 [SMILES: c1ccc(C2CCN([C@@H]3COC4(CNC4)C3)CC2)c(O[C@@H]2CCOC2)c1] | 0.46 LCMS Method 1 | 359.2 [M + H]⁺ | 359.6 [M + H]⁺ |
| 7Q | 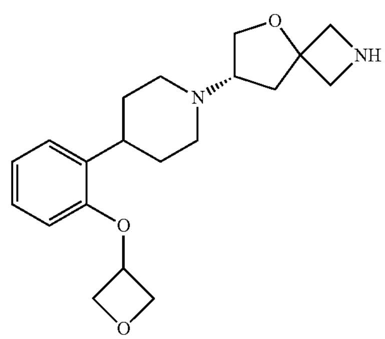 [SMILES: c1ccc(C2CCN([C@@H]3COC4(CNC4)C3)CC2)c(OC2COC2)c1] | 0.45 LCMS Method 1 | 345.2 [M + H]⁺ | 345.2 [M + H]⁺ |
| 7R | 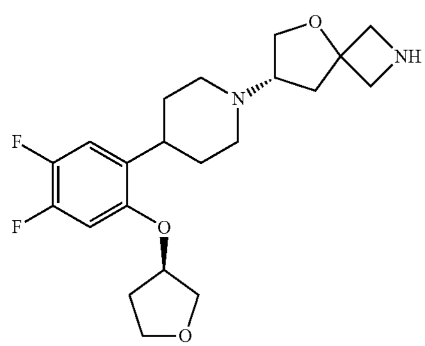 [SMILES: Fc1cc(O[C@@H]2CCOC2)c(C2CCN([C@@H]3COC4(CNC4)C3)CC2)cc1F] | 0.85 LCMS Method 1 | 395.2 [M + H]⁺ | 395.4 [M + H]⁺ |
| 7S | 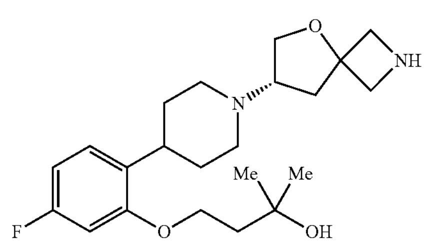 [SMILES: CC(C)(O)CCOc1cc(F)ccc1C1CCN([C@@H]2COC3(CNC3)C2)CC1] | 0.46 LCMS Method 1 | 393.3 [M + H]⁺ | 393.2 [M + H]⁺ |

TABLE 6-continued

Intermediates 7C to 7QQ

| Intermediate | Structure | Retention time (min) and Method | Expected Mass | Observed Mass |
|---|---|---|---|---|
| 7T | 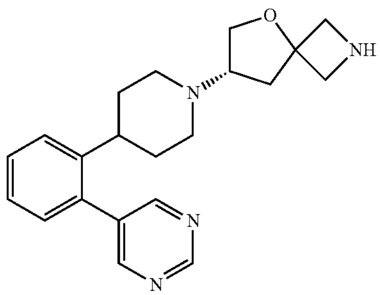 [SMILES: c1ccc(C2CCN([C@@H]3COC4(CNC4)C3)CC2)c(-c2cncnc2)c1] | 0.88 LCMS Method 2 | 351.2 [M + H]⁺ | 351.6 [M + H]⁺ |
| 7U | 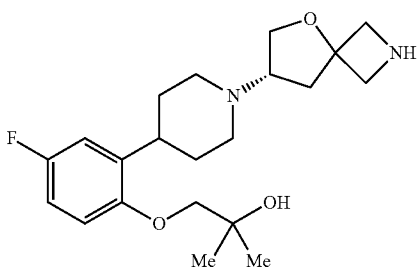 [SMILES: CC(C)(O)COc1ccc(F)cc1C1CCN([C@@H]2COC3(CNC3)C2)CC1] | 0.45 LCMS Method 1 | 379.2 [M + H]⁺ | 379.5 [M + H]⁺ |
| 7V | 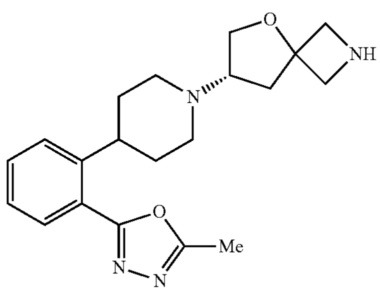 [SMILES: Cc1nnc(-c2ccccc2C2CCN([C@@H]3COC4(CNC4)C3)CC2)o1] | 0.46 LCMS Method 1 | 355.2 [M + H]⁺ | 355.3 [M + H]⁺ |
| 7W | 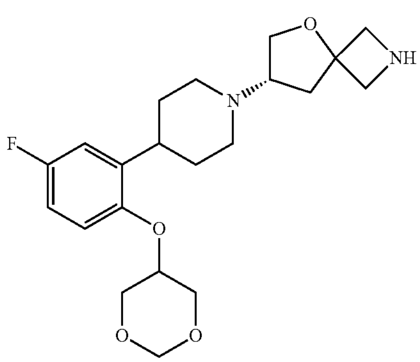 [SMILES: Fc1ccc(OC2COCOC2)c(C2CCN([C@@H]3COC4(CNC4)C3)CC2)c1] | 0.48 LCMS Method 1 | 393.2 [M + H]⁺ | 393.4 [M + H]⁺ |
| 7X | 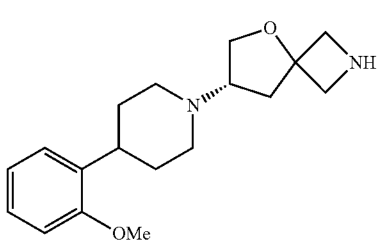 [SMILES: COc1ccccc1C1CCN([C@@H]2COC3(CNC3)C2)CC1] | 0.86 LCMS Method 2 | 303.2 [M + H]⁺ | 303.3 [M + H]⁺ |

TABLE 6-continued

Intermediates 7C to 7QQ

| Intermediate | Structure | Retention time (min) and Method | Expected Mass | Observed Mass |
|---|---|---|---|---|
| 7Y | 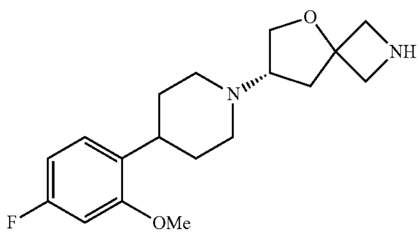 [SMILES: COc1cc(F)ccc1C1CCN([C@@H]2COC3(CNC3)C2)CC1] | 0.42 LCMS Method 1 | 321.2 [M + H]⁺ | 321.2 [M + H]⁺ |
| 7Z | 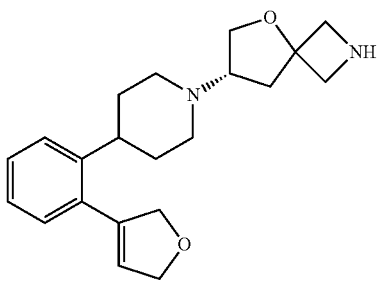 [SMILES: C1=C(c2ccccc2C2CCN([C@@H]3COC4(CNC4)C3)CC2)COC1] | 0.80 LCMS Method 2 | 341.2 [M + H]⁺ | 341.2 [M + H]⁺ |
| 7AA | 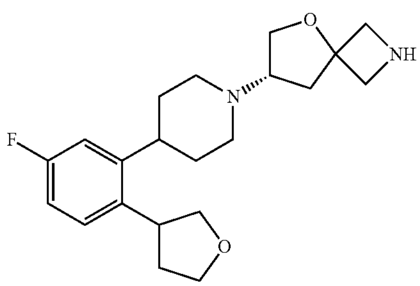 [SMILES: Fc1ccc(C2CCOC2)c(C2CCN([C@@H]3COC4(CNC4)C3)CC2)c1] | 0.49 LCMS Method 1 | 361.2 [M + H]⁺ | 361.2 [M + H]⁺ |
| 7BB | 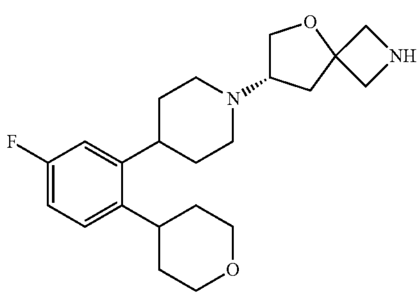 [SMILES: Fc1ccc(C2CCOCC2)c(C2CCN([C@@H]3COC4(CNC4)C3)CC2)c1] | 0.53 LCMS Method 1 | 375.2 [M + H]⁺ | 375.2 [M + H]⁺ |
| 7CC | 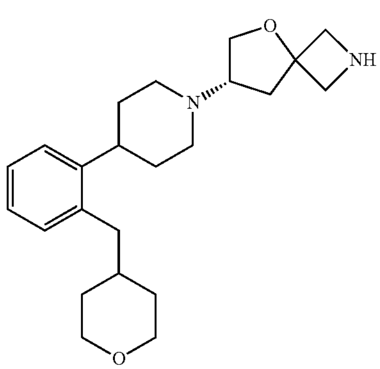 [SMILES: c1ccc(C2CCN([C@@H]3COC4(CNC4)C3)CC2)c(CC2CCOCC2)c1] | 0.51 LCMS Method 1 | 371.3 [M + H]⁺ | 371.4 [M + H]⁺ |

TABLE 6-continued

Intermediates 7C to 7QQ

| Intermediate | Structure | Retention time (min) and Method | Expected Mass | Observed Mass |
|---|---|---|---|---|
| 7DD | 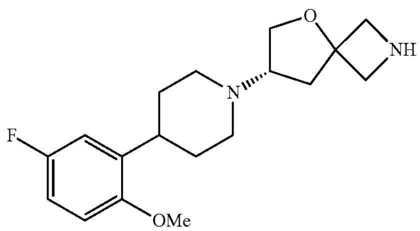 [SMILES: COc1ccc(F)cc1C1CCN([C@@H]2COC3(CNC3)C2)CC1] | 0.49 LCMS Method 1 | 321.2 [M + H]+ | 321.1 [M + H]+ |
| 7EE | 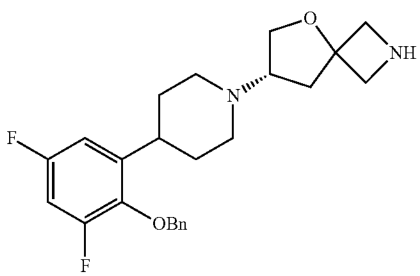 [SMILES: Fc1cc(F)c(OCc2ccccc2)c(C2CCN([C@@H]3COC4(CNC4)C3)CC2)c1] | 0.63 LCMS Method 1 | 415.5 [M + H]+ | 415.2 [M + H]+ |
| 7FF | 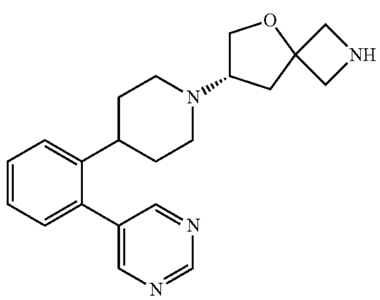 [SMILES: c1ccc(C2CCN([C@@H]3COC4(CNC4)C3)CC2)c(-c2cncnc2)c1] | 0.44 LCMS Method 1 | 351.2 [M + H]+ | 351.6 [M + H]+ |
| 7GG | 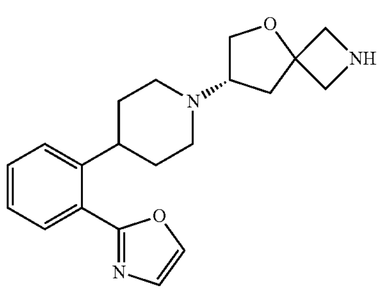 [SMILES: c1ccc(C2CCN([C@@H]3COC4(CNC4)C3)CC2)c(-c2ncco2)c1] | 0.44 LCMS Method 1 | 340.2 [M + H]+ | 340.3 [M + H]+ |
| 7HH | 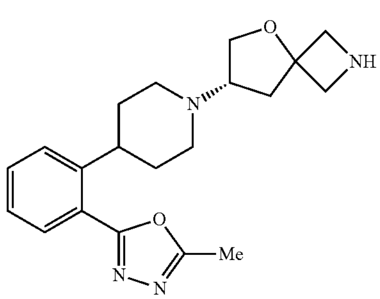 [SMILES: Cc1nnc(-c2ccccc2C2CCN([C@@H]3COC4(CNC4)C3)CC2)o1] | 0.43 LCMS Method 1 | 355.2 [M + H]+ | 355.3 [M + H]+ |

TABLE 6-continued
Intermediates 7C to 7QQ
| Intermediate | Structure | Retention time (min) and Method | Expected Mass | Observed Mass |
|---|---|---|---|---|
| 7II | 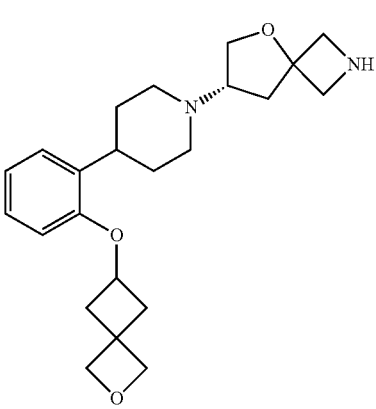 [SMILES: c1ccc(C2CCN([C@@H]3COC4(CNC4)C3)CC2)c(OC2CC3(COC3)C2)c1] | 0.48 LCMS Method 1 | 385.3 [M + H]⁺ | 385.4 [M + H]⁺ |
| 7JJ | 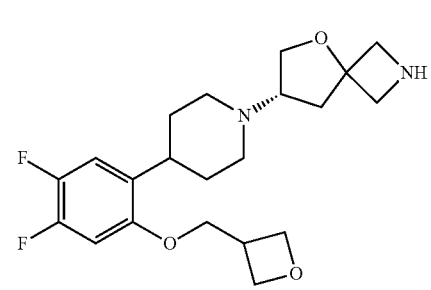 [SMILES: Fc1cc(OCC2COC2)c(C2CCN([C@@H]3COC4(CNC4)C3)CC2)cc1F] | 0.50 LCMS Method 1 | 395.2 [M + H]⁺ | 395.4 [M + H]⁺ |
| 7KK | 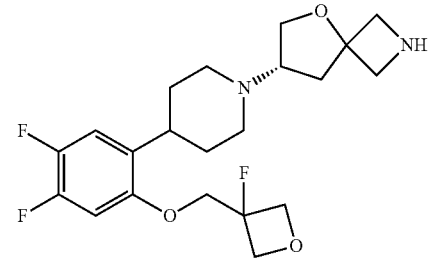 [SMILES: Fc1cc(OCC2(F)COC2)c(C2CCN([C@@H]3COC4(CNC4)C3)CC2)cc1F] | 0.51 LCMS Method 1 | 413.2 [M + H]⁺ | 413.5 [M + H]⁺ |
| 7LL | 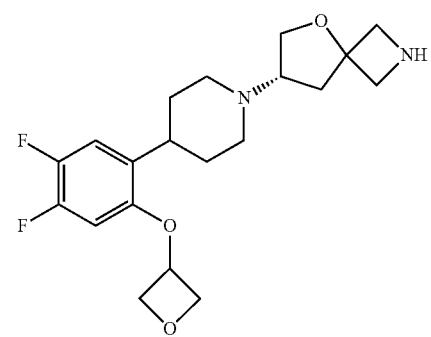 [SMILES: Fc1cc(OC2COC2)c(C2CCN([C@@H]3COC4(CNC4)C3)CC2)cc1F] | 0.45 LCMS Method 1 | 381.2 [M + H]⁺ | 381.1 [M + H]⁺ |

TABLE 6-continued

Intermediates 7C to 7QQ

| Intermediate | Structure | Retention time (min) and Method | Expected Mass | Observed Mass |
|---|---|---|---|---|
| 7MM | 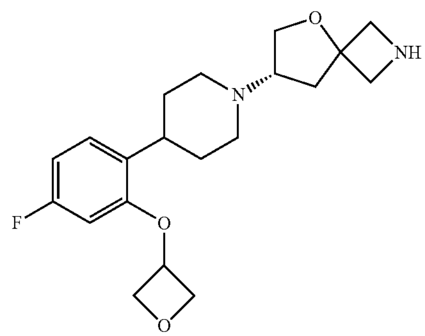 [SMILES: Fc1ccc(C2CCN([C@@H]3COC4(CNC4)C3)CC2)c(OC2COC2)c1] | 0.44 LCMS Method 1 | 363.2 [M + H]⁺ | 363.3 [M + H]⁺ |
| 7NN | 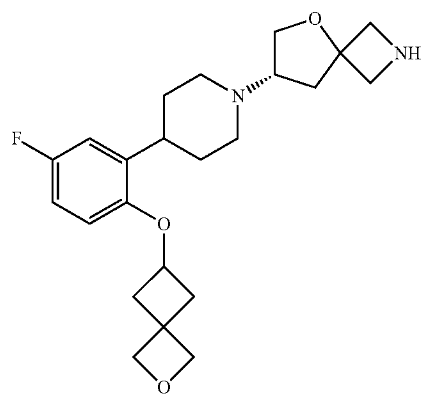 [SMILES: Fc1ccc(OC2CC3(COC3)C2)c(C2CCN([C@@H]3COC4(CNC4)C3)CC2)c1] | 0.50 LCMS Method 1 | 403.2 [M + H]⁺ | 403.4 [M + H]⁺ |
| 7OO | 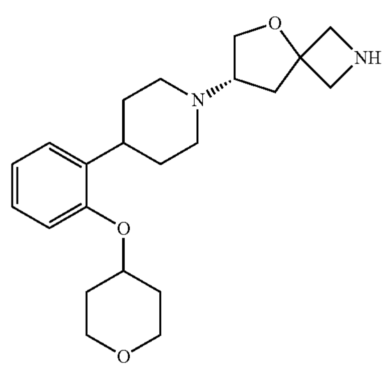 [SMILES: c1ccc(C2CCN([C@@H]3COC4(CNC4)C3)CC2)c(OC2CCOCC2)c1] | 0.52 LCMS Method 1 | 373.3 [M + H]⁺ | 373.6 [M + H]⁺ |
| 7PP | 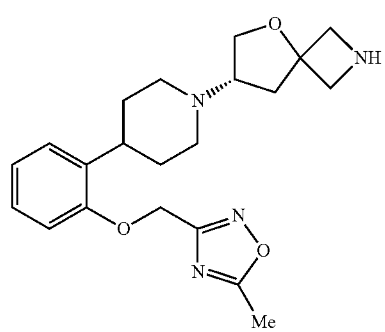 [SMILES: Cc1nc(COc2ccccc2C2CCN([C@@H]3COC4(CNC4)C3)CC2)no1] | 0.43 LCMS Method 1 | 385.2 [M + H]⁺ | 385.2 [M + H]⁺ |

TABLE 6-continued

Intermediates 7C to 7QQ

| Intermediate | Structure | Retention time (min) and Method | Expected Mass | Observed Mass |
|---|---|---|---|---|
| 7QQ | 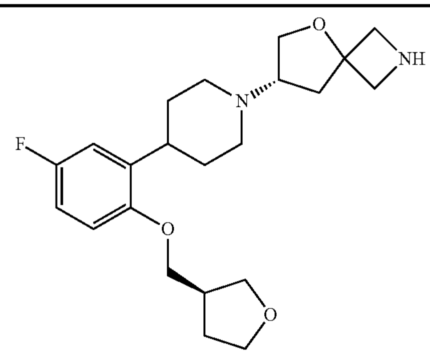 | 0.94 LCMS Method 2 | 391.2 [M + H]+ | 391.2 [M + H]+ |

Intermediate 8A: (S)-2-(1-(2-(1,3,4-thiadiazol-2-yl)-5-oxa-2-azaspiro[3.4]octan-7-yl)piperidin-4-yl)-4-fluorophenol Intermediate 8B: (S)-7-(4-(2-(benzyloxy)-5-fluorophenyl)piperidin-1-yl)-2-(1,3,4-oxadiazol-2-yl)-5-oxa-2-azaspiro[3.4]octane

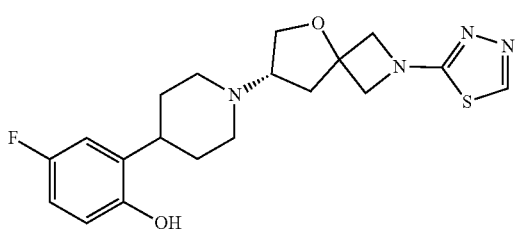 [SMILES: Oc1ccc(F)cc1C1CCN([C@@H]2COC3(C2)CN(c2nncs2)C3)CC1]

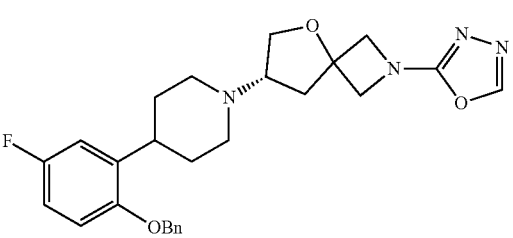 [SMILES: Fc1ccc(OCc2ccccc2)c(C2CCN([C@@H]3COC4(C3)CN(c3nnco3)C4)CC2)c1]

tert-butyl (S)-7-(4-(5-fluoro-2-hydroxyphenyl)piperidin-1-yl)-5-oxa-2-azaspiro[3.4]octane-2-carboxylatefluorophenol (Intermediate 4A, 619 mg, 1.523 mmol) was dissolved in DCM (3 mL) and TFA (1.0 mL) was added. The reaction is stirred was stirred at RT for one hour and additional TFA (1.0 mL) was added and the reaction was stirred for another hour at RT. The reaction was then concentrated and the crude was dissolved in 2% aqueous TPGS-750-M (6.8 mL) and THF (0.76 mL) and K$_3$PO$_4$ (970 mg, 4.57 mmol) and 2-bromo-1,3,4-thiadiazole (503 mg, 3.05 mmol) were added. The reaction was stirred at 60° C. for 40 minutes and then the reaction was cooled to RT, diluted with saturated aq. NaHCO$_3$ and extracted with EtOAc. The combined organic layers were dried over MgSO$_4$, filtered and concentrated. The crude was purified by FCC (0-10% MeOH (10% NH$_4$OH)/DCM) to yield the title intermediate (78 mg, 0.200 mmol) as a white solid.

LCMS: Rt=0.75 min (LCMS Method 2); MS m/z 391.1 [M+H]+.

$^1$H NMR (CD$_3$OD) δ 8.66 (s, 1H), 6.90-6.79 (m, 1H), 6.77-6.62 (m, 2H), 4.36-4.03 (m, 5H), 3.84-3.72 (m, 1H), 3.17-3.05 (m, 3H), 3.03-2.82 (m, 2H), 2.62-2.50 (m, 1H), 2.35-2.13 (m, 3H), 1.93-1.79 (m, 2H), 1.79-1.61 (m, 2H).

(S)-7-(4-(2-(benzyloxy)-5-fluorophenyl)piperidin-1-yl)-5-oxa-2-azaspiro[3.4]octane (Intermediate 7B, 1.00 g, 2.52 mmol) was dissolved in THF (25 mL). The reaction solution was cooled in −5° C. in an acetone-ice bath. DIPEA (0.97 mL, 5.55 mmol) was added followed by ethyl 5-bromo-1,3,4-oxadiazole-2-carboxylate (0.725 g, 3.28 mmol) was then added as a solid. The mixture was stirred for 30 min at −5° C. and then the reaction was concentrated under reduced pressure. EtOAc was added to the residue and the organic phase was washed with water and the water layer was extracted with EtOAc. The combined organics were washed with brine, dried over sodium sulfate and concentrated. The residue was dissolved in THF (25 mL) and treated with LiOH (0.36 g, 15.1 mmol) dissolved in water (8.3 mL) dropwise over 3 minutes. The reaction mixture was then stirred at RT overnight. Next, the reaction was cooled to −10° C. and aq 1M HCl was added over a period of 3 hours until pH 2 was reached. The reaction was then poured into EtOAc and basified using 2M Na$_2$CO$_3$. The organic layer was separated and dried over magnesium sulfate, filtered and concentrated. The residue was then purified by FCC (0-10% MeOH (1% NH$_4$OH)/DCM) to yield the title intermediate (655 mg, 1.325 mmol).

LCMS: Rt: 2.60 min (LCMS Method 4); MS m/z 465.4 [M+H]+.

The following compound in Table 7 was prepared using a similar procedure and the relevant starting materials:

TABLE 7

| | | Intermediate 8C | | |
|---|---|---|---|---|
| Intermediate | Structure | Retention time (min) and Method | Expected Mass | Observed Mass |
| 8C | ![structure] | 0.94 LCMS Method 1 | 483.3 [M + H]⁺ | 483.2 [M + H]⁺ |

Intermediate 9A: (S)-tert-butyl 7-(4-(2-(((trifluoromethyl)sulfonyl)oxy)phenyl)piperidin-1-yl)-5-oxa-2-azaspiro[3.4]octane-2-carboxylate

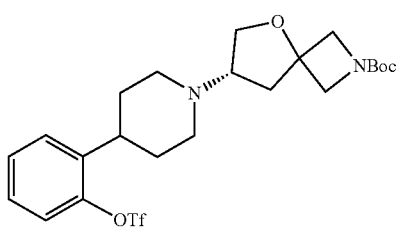 [SMILES: CC(C)(C)OC(=O)N1CC2(C[C@H](N3CCC(c4ccccc4OS(=O)(=O)C(F)(F)F)CC3)CO2)C1]

(S)-tert-butyl 7-(4-(2-hydroxyphenyl)piperidin-1-yl)-5-oxa-2-azaspiro[3.4]octane-2-carboxylate (Intermediate 4E, 1.00 g, 2.60 mmol) was dissolved in DCM (10 mL) and pyridine (0.42 mL, 5.2 mmol) was added and the solution was cooled to 0° C. The reaction was stirred at 0° C. for 10 min and then trifluoromethanesulfonic anhydride (2.337 mL, 2.337 mmol, 1M in DCM) was added dropwise. The mixture was warmed to room temperature and then stirred for 2 hours. Additional pyridine (0.21 mL, 2.6 mmol) was added and the reaction was cooled to 0° C. and stirred for 10 min. Then trifluoromethanesulfonic anhydride (1.17 mL, 1.17 mmol, 1M in DCM) was added dropwise. The reaction was stirred at room temperature for 30 minutes, then pyridine (0.21 mL, 2.6 mmol) was added and the reaction was cooled to 0° C. and stirred for 10 min. Trifluoromethanesulfonic anhydride (1.17 mL, 1.17 mmol, 1M in DCM) was added at 0° C. and the reaction was warmed and stirred at room temperature for 20 minutes. The reaction was then cooled to 0° C., diluted with DCM, quenched with 10% aq. HCl. The layers were separated and the DCM layer was washed with sat. aq. NaHCO₃, brine, dried with MgSO₄, filtered, and evaporated. The residue was purified by FCC (0-10% MeOH/DCM) to afford the title intermediate (1.30 g, 2.28 mmol).

LCMS: Rt: 3.01 min (LCMS Method 4); MS m/z 521.5 [M+H]⁺.

The following compound in Table 8 was prepared using a similar procedure and the relevant starting materials:

TABLE 8

| | | Intermediate 9B | | |
|---|---|---|---|---|
| Intermediate | Structure | Retention time (min) and Method | Expected Mass | Observed Mass |
| 9B | ![structure] | 1.29 LCMS Method 2 | 539.0 [M + H]⁺ | 539.2 [M + H]⁺ |

Intermediate 10A: tert-butyl (S)-7-(4-(2-(pyrimidin-5-yl)phenyl)piperidin-1-yl)-5-oxa-2-azaspiro[3.4]octane-2-carboxylate

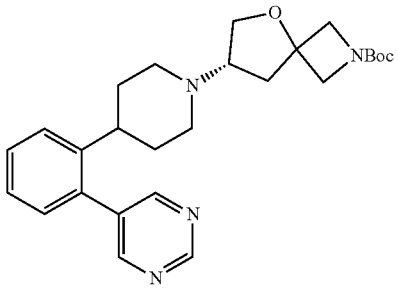 [SMILES: CC(C)(C)OC(=O)N1CC2(C[C@H](N3CCC(c4ccccc4-c4cncnc4)CC3)CO2)C1]

In an oven-dried glass microwave vial, XPhos Pd G2 (12 mg, 0.015 mmol), XPhos (15 mg, 0.031 mmol), tetrahydroxydiboron (44 mg, 0.46 mmol), and potassium acetate (37 mg, 0.62 mmol) were added. The vessel was sealed, then evacuated and back-filled with nitrogen gas (the process was repeated four times). EtOH (3 mL) was added via syringe, followed by a solution of tert-butyl (S')-7-(4-(2-(((trifluoromethyl)sulfonyl)oxy)phenyl)piperidin-1-yl)-5-oxa-2-azaspiro[3.4]octane-2-carboxylate (Intermediate 9A, 80 mg, 0.15 mmol) in EtOH (3 mL). The reaction mixture was stirred in the microwave at 80° C. for 2 hours. Next, potassium carbonate (64 mg, 0.46 mmol) in water (1 mL, pre-degassed) was added, followed by a solution of 5-bromopyrimidine (37 mg, 0.23 mmol) in THE (2 mL, degassed). The reaction mixture was stirred in the microwave at 80° C. for 14 hours, then filtered, and evaporated under reduced pressure. The residue was purified by FCC (0-100% EtOAc (100 (1000 NH$_4$OH in MeOH))/heptane) to afford the title intermediate (53 mg, 0.12 mmol).

LCMS: Rt: 097 mL (LCMS Method 2); MS m/z 451.3 [M+H]$^+$.

The following compounds in Table 9 were prepared using a similar procedure and the relevant starting materials:

TABLE 9

Intermediates 10B to 10E

| Intermediate | Structure | Retention time (min) and Method | Expected Mass | Observed Mass |
| --- | --- | --- | --- | --- |
| 10B | 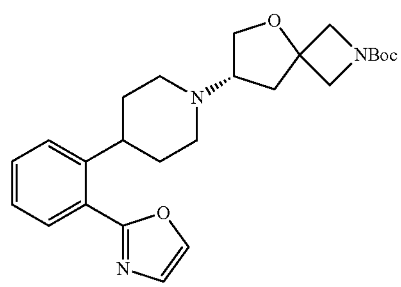 [SMILES: CC(C)(C)OC(=O)N1CC2(C[C@H](N3CCC(c4ccccc4-c4ncco4)CC3)CO2)C1] | 1.12 LCMS Method 2 | 440.3 [M + H]$^+$ | 440.4 [M + H]$^+$ |
| 10C | 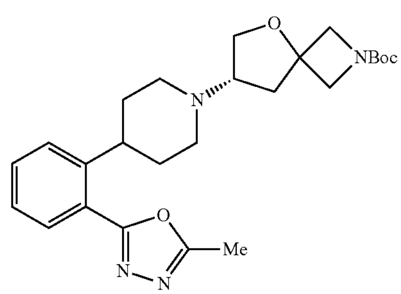 [SMILES: Cc1nnc(-c2ccccc2C2CCN([C@@H]3COC4(C3)CN(C(=O)OC(C)(C)C)C4)CC2)o1] | 1.01 LCMS Method 2 | 455.3 [M + H]$^+$ | 455.4 [M + H]$^+$ |
| 10D | 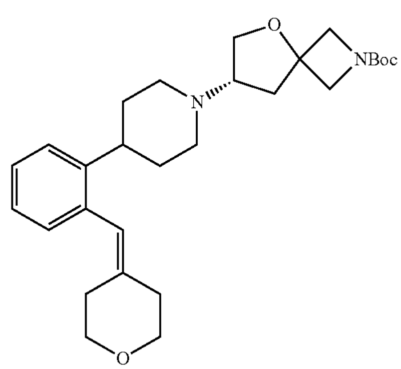 [SMILES: CC(C)(C)OC(=O)N1CC2(C[C@H](N3CCC(c4ccccc4C=C4CCOCC4)CC3)CO2)C1] | 1.19 LCMS Method 2 | 469.4 [M + H]$^+$ | 469.3 [M + H]$^+$ |

TABLE 9-continued

Intermediates 10B to 10E

| Intermediate | Structure | Retention time (min) and Method | Expected Mass | Observed Mass |
|---|---|---|---|---|
| 10E | 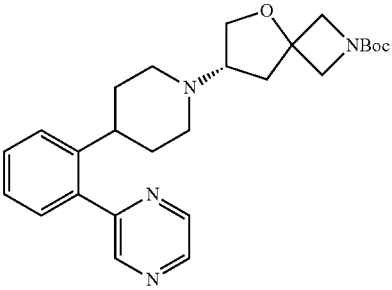 [SMILES: CC(C)(C)OC(=O)N1CC2(C[C@H](N3CCC(c4ccccc4-c4cnccn4)CC3)CO2)C1] | 1.00 LCMS Method 2 | 451.3 [M + H]⁺ | 451.6 [M + H]⁺ |

Intermediate 11A: (S)-7-(4-(2-((2-oxaspiro[3.3]heptan-6-yl)oxy)-5-fluorophenyl)piperidin-1-yl)-5-oxa-2-azaspiro[3.4]octane-2-carbonitrile

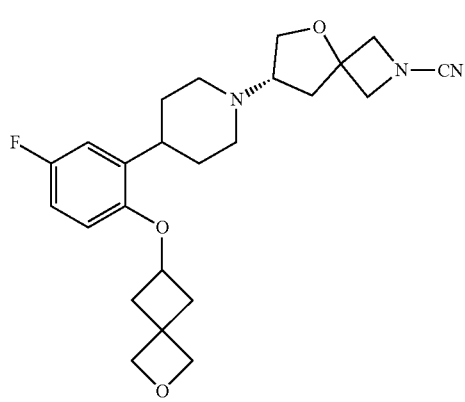 [SMILES: N#CN1CC2(C[C@H](N3CCC(c4cc(F)ccc4OC4CC5(COC5)C4)CC3)CO2)C1]

In a round bottom flask, a solution of (S)-7-(4-(2-((2-oxaspiro[3.3]heptan-6-yl)oxy)-5-fluorophenyl)piperidin-1-yl)-5-oxa-2-azaspiro[3.4]octane (Intermediate 7NN, 0.136 g, 0.338 mmol) in DCM (3.4 mL) was placed under nitrogen. Triethylamine (0.240 mL, 1.689 mmol) was added followed by cyanogen bromide (0.054 g, 0.507 mmol). The reaction was stirred for 2.5 hours and it was then quenched with 0.1N NaOH solution to pH>12 and extracted with DCM. The combined organic layers were washed with 0.1N NaOH solution and brine, dried with MgSO₄, filtered and concentrated. The residue was purified by FCC (0-100% 10% 7N NH₃ in MeOH/DCM) to yield the title intermediate as a white solid (115 mg, 0.269 mmol).

LCMS: Rt: 0.95 min (LCMS Method 2); MS m/z 428.5 [M+H]⁺.

The following compounds in Table 10 were prepared in a similar manner, using the relevant starting materials:

TABLE 10

Intermediates 11B to 11C

| Intermediate | Structure | Retention time (min) and LCMS Method | Expected mass | Observed mass |
|---|---|---|---|---|
| 11B | 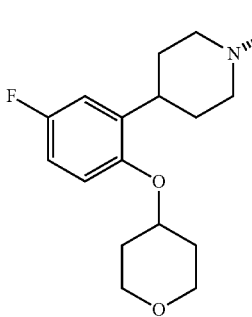 | 0.95 LCMS Method 2 | 416.2 [M + H]⁺ | 416.2 [M + H]⁺ |

TABLE 10-continued

Intermediates 11B to 11C

| Intermediate | Structure | Retention time (min) and LCMS Method | Expected mass | Observed mass |
|---|---|---|---|---|
| 11C | 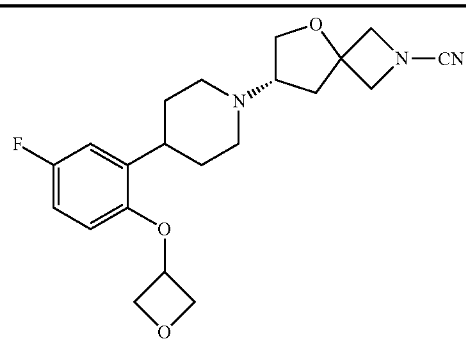 | 0.87 LCMS Method 2 | 388.2 [M + H]+ | 388.3 [M + H]+ |

Intermediate 12A: (S)-7-(4-(2-((2-oxaspiro[3.3]heptan-6-yl)oxy)-5-fluorophenyl)piperidin-1-yl)-N-hydroxy-5-oxa-2-azaspiro[3.4]octane-2-carboximidamide

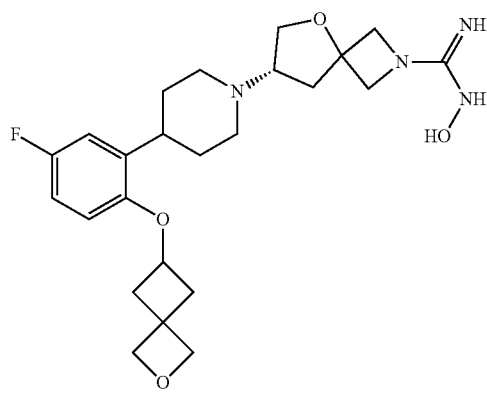 [SMILES: N=C(NO)N1CC2(C[C@H](N3CCC(c4cc(F)ccc4OC4CC5(COC5)C4)CC3)CO2)C1]

In a 100 mL round bottom flask, a solution of (S)-7-(4-(2-((2-oxaspiro[3.3]heptan-6-yl)oxy)-5-fluorophenyl)piperidin-1-yl)-5-oxa-2-azaspiro[3.4]octane-2-carbonitrile (Intermediate 11A, 115 mg, 0.269 mmol) in THF (2.7 mL) was added K₂CO₃ (112 mg, 0.807 mmol) followed by hydroxylamine hydrochloride (33.6 mg, 0.484 mmol). The reaction was stirred at 50° C. for 5 hours and then at RT for 17 hours. Additional hydroxylamine hydrochloride (6.6 mg, 0.09 mmol) was added and the reaction was stirred at 50° C. for 40 minutes and then the reaction was concentrated and the residue was taken up in 10:1 DCM:MeOH, filtered through celite and concentrated. The resulting clear oil was dried under high vacuum overnight to afford a yellow solid that was used without further purification (119 mg, 0.259 mmol).

LCMS: Rt: 0.84 min (LCMS Method 2); MS m/z 461.4 [M+H]+.

The following compounds in Table 11 were prepared in a similar manner, using the relevant starting materials:

TABLE 11

Intermediates 12B to 12C

| Intermediate | Structure | Retention time (min) and LCMS Method | Expected mass | Observed mass |
|---|---|---|---|---|
| 12B | 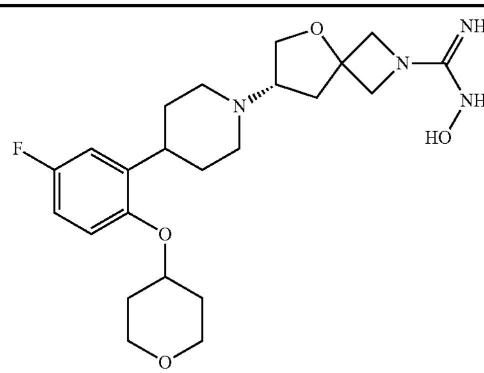 | 0.84 LCMS Method 2 | 449.3 [M + H]+ | 449.4 [M + H]+ |

TABLE 11-continued

Intermediates 12B to 12C

| Intermediate | Structure | Retention time (min) and LCMS Method | Expected mass | Observed mass |
|---|---|---|---|---|
| 12C | 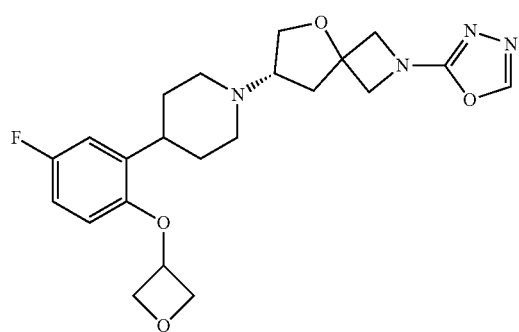 | 0.76 min LCMS Method 2 | 421.2 [M + H]⁺ | 421.3 [M + H]⁺ |

Example 1A: (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane

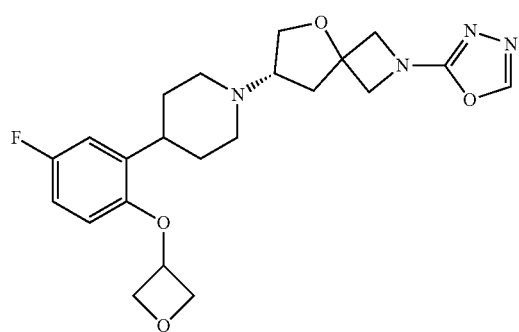

(S)-7-(4-(5-fluoro-2-(oxetan-3-yloxy)phenyl)piperidin-1-yl)-5-oxa-2-azaspiro[3.4]octane (Intermediate 7A, 540 mg, 1.49 mmol) was dissolved in 2% aqueous TPGS-750-M (2.6 mL) and THF (0.3 mL). Next, ethyl 5-bromo-1,3,4-oxadiazole-2-carboxylate (329 mg, 1.49 mmol) and potassium phosphate tribasic (949 mg, 4.47 mmol) were added. The mixture was stirred at room temperature overnight, and then 2M LiOH (2.2 mL, 4.5 mmol) was added and the reaction was stirred at room temperature overnight. MeOH (6 mL) was added followed by 4N HCl solution to adjust the reaction to pH=2; then stirred at room temperature for 4 hours. The reaction was then adjusted to pH>8 and the aqueous layer was extracted with DCM and the combined organic layers were dried over MgSO₄, filtered and concentrated in vacuo. The residue was purified by FCC (0-10% MeOH/DCM) and further purified by preparative HPLC (XBridge 30×50 mm 5 μm 15-40% MeCN/H₂O (5 mM NH₄OH), 75 mL/min) to afford the title compound (214 mg, 0.495 mmol).

LCMS: Rt: 1.77 min (LCMS Method 4); MS m/z 431.1 [M+H]⁺.

$^1$H NMR (DMSO-d$_6$) δ 8.65 (s, 1H), 7.04 (dd, J=9.8, 2.9 Hz, 1H), 6.98-6.86 (m, 1H), 6.56 (dd, J=8.9, 4.6 Hz, 1H), 5.30-5.19 (m, 1H), 4.91 (t, J=6.6 Hz, 2H), 4.59-4.47 (m, 2H), 4.22 (d, J=8.7 Hz, 1H), 4.18-4.09 (m, 2H), 4.02 (d, J=8.6 Hz, 1H), 3.94 (t, J=7.6 Hz, 1H), 3.62 (t, J=7.8 Hz, 1H), 3.05-2.74 (m, 4H), 2.45-2.36 (m, 1H), 2.17-2.00 (m, 3H), 1.81-1.51 (m, 4H).

Example 1B: (S)-7-(4-(5-fluoro-2-(((R)-tetrahydrofuran-3-yl)methoxy)phenyl)piperidin-1-yl)-2-(1,3,4-oxadiazol-2-yl)-5-oxa-2-azaspiro[3.4]octane

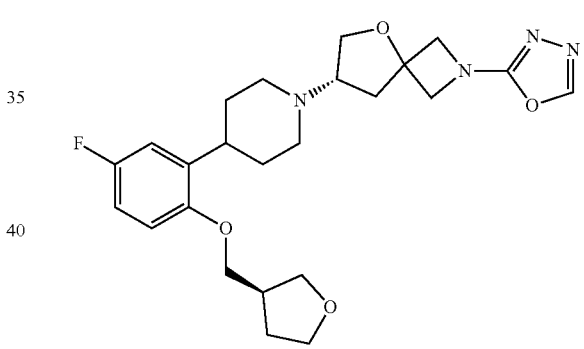

(S)-tert-butyl 7-(4-(5-fluoro-2-(((R)-tetrahydrofuran-3-yl)methoxy)phenyl)piperidin-1-yl)-5-oxa-2-azaspiro[3.4]octane-2-carboxylate (Intermediate 6B, 217 mg, 0.442 mmol) was dissolved in DCM (4.4 mL) and TFA (0.68 mL, 8.85 mmol) was added. The reaction was stirred for 4 hours and then it was concentrated and the residue was dissolved in DCM. The organic phase was washed with 1N NaOH and brine and concentrated. Part of this material (97 mg, 0.248 mmol) was then dissolved in THF (0.05 mL) and 2% aqueous TPGS-750-M (0.45 mL) and ethyl 5-bromo-1,3,4-oxadiazole-2-carboxylate (54 mg, 0.248 mmol) and K₃PO₄ (52.7 mg, 0.248 mmol) were added. The reaction was treated similarly to Example 1A and the crude was purified by FCC (0-7% MeOH/DCM) and by preparative HPLC (C18 OBD 30×50 mm 5 μm column, 75 mL/min, 25-50% MeCN/H₂O (5 mM NH₄OH) to yield the title compound (43 mg, 0.092 mmol).

LCMS: Rt: 2.05 min (LCMS Method 4); MS m/z 459.1 [M+H]⁺.

$^1$H NMR (DMSO-d$_6$) δ: 8.64 (s, 1H), 6.92-7.02 (m, 3H), 4.22 (d, J=8.8 Hz, 1H), 4.13 (dd, J=8.6, 2.7 Hz, 2H), 4.02 (d,

J=8.3 Hz, 1H), 3.98-3.91 (m, 2H), 3.90-3.80 (m, 2H), 3.76 (td, J=8.1, 5.4 Hz, 1H), 3.72-3.65 (m, 1H), 3.65-3.58 (m, 1H), 3.53 (dd, J=8.3, 5.9 Hz, 1H), 3.04-2.91 (m, 2H), 2.89-2.74 (m, 2H), 2.70-2.61 (m, 1H), 2.45-2.37 (m, 1H), 2.13-1.97 (m, 4H), 1.74-1.63 (m, 3H), 1.63-1.51 (m, 2H).

Example 1C: ethyl 5-((S)-7-(4-(2-(((R)-1,4-dioxan-2-yl)methoxy)-5-fluorophenyl)piperidin-1-yl)-5-oxa-2-azaspiro[3.4]octan-2-yl)-1,3,4-oxadiazole-2-carboxylate

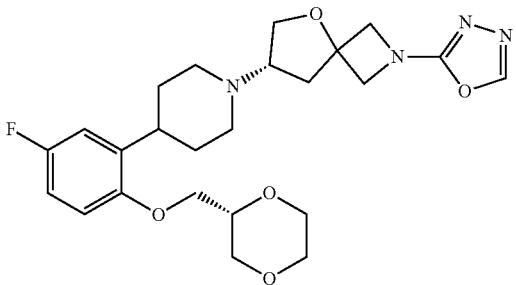 [SMILES: Fc1ccc(OC[C@H]2COCCO2)c(C2CCN([C@@H]3COC4(C3)CN(c3nnco3)C4)CC2)c1]

(S)-7-(4-(2-(((R)-1,4-dioxan-2-yl)methoxy)-5-fluorophenyl)piperidin-1-yl)-5-oxa-2-azaspiro[3.4]octane (Intermediate 7C, 84 mg, 0.21 mmol) was dissolved in 2% aqueous TPGS-750-M (372 μL) and THF (41 μL). Ethyl 5-bromo-1,3,4-oxadiazole-2-carboxylate (46 mg, 0.21 mmol) and potassium phosphate tribasic (44 mg, 0.21 mmol) were added and the reaction was treated in a similar fashion to Example 1A. The crude was purified by FCC (0-7% MeOH/DCM) and by preparative HPLC (XBridge 30×50 mm 5 μm 25-50% MeCN/H2O (5 mM NH4OH), 75 mL/min) to afford the title compound (28 mg, 0.058 mmol).

LCMS: Rt: 1.90 min (LCMS Method 4); MS m/z 475.2 [M+H]+.

1H NMR (DMSO-$d_6$) δ 8.64 (s, 1H), 7.02-6.92 (m, 3H), 4.22 (d, J=8.8 Hz, 1H), 4.13 (dd, J=8.3, 3.9 Hz, 2H), 4.04-3.89 (m, 4H), 3.81-3.88 (m, 2H), 3.80-3.74 (m, 1H), 3.71-3.65 (m, 1H), 3.64-3.58 (m, 2H), 3.53-3.43 (m, 2H), 3.03-2.92 (m, 2H), 2.88-2.75 (m, 2H), 2.41 (dd, J=12.7, 7.3 Hz, 1H), 2.12-2.01 (m, 3H), 1.75-1.66 (m, 2H), 1.65-1.51 (m, 2H).

Example 1D: (S)-7-(4-(5-fluoro-2-(((R)-tetrahydrofuran-3-yl)oxy)phenyl)piperidin-1-yl)-2-(1,3,4-oxadiazol-2-yl)-5-oxa-2-azaspiro[3.4]octane

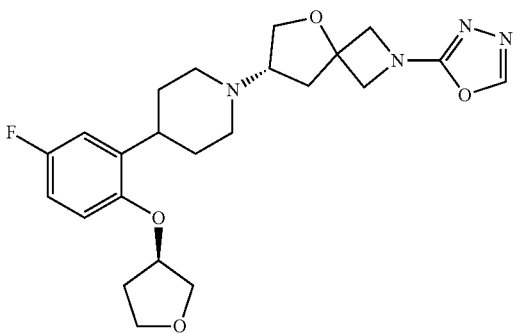

(S)-7-(4-(2-(((R)-1,4-dioxan-2-yl)methoxy)-5-fluorophenyl)piperidin-1-yl)-5-oxa-2-azaspiro[3.4]octane (Intermediate 7D, 84 mg, 0.21 mmol) was dissolved in 2% aqueous TPGS-750-M (372 μL) and THF (41 μL). Ethyl 5-bromo-1,3,4-oxadiazole-2-carboxylate (46 mg, 0.21 mmol) and potassium phosphate tribasic (44 mg, 0.21 mmol) were added and the reaction was treated similarly to Example 1A. The crude was purified by FCC (0-7% MeOH/DCM) followed by preparative HPLC (XBridge 30×50 mm 5 μm 25-50% MeCN/H2O (5 mM NH4OH), 75 mL/min) to afford the title compound (36 mg, 0.058 mmol).

LCMS: Rt: 1.91 min (LCMS Method 4); MS m/z 445.1 [M+H]+.

1H NMR (400 MHz, DMSO-$d_6$) δ 8.65 (s, 1H), 7.07-6.88 (m, 3H), 5.01 (t, J=5.3 Hz, 1H), 4.22 (d, J=8.7 Hz, 1H), 4.18-4.09 (m, 2H), 4.02 (d, J=8.4 Hz, 1H), 3.93 (t, J=7.6 Hz, 1H), 3.89-3.71 (m, 4H), 3.67-3.57 (m, 1H), 3.03-2.90 (m, 2H), 2.80 (t, J=12.7 Hz, 2H), 2.40 (dd, J=12.8, 7.9 Hz, 1H), 2.18 (m, 1H), 2.12-1.89 (m, 4H), 1.63 (m, 4H).

Example 1E: (S)-3-(2-(1-(2-(1,3,4-oxadiazol-2-yl)-5-oxa-2-azaspiro[3.4]octan-7-yl)piperidin-4-yl)-4-fluorophenoxy)-2,2-dimethylpropanenitrile

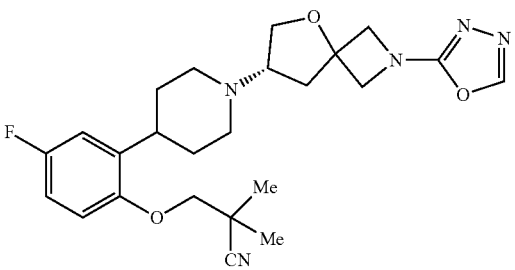 [SMILES: CC(C)(C#N)COc1ccc(F)cc1C1CCN([C@@H]2COC3(C2)CN(c2nnco2)C3)CC1]

(S)-3-(2-(1-(5-oxa-2-azaspiro[3.4]octan-7-yl)piperidin-4-yl)-4-fluorophenoxy)-2,2-dimethylpropanenitrile (Intermediate 7E, 20 mg, 0.052 mmol), ethyl 5-bromo-1,3,4-oxadiazole-2-carboxylate (14 mg, 0.062 mmol) and potassium phosphate tribasic (13 mg, 0.062 mmol) were dissolved in 2% aqueous TPGS-750-M (0.7 mL and THF (0.18 mL). The reaction was stirred at room temperature for 4 days, then 0.5 mL of MeOH and LiOH monohydrate (13 mg, 0.31 mmol) were added and the reaction was stirred at room temperature for 1 hour. 6M HCl was added to adjust the pH to 4 and the reaction was stirred at room temperature for 1 hour. The reaction was then basified with a solution of sodium bicarbonate, extracted with EtOAc and concentrated under reduced pressure. The residue was purified by preparative HPLC (XBridge 30×50 mm 5 μm 25-50% MeCN/H2O (5 mM NH4OH), 75 mL/min) to afford the title compound (2.8 mg, 0.0060 mmol).

LCMS: Rt: 2.09 min (LCMS Method 4); MS m/z 456.3 [M+H]+.

1H NMR (CD3OD) δ 8.39 (s, 1H), 7.02-6.81 (m, 3H), 4.35-4.24 (m, 2H), 4.23-4.12 (m, 2H), 4.11-4.03 (m, 1H), 3.95 (s, 2H), 3.81-3.71 (m, 1H), 3.12-3.04 (m, 3H), 2.95-2.85 (m, 1H), 2.62-2.51 (m, 1H), 2.34-2.20 (m, 2H), 2.18-2.08 (m, 1H), 1.98-1.85 (m, 2H), 1.77-1.62 (m, 2H), 1.50 (s, 6H).

Example 1F: (S)-7-(4-(2-(((S)-1,4-dioxan-2-yl)methoxy)-5-fluorophenyl)piperidin-1-yl)-2-(1,3,4-oxadiazol-2-yl)-5-oxa-2-azaspiro[3.4]octane

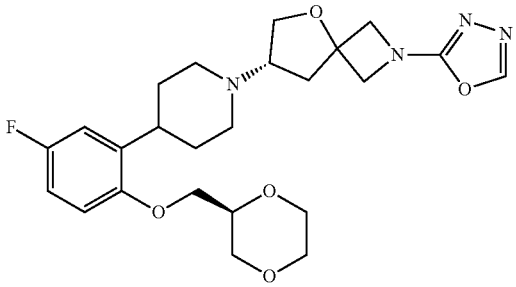

(S)-7-(4-(2-(((S)-1,4-dioxan-2-yl)methoxy)-5-fluorophenyl)piperidin-1-yl)-5-oxa-2-azaspiro[3.4]octane (Intermediate 7F, 84 mg, 0.21 mmol), ethyl 5-bromo-1,3,4-oxadiazole-2-carboxylate (46 mg, 0.21 mmol) and potassium phosphate tribasic (44 mg, 0.21 mmol) were dissolved in 2% aqueous TPGS-750-M (0.37 mL) and THF (0.041 mL). The reaction was treated similarly to Example 1A. The crude was by purified by FCC (0-10% MeOH/DCM) and further by preparative HPLC (XBridge 30×50 mm 5 μm 25-50% MeCN/H$_2$O (5 mM NH$_4$OH), 75 mL/min) to afford the title compound (29 mg, 0.059 mmol).

LCMS: Rt: 1.90 min (LCMS Method 4); MS m/z 475.1 [M+H]$^+$.

$^1$H NMR (DMSO-d$_6$) δ 8.64 (s, 1H), 7.03-6.92 (m, 3H), 4.22 (d, J=8.8 Hz, 1H), 4.16-4.09 (m, 2H), 4.05-3.89 (m, 4H), 3.88-3.80 (m, 2H), 3.80-3.74 (m, 1H), 3.72-3.58 (m, 3H), 3.53-3.43 (m, 2H), 3.03-2.92 (m, 2H), 2.88-2.75 (m, 2H), 2.41 (dd, J=13.0, 7.1 Hz, 1H), 2.13-2.01 (m, 3H), 1.78-1.63 (m, 2H), 1.63-1.51 (m, 2H).

Example 1G: (S)-7-(4-(5-fluoro-2-((tetrahydro-2H-pyran-4-yl)oxy)phenyl)piperidin-1-yl)-2-(1,3,4-oxadiazol-2-yl)-5-oxa-2-azaspiro[3.4]octane

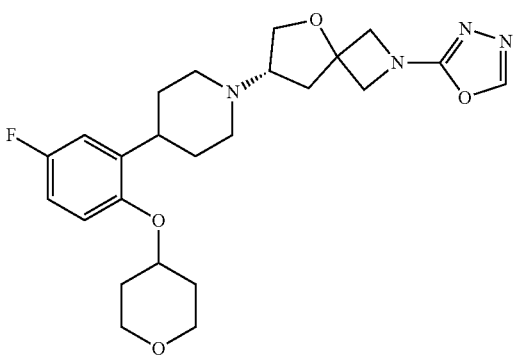

(S)-7-(4-(5-fluoro-2-((tetrahydro-2H-pyran-4-yl)oxy)phenyl)piperidin-1-yl)-5-oxa-2-azaspiro[3.4]octane (Intermediate 7G, 70 mg, 0.18 mmol), ethyl 5-bromo-1,3,4-oxadiazole-2-carboxylate (40 mg, 0.18 mmol) and potassium phosphate tribasic (38 mg, 0.18 mmol) were dissolved in 2% aqueous TPGS-750-M (0.32 mL) and THF (0.036 mL). The reaction was treated similarly to Example 1A and the crude was purified by FCC (0-10% MeOH/DCM) and further by preparative HPLC (XBridge 30×50 mm 5 μm 25-50% MeCN/H$_2$O (5 mM NH$_4$OH) 75 mL/min) to afford the title compound (21 mg, 0.044 mmol).

LCMS: Rt: 1.58 min (LCMS Method 4); MS m/z 459.3 [M+H]$^+$.

$^1$H NMR (DMSO-d$_6$) δ 8.64 (s, 1H), 7.07-6.90 (m, 3H), 4.53 (m, 1H), 4.22 (d, J=8.8 Hz, 1H), 4.15-4.10 (m, 2H), 4.02 (d, J=8.3 Hz, 1H), 3.94 (dd, J=8.3, 6.8 Hz, 1H), 3.85-3.76 (m, 2H), 3.66-3.59 (m, 1H), 3.50 (m, 2H), 3.02-2.93 (m, 2H), 2.92-2.77 (m, 2H), 2.40 (dd, J=12.7, 7.3 Hz, 1H), 2.12-2.02 (m, 3H), 1.98-1.88 (m, 2H), 1.75-1.65 (m, 2H), 1.64-1.53 (m, 4H).

Example 1H: (S)-7-(4-(5-fluoro-2-(((S)-tetrahydrofuran-3-yl)oxy)phenyl)piperidin-1-yl)-2-(1,3,4-oxadiazol-2-yl)-5-oxa-2-azaspiro[3.4]octane

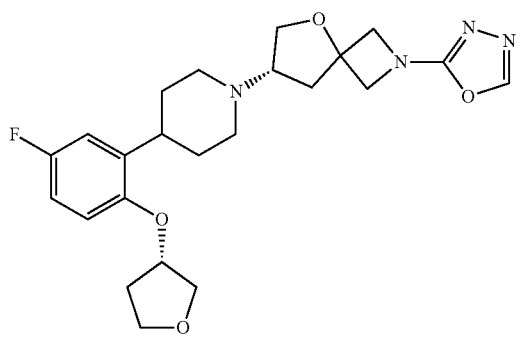

(S)-tert-butyl 7-(4-(5-fluoro-2-(((S)-tetrahydrofuran-3-yl)oxy)phenyl)piperidin-1-yl)-5-oxa-2-azaspiro[3.4]octane-2-carboxylate (Intermediate 7H, 91 mg, 0.24 mmol), ethyl 5-bromo-1,3,4-oxadiazole-2-carboxylate (53 mg, 0.24 mmol) and potassium phosphate tribasic (51 mg, 0.24 mmol) were dissolved in 2% aqueous TPGS-750-M (0.44 mL) and THF (0.048 mL). The reaction was treated similarly to Example 1A and the crude was purified by FCC (0-10% MeOH/DCM) and further by preparative HPLC (XBridge 30×50 mm 5 μm 25-50% MeCN/H$_2$O (5 mM NH$_4$OH), 75 mL/min) to give the title compound (42 mg, 0.092 mmol).

LCMS: Rt: 1.91 min (LCMS Method 4); MS m/z 445.1 [M+H]$^+$.

$^1$H NMR (400 MHz, DMSO-d$_6$) δ 8.65 (s, 1H), 7.04-6.90 (m, 3H), 5.05-4.98 (m, 1H), 4.22 (d, J=8.8 Hz, 1H), 4.15-4.09 (m, 2H), 4.02 (d, J=8.5 Hz, 1H), 3.96-3.90 (m, 1H), 3.89-3.82 (m, 1H), 3.82-3.71 (m, 3H), 3.66-3.57 (m, 1H), 3.02-2.91 (m, 2H), 2.85-2.74 (m, 2H), 2.42-2.36 (m, 1H), 2.26-2.12 (m, 1H), 2.10-1.90 (m, 4H), 1.75-1.48 (m, 4H).

Example 1I: (S)-7-(4-(5-fluoro-2-(((S)-tetrahydrofuran-3-yl)methoxy)phenyl)piperidin-1-yl)-2-(1,3,4-oxadiazol-2-yl)-5-oxa-2-azaspiro[3.4]octane

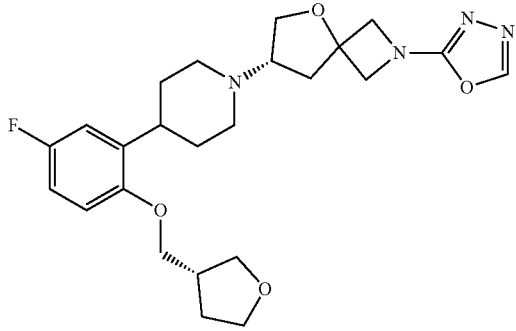

(S)-7-(4-(5-fluoro-2-(((S)-tetrahydrofuran-3-yl)methoxy)phenyl)piperidin-1-yl)-5-oxa-2-azaspiro[3.4]octane (Intermediate 7J, 81 mg, 0.21 mmol), ethyl 5-bromo-1,3,4-oxadiazole-2-carboxylate (46 mg, 0.21 mmol) and potassium phosphate tribasic (44 mg, 0.21 mmol) were dissolved in a mixture of 2% aqueous TPGS-750-M (0.37 mL) and THE (0.042 mL) and the reaction was treated similarly to Example 1A. The residue was purified by purified by FCC (0-10% MeOH/DCM) and further by preparative HPLC (XBridge 30×50 mm 5 μm 25-50% MeCN/H$_2$O (5 mM NH$_4$OH), 75 mL/min), to afford the title compound (30 mg, 0.064 mmol).

LCMS: Rt: 2.05 min (LCMS Method 4); MS m/z 459.5 [M+H]$^+$.

$^1$H NMR (DMSO-d$_6$) δ 8.64 (s, 1H), 7.01-6.93 (m, 3H), 4.21 (d, J=8.8 Hz, 1H), 4.12 (dd, J=8.3, 2.4 Hz, 2H), 4.02 (d, J=8.3 Hz, 1H), 3.97-3.91 (m, 2H), 3.90-3.80 (m, 2H), 3.79-3.73 (m, 1H), 3.72-3.65 (m, 1H), 3.64-3.58 (m, 1H), 3.52 (dd, J=8.6, 6.1 Hz, 1H), 3.01-2.92 (m, 2H), 2.88-2.76 (m, 2H), 2.71-2.59 (m, 1H), 2.40 (dd, J=13.0, 7.1 Hz, 1H), 2.11-1.96 (m, 4H), 1.75-1.63 (m, 3H), 1.62-1.51 (m, 2H).

Example 1J: (S)-7-(4-(5-fluoro-2-((tetrahydro-2H-pyran-4-yl)methoxy)phenyl)piperidin-1-yl)-2-(1,3,4-oxadiazol-2-yl)-5-oxa-2-azaspiro[3.4]octane

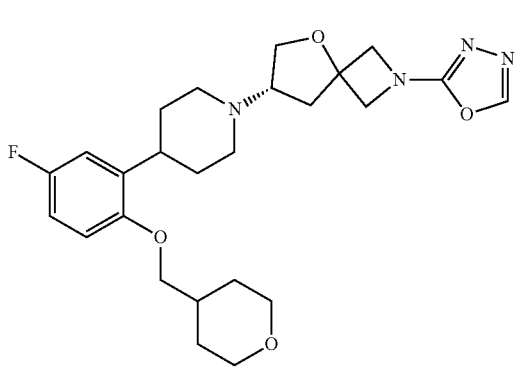 [SMILES: Fc1ccc(OCC2CCOCC2)c(C2CCN([C@@H]3COC4(C3)CN(c3nnco3)C4)CC2)c1]

(S)-7-(4-(5-fluoro-2-((tetrahydro-2H-pyran-4-yl)methoxy)phenyl)piperidin-1-yl)-5-oxa-2-azaspiro[3.4]octane (Intermediate 7I, 197 mg, 0.453 mmol), ethyl 5-bromo-1,3,4-oxadiazole-2-carboxylate (120 mg, 0.54 mmol) and DIPEA (0.16 mL, 0.91 mmol) were dissolved in THE (2.3 mL). The reaction was stirred for 2 h, and then evaporated under reduce pressure. The residue was dissolved in EtOAc, washed with water, dried over MgSO$_4$, filtered and concentrated under reduced pressure. The residue was dissolved in a mixture of THF (2 mL) and water (1 mL) and LiOH (114 mg, 2.72 mmol) was added. The reaction was stirred at room temperature for 1 hour and then aq 6M HCl (0.76 mL) was added to adjust the pH to 2 and the reaction was stirred at room temperature for 1 h. Subsequently, the reaction was basified (pH>8) with a saturated solution of sodium carbonate. The residue was diluted with EtOAc, washed with brine and evaporated under reduced pressure. The residue was purified by FCC (0-10% MeOH (10% NH$_4$OH)/DCM) to afford the title compound (157 mg, 0.33 mmol).

LCMS: Rt: 2.16 min (LCMS Method 4); MS m/z 473.7 [M+H]$^+$.

$^1$H NMR (400 MHz, CD$_3$OD) δ 8.38 (s, 1H), 6.88 (m, 3H), 4.29 (q, J=8.8 Hz, 2H), 4.16 (q, J=8.6 Hz, 2H), 4.10-4.03 (m, 1H), 3.99 (dd, J=10.8, 3.4 Hz, 2H), 3.83 (d, J=6.0 Hz, 2H), 3.78-3.71 (m, 1H), 3.52-3.43 (m, 2H), 3.14-2.84 (m, 4H), 2.54 (dd, J=12.9, 7.4 Hz, 1H), 2.28-1.99 (m, 4H), 1.91-1.59 (m, 6H), 1.51 (m, 2H).

Example 1K: (S)-7-(4-(5-fluoro-2-(3-methoxy-3-methylbutoxy)phenyl)piperidin-1-yl)-2-(1,3,4-oxadiazol-2-yl)-5-oxa-2-azaspiro[3.4]octane

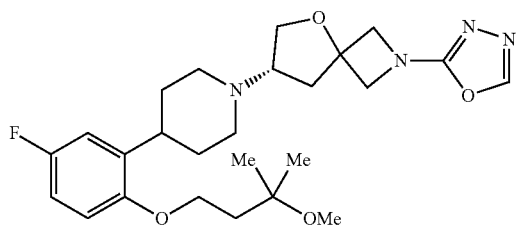 [SMILES: COC(C)(C)CCOc1ccc(F)cc1C1CCN([C@@H]2COC3(C2)CN(c2nnco2)C3)CC1]

(S)-7-(4-(5-fluoro-2-(3-methoxy-3-methylbutoxy)phenyl)piperidin-1-yl)-5-oxa-2-azaspiro[3.4]octane (Intermediate 7M, 79 mg, 0.19 mmol), ethyl 5-bromo-1,3,4-oxadiazole-2-carboxylate (43 mg, 0.19 mmol), and K$_3$PO$_4$ were dissolved in a mixture of 2% aqueous TPGS-750-M (0.35 mL) and THE (0.039 mL). The reaction was treated similarly to Example 1A and was then purified by preparative HPLC (XBridge 30×50 mm 5 μm 10-30% MeCN/H$_2$O (5 mM NH$_4$OH), 75 mL/min), to afford the title compound (11 mg, 0.022 mmol).

LCMS: Rt: 2.38 min (LCMS Method 4); MS m/z 475.4 [M+H]$^+$.

$^1$H NMR (DMSO-d$_6$) δ 8.64 (s, 1H), 7.01-6.9 (m, 3H), 4.21 (d, J=8.8 Hz, 1H), 4.12 (dd, J=8.6, 2.2 Hz, 2H), 4.05-3.97 (m, 3H), 3.93 (dd, J=8.3, 6.8 Hz, 1H), 3.61 (t, J=7.8 Hz, 1H), 3.11 (s, 3H), 3.01-2.90 (m, 2H), 2.90-2.75 (m, 2H), 2.40 (dd, J=12.7, 7.3 Hz, 1H), 2.10-1.98 (m, 3H), 1.91 (t, J=6.8 Hz, 2H), 1.73-1.51 (m, 4H), 1.17 (s, 6H).

Example 1L: (S)-7-(4-(5-fluoro-2-(2-methoxy-ethoxy)phenyl)piperidin-1-yl)-2-(1,3,4-oxadiazol-2-yl)-5-oxa-2-azaspiro[3.4]octane

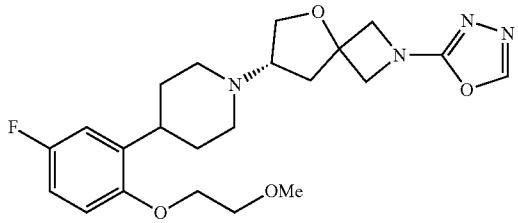 [SMILES: COCCOc1ccc(F)cc1C1CCN([C@@H]2COC3(C2)CN(c2nnco2)C3)CC1]

To a solution of (S)-7-(4-(5-fluoro-2-(2-methoxyethoxy)phenyl)piperidin-1-yl)-5-oxa-2-azaspiro[3.4]octane (Intermediate 7N, 61 mg, 0.17 mmol) in a mixture of 2% aqueous TPGS-750-M (0.30 mL) and THF (0.034 mL), was added ethyl 5-bromo-1,3,4-oxadiazole-2-carboxylate (37 mg, 0.17 mmol), followed by potassium phosphate tribasic (36 mg, 0.17 mmol). The reaction was treated similarly to Example 1A and the crude was purified by preparative HPLC (XBridge 30×50 mm 5 μm 25-50% MeCN/H$_2$O (5 mM NH$_4$OH), 75 mL/min), to afford the title compound (16 mg, 0.036 mmol).

LCMS: Rt: 1.95 min (LCMS Method 4); MS m/z 433.2 [M+H]$^+$.

$^1$H NMR (400 MHz, DMSO-d$_6$) δ 8.64 (s, 1H), 7.04-6.91 (m, 3H), 4.27-3.89 (m, 7H), 3.71-3.57 (m, 3H), 3.33 (s, 3H), 3.01-2.74 (m, 4H), 2.40 (dd, J=12.8, 7.3 Hz, 1H), 2.04 (m, 3H), 1.77-1.65 (m, 2H), 1.56 (m, 2H).

Example 1M: (S)-7-(4-(2-((1,3-dioxan-5-yl)oxy)-5-fluorophenyl)piperidin-1-yl)-2-(1,3,4-oxadiazol-2-yl)-5-oxa-2-azaspiro[3.4]octane

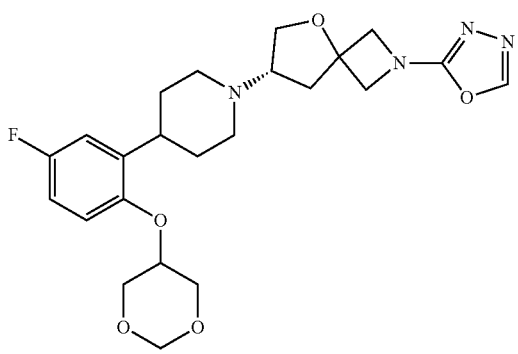 [SMILES: Fc1ccc(OC2COCOC2)c(C2CCN([C@@H]3COC4(C3)CN(c3nnco3)C4)CC2)c1]

To a solution of (S)-7-(4-(2-((1,3-dioxan-5-yl)oxy)-5-fluorophenyl)piperidin-1-yl)-5-oxa-2-azaspiro[3.4]octane (Intermediate 7W, 99 mg, 0.25 mmol) in a mixture of 2% aqueous TPGS-750-M (0.454 mL) and THF (0.05 mL), was added ethyl 5-bromo-1,3,4-oxadiazole-2-carboxylate (56 mg, 0.25 mmol) followed by potassium phosphate tribasic (161 mg, 0.757 mmol). The reaction was treated similarly to Example 1A and the crude was purified by FCC (0-7% MeOH/DCM) and further by preparative HPLC (XBridge 30×50 mm 5 μm 25-50% MeCN/H$_2$O (5 mM NH$_4$OH) 75 mL/min), to afford the title compound (9.0 mg, 0.018 mmol).

LCMS: Rt: 0.87 min (LCMS Method 4); MS m/z 461.5 [M+H]$^+$.

$^1$H NMR (DMSO-d$_6$) δ 8.64 (s, 1H), 7.03-6.93 (m, 3H), 4.99-4.85 (m, 2H), 4.41-4.33 (m, 1H), 4.21 (d, J=8.3 Hz, 1H), 4.16-4.09 (m, 2H), 4.05-3.99 (m, 4H), 3.98-3.90 (m, 1H), 3.76-3.68 (m, 1H), 3.61 (t, J=7.8 Hz, 1H), 3.02-2.90 (m, 2H), 2.88-2.75 (m, 2H), 2.40 (dd, J=13.2, 7.3 Hz, 1H), 2.12-1.98 (m, 3H), 1.77-1.65 (m, 2H), 1.64-1.49 (m, 2H).

Example 1N: (S)-4-(2-(1-(2-(1,3,4-oxadiazol-2-yl)-5-oxa-2-azaspiro[3.4]octan-7-yl)piperidin-4-yl)-4-fluorophenoxy)-2-methylbutan-2-ol

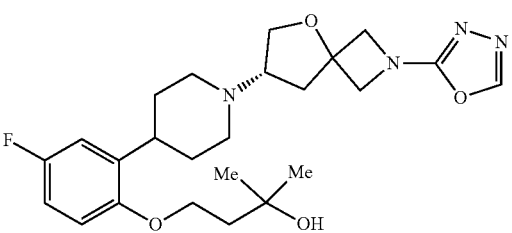 [SMILES: CC(C)(O)CCOc1ccc(F)cc1C1CCN([C@@H]2COC3(C2)CN(c2nnco2)C3)CC1]

To a solution of (S)-4-(2-(1-(5-oxa-2-azaspiro[3.4]octan-7-yl)piperidin-4-yl)-4-fluorophenoxy)-2-methylbutan-2-ol (Intermediate 7O, 147 mg, 0.38 mmol) in a mixture of 2% aqueous TPGS-750-M (0.674 mL) and THF (75 μL), was added ethyl 5-bromo-1,3,4-oxadiazole-2-carboxylate (83 mg, 0.38 mmol) followed by potassium phosphate tribasic (79 mg, 0.38 mmol). The reaction was treated similarly to Example 1A and then the crude was purified by FCC (0-10% MeOH/DCM) and further by preparative HPLC (XBridge 30×50 mm 5 μm 10-30% MeCN/H$_2$O (5 mM NH$_4$OH) 75 mL/min), to afford the title compound (88 mg, 0.19 mmol).

LCMS: Rt: 1.93 min (LCMS Method 4); MS m/z 461.2 [M+H]$^+$.

$^1$H NMR (400 MHz, CD$_3$OD) δ 8.38 (s, 1H), 7.02-6.77 (m, 3H), 4.36-4.22 (m, 2H), 4.17 (q, J=8.7 Hz, 2H), 4.07 (dd, J=8.7, 6.9 Hz, 1H), 3.76 (d, J=4.7 Hz, 3H), 3.08 (m, 3H), 2.90 (d, J=11.3 Hz, 1H), 2.55 (dd, J=13.0, 7.4 Hz, 1H), 2.24 (m, 2H), 2.14 (dd, J=13.0, 8.4 Hz, 1H), 1.85 (d, J=10.9 Hz, 2H), 1.80-1.60 (m, 2H), 1.34 (s, 6H).

Example 1O: (S)-2-(1,3,4-oxadiazol-2-yl)-7-(4-(2-(((R)-tetrahydrofuran-3-yl)oxy)phenyl)piperidin-1-yl)-5-oxa-2-azaspiro[3.4]octane

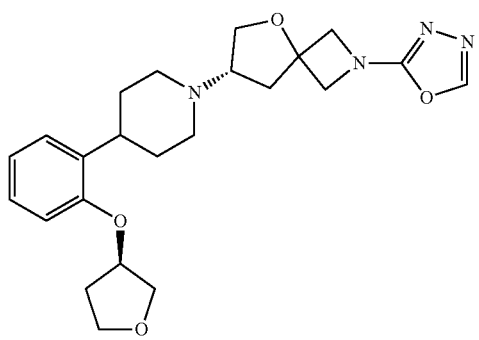 [SMILES: c1ccc(C2CCN([C@@H]3COC4(C3)CN(c3nnco3)C4)CC2)c(O[C@@H]2CCOC2)c1]

To a solution of (S)-7-(4-(2-(((R)-tetrahydrofuran-3-yl)oxy)phenyl)piperidin-1-yl)-5-oxa-2-azaspiro[3.4]octane (Intermediate 7P, 179 mg, 0.499 mmol) in a mixture of 2% aqueous TPGS-750-M (890 μL), and THF (100 μL) was added ethyl 5-bromo-1,3,4-oxadiazole-2-carboxylate (110 mg, 0.499 mmol) followed by potassium phosphate tribasic (106 mg, 0.499 mmol). The reaction was treated similarly to Example 1A and the crude was purified by FCC (0-10% MeOH/DCM) and further by preparative HPLC (XBridge 30×50 mm 5 μm 25-50% MeCN/H$_2$O (5 mM NH$_4$OH) 75 mL/min) to afford the title compound (58 mg, 0.13 mmol).

LCMS: Rt: 1.87 min (LCMS Method 4); MS m/z 427.2 [M+H]$^+$.

$^1$H NMR (DMSO-d$_6$) δ 8.64 (s, 1H), 7.20-7.10 (m, 2H), 6.96-6.85 (m, 2H), 5.07-5.00 (m, 1H), 4.22 (d, J=8.8 Hz, 1H), 4.12 (dd, J=8.3, 2.9 Hz, 2H), 4.02 (d, J=8.3 Hz, 1H), 3.97-3.85 (m, 2H), 3.84-3.72 (m, 3H), 3.62 (t, J=7.8 Hz, 1H), 3.01-2.91 (m, 2H), 2.87-2.74 (m, 2H), 2.40 (dd, J=12.7, 7.3 Hz, 1H), 2.26-2.15 (m, 1H), 2.12-2.00 (m, 3H), 2.00-1.92 (m, 1H), 1.74-1.51 (m, 4H).

Example 1P: (S)-2-(1,3,4-oxadiazol-2-yl)-7-(4-(2-(oxetan-3-yloxy)phenyl)piperidin-1-yl)-5-oxa-2-azaspiro[3.4]octane

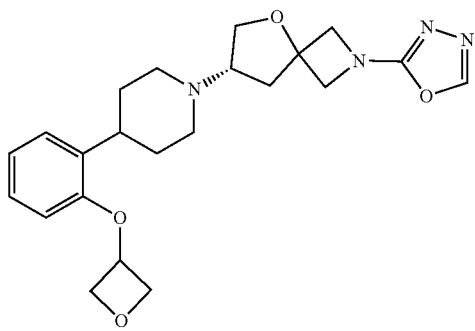 [SMILES: c1ccc(C2CCN([C@@H]3COC4(C3)CN(c3nnco3)C4)CC2)c(OC2COC2)c1]

To a solution of (S)-7-(4-(2-(oxetan-3-yloxy)phenyl)piperidin-1-yl)-5-oxa-2-azaspiro[3.4]octane (Intermediate 7Q, 97 mg, 0.28 mmol) in a mixture of 2% aqueous TPGS-750-M (510 μL), and THF (60 μL) was added ethyl 5-bromo-1,3,4-oxadiazole-2-carboxylate (62 mg, 0.28 mmol) followed by potassium phosphate tribasic (60 mg, 0.28 mmol). The reaction was treated similarly to Example 1A and then the crude was purified by FCC (0-10% MeOH/DCM) and further by preparative HPLC (XBridge 30×50 mm 5 μm 15-40% MeCN/H$_2$O (5 mM NH$_4$OH) 75 mL/min) to afford the title compound (27 mg, 0.062 mmol).

LCMS: Rt: 1.74 min (LCMS Method 4); MS m/z 413.2 [M+H]$^+$.

$^1$H NMR (DMSO-d$_6$) δ 8.65 (s, 1H), 7.24-7.18 (m, 1H), 7.15-7.07 (m, 1H), 6.98-6.88 (m, 1H), 6.53 (d, J=8.3 Hz, 1H), 5.32-5.22 (m, 1H), 4.93 (t, J=6.6 Hz, 2H), 4.58-4.47 (m, 2H), 4.27-4.19 (m, 1H), 4.17-4.09 (m, 2H), 4.16-4.00 (m, 1H), 3.98-3.91 (m, J=7.6, 7.6 Hz, 1H), 3.69-3.59 (m, 1H), 3.04-2.85 (m, 3H), 2.85-2.77 (m, 1H), 2.46-2.37 (m, 1H), 2.17-2.02 (m, 3H), 1.81-1.68 (m, 2H), 1.68-1.56 (m, 2H).

Example 1Q: (S)-7-(4-(2-methoxyphenyl)piperidin-1-yl)-2-(1,3,4-oxadiazol-2-yl)-5-oxa-2-azaspiro[3.4]octane

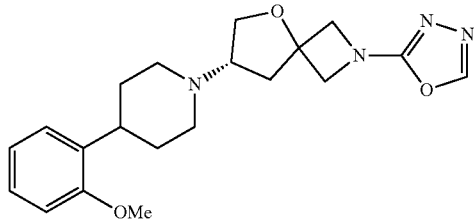 [SMILES: COc1ccccc1C1CCN([C@@H]2COC3(C2)CN(c2nnco2)C3)CC1]

To a solution of (S)-7-(4-(2-methoxyphenyl)piperidin-1-yl)-5-oxa-2-azaspiro[3.4]octane (Intermediate 7X, 81 mg, 0.27 mmol) in a mixture of 2% aqueous TPGS-750-M (480 μL), and THF (50 μL) was added ethyl 5-bromo-1,3,4-oxadiazole-2-carboxylate (59 mg, 0.27 mmol) followed by potassium phosphate tribasic (57 mg, 0.27 mmol). The reaction was treated similarly to Example 1A and the crude was purified by FCC (0-10% MeOH/DCM) and further by preparative HPLC (XBridge 30×50 mm 5 μm 15-40% MeCN/H$_2$O (5 mM NH$_4$OH) 75 mL/min) to afford the title compound (10 mg, 0.026 mmol).

LCMS: Rt: 1.94 min (LCMS Method 4); MS m/z 371.0 [M+H]$^+$.

$^1$H NMR (DMSO-d$_6$) δ 8.64 (s, 1H), 7.22-7.11 (m, 2H), 6.99-6.83 (m, 2H), 4.22 (d, J=8.8 Hz, 1H), 4.13 (dd, J=8.1, 3.2 Hz, 2H), 4.02 (d, J=8.3 Hz, 1H), 3.93 (dd, J=8.3, 6.8 Hz, 1H), 3.77 (s, 3H), 3.62 (t, J=7.8 Hz, 1H), 3.03-2.91 (m, 2H), 2.90-2.81 (m, 1H), 2.80-2.73 (m, 1H), 2.39 (dd, J=12.7, 7.3 Hz, 1H), 2.12-1.97 (m, 3H), 1.74-1.47 (m, 4H).

Example 1R: (S)-7-(4-(4,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane

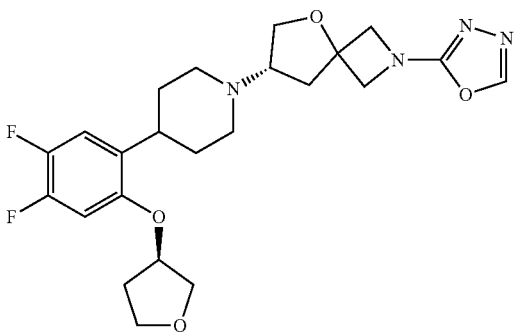

To a solution of (S)-7-(4-(4,5-difluoro-2-(((R)-tetrahydrofuran-3-yl)oxy)phenyl)piperidin-1-yl)-5-oxa-2-azaspiro[3.4]octane (Intermediate 7R, 96 mg, 0.24 mmol) in a mixture of 2% aqueous TPGS-750-M (440 μL), and THF (50 μL) was added ethyl 5-bromo-1,3,4-oxadiazole-2-carboxylate (54 mg, 0.24 mmol) followed by potassium phosphate tribasic (52 mg, 0.24 mmol). The reaction was treated similarly to Example 1A and the crude was purified by FCC (0-7% MeOH/DCM) and further by preparative HPLC (XBridge 30×50 mm 5 μm 25-50% MeCN/H$_2$O (5 mM NH$_4$OH) 75 mL/min) to afford the title compound (35 mg, 0.073 mmol).

LCMS: Rt: 2.01 min (LCMS Method 4); MS m/z 463.1 [M+H]⁺.

¹H NMR (400 MHz, DMSO-d₆) δ 8.64 (s, 1H), 7.22 (dd, J=12.1, 9.2 Hz, 1H), 7.12 (dd, J=12.8, 7.2 Hz, 1H), 5.08-5.01 (m, 1H), 4.21 (d, J=8.7 Hz, 1H), 4.12 (dd, J=8.5, 2.5 Hz, 2H), 4.02 (d, J=8.4 Hz, 1H), 3.93 (dd, J=8.5, 6.6 Hz, 1H), 3.86 (dd, J=10.3, 4.4 Hz, 1H), 3.83-3.71 (m, 3H), 3.60 (dd, J=8.6, 7.0 Hz, 1H), 3.01-2.91 (m, 2H), 2.82-2.70 (m, 2H), 2.39 (dd, J=12.9, 7.2 Hz, 1H), 2.27-2.14 (m, 1H), 2.09-1.89 (m, 4H), 1.72-1.48 (m, 4H).

Example 1S: (S)-7-(4-(4-fluoro-2-methoxyphenyl)piperidin-1-yl)-2-(1,3,4-oxadiazol-2-yl)-5-oxa-2-azaspiro[3.4]octane

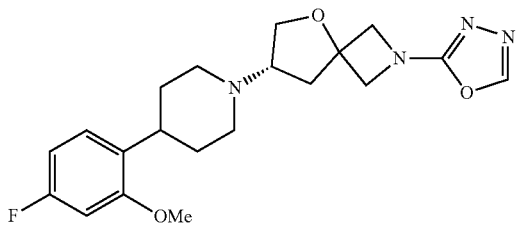

To a solution of (S)-7-(4-(4-fluoro-2-methoxyphenyl)piperidin-1-yl)-5-oxa-2-azaspiro[3.4]octane (Intermediate 7Y, 279 mg, 0.87 mmol) in a mixture of 2% aqueous TPGS-750-M (1.6 mL), and THF (175 μL) was added ethyl 5-bromo-1,3,4-oxadiazole-2-carboxylate (192 mg, 0.87 mmol) followed by potassium phosphate tribasic (185 mg, 0.87 mmol). The mixture was treated similarly to Example 1A and the crude was purified by FCC (0-7% MeOH/DCM) and further by preparative HPLC (XBridge 30×50 mm 5 μm 25-50% MeCN/H₂O (5 mM NH₄OH) 75 mL/min) to afford the title compound (105 mg, 0.27 mmol).

LCMS: Rt: 2.04 min (LCMS Method 4); MS m/z 389.2 [M+H]⁺.

¹H NMR (DMSO-d₆) δ 8.64 (s, 1H), 7.16 (dd, J=8.3, 7.3 Hz, 1H), 6.84 (dd, J=11.2, 2.4 Hz, 1H), 6.74-6.62 (m, 1H), 4.22 (d, J=8.8 Hz, 1H), 4.16-4.08 (m, 2H), 4.02 (d, J=8.3 Hz, 1H), 3.97-3.89 (m, 1H), 3.78 (s, 3H), 3.68-3.56 (m, 1H), 3.03-2.89 (m, 2H), 2.86-2.72 (m, 2H), 2.43-2.36 (m, 1H), 2.13-1.95 (m, 3H), 1.74-1.51 (m, 4H).

Example 1T: (S)-4-(2-(1-(2-(1,3,4-oxadiazol-2-yl)-5-oxa-2-azaspiro[3.4]octan-7-yl)piperidin-4-yl)-5-fluorophenoxy)-2-methylbutan-2-ol

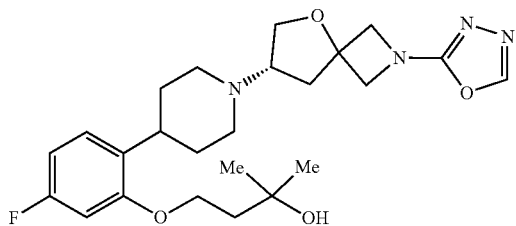 [SMILES: CC(C)(O)CCOc1cc(F)ccc1C1CCN([C@@H]2COC3(C2)CN(c2nnco2)C3)CC1]

To a solution of (S)-4-(2-(1-(5-oxa-2-azaspiro[3.4]octan-7-yl)piperidin-4-yl)-5-fluorophenoxy)-2-methylbutan-2-ol (Intermediate 7S, 141 mg, 0.36 mmol) in a mixture of 2% aqueous TPGS-750-M (0.65 mL), and THF (70 μL) was added ethyl 5-bromo-1,3,4-oxadiazole-2-carboxylate (79 mg, 0.36 mmol) followed by potassium phosphate tribasic (76 mg, 0.36 mmol). The reaction was treated similarly to Example 1A and the crude was purified by FCC (0-10% MeOH/DCM) and further by preparative HPLC (XBridge 30×50 mm 5 μm 25-50% MeCN/H₂O (5 mM NH₄OH) 75 mL/min) to afford the title compound (44 mg, 0.094 mmol).

LCMS: Rt: 1.97 min (LCMS Method 4); MS m/z 461.4 [M+H]⁺.

¹H NMR (DMSO-d₆) δ 8.60-8.67 (m, 1H), 7.20-7.09 (m, 1H), 6.89-6.79 (m, 1H), 6.71-6.63 (m, 1H), 4.41-4.34 (m, 1H), 4.27-3.99 (m, 7H), 3.98-3.88 (m, 1H), 3.67-3.57 (m, 1H), 3.30-3.28 (m, 1H), 3.05-2.89 (m, 2H), 2.87-2.71 (m, 2H), 2.45-2.36 (m, 1H), 2.13-1.96 (m, 3H), 1.75-1.48 (m, 4H), 1.22-1.12 (m, 6H).

Example 1U: (S)-1-(2-(1-(2-(1,3,4-oxadiazol-2-yl)-5-oxa-2-azaspiro[3.4]octan-7-yl)piperidin-4-yl)-4-fluorophenoxy)-2-methylpropan-2-ol

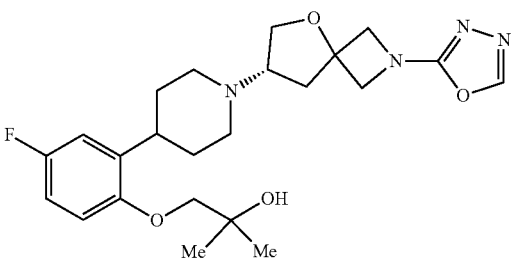 [SMILES: CC(C)(O)COc1ccc(F)cc1C1CCN([C@@H]2COC3(C2)CN(c2nnco2)C3)CC1]

(S)-1-(2-(1-(5-oxa-2-azaspiro[3.4]octan-7-yl)piperidin-4-yl)-4-fluorophenoxy)-2-methylpropan-2-ol (Intermediate 7U, 67 mg, 0.18 mmol), ethyl 5-bromo-1,3,4-oxadiazole-2-carboxylate (39 mg, 0.18 mmol), and potassium phosphate tribasic (38 mg, 0.18 mmol) were suspended in a mixture of 2% aqueous TPGS-750-M (1.6 mL), and THF (0.16 mL). The reaction was treated similarly to Example 1A and the crude was purified by and preparative HPLC (XBridge 30×50 mm 5 μm 25-50% MeCN/H₂O (5 mM NH₄OH) 75 mL/min), to afford the title compound (6.2 mg, 0.013 mmol).

LCMS: Rt: 1.85 min (LCMS Method 4); MS m/z 447.6 [M+H]⁺.

¹H NMR (400 MHz, CD₃OD) δ 8.38 (s, 1H), 6.94-6.83 (m, 3H), 4.35-4.24 (m, 2H), 4.17 (q, J=8.7 Hz, 2H), 4.07 (dd, J=8.7, 6.9 Hz, 1H), 3.76 (d, J=4.7 Hz, 3H), 3.15-3.04 (m, 3H), 2.90 (d, J=11.3 Hz, 1H), 2.55 (dd, J=13.0, 7.4 Hz, 1H), 2.24 (m, 2H), 2.14 (dd, J=13.0, 8.4 Hz, 1H), 1.93-1.81 (m, 2H), 1.77-1.62 (m, 2H), 1.34 (s, 6H).

Example 1V: (S)-7-(4-(5-fluoro-2-methoxyphenyl)piperidin-1-yl)-2-(1,3,4-oxadiazol-2-yl)-5-oxa-2-azaspiro[3.4]octane

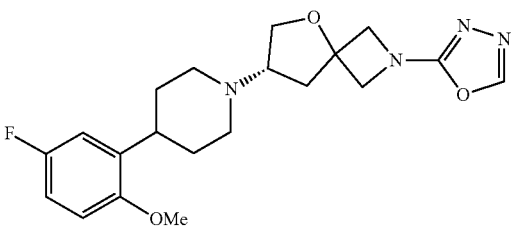

(S)-7-(4-(5-fluoro-2-methoxyphenyl)piperidin-1-yl)-5-oxa-2-azaspiro[3.4]octane (Intermediate 7DD, 116 mg, 0.362 mmol), ethyl 5-bromo-1,3,4-oxadiazole-2-carboxylate (80 mg, 0.362 mmol), and potassium phosphate tribasic (77 mg, 0.362 mmol) were dissolved in a mixture of 2% aqueous TPGS-750-M (0.65 mL), and THF (0.07 mL). The reaction was treated similarly to Example 1A and the residue was purified by FCC (0-10% MeOH/DCM), and by further by preparative HPLC (XBridge 30×50 mm 5 μm 25-50% MeCN/H$_2$O (5 mM NH$_4$OH) 75 mL/min), to afford the title compound (39 mg, 0.097 mmol).

LCMS: Rt: 1.98 min (LCMS Method 4); MS m/z 389.3 [M+H]$^+$.

$^1$H NMR (400 MHz, DMSO-d$_6$) δ 8.64 (s, 1H), 7.13-6.82 (m, 3H), 4.22 (d, J=8.6 Hz, 1H), 4.15-4.09 (m, 2H), 4.02 (d, J=8.4 Hz, 1H), 3.93 (dd, J=8.6, 6.8 Hz, 1H), 3.76 (s, 3H), 3.62 (dd, J=8.5, 7.1 Hz, 1H), 3.04-2.90 (m, 2H), 2.90-2.72 (m, 2H), 2.39 (dd, J=12.9, 7.3 Hz, 1H), 2.12-1.99 (m, 3H), 1.73-1.51 (m, 4H).

Example 1W: (S)-2-(1,3,4-oxadiazol-2-yl)-7-(4-(2-(pyrimidin-5-yl)phenyl)piperidin-1-yl)-5-oxa-2-azaspiro[3.4]octane

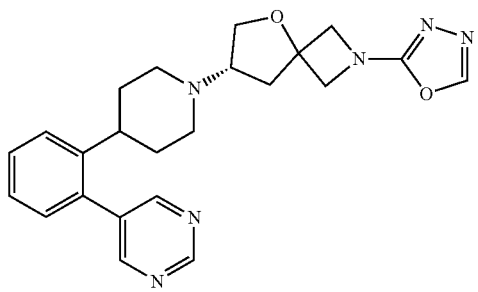 [SMILES: c1ccc(C2CCN([C@@H]3COC4(C3)CN(c3nnco3)C4)CC2)c(-c2cncnc2)c1]

(S)-7-(4-(2-(pyrimidin-5-yl)phenyl)piperidin-1-yl)-5-oxa-2-azaspiro[3.4]octane (Intermediate 7FF, 34 mg, 0.097 mmol), ethyl 5-bromo-1,3,4-oxadiazole-2-carboxylate (28 mg, 0.13 mmol), and potassium phosphate tribasic (31 mg, 0.15 mmol) were dissolved in a mixture of 2% aqueous TPGS-750-M (0.30 mL), and THF (0.030 mL). The reaction was treated similarly to Example 1A and the residue was purified by preparative HPLC (XBridge 30×50 mm 5 μm 25-40% MeCN/H$_2$O (5 mM NH$_4$OH) 75 mL/min) to afford the title compound (17 mg, 0.041 mmol).

LCMS: Rt: 1.52 min (LCMS Method 4); MS m/z 419.4 [M+H]$^+$.

$^1$H NMR (400 MHz, CD$_2$Cl$_2$) δ 9.23 (s, 1H), 8.72 (s, 2H), 7.96 (s, 1H), 7.49 (m, 2H), 7.41-7.30 (m, 1H), 7.22 (dd, J=7.6, 1.2 Hz, 1H), 4.21 (s, 2H), 4.20-4.07 (m, 2H), 4.00 (dd, J=8.5, 6.7 Hz, 1H), 3.73 (t, J=8.0 Hz, 1H), 3.07-2.90 (m, 2H), 2.85-2.68 (m, 1H), 2.54 (m, 1H), 2.40 (dd, J=12.9, 7.1 Hz, 1H), 2.13 (dd, J=12.6, 8.1 Hz, 1H), 1.96 (q, J=11.1, 10.6 Hz, 2H), 1.84 (d, J=13.2 Hz, 2H), 1.77-1.67 (m, 2H).

Example 1X: (S)-2-(1,3,4-oxadiazol-2-yl)-7-(4-(2-(oxazol-2-yl)phenyl)piperidin-1-yl)-5-oxa-2-azaspiro[3.4]octane

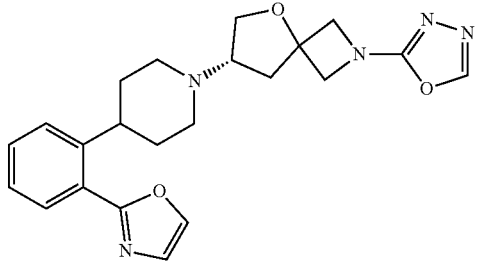 [SMILES: c1ccc(C2CCN([C@@H]3COC4(C3)CN(c3nnco3)C4)CC2)c(-c2ncco2)c1]

(S)-7-(4-(2-(oxazol-2-yl)phenyl)piperidin-1-yl)-5-oxa-2-azaspiro[3.4]octane (Intermediate 7GG, 25 mg, 0.074 mmol), ethyl 5-bromo-1,3,4-oxadiazole-2-carboxylate (21 mg, 0.096 mmol), and potassium phosphate tribasic (20 mg, 0.096 mmol) were dissolved in a mixture of 2% aqueous TPGS-750-M (0.30 mL), and THF (0.030 mL). The reaction was treated similarly to Example 1A the crude was purified by preparative HPLC (XBridge 30×50 mm 5 μm 25-50% MeCN/H$_2$O (5 mM NH$_4$OH) 75 mL/min) to afford the title compound (13 mg, 0.032 mmol).

LCMS: Rt: 1.78 min (LCMS Method 4); MS m/z 408.6 [M+H]$^+$.

$^1$H NMR (400 MHz, CD$_3$OD) δ 8.38 (s, 1H), 8.01 (s, 1H), 7.76 (d, J=7.3 Hz, 1H), 7.49 (d, J=4.0 Hz, 2H), 7.38-7.22 (m, 2H), 4.36-4.23 (m, 2H), 4.16 (q, J=8.6 Hz, 2H), 4.06 (dd, J=8.7, 6.9 Hz, 1H), 3.76 (dd, J=8.6, 7.4 Hz, 1H), 3.55-3.40 (m, 1H), 3.09 (m, 2H), 2.88 (dd, J=11.5, 2.3 Hz, 1H), 2.53 (dd, J=13.1, 7.4 Hz, 1H), 2.30-2.05 (m, 3H), 1.82 (m, 4H).

Example 1Y: (S)-7-(4-(2-(5-methyl-1,3,4-oxadiazol-2-yl)phenyl)piperidin-1-yl)-2-(1,3,4-oxadiazol-2-yl)-5-oxa-2-azaspiro[3.4]octane

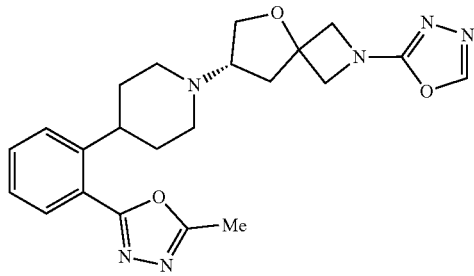 [SMILES: Cc1nnc(-c2ccccc2C2CCN([C@@H]3COC4(C3)CN(c3nnco3)C4)CC2)o1]

(S)-7-(4-(2-(5-methyl-1,3,4-oxadiazol-2-yl)phenyl)piperidin-1-yl)-5-oxa-2-azaspiro[3.4]octane octane (Intermediate 7HH, 7.0 mg, 0.020 mmol), ethyl 5-bromo-1,3,4-oxadiazole-2-carboxylate (5.7 mg, 0.026 mmol), and potassium phosphate tribasic (5.5 mg, 0.026 mmol) were dissolved in a mixture of 2% aqueous TPGS-750-M (0.60 mL), and THF (0.060 mL). The reaction was treated similarly to Example 1A and the crude was purified by preparative HPLC (XBridge Peptide BEH C18 5 μm 19×150 mm 25-40% MeCN/H$_2$O (5 mM NH$_4$OH) 30 mL/min) to afford the title compound (1 mg, 0.002 mmol).

LCMS: Rt: 1.58 min (LCMS Method 4); MS m/z 423.2 [M+H]$^+$.

¹H NMR (400 MHz, CD₃OD) δ 8.38 (s, 1H), 7.81 (d, J=8.2 Hz, 1H), 7.63-7.48 (m, 2H), 7.38 (m, 1H), 4.36-4.24 (m, 2H), 4.18 (t, J=8.7 Hz, 2H), 4.07 (dd, J=8.8, 6.9 Hz, 1H), 3.77 (dd, J=8.7, 7.4 Hz, 1H), 3.62-3.45 (m, 1H), 3.18-3.03 (m, 2H), 2.96-2.83 (m, 1H), 2.63 (s, 3H), 2.55 (dd, J=13.0, 7.4 Hz, 1H), 2.33-2.07 (m, 3H), 1.86 (m, 4H).

Example 2A: (S)-7-(4-(5-fluoro-2-(oxetan-3-yl-methoxy)phenyl)piperidin-1-yl)-2-(1,3,4-thiadiazol-2-yl)-5-oxa-2-azaspiro[3.4]octane

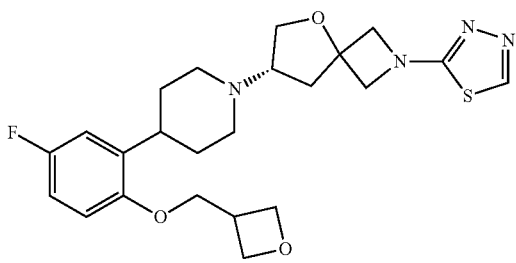 [SMILES: Fc1ccc(OCC2COC2)c(C2CCN([C@@H]3COC4(C3)CN(c3nncs3)C4)CC2)c1]

(S)-2-(1-(2-(1,3,4-thiadiazol-2-yl)-5-oxa-2-azaspiro[3.4] octan-7-yl)piperidin-4-yl)-4-fluorophenol (Intermediate 8A, 11 mg, 0.028 mmol), 3-(iodomethyl)oxetane (14 mg, 0.070 mmol) and cesium carbonate (14 mg, 0.042 mmol) were dissolved in MeCN (0.5 mL). The reaction was stirred at 60° C. overnight, and then concentrated under reduced pressure, and the crude was purified by preparative HPLC (X-bridge C18 OBD 30×50 mm 5 μm 25-50% MeCN/H₂O (5 mM NH₄OH) 75 mL/min) to afford the title compound (6.2 mg, 0.013 mmol).

LCMS: Rt: 1.91 min (LCMS Method 4); MS m/z 461.1 [M+H]⁺.

¹H NMR (CD₃OD) δ 8.66 (s, 1H), 6.94 (d, J=4.4 Hz, 3H), 4.92-4.87 (m, 2H), 4.71-4.59 (m, 2H), 4.33-4.01 (m, 7H), 3.86-3.73 (m, 1H), 3.53-3.41 (m, 1H), 3.15-2.95 (m, 3H), 2.93-2.84 (m, 1H), 2.61-2.47 (m, 1H), 2.32-2.11 (m, 3H), 1.93-1.79 (m, 2H), 1.78-1.58 (m, 2H).

Example 2B: (S)-7-(4-(5-fluoro-2-((3-methyloxetan-3-yl)methoxy)phenyl)piperidin-1-yl)-2-(1,3,4-thiadiazol-2-yl)-5-oxa-2-azaspiro[3.4]octane

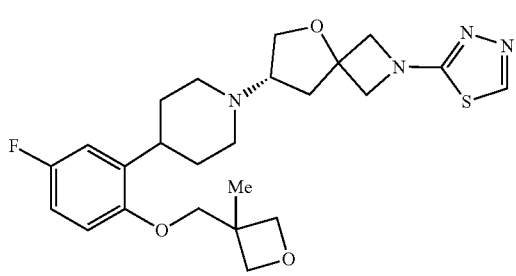 [SMILES: CC1(COc2ccc(F)cc2C2CCN([C@@H]3COC4(C3)CN(c3nncs3)C4)CC2)COC1]

(S)-2-(1-(2-(1,3,4-thiadiazol-2-yl)-5-oxa-2-azaspiro[3.4] octan-7-yl)piperidin-4-yl)-4-fluorophenol (Intermediate 8A, 15 mg, 0.038 mmol) was dissolved in acetonitrile (0.75 mL), and 3-(bromomethyl)-3-methyloxetane (13 mg, 0.077 mmol) was added followed by cesium carbonate (19 mg, 0.058 mmol). The reaction was stirred at 60° C. overnight, concentrated under reduced pressure, and purified by preparative HPLC (X-bridge C18 OBD 30×50 mm 5 μm 25-50% MeCN/H₂O (5 mM NH₄OH) 75 mL/min) to afford the title compound (4.5 mg, 0.0093 mmol).

LCMS: Rt: 2.08 min (LCMS Method 4); MS m/z 475.2 [M+H]⁺.

¹H NMR (CD₃OD) δ 8.66 (s, 1H), 7.03-6.82 (m, 3H), 4.73-4.66 (m, 2H), 4.51-4.43 (m, 2H), 4.33-4.05 (m, 5H), 4.01 (s, 2H), 3.83-3.72 (m, 1H), 3.16-2.98 (m, 3H), 2.95-2.85 (m, 1H), 2.65-2.47 (m, 1H), 2.30-2.08 (m, 3H), 1.94-1.81 (m, 2H), 1.79-1.60 (m, 2H), 1.45 (s, 3H).

Example 2C: (S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate or (S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate and Example 2D: (S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate or (S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate

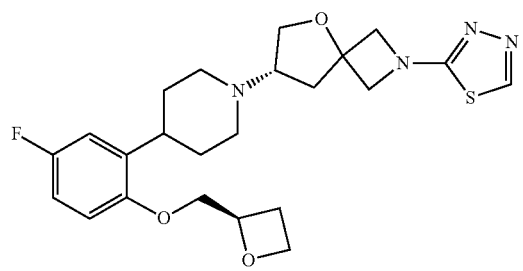

(R) oxetane isomer

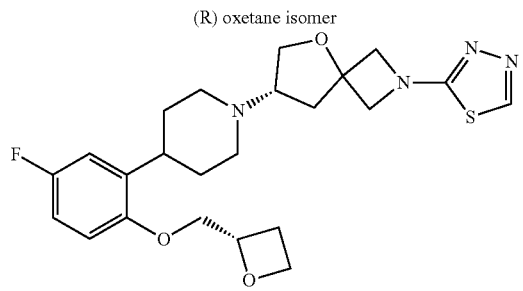

(S) oxetane isomer (S)-2-(1-(2-(1,3,4-thiadiazol-2-yl)-5-oxa-2-azaspiro[3.4] octan-7-yl)piperidin-4-yl)-4-fluorophenol (Intermediate 8A, 30 mg, 0.077 mmol) was dissolved in acetonitrile (1.2 mL), and 2-(bromomethyl)oxetane (10 mg, 0.066 mmol), and cesium carbonate (38 mg, 0.12 mmol) were added. The reaction was stirred at 60° C. overnight, then additional 2-(bromomethyl)oxetane (20 mg, 0.13 mmol) was added, and the reaction was heated at 60° C. overnight. Additional 2-(Bromomethyl)oxetane (40 mg, 0.077 mmol) was added followed by cesium carbonate (25 mg, 0.077 mmol), and the reaction was heated at 75° C. overnight. The reaction was concentrated under reduced pressure and purified by preparative HPLC (XBridge Peptide BEH C18 5 μm 19×150 mm 30-45% MeCN/H₂O (10 mM NH₄OH) 30 mL/min) to afford the separated diastereoisomers as TFA salts: Peak 1 (Example 2C, 4.5 mg, 0.0093 mmol) and Peak 2 (Example 2D, 3.6 mg, 0.0061 mmol).

Example 2C

LCMS: Rt: 1.92 min (LCMS Method 4); MS m/z 461.2 [M+H]⁺.

¹H NMR (CD₃OD) δ 8.66 (s, 1H), 6.96-6.90 (m, 2H), 6.90-6.83 (m, 1H), 4.33-4.21 (m, 2H), 4.20-4.03 (m, 5H), 3.82-3.73 (m, 1H), 3.18-2.97 (m, 4H), 2.95-2.86 (m, 1H), 2.85-2.79 (m, 1H), 2.61-2.51 (m, 2H), 2.30-2.02 (m, 4H), 1.98-1.79 (m, 3H), 1.70 (br s, 2H).

Example 2D

LCMS: Rt: 2.02 min (LCMS Method 4); MS m/z 461.6 [M+H]⁺.

¹H NMR (CD₃OD) δ 8.66 (s, 1H), 6.99-6.92 (m, 2H), 6.91-6.83 (m, 1H), 5.25-5.09 (m, 1H), 4.79-4.63 (m, 2H), 4.32-4.21 (m, 2H), 4.19-4.03 (m, 5H), 3.83-3.73 (m, 1H), 3.18-3.05 (m, 3H), 2.96-2.88 (m, 1H), 2.87-2.69 (m, 2H), 2.62-2.50 (m, 1H), 2.30-2.10 (m, 3H), 1.99-1.82 (m, 2H), 1.79-1.62 (m, 2H).

Example 2E: (S)-7-(4-(5-fluoro-2-((5-methyl-1,3,4-thiadiazol-2-yl)methoxy)phenyl)piperidin-1-yl)-2-(1,3,4-oxadiazol-2-yl)-5-oxa-2-azaspiro[3.4]octane

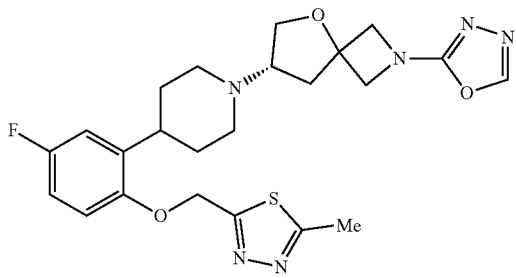 [SMILES: Cc1nnc(COc2ccc(F)cc2C2CCN([C@@H]3COC4(C3)CN(c3nnco3)C4)CC2)s1]

(S)-2-(1-(2-(1,3,4-oxadiazol-2-yl)-5-oxa-2-azaspiro[3.4]octan-7-yl)piperidin-4-yl)-4-fluorophenol, (Intermediate 4F, 14 mg, 0.037 mmol) was dissolved in acetonitrile (1 mL) and 2-(chloromethyl)-5-methyl-1,3,4-thiadiazole (7.2 mg, 0.049 mmol) was added followed by cesium carbonate (18 mg, 0.056 mmol). The reaction was stirred at room temperature for 18 hours and was then concentrated under reduced pressure and purified by preparative HPLC (XBridge 30×50 mm 5 μm 15-40% MeCN/H₂O (5 mM NH₄OH) 75 mL/min) to yield the title compound (9.8 mg, 0.020 mmol) as a white solid.

LCMS: Rt: 1.78 min (LCMS Method 4); MS m/z 487.3 [M+H]⁺.

¹H NMR (CD₃OD) δ 8.39 (s, 1H), 7.09-7.04 (m, 1H), 7.01-6.95 (m, 1H), 6.95-6.87 (m, 1H), 5.49 (d, J=3.4 Hz, 2H), 4.35-4.23 (m, 2H), 4.22-4.12 (m, 2H), 4.10-4.02 (m, 1H), 3.81-3.70 (m, 1H), 3.17-2.95 (m, 3H), 2.94-2.86 (m, 1H), 2.79 (s, 3H), 2.61-2.47 (m, 1H), 2.29-2.08 (m, 3H), 1.93-1.78 (m, 2H), 1.77-1.61 (m, 2H).

Example 2F: (S)-7-(4-(5-fluoro-2-((5-methyl-1,3,4-oxadiazol-2-yl)methoxy)phenyl)piperidin-1-yl)-2-(1,3,4-oxadiazol-2-yl)-5-oxa-2-azaspiro[3.4]octane

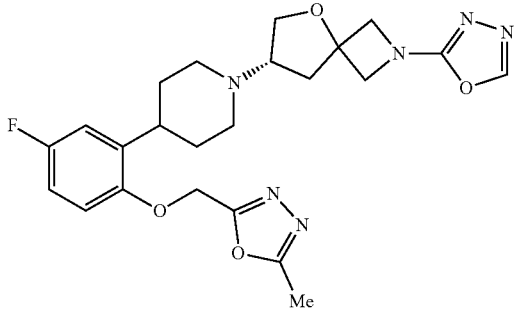 [SMILES: Cc1nnc(COc2ccc(F)cc2C2CCN([C@@H]3COC4(C3)CN(c3nnco3)C4)CC2)o1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 20.2 mg, 0.054 mmol) was dissolved in DMF (0.5 mL) and 2-(chloromethyl)-5-methyl-1,3,4-oxadiazole (8.9 mg, 0.065 mmol) and cesium carbonate (35.2 mg, 0.108 mmol) were added. The resulting reaction mixture was stirred at room temperature for 18 hours. It was then was diluted with EtOAc, and was washed with water and the organic layer was concentrated under reduced pressure. The residue was purified by preparative HPLC (XBridge 30×50 mm 5 μm 15-40% MeCN/H₂O (5 mM NH₄OH) 75 mL/min) to yield the title compound (15 mg, 0.032 mmol).

LCMS: Rt: 0.87 min (LCMS Method 3), MS m/z 471.3 [M+H]⁺.

¹H NMR (400 MHz, CD₃OD) δ 8.38 (s, 1H), 7.08 (dd, J=9.0, 4.6 Hz, 1H), 6.97 (dd, J=9.7, 3.1 Hz, 1H), 6.93-6.86 (m, 1H), 5.29 (s, 2H), 4.34-4.23 (m, 2H), 4.16 (q, J=8.6 Hz, 2H), 4.05 (dd, J=8.6, 7.0 Hz, 1H), 3.75 (dd, J=8.4, 7.6 Hz, 1H), 3.13-2.94 (m, 3H), 2.87 (d, J=10.8 Hz, 1H), 2.56 (s, 3H), 2.55-2.48 (m, 1H), 2.26-2.09 (m, 3H), 1.80 (m, 2H), 1.76-1.62 (m, 2H).

Example 2G: (S)-7-(4-(5-fluoro-2-((3-methylisoxazol-5-yl)methoxy)phenyl)piperidin-1-yl)-2-(1,3,4-oxadiazol-2-yl)-5-oxa-2-azaspiro[3.4]octane

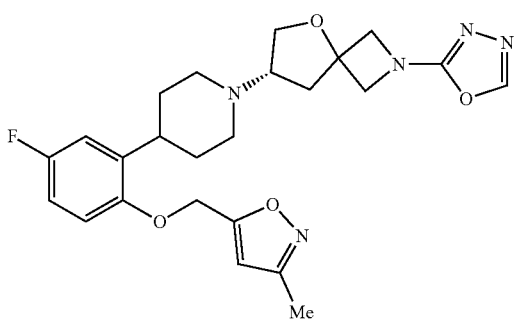 [SMILES: Cc1cc(COc2ccc(F)cc2C2CCN([C@@H]3COC4(C3)CN(c3nnco3)C4)CC2)on1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 18.6 mg, 0.050 mmol) was dissolved in DMF (0.5 mL) and then 5-(chloromethyl)-3-methylisoxazole (8.26 mg, 0.060 mmol) and cesium carbonate (32.4 mg, 0.099 mmol) were added. The resulting reaction mixture was stirred at room temperature for 18 hr. The reaction was then diluted with EtOAc, and washed with water and the organic layer was concentrated under reduced pressure. The residue was purified by preparative HPLC (XBridge 30×50 mm 5 μm 25-50% MeCN/H₂O (5 mM NH₄OH) 75 mL/min) to yield the title compound (13.8 mg, 0.029 mmol).

LCMS: Rt: 1.08 min (LCMS Method 3); MS m/z 470.2 [M+H]⁺.

¹H NMR (400 MHz, CD₃OD) δ 8.38 (s, 1H), 7.03 (dd, J=9.0, 4.6 Hz, 1H), 6.97-6.84 (m, 2H), 6.33 (s, 1H), 5.17 (s, 2H), 4.34-4.24 (m, 2H), 4.16 (q, J=8.8 Hz, 2H), 4.06 (dd, J=8.6, 7.0 Hz, 1H), 3.75 (dd, J=8.5, 7.6 Hz, 1H), 3.14-3.03 (m, 2H), 2.98 (m, 1H), 2.87 (d, J=10.6 Hz, 1H), 2.53 (dd, J=13.0, 7.4 Hz, 1H), 2.28 (s, 3H), 2.25-2.08 (m, 3H), 1.84-1.75 (m, 2H), 1.68 (m, 2H).

Example 2H: (S)-7-(4-(5-fluoro-2-(oxetan-3-yl-methoxy)phenyl)piperidin-1-yl)-2-(1,3,4-oxadiazol-2-yl)-5-oxa-2-azaspiro[3.4]octane

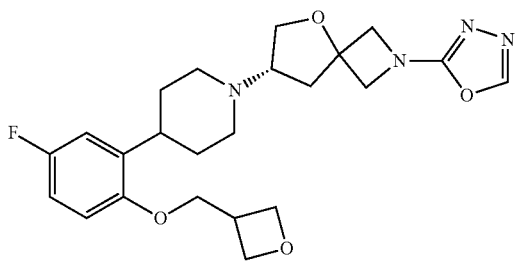 [SMILES: Fc1ccc(OCC2COC2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 18.3 mg, 0.049 mmol) was dissolved in 0.5 mL of DMF and 3-(iodomethyl)oxetane (19.36 mg, 0.098 mmol) and cesium carbonate (31.8 mg, 0.098 mmol) were added. The resulting reaction mixture was stirred at room temperature for 18 h. The reaction then was diluted with EtOAc, and washed with water and was concentrated under reduced pressure.

The residue was then purified by preparative HPLC (XBridge 30×50 mm 5 μm 25-50% MeCN/H₂O (5 mM NH₄OH) 75 mL/min) to yield the title compound (12.1 mg, 0.027 mmol).

LCMS: Rt: 0.97 min (LCMS Method 3); MS m/z 445.4 [M+H]⁺.

¹H NMR (400 MHz, CD₃OD) δ 8.38 (s, 1H), 7.02-6.78 (m, 3H), 4.88 (dd, J=8.0, 6.1 Hz, 2H), 4.64 (t, J=6.0 Hz, 2H), 4.34-4.23 (m, 2H), 4.17 (dd, J=8.9, 7.4 Hz, 4H), 4.06 (dd, J=8.6, 7.0 Hz, 1H), 3.75 (dd, J=8.4, 7.6 Hz, 1H), 3.47 (m, 1H), 3.14-2.97 (m, 3H), 2.88 (d, J=10.8 Hz, 1H), 2.53 (dd, J=13.0, 7.4 Hz, 1H), 2.27-2.08 (m, 3H), 1.84 (m, 2H), 1.68 (m, 2H).

Example 2I: (S)-7-(4-(5-fluoro-2-(pyrimidin-2-yl-methoxy)phenyl)piperidin-1-yl)-2-(1,3,4-oxadiazol-2-yl)-5-oxa-2-azaspiro[3.4]octane

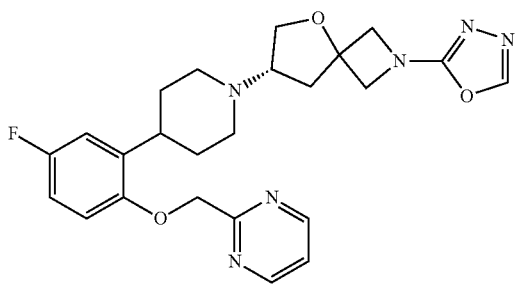 [SMILES: Fc1ccc(OCc2ncccn2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 20.5 mg, 0.055 mmol) was dissolved in 0.5 mL of DMF and then 2-(chloromethyl)pyrimidine (8.89 mg, 0.066 mmol) and cesium carbonate (35.7 mg, 0.110 mmol) were added. The resulting reaction mixture was stirred at room temperature for 18 hours and it was then was diluted with EtOAc, washed with water and was concentrated under reduced pressure. The residue was purified by preparative HPLC (XBridge 30×50 mm 5 μm 15-40% MeCN/H₂O (5 mM NH₄OH) 75 mL/min) to yield the title compound (16 mg, 0.034 mmol).

LCMS: Rt: 0.92 min (LCMS Method 3); MS m/z 467.4 [M+H]⁺.

¹H NMR (400 MHz, CD₃OD) δ 8.81 (d, J=4.9 Hz, 2H), 8.38 (s, 1H), 7.44 (t, J=4.9 Hz, 1H), 6.97-6.90 (m, 2H), 6.81 (m, 1H), 5.27 (s, 2H), 4.34-4.23 (m, 2H), 4.16 (q, J=8.6 Hz, 2H), 4.05 (dd, J=8.6, 7.0 Hz, 1H), 3.80-3.70 (m, 1H), 3.10 (m, 3H), 2.87 (d, J=10.7 Hz, 1H), 2.53 (dd, J=13.0, 7.4 Hz, 1H), 2.28-2.08 (m, 3H), 1.88 (m, 2H), 1.69 (m, 2H).

Example 2J: (S)-7-(4-(5-fluoro-2-((3-fluorooxetan-3-yl)methoxy)phenyl)piperidin-1-yl)-2-(1,3,4-oxadiazol-2-yl)-5-oxa-2-azaspiro[3.4]octane

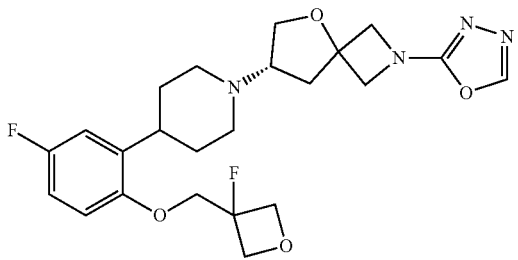 [SMILES: Fc1ccc(OCC2(F)COC2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 17.4 mg, 0.046 mmol) was dissolved in DMF (0.5 mL) and then 3-fluorooxetan-3-yl)methyl 4-methylbenzenesulfonate (commercially available, 13.3 mg, 0.051 mmol) and cesium carbonate (30.3 mg, 0.093 mmol) were added. The resulting reaction mixture was stirred at 50° C. overnight and it was then diluted with EtOAc, washed with water and concentrated under reduced pressure. The residue was purified by preparative HPLC (XBridge 30×50 mm 5 μm 25-50% MeCN/H₂O (5 mM NH₄OH) 75 mL/min) to yield the title compound (2.7 mg, 0.0058 mmol).

LCMS: Rt: 1.01 min (LCMS Method 3); MS m/z 463.7 [M+H]⁺.

¹H NMR (400 MHz, CD₃OD) δ 8.38 (s, 1H), 7.03-6.84 (m, 3H), 4.84-4.72 (m, 4H), 4.39-4.23 (m, 4H), 4.16 (q, J=8.6 Hz, 2H), 4.06 (dd, J=8.6, 7.0 Hz, 1H), 3.75 (dd, J=8.4, 7.6 Hz, 1H), 3.13-3.04 (m, 2H), 2.97 (m, 1H), 2.89 (d, J=10.9 Hz, 1H), 2.54 (dd, J=13.0, 7.4 Hz, 1H), 2.27-2.07 (m, 3H), 1.84 (m, 2H), 1.67 (m, 2H).

Example 2K: (S)-7-(4-(5-fluoro-2-((3-methyloxetan-3-yl)methoxy)phenyl)piperidin-1-yl)-2-(1,3,4-oxadiazol-2-yl)-5-oxa-2-azaspiro[3.4]octane

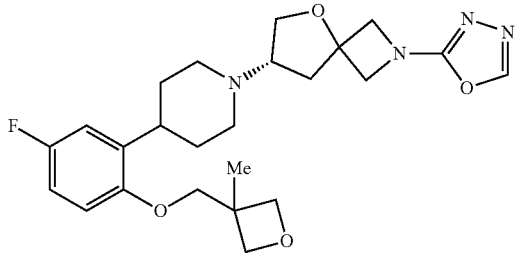 [SMILES: CC1(COc2ccc(F)cc2C2CCN([C@@H]3COC4(C3)CN(c3nnco3)C4)CC2)COC1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 19 mg, 0.051 mmol) was dissolved in acetonitrile (1.0 mL) and 3-(bromomethyl)-3-methyloxetane (16.8 mg, 0.101 mmol) and cesium carbonate (25 mg, 0.076 mmol) were added. The reaction was stirred at 80° C. overnight. It was then concentrated under reduced pressure and purified by preparative HPLC (XBridge 30×50 mm 5 μm 25-50% MeCN/H$_2$O (5 mM NH$_4$OH) 75 mL/min) to yield the title compound (10.7 mg, 0.023 mmol).

LCMS: Rt: 2.00 min (LCMS Method 4); MS m/z 459.2 [M+H]$^+$.

$^1$H NMR (CD$_3$OD) δ 8.39 (s, 1H), 6.81-7.02 (m, 3H), 4.66-4.72 (m, 2H), 4.48 (s, 2H), 4.24-4.35 (m, 2H), 4.12-4.21 (m, 2H), 4.03-4.10 (m, 1H), 4.01 (s, 2H), 3.71-3.80 (m, 1H), 2.98-3.17 (m, 3H), 2.83-2.95 (m, 1H), 2.47-2.60 (m, 1H), 2.08-2.29 (m, 3H), 1.80-1.93 (m, 2H), 1.59-1.76 (m, 2H), 1.45 (s, 3H).

Example 2L: (S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane

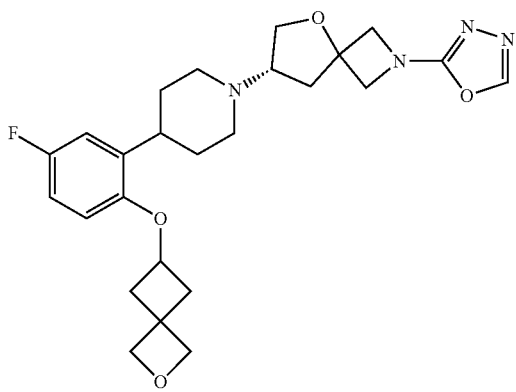 [SMILES: Fc1ccc(OC2CC3(COC3)C2)c(C2CCN([C@@H]3COC4(C3)CN(c3nnco3)C4)CC2)c1]

Step 1: 2-oxaspiro[3.3]heptan-6-yl 4-methylbenzenesulfonate

To a solution of 2-oxaspiro[3.3]heptan-6-ol (500 mg, 4.38 mmol), DMAP (53 mg, 0.438 mmol) and triethylamine (1.53 mL, 10.95 mmol) in DCM (15 mL) at 0° C., was added 4-methylbenzene-1-sulfonyl chloride (877 mg, 4.60 mmol). The reaction was stirred at room temperature for 18 hours. The reaction mixture was then washed with 1N HCl solution, dried over MgSO$_4$ and concentrated under reduced pressure. The residue was purified by FCC (0→60% EtOAc/heptanes) to afford title intermediate (1.04 g, 3.68 mmol) as a white solid.

LCMS: Rt: 0.87 min (LCMS Method 2); MS m/z 269.3 [M+H]$^+$.

Step 2: (S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane To a MeCN (5 mL) solution of (S)-2-(1-(2-(1,3,4-oxadiazol-2-yl)-5-oxa-2-azaspiro[3.4]octan-7-yl)piperidin-4-yl)-4-fluorophenol (Intermediate 4F, 100 mg, 0.267 mmol) and 2-oxaspiro[3.3]heptan-6-yl 4-methylbenzenesulfonate (79 g, 0.294 mmol), was added Cs$_2$CO$_3$ (348 mg, 1.07 mmol). The resulting mixture was stirred at 80° C. for 18 hours. The crude was concentrated under reduced pressure and it was then diluted with EtOAc and washed with water. The combined organics were concentrated under reduced pressure and the crude was purified by FCC (0-8% MeOH (1% NH$_4$OH)/DCM). The isolated material was dissolved in 3:7 MeCN:water and freeze dried to give the title compound (52 mg, 0.105 mmol) as a white solid. The stereochemistry of this compound was confirmed by X-ray crystallography.

[α]$_D^{25}$=−11.04 0 (c=1.0400 w/v %, CH$_3$OH).

LCMS: Rt: 1.96 min (LCMS Method 4); MS m/z 471.4 [M+H]$^+$.

$^1$H NMR (400 MHz, CD$_3$OD) δ 8.38 (s, 1H), 6.90 (dd, J=9.8, 3.0 Hz, 1H), 6.82 (td, J=8.5, 3.1 Hz, 1H), 6.70 (dd, J=9.0, 4.6 Hz, 1H), 4.75, (s, 2H), 4.68 (s, 2H), 4.53 (p, J=6.6 Hz, 1H), 4.38-4.23 (m, 2H), 4.16 (q, J=8.6 Hz, 2H), 4.06 (dd, J=8.7, 6.9 Hz, 1H), 3.76 (t, J=8.0 Hz, 1H), 3.17-3.04 (m, 2H), 3.03-2.85 (m, 2H), 2.85-2.75 (m, 2H), 2.54 (dd, J=13.2, 7.6 Hz, 1H), 2.36-2.09 (m, 5H), 1.87-1.74 (m, 2H), 1.67 (m, 2H).

Example 2M: (S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane

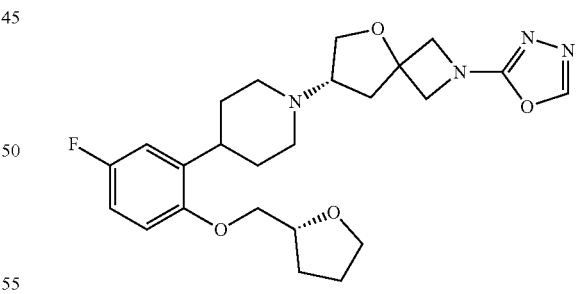

Step 1: (R)-(tetrahydrofuran-2-yl)methyl 4-methylbenzenesulfonate (R)-(tetrahydrofuran-2-yl)methanol (400 mg, 3.92 mmol) was dissolved in DCM (6 mL) and 4-methylbenzenesulfonyl chloride (896 mg, 4.70 mmol), triethylamine (0.82 mL, 5.9 mmol) and DMAP (24 mg, 0.20 mmol) were added. The reaction was stirred at room temperature for 18 hours. The reaction was neutralized with a saturated solution of NH$_4$Cl and extracted with DCM. The combined DCM layers were dried over MgSO₄, filtered and concentrated under vacuum. The residue was purified by FCC (0-50% EtOAc/heptanes) to afford the title intermediate (925 mg, 3.61 mmol) as a colorless oil.

LCMS: Rt: 0.92 min (LCMS Method 1), MS m/z 257.1 [M+H]⁺.

Step 2: (S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane (S)-2-(1-(2-(1,3,4-oxadiazol-2-yl)-5-oxa-2-azaspiro[3.4]octan-7-yl)piperidin-4-yl)-4-fluorophenol (Intermediate 4F, 15 mg, 0.040 mmol) was dissolved in acetonitrile (1 mL) and (R)-(tetrahydrofuran-2-yl)methyl 4-methylbenzenesulfonate (13 mg, 0.052 mmol) was added followed by cesium carbonate (20 mg, 0.060 mmol). The reaction was stirred at 75° C. for 18 hours. The reaction was concentrated under reduced pressure and purified by preparative HPLC (XBridge 30×50 mm 5 µm 10-30% MeCN/H₂O (0.1% formic acid) 75 mL/min) to yield the title compound (4.9 mg, 0.0011 mol) as a white solid.

LCMS: Rt: 2.09 min (LCMS Method 4); MS m/z 459.4 [M+H]⁺.

¹H NMR (CD₃OD) δ 8.39 (s, 1H), 6.99-6.77 (m, 3H), 4.35-4.23 (m, 3H), 4.21-4.12 (m, 2H), 4.11-4.04 (m, 1H), 4.02-3.89 (m, 3H), 3.87-3.72 (m, 2H), 3.15-2.98 (m, 3H), 2.94-2.85 (m, 1H), 2.60-2.50 (m, 1H), 2.29-1.80 (m, 9H), 1.76-1.59 (m, 2H).

Example 2N: (S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane or (S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane and
Example 2O: (S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane or (S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane

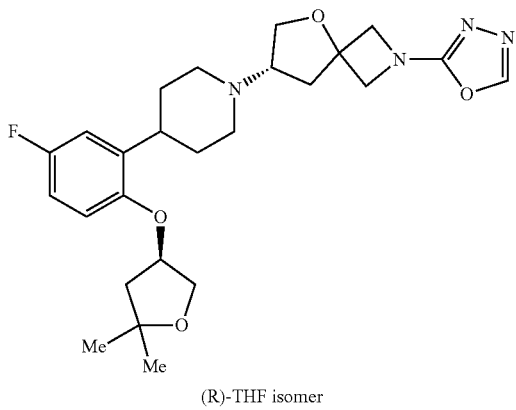

(R)-THF isomer

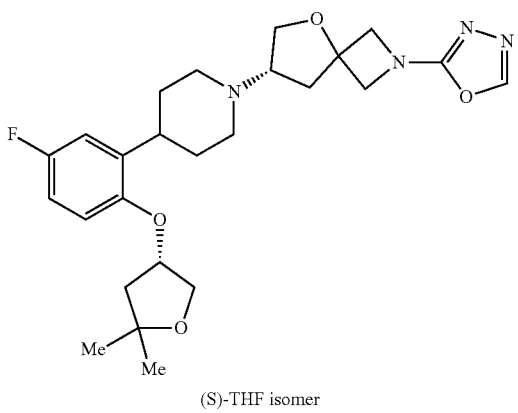

(S)-THF isomer

To a DMF (1.1 mL) solution of (S)-2-(1-(2-(1,3,4-oxadiazol-2-yl)-5-oxa-2-azaspiro[3.4]octan-7-yl)piperidin-4-yl)-4-fluorophenol (Intermediate 4F, 100 mg, 0.267 mmol) and cesium carbonate (261 mg, 0.801 mmol) was added 5,5-dimethyltetrahydrofuran-3-yl 4-methylbenzenesulfonate (Intermediate 5N, 72.2 mg, 0.267 mmol). The resulting mixture was stirred at 80° C. for 18 hours. The crude was diluted with EtOAc, washed with water and concentrated under reduced pressure. The residue was purified by FCC (0-10% MeOH/DCM), then by preparative HPLC (XBridge 30×50 mm 5 µm 25-50% MeCN/H₂O (5 mM NH₄OH) 75 mL/min). The two diastereomers were then separated by preparative SFC (ChiralPak IG 21×250 mm column, 30% IPA, Flow rate: 80 g per minute). Peak 1 was isolated and concentrated to give Example 2N (19 mg, 0.039 mmol) and Peak 2 was isolated to give Example 2O (9 mg, 0.019 mmol)

Example 2N

SFC: Rt: 3.29 min (Chiralpak IG 4.6×100 mm 5 m, 5→55% IPA with 10 mM NH₄OH/CO₂, 5 mL/min). LCMS: Rt: 2.21 min (LCMS Method 4); MS m/z 473.3 [M+H]⁺.

¹H NMR (400 MHz, DMSO-d₆) δ 8.65 (s, 1H), 7.04-6.86 (m, 3H), 5.01 (m, 1H), 4.22 (d, J=8.9 Hz, 1H), 4.13 (dd, J=8.3, 2.7 Hz, 2H), 4.09-3.99 (m, 2H), 3.94 (dd, J=8.5, 6.6 Hz, 1H), 3.83-3.74 (m, 1H), 3.68-3.57 (m, 1H), 3.06-2.91 (m, 2H), 2.91-2.75 (m, 2H), 2.41 (dd, J=12.9, 7.2 Hz, 1H), 2.13 (dd, J=13.7, 6.7 Hz, 1H), 2.09-1.98 (m, 3H), 1.89 (dd, J=13.8, 1.6 Hz, 1H), 1.76-1.65 (m, 2H), 1.59 (m, 2H), 1.31 (s, 3H), 1.22 (s, 3H).

Example 2O

SFC: Rt: 3.41 min (Chiralpak IG 4.6×100 mm 5 m, 5→55% IPA with 10 mM NH₄OH/CO₂, 5 mL/min). LCMS: Rt: 2.23 min (LCMS Method 4); MS m/z 473.5 [M+H]⁺.

¹H NMR (400 MHz, DMSO-d₆) δ 8.65 (s, 1H), 7.12-6.80 (m, 3H), 5.01 (m, 1H), 4.22 (d, J=8.7 Hz, 1H), 4.13 (dd, J=8.5, 4.6 Hz, 2H), 4.08-3.98 (m, 2H), 3.94 (dd, J=8.5, 6.7 Hz, 1H), 3.78 (dt, J=10.1, 1.3 Hz, 1H), 3.65-3.57 (m, 1H), 2.95 (p, J=7.0 Hz, 2H), 2.92-2.75 (m, 2H), 2.41 (dd, J=12.9, 7.2 Hz, 1H), 2.13 (dd, J=13.6, 6.6 Hz, 1H), 2.09-1.97 (m, 3H), 1.94-1.85 (m, 1H), 1.70 (m, 2H), 1.57 (m, 2H), 1.31 (s, 3H), 1.22 (s, 3H).

Example 2P: (S)-7-(4-(2-((3-ethyloxetan-3-yl)methoxy)-5-fluorophenyl)piperidin-1-yl)-2-(1,3,4-oxadiazol-2-yl)-5-oxa-2-azaspiro[3.4]octane

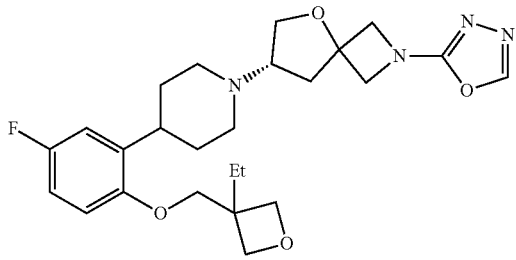 [SMILES: CCC1(COc2ccc(F)cc2C2CCN([C@@H]3COC4(C3)CN(c3nnco3)C4)CC2)COC1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 16 mg, 0.042 mmol) was dissolved in acetonitrile (1.0 mL) and (3-ethyloxetan-3-yl)methyl 4-methylbenzenesulfonate (Intermediate 5N, 15 mg, 0.055 mmol) and cesium carbonate (21 mg, 0.064 mmol) were added. The reaction was stirred at 80° C. for 18 hours and then the reaction was concentrated under reduced pressure. The residue was dissolved in DCM and a saturated solution of sodium bicarbonate. The layers were separated and the aqueous layer was extracted with DCM and the combined organics were concentrated under reduced pressure. The residue was then purified by preparative HPLC (XBridge 30×50 mm 5 μm 25-50% MeCN/H$_2$O (5 mM NH$_4$OH) 75 mL/min) to afford the title compound (13.4 mg, 0.027 mmol) as a white solid.

LCMS: Rt: 2.18 min (LCMS Method 4); MS m/z 473.5 [M+H]$^+$.

$^1$H NMR (CD$_3$OD) δ 8.39 (s, 1H), 7.03-6.82 (m, 3H), 4.67-4.61 (m, 2H), 4.54-4.47 (m, 2H), 4.34-4.24 (m, 2H), 4.21-4.12 (m, 2H), 4.08 (s, 3H), 3.80-3.70 (m, 1H), 3.16-2.96 (m, 3H), 2.94-2.85 (m, 1H), 2.60-2.48 (m, 1H), 2.28-2.09 (m, 3H), 1.91 (d, J=7.3 Hz, 4H), 1.76-1.59 (m, 2H), 0.98 (t, J=7.6 Hz, 3H).

Example 2Q: (S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane or (S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane and Example 2R: (S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane or (S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane

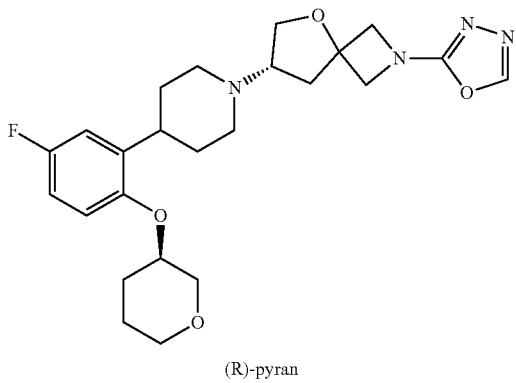

(R)-pyran

-continued

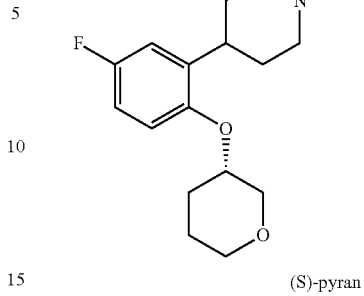

(S)-pyran (S)-2-(1-(2-(1,3,4-oxadiazol-2-yl)-5-oxa-2-azaspiro[3.4]octan-7-yl)piperidin-4-yl)-4-fluorophenol (Intermediate 4F, 100 mg, 0.267 mmol) was dissolved in DMF (1.1 mL) and cesium carbonate (261 mg, 0.801 mmol) was added followed by tetrahydro-2H-pyran-3-yl 4-methylbenzenesulfonate (Intermediate 5 L, 68.5 mg, 0.267 mmol). The resulting mixture was stirred at 80° C. for 18 hours and then diluted with EtOAc, washed with water and concentrated under reduced pressure. The residue was purified by FCC (0-10% MeOH/DCM) and further by preparative HPLC (XBridge 30×50 mm 5 μm 25-50% MeCN/H$_2$O (5 mM NH$_4$OH) 75 mL/min). The diastereomers were then separated by SFC (ChiralPak IG 21×250 mm column, 21% MeOH, Flow rate: 80 g per minute). Peak 1 was isolated to give Example 2Q (8.0 mg, 0.017 mmol) and peak 2 was isolated to give Example 2R (7.0 mg, 0.015 mmol)

Example 2Q

SFC: Rt: 3.14 min (Chiralpak IA 4.6×100 mm 5 m, 5→55% MeOH with 10 mM NH$_4$OH/CO$_2$, 5 mL/min). LCMS: Rt: 2.10 min (LCMS Method 4); MS m/z 459.5 [M+H]$^+$.

$^1$H NMR (DMSO-d$_6$) δ 8.64 (s, 1H), 7.03-6.90 (m, 3H), 4.36-4.28 (m, 1H), 4.24-4.19 (m, 1H), 4.15-4.10 (m, 2H), 4.05-4.00 (m, 1H), 3.97-3.90 (m, 1H), 3.75-3.69 (m, 1H), 3.65-3.54 (m, 3H), 3.54-3.47 (m, 1H), 3.03-2.84 (m, 3H), 2.83-2.74 (m, 1H), 2.45-2.36 (m, 1H), 2.11-1.93 (m, 4H), 1.86-1.65 (m, 4H), 1.65-1.46 (m, 3H).

Example 2R

SFC: Rt: 3.35 min (Chiralpak IA 4.6×100 mm 5 m, 5→55% MeOH with 10 mM NH$_4$OH/CO$_2$, 5 mL/min). LCMS: Rt: 2.09 min (LCMS Method 4); MS m/z 459.1 [M+H]$^+$.

$^1$H NMR (DMSO-d$_6$) δ 8.66-8.62 (m, 1H), 7.04-6.89 (m, 3H), 4.27-4.28 (m, 1H), 4.25-4.19 (m, 1H), 4.16-4.09 (m, 2H), 4.05-4.00 (m, 1H), 3.97-3.90 (m, 1H), 3.76-3.70 (m, 1H), 3.65-3.55 (m, 3H), 3.55-3.47 (m, 1H), 3.01-2.84 (m, 3H), 2.84-2.75 (m, 1H), 2.45-2.37 (m, 1H), 2.11-1.93 (m, 4H), 1.87-1.64 (m, 4H), 1.64-1.47 (m, 3H).

Example 2S: (S)-7-(4-(2-((2-oxaspiro[3.3]heptan-6-yl)methoxy)-5-fluorophenyl)piperidin-1-yl)-2-(1,3,4-oxadiazol-2-yl)-5-oxa-2-azaspiro[3.4]octane

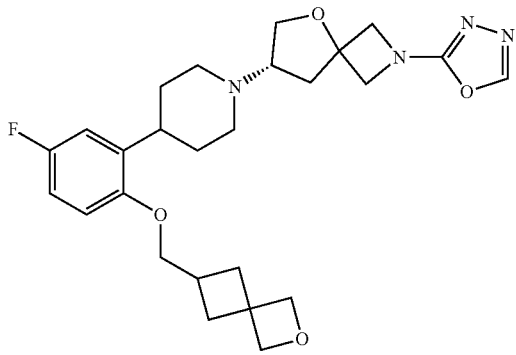 [SMILES: Fc1ccc(OCC2CC3(COC3)C2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 40 mg, 0.11 mmol), cesium carbonate (139 mg, 0.427 mmol) and (2-oxaspiro[3.3]heptan-6-yl)methyl 4-methylbenzenesulfonate (Intermediate 5A, 36.2 mg, 0.128 mmol) were dissolved in DMF (10 mL). The resulting mixture was stirred at 80° C. for 16 hours. The crude was diluted with EtOAc, washed with water and the organic layer was concentrated under reduced pressure. The residue was purified by preparative HPLC (XBridge 30×50 mm 5 μm 35-60% MeCN/H$_2$O (5 mM NH$_4$OH) 75 mL/min) to afford the title compound (23 mg, 0.047 mmol).

LCMS: Rt: 2.18 min (LCMS Method 4); MS m/z 485.5 [M+H]$^+$.

$^1$H NMR (400 MHz, CD$_3$OD) δ 8.29 (s, 1H), 6.89-6.64 (m, 3H), 4.66 (s, 2H), 4.54 (s, 2H), 4.20 (d, J=10.3 Hz, 2H), 4.07 (d, J=8.6 Hz, 2H), 4.02-3.92 (m, 1H), 3.82-3.60 (m, 3H), 3.07-2.73 (m, 4H), 2.56-2.40 (m, 2H), 2.33 (m, 2H), 2.19-1.97 (m, 5H), 1.80-1.48 (m, 4H).

Example 2T: (S)-7-(4-(2-((5-ethyl-1,3,4-thiadiazol-2-yl)methoxy)-5-fluorophenyl)piperidin-1-yl)-2-(1,3,4-oxadiazol-2-yl)-5-oxa-2-azaspiro[3.4]octane

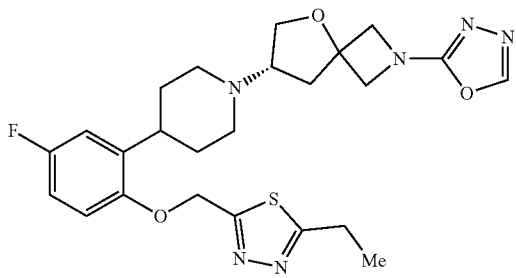 [SMILES: CCc1nnc(COc2ccc(F)cc2C2CCN([C@@H]3COC4(C3)CN(c3nnco3)C4)CC2)s1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 13 mg, 0.035 mmol) was dissolved in acetonitrile (1.0 mL) and 2-(chloromethyl)-5-ethyl-1,3,4-thiadiazole (11.3 mg, 0.069 mmol) and cesium carbonate (17 mg, 0.052 mmol) were added. The reaction was stirred at room temperature for 16 hours and then the solvent was concentrated under reduced pressure and the residue was purified by preparative HPLC (XBridge 30×50 mm 5 μm 25-50% MeCN/H$_2$O (5 mM NH$_4$OH) 75 mL/min) to afford the title compound (4.0 mg, 0.0080 mmol) as a white solid.

LCMS: Rt: 1.93 min (LCMS Method 4); MS m/z 501.7 [M+H]$^+$.

$^1$H NMR (CD$_3$OD) δ 8.39 (s, 1H), 7.10-7.04 (m, 1H), 7.01-6.96 (m, 1H), 6.95-6.88 (m, 1H), 5.49 (s, 2H), 4.37-4.25 (m, 2H), 4.22-4.13 (m, 2H), 4.11-4.02 (m, 1H), 3.82-3.72 (m, 1H), 3.18 (s, 4H), 3.06-2.95 (m, 1H), 2.93-2.84 (m, 1H), 2.62-2.48 (m, 1H), 2.30-2.10 (m, 3H), 1.93-1.79 (m, 2H), 1.77-1.62 (m, 2H), 1.48-1.38 (m, 3H).

Example 2U: (S)-3-((2-(1-(2-(1,3,4-oxadiazol-2-yl)-5-oxa-2-azaspiro[3.4]octan-7-yl)piperidin-4-yl)-4-fluorophenoxy)methyl)oxetan-3-ol

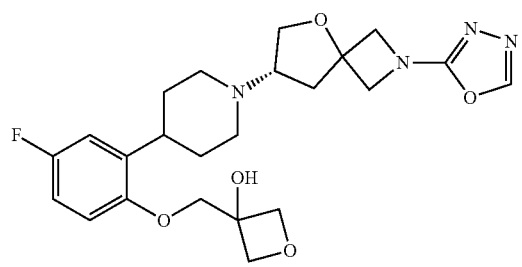 [SMILES: OC1(COc2ccc(F)cc2C2CCN([C@@H]3COC4(C3)CN(c3nnco3)C4)CC2)COC1]

(S)-2-(1-(2-(1,3,4-oxadiazol-2-yl)-5-oxa-2-azaspiro[3.4]octan-7-yl)piperidin-4-yl)-4-fluorophenol (Intermediate 4F, 36 mg, 0.096 mmol) was dissolved in MeCN (1.5 mL) and (3-hydroxyoxetan-3-yl)methyl 4-methylbenzenesulfonate (Intermediate 5J, 30 mg, 0.12 mmol) and cesium carbonate (47 mg, 0.14 mmol) were added. The reaction was stirred at 70° C. for 3 days and then the solvent was removed under reduced pressure. The residue was diluted with DCM and a saturated solution of NaHCO$_3$. The layers were separated and the aqueous layer was extracted with DCM and the combined organic layers were concentrated under reduced pressure. The residue was purified by preparative HPLC (XBridge 30×50 mm 5 μm 15-40% MeCN/H$_2$O (5 mM NH$_4$OH) 75 mL/min) to afford the title compound (12.4 mg, 0.027 mmol) as a white solid.

LCMS: Rt: 1.54 min (LCMS Method 4); MS m/z 461.4 [M+H]$^+$.

$^1$H NMR (CD$_3$OD) δ 8.39 (s, 1H), 7.05-6.83 (m, 3H), 4.74-4.69 (m, 2H), 4.68-4.63 (m, 2H), 4.36-4.25 (m, 2H), 4.22-4.13 (m, 2H), 4.12-4.03 (m, 3H), 3.81-3.72 (m, 1H), 3.15-3.04 (m, 3H), 2.94-2.83 (m, 1H), 2.60-2.49 (m, 1H), 2.33-2.06 (m, 3H), 1.94-1.80 (m, 2H), 1.77-1.60 (m, 1H).

Example 2V: 2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol or 2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol and Example 2W 2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol or 2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol

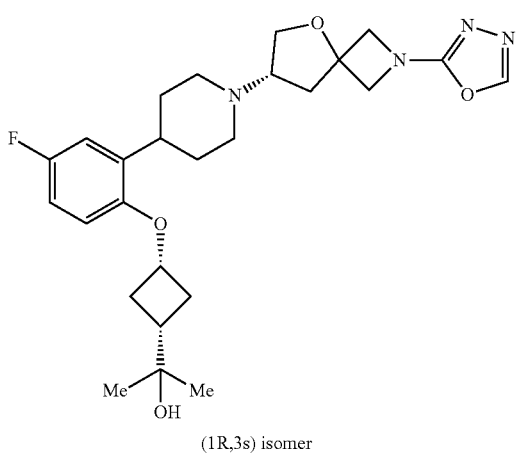
(1R,3s) isomer

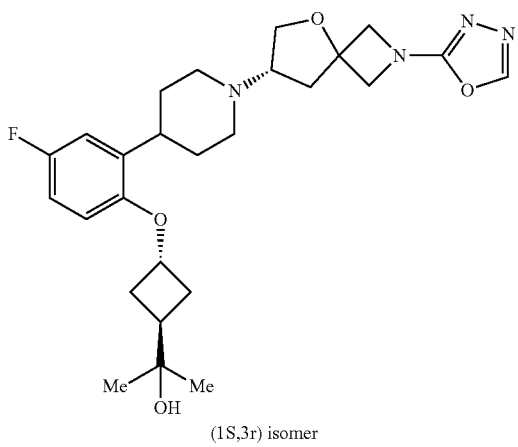
(1S,3r) isomer

Step 1: methyl (S)-3-(2-(1-(2-(1,3,4-oxadiazol-2-yl)-5-oxa-2-azaspiro[3.4]octan-7-yl)piperidin-4-yl)-4-fluorophenoxy)cyclobutane-1-carboxylate (S)-2-(1-(2-(1,3,4-oxadiazol-2-yl)-5-oxa-2-azaspiro[3.4]octan-7-yl)piperidin-4-yl)-4-fluorophenol (Intermediate 4F, 50 mg, 0.13 mmol) and methyl 3-(tosyloxy)cyclobutane-1-carboxylate (Intermediate 5Q, 102 mg, 0.200 mmol) were dissolved in acetonitrile (2 mL), and cesium carbonate (218 mg, 0.668 mmol) was added. The reaction was stirred at 80° C. for 16 hours and then concentrated and diluted with EtOAc, washed with water, and concentrated under reduced pressure. The residue was purified by FCC (0-5% MeOH/DCM) to afford the title intermediate (56 mg, 0.11 mmol).

LCMS: Rt: 0.97 min (LCMS Method 2); MS m/z 487.4 [M+H]$^+$.

Step 2: 2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol or 2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol Methyl (S)-3-(2-(1-(2-(1,3,4-oxadiazol-2-yl)-5-oxa-2-azaspiro[3.4]octan-7-yl)piperidin-4-yl)-4-fluorophenoxy)cyclobutane-1-carboxylate (50 mg, 0.078 mmol) was dissolved in THF (2 mL) at −10° C., and methylmagnesium chloride (0.057 mL, 0.173 mmol, 3M THF) was added. The reaction was slowly warmed to 0° C. and stirred for 1 hour. The reaction was then neutralized with a saturated solution of ammonium chloride and extracted with EtOAc. The combined organic layers were concentrated under reduced pressure and the residue was purified by preparative HPLC (X-Bridge 30×50 mm 5 μm 25-50% MeCN/H$_2$O (5 mM NH$_4$OH) 75 mL/min) to afford the separated diastereomers. The initial peak being Example 2V (5.0 mg, 0.0099 mmol) and the trailing peak being Example 2W (8 mg, 0.016 mmol).

Example 2V

LCMS: Rt: 2.11 min (LCMS Method 4); MS m/z 487.5 [M+H]$^+$.

$^1$H NMR (400 MHz, CD$_3$OD) δ 8.38 (s, 1H), 6.97-6.75 (m, 2H), 6.64 (dd, J=9.0, 4.6 Hz, 1H), 4.63 (m, 1H), 4.41-4.26 (m, 2H), 4.23-4.14 (m, 2H), 4.07 (dd, J=8.7, 6.9 Hz, 1H), 3.77 (dd, J=8.7, 7.4 Hz, 1H), 3.17-2.86 (m, 4H), 2.64-2.53 (m, 1H), 2.51-2.33 (m, 3H), 2.31-2.09 (m, 5H), 1.95-1.59 (m, 4H), 1.16 (s, 6H).

Example 2W

LCMS: Rt: 2.14 min (LCMS Method 4); MS m/z 487.4 [M+H]$^+$.

$^1$H NMR (400 MHz, CD$_3$OD) δ 8.38 (s, 1H), 6.97-6.65 (m, 3H), 4.59-4.40 (m, 1H), 4.37-4.24 (m, 2H), 4.17 (q, J=8.6 Hz, 2H), 4.06 (dd, J=8.6, 7.0 Hz, 1H), 3.76 (dd, J=8.6, 7.3 Hz, 1H), 3.17-2.79 (m, 4H), 2.54 (dd, J=13.0, 7.4 Hz, 1H), 2.40 (m, 2H), 2.28-2.10 (m, 3H), 2.09-1.92 (m, 3H), 1.83 (m, 2H), 1.68 (m, 2H), 1.12 (s, 6H).

Example 2X: (S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane or (S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane and Example 2Y: (S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane or (S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane

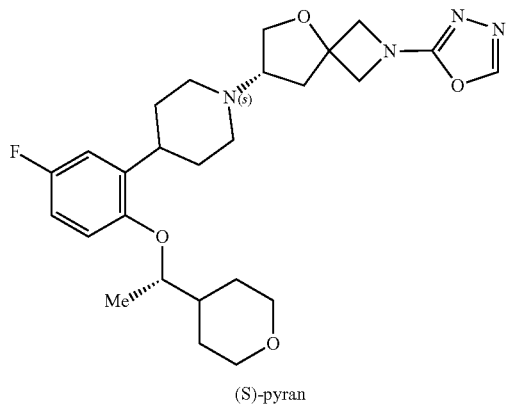

(S)-pyran

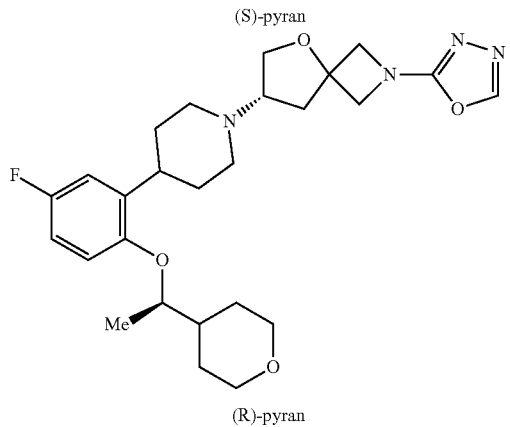

(R)-pyran (S)-2-(1-(2-(1,3,4-oxadiazol-2-yl)-5-oxa-2-azaspiro[3.4]octan-7-yl)piperidin-4-yl)-4-fluorophenol (Intermediate 4F, 73 mg, 0.20 mmol), 1-(tetrahydro-2H-pyran-4-yl)ethyl 4-methylbenzenesulfonate (Intermediate 5R, 83 mg, 0.29 mmol) were dissolved in acetonitrile (8 mL), and cesium carbonate (127 mg, 0.390 mmol) was added. The reaction was stirred at 80° C. for 16 hours and then filtered. The filtrate was evaporated under reduced pressure and the residue was purified by FCC (0-100% EtOAc (0.1% 7N NH$_3$ in MeOH)/DCM; then 0-3% DCM/MeOH). The diastereomers were then separated by chiral SFC (ChiralPak IF 21×250 mm column, 30% MeOH:IPA 1:1 with 10 mM NH$_4$OH, Flow rate: 80 g per minute). The initial peak was isolated to give Example 2X (17 mg, 0.034 mmol) and the trailing peak was isolated to give Example 2Y (17 mg, 0.034 mmol).

Example 2X

SFC: Rt: 2.78 min (Chiralpak IF 3×100 mm 5 m, 5→55% MeOH:IPA 1:1 with 10 mM NH$_4$OH/CO$_2$, 2.5 mL/min).
LCMS: Rt: 2.28 min (LCMS Method 4); MS m/z 487.3 [M+H]$^+$.

$^1$H NMR (400 MHz, CD$_3$OD) δ 8.38 (s, 1H), 7.06-6.56 (m, 3H), 4.35-4.21 (m, 3H), 4.17 (q, J=8.6 Hz, 2H), 4.11-3.94 (m, 3H), 3.76 (dd, J=8.5, 7.4 Hz, 1H), 3.44 (m, 2H), 3.21-2.85 (m, 4H), 2.55 (dd, J=12.9, 7.3 Hz, 1H), 2.32-2.07 (m, 3H), 1.92-1.77 (m, 4H), 1.76-1.42 (m, 5H), 1.21 (d, J=6.0 Hz, 3H).

Example 2Y

SFC: Rt: 2.93 min (Chiralpak IF 3×100 mm 5 m, 5→55% MeOH:IPA 1:1 with 10 mM NH$_4$OH/CO$_2$, 2.5 mL/min).
LCMS: Rt: 2.33 min (LCMS Method 4); MS m/z 487.4 [M+H]$^+$.

1H NMR (400 MHz, CD$_3$OD) δ 8.38 (s, 1H), 7.31-6.49 (m, 3H), 4.38-4.22 (m, 3H), 4.17 (q, J=8.6 Hz, 2H), 4.10-3.92 (m, 3H), 3.76 (dd, J=8.7, 7.4 Hz, 1H), 3.44 (m, 2H), 3.22-2.75 (m, 4H), 2.55 (dd, J=13.1, 7.3 Hz, 1H), 2.38-2.08 (m, 3H), 2.01-1.79 (m, 4H), 1.76-1.43 (m, 5H), 1.22 (d, J=6.0 Hz, 3H).

Example 2Z: (7S)-7-(4-(2-((3-oxabicyclo[3.1.0]hexan-6-yl)methoxy)-5-fluorophenyl)piperidin-1-yl)-2-(1,3,4-oxadiazol-2-yl)-5-oxa-2-azaspiro[3.4]octane

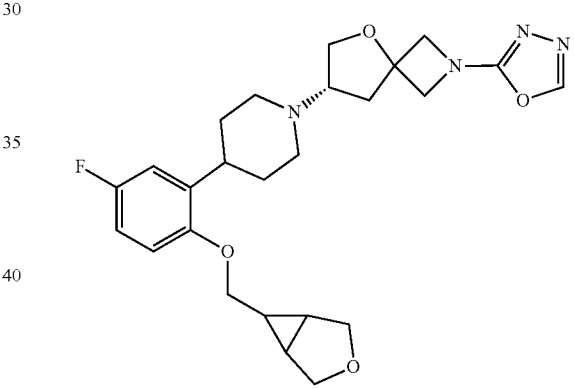

(S)-2-(1-(2-(1,3,4-oxadiazol-2-yl)-5-oxa-2-azaspiro[3.4]octan-7-yl)piperidin-4-yl)-4-fluorophenol (Intermediate 4F, 38 mg, 0.10 mmol) and (3-oxabicyclo[3.1.0]hexan-6-yl)methyl 4-methylbenzenesulfonate (Intermediate 5K, 55 mg, 0.15 mmol) were dissolved in acetonitrile (2 mL), and cesium carbonate (66 mg, 0.20 mmol) was added. The reaction was stirred at 80° C. for 16 hours and then filtered. The filtrate was concentrated under reduced pressure and the residue was purified by preparative HPLC (X-bridge C18 OBD 30×50 mm 5 μm column 25-50% MeCN/H$_2$O (5 mM NH$_4$OH) 75 mL/min) to afford the title compound (19 mg, 0.040 mmol).

LCMS: Rt: 2.11 min (LCMS Method 4); MS m/z 471.4 [M+H]$^+$.

$^1$H NMR (400 MHz, CD$_3$OD) δ 8.38 (s, 1H), 7.03-6.29 (m, 3H), 4.36-4.23 (m, 2H), 4.17 (q, J=8.5 Hz, 2H), 4.07 (dd, J=8.7, 6.9 Hz, 1H), 3.96-3.84 (m, 4H), 3.81-3.64 (m, 3H), 3.17-2.96 (m, 3H), 2.90 (m, 1H), 2.55 (dd, J=13.1, 7.3 Hz, 1H), 2.31-2.07 (m, 3H), 1.84 (m, 2H), 1.77-1.59 (m, 4H), 1.16 (m, 1H).

Example 2AA: (S)-7-(4-(2-((2-oxaspiro[3.3]heptan-6-yl)oxy)-3,5-difluorophenyl)piperidin-1-yl)-2-(1,3,4-oxadiazol-2-yl)-5-oxa-2-azaspiro[3.4]octane

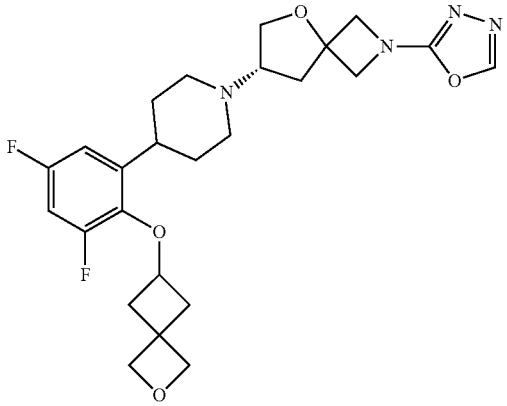 [SMILES: Fc1cc(F)c(OC2CC3(COC3)C2)c(C2CCN([C@@H]3COC4(C3)CN(c3nnco3)C4)CC2)c1]

In a 40 mL vial, to a solution of (S)-2-(1-(2-(1,3,4-oxadiazol-2-yl)-5-oxa-2-azaspiro[3.4]octan-7-yl)piperidin-4-yl)-4,6-difluorophenol (Intermediate 4C, 0.082 g, 0.209 mmol) in MeCN (2.1 mL) under nitrogen was added a solution of 2-oxaspiro[3.3]heptan-6-yl 4-methylbenzenesulfonate (Step 1 from Example 2K, 0.062 g, 0.230 mmol) in MeCN (0.5 mL) followed by Cs₂CO₃ (0.272 g, 0.836 mmol) and this was stirred at 80° C. for 6 hours. The reaction was then cooled to RT and diluted with EtOAc and water. The layers were separated and the aq phase was extracted with EtOAc, and the combined organic layers were dried with MgSO₄, filtered and concentrated. The residue was purified by FCC (0-15% MeOH (10% NH₄OH)/EtOAc) to yield the title compound as a white solid.

LCMS: Rt: 1.20 min (LCMS Method 3); MS m/z 489.3 [M+H]⁺.

¹H NMR (400 MHz, CD₃OD) δ 8.38 (s, 1H), 6.89-6.74 (m, 2H), 4.67 (d, J=1.8 Hz, 4H), 4.42-4.24 (m, 3H), 4.17 (q, J=8.6 Hz, 2H), 4.06 (dd, J=8.8, 6.9 Hz, 1H), 3.77 (dd, J=8.8, 7.3 Hz, 1H), 3.17-3.05 (m, 2H), 3.05-2.86 (m, 2H), 2.69 (m, 2H), 2.55 (dd, J=13.0, 7.4 Hz, 1H), 2.39 (ddd, J=10.2, 7.2, 3.4 Hz, 2H), 2.31-2.09 (m, 3H), 1.85-1.58 (m, 4H).

Example 2BB: (S)-7-(4-(3,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane

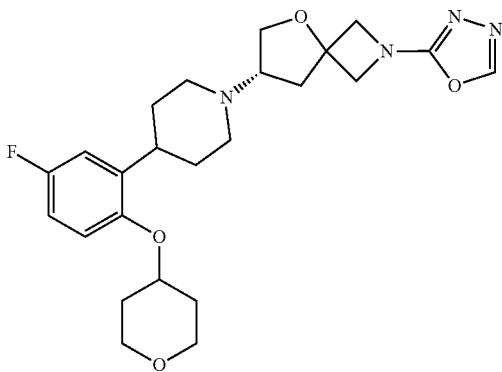 [SMILES: Fc1ccc(OC2CCOCC2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4,6-difluorophenol (Intermediate 4C, 32 mg, 0.082 mmol), tetrahydro-2H-pyran-4-yl 4-methylbenzenesulfonate (23 mg, 0.090 mmol) and cesium carbonate (106 mg, 0.326 mmol) were suspended in acetonitrile (0.8 mL). The reaction was stirred at 80° C. overnight and then cooled to room temperature and diluted with EtOAc and water. The aqueous layer was extracted with EtOAc, and the combined organic layers were dried with magnesium sulfate, filtered and concentrated. The residue was purified by FCC (0-20% MeOH (10% NH₄OH)/EtOAc) and by preparative HPLC (X-bridge C18 OBD 30×50 mm 5 μm column 25-50% MeCN/H₂O (5 mM NH₄OH) 75 mL/min) to afford the title compound (27 mg, 0.058 mmol) as a white solid.

LCMS: Rt: 1.98 min (LCMS Method 4); MS m/z 477.4 [M+H]⁺.

¹H NMR (400 MHz, CD₃OD) δ 8.38 (s, 1H), 6.90-6.77 (m, 2H), 4.35-4.12 (m, 5H), 4.06 (dd, J=8.6, 6.9 Hz, 1H), 3.97 (dt, J=12.0, 4.3 Hz, 2H), 3.76 (dd, J=8.7, 7.3 Hz, 1H), 3.48 (m, 2H), 3.16-3.01 (m, 3H), 2.90 (m, 1H), 2.54 (dd, J=12.9, 7.4 Hz, 1H), 2.27-2.09 (m, 3H), 2.03-1.93 (m, 2H), 1.87-1.58 (m, 6H).

Example 2CC: (S)-7-(4-(3,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane

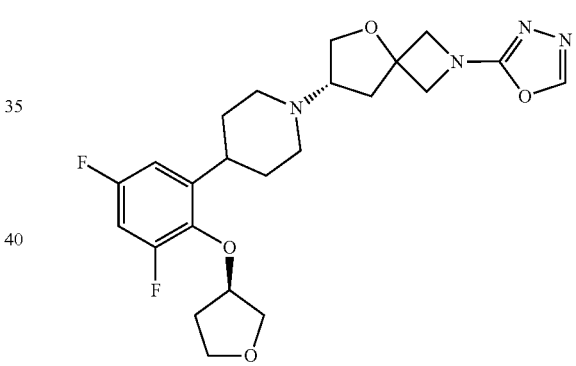

(S)-2-(1-(2-(1,3,4-oxadiazol-2-yl)-5-oxa-2-azaspiro[3.4]octan-7-yl)piperidin-4-yl)-4,6-difluorophenol (Intermediate 4C, 32 mg, 0.082 mmol), (S)-tetrahydrofuran-3-yl 4-methylbenzenesulfonate (Intermediate 5C) 22 mg, 0.090 mmol) and cesium carbonate (106 mg, 0.326 mmol) were suspended in acetonitrile (0.8 mL). The reaction was stirred at 80° C. for 80 minutes then cooled at room temperature and diluted with EtOAc and water. The aq layer was extracted with EtOAc, and the combined organic layers were dried with magnesium sulfate, filtered and concentrated. The residue was purified by FCC (0-20% MeOH (10% NH₄OH)/EtOAc) to afford the title compound (27 mg, 0.058 mmol) as a white solid.

LCMS: Rt: 1.98 min (LCMS Method 4); MS m/z 463.2 [M+H]⁺.

¹H NMR (400 MHz, CD₃OD) δ 8.38 (s, 1H), 6.94-6.75 (m, 2H), 5.03-4.94 (m, 1H), 4.35-4.23 (m, 2H), 4.17 (q, J=8.6 Hz, 2H), 4.10-3.99 (m, 2H), 3.96-3.86 (m, 2H), 3.80-3.69 (m, 2H), 3.15-2.98 (m, 3H), 2.95-2.84 (m, 1H), 2.55 (dd, J=13.0, 7.4 Hz, 1H), 2.27-2.08 (m, 5H), 1.85-1.56 (m, 4H).

Example 2DD: (S)-7-(4-(3,5-difluoro-2-(oxetan-3-ylmethoxy)phenyl)piperidin-1-yl)-2-(1,3,4-oxadiazol-2-yl)-5-oxa-2-azaspiro[3.4]octane

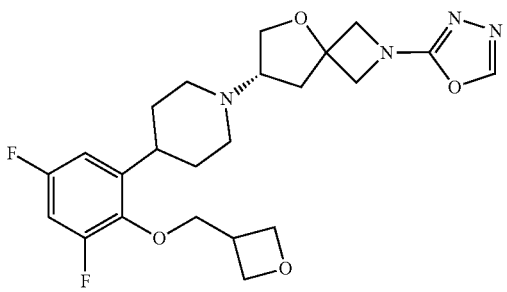 [SMILES: Fc1cc(F)c(OCC2COC2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4,6-difluorophenol (Intermediate 4C, 32 mg, 0.082 mmol), oxetan-3-ylmethyl 4-methylbenzenesulfonate (22 mg, 0.090 mmol) and cesium carbonate (106 mg, 0.326 mmol) were suspended in acetonitrile (0.8 mL). The reaction was stirred at 80° C. for 20 minutes then cooled at room temperature and diluted with EtOAc and water. The aqueous layer was extracted with EtOAc, and the combined organic layers were dried with magnesium sulfate, filtered and concentrated. The residue was purified by FCC (0-20% MeOH (10% NH$_4$OH)/EtOAc) to afford the title compound (23 mg, 0.049 mmol) as a white solid.

LCMS: Rt: 1.89 min (LCMS Method 4); MS m/z 463.5 [M+H]$^+$.

$^1$H NMR (400 MHz, CD$_3$OD) δ 8.38 (s, 1H), 6.92-6.77 (m, 2H), 4.88 (dd, J=8.0, 6.1 Hz, 2H), 4.63 (t, J=6.0 Hz, 2H), 4.35-4.23 (m, 2H), 4.23-4.12 (m, 4H), 4.06 (dd, J=8.7, 6.8 Hz, 1H), 3.76 (dd, J=8.7, 7.2 Hz, 1H), 3.44 (m, 1H), 3.17-2.95 (m, 3H), 2.95-2.86 (m, 1H), 2.54 (dd, J=13.1, 7.4 Hz, 1H), 2.28-2.09 (m, 3H), 1.88-1.62 (m, 4H).

Example 2EE: (S)-7-(4-(3,5-difluoro-2-(oxetan-3-yloxy)phenyl)piperidin-1-yl)-2-(1,3,4-oxadiazol-2-yl)-5-oxa-2-azaspiro[3.4]octane

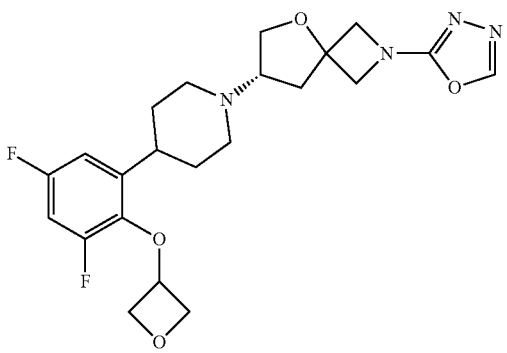 [SMILES: Fc1cc(F)c(OC2COC2)c(C2CCN([C@@H]3COC4(C3)CN(c3nnco3)C4)CC2)c1]

(S)-2-(1-(2-(1,3,4-oxadiazol-2-yl)-5-oxa-2-azaspiro[3.4]octan-7-yl)piperidin-4-yl)-4,6-difluorophenol (Intermediate 4C, 32 mg, 0.082 mmol), oxetan-3-yl 4-methylbenzenesulfonate (commercially available, 20 mg, 0.090 mmol) and cesium carbonate (106 mg, 0.326 mmol) were suspended in acetonitrile (0.8 mL). The reaction was stirred at 80° C. for 6 hours then cooled at room temperature and diluted with EtOAc and water. The aqueous layer was extracted with EtOAc, and the combined organic layers were dried with magnesium sulfate, filtered and concentrated. The residue was purified by FCC (0-20% MeOH (10% NH$_4$OH)/EtOAc) to afford the title compound (15 mg, 0.033 mmol) as a white solid.

LCMS: Rt: 1.87 min (LCMS Method 4); MS m/z 449.5 [M+H]$^+$.

$^1$H NMR (400 MHz, CD$_3$OD) δ 8.38 (s, 1H), 6.93-6.75 (m, 2H), 5.15-5.00 (m, 1H), 4.91 (dd, J=7.5, 6.1 Hz, 2H), 4.83-4.77 (m, 2H), 4.35-4.22 (m, 2H), 4.17 (q, J=8.7 Hz, 2H), 4.06 (dd, J=8.8, 6.9 Hz, 1H), 3.77 (dd, J=8.8, 7.3 Hz, 1H), 3.16-2.95 (m, 3H), 2.95-2.85 (m, 1H), 2.54 (dd, J=13.0, 7.4 Hz, 1H), 2.23 (m, 2H), 2.14 (dd, J=13.0, 8.3 Hz, 1H), 1.86-1.59 (m, 4H).

Example 2FF: (S)-7-(4-(4,5-difluoro-2-(oxetan-3-yloxy)phenyl)piperidin-1-yl)-2-(1,3,4-oxadiazol-2-yl)-5-oxa-2-azaspiro[3.4]octane

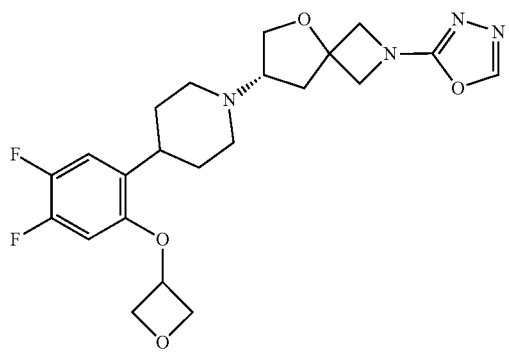 [SMILES: Fc1cc(OC2COC2)c(C2CCN([C@@H]3COC4(C3)CN(c3nnco3)C4)CC2)cc1F]

(S)-2-(1-(2-(1,3,4-oxadiazol-2-yl)-5-oxa-2-azaspiro[3.4]octan-7-yl)piperidin-4-yl)-4,5-difluorophenol (Intermediate 4D, 28 mg, 0.071 mmol), oxetan-3-yl 4-methylbenzenesulfonate (21 mg, 0.093 mmol) and cesium carbonate (70 mg, 0.21 mmol) were suspended in acetonitrile (2 mL). The reaction was stirred at 80° C. overnight, cooled to room temperature, filtered and concentrated. The residue was purified by preparative HPLC (X-bridge C18 OBD 30×50 mm 5 μm column 25-50% MeCN/H$_2$O (5 mM NH$_4$OH) 75 mL/min), then by preparative HPLC (X-bridge C18 OBD 30×50 mm 5 μm column 10-30% MeCN/H$_2$O (0.1% formic acid) 75 mL/min) to afford the title compound (6 mg, 0.012 mmol) as a formate salt.

LCMS: Rt: 1.87 min (LCMS Method 4); MS m/z 449.3 [M+H]$^+$.

$^1$H NMR (400 MHz, CD$_3$OD) δ 8.38 (d, J=6.3 Hz, 1H), 7.13 (dd, J=11.7, 8.9 Hz, 1H), 6.53 (dd, J=12.2, 6.8 Hz, 1H), 5.26 (m, 1H), 5.02 (t, J=6.8 Hz, 2H), 4.67 (dd, J=7.5, 4.8 Hz, 2H), 4.42-4.00 (m, 5H), 3.86 (dd, J=9.1, 6.7 Hz, 1H), 3.29-2.78 (m, 4H), 2.61 (dd, J=13.3, 7.5 Hz, 1H), 2.43 (m, 2H), 2.22 (dd, J=13.3, 7.8 Hz, 1H), 1.96-1.51 (m, 4H).

Example 2GG: (S)-7-(4-(4,5-difluoro-2-((tetra-hydro-2H-pyran-4-yl)oxy)phenyl)piperidin-1-yl)-2-(1,3,4-oxadiazol-2-yl)-5-oxa-2-azaspiro[3.4]octane

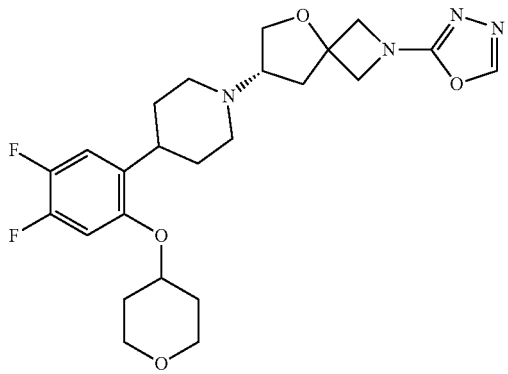 [SMILES: Fc1cc(OC2CCOCC2)c(C2CCN([C@@H]3COC4(C3)CN(c3nnco3)C4)CC2)cc1F]

(S)-2-(1-(2-(1,3,4-oxadiazol-2-yl)-5-oxa-2-azaspiro[3.4]octan-7-yl)piperidin-4-yl)-4,5-difluorophenol (Intermediate 4D, 28 mg, 0.071 mmol), tetrahydro-2H-pyran-4-yl 4-methylbenzenesulfonate (commercially available, 24 mg, 0.093 mmol) and cesium carbonate (70 mg, 0.21 mmol) were suspended in acetonitrile (2 mL). The reaction was stirred at 80° C. overnight then cooled to room temperature, filtered and concentrated. The residue was purified by preparative HPLC (X-bridge C18 OBD 30×50 mm 5 μm column 25-50% MeCN/H$_2$O (5 mM NH$_4$OH) 75 mL/min), and further by preparative HPLC (X-bridge C18 OBD 30×50 mm 5 μm column 10-30% MeCN/H$_2$O (0.1% formic acid) 75 mL/min) to afford the title compound (14 mg, 0.027 mmol).

LCMS: Rt: 2.11 min (LCMS Method 4); MS m/z 477.3 [M+H]$^+$.

$^1$H NMR (400 MHz, CD$_3$OD) δ 8.39 (s, 1H), 7.07 (dd, J=11.8, 9.2 Hz, 1H), 7.02-6.88 (m, 1H), 4.54 (m, 1H), 4.40-4.25 (m, 2H), 4.23-4.04 (m, 3H), 4.02-3.77 (m, 3H), 3.61 (m, 2H), 3.29-3.14 (m, 2H), 3.01 (m, 2H), 2.59 (dd, J=13.2, 7.4 Hz, 1H), 2.36 (m, 2H), 2.19 (dd, J=13.3, 7.9 Hz, 1H), 2.03 (m, 2H), 1.87 (m, 2H), 1.72 (m, 4H).

Example 2HH: ((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol or ((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol and Example 2II ((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol or ((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol

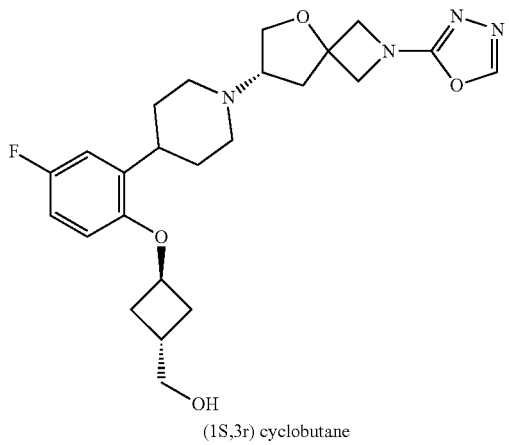

(1S,3r) cyclobutane

-continued

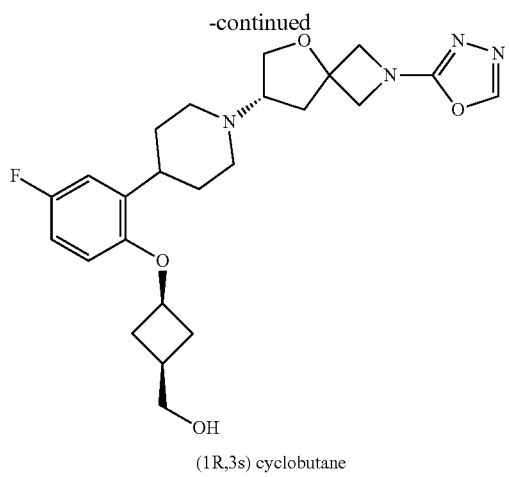

(1R,3s) cyclobutane

Methyl (S)-3-(2-(1-(2-(1,3,4-oxadiazol-2-yl)-5-oxa-2-azaspiro[3.4]octan-7-yl)piperidin-4-yl)-4-fluorophenoxy)cyclobutane-1-carboxylate (Example 2U, Step 1, 29 mg, 0.060 mmol) was dissolved in THF (2 mL) and LiBH$_4$ (2.6 mg, 0.12 mmol) was added at 0° C. The reaction was warmed up slowly to room temperature, stirred overnight and neutralized with a saturated solution of ammonium chloride, extracted EtOAc and the combined organic layers were concentrated. The residue was purified by preparative HPLC (XSelect CSH C18 5 μm 19×150 mm column 15-30% MeCN/H$_2$O (0.1% TFA), 25 mL/min) to afford peak 1 and peak 2. Peak 1 was free-based with PL-HCO3 MP resin column (eluting with methanol) and concentrated to afford Example 2HH (2.0 mg, 0.0043 mmol). Peak 2 was further purified by preparative HPLC (X-bridge C18 OBD 30×50 mm 5 μm column 35-60% MeCN/H$_2$O (5 mM NH$_4$OH), 75 mL/min) to yield Example 2II (2 mg, 0.0043 mmol).

Example 2HH

LCMS: Rt: 1.88 min (LCMS Method 4); MS m/z 459.5 [M+H]$^+$.

$^1$H NMR (400 MHz, CD$_3$OD) δ 8.38 (s, 1H), 6.90 (dd, J=9.8, 3.1 Hz, 1H), 6.81 (td, J=8.4, 3.1 Hz, 1H), 6.65 (dd, J=8.9, 4.5 Hz, 1H), 4.73 (p, J=6.4 Hz, 1H), 4.36-4.24 (m, 2H), 4.17 (q, J=8.7 Hz, 2H), 4.07 (dd, J=8.7, 6.9 Hz, 1H), 3.76 (dd, J=8.7, 7.4 Hz, 1H), 3.62 (d, J=6.7 Hz, 2H), 3.09 (t, J=7.6 Hz, 2H), 3.06-2.94 (m, 1H), 2.90 (d, J=11.2 Hz, 1H), 2.55 (dd, J=13.0, 7.5 Hz, 1H), 2.53-2.40 (m, 1H), 2.39-2.29 (m, 2H), 2.29-2.09 (m, 5H), 1.84 (m, 2H), 1.78-1.61 (m, 2H).

Example 2II

LCMS: Rt: 1.84 min (LCMS Method 4); MS m/z 459.5 [M+H]$^+$.

$^1$H NMR (400 MHz, CD$_3$OD) δ 8.41 (s, 1H), 6.92 (dd, J=9.8, 3.0 Hz, 1H), 6.84 (td, J=8.3, 3.1 Hz, 1H), 6.77 (dd, J=8.9, 4.8 Hz, 1H), 4.58 (p, J=7.0 Hz, 1H), 4.40-4.26 (m, 2H), 4.19 (q, J=8.7 Hz, 2H), 4.09 (dd, J=8.8, 6.9 Hz, 1H), 3.85-3.75 (m, 1H), 3.57 (d, J=5.9 Hz, 2H), 3.19-3.08 (m, 2H), 3.00 (m, 1H), 2.92 (d, J=11.4 Hz, 1H), 2.57 (m, 3H), 2.36-2.12 (m, 4H), 1.87 (m, 4H), 1.71 (m, 2H).

Example 3A: (S)-2-(1,3,4-oxadiazol-2-yl)-7-(4-(2-((S)-tetrahydrofuran-3-yl)phenyl)piperidin-1-yl)-5-oxa-2-azaspiro[3.4]octane or (S)-2-(1,3,4-oxadiazol-2-yl)-7-(4-(2-((R)-tetrahydrofuran-3-yl)phenyl) piperidin-1-yl)-5-oxa-2-azaspiro[3.4]octane and Example 3B: (S)-2-(1,3,4-oxadiazol-2-yl)-7-(4-(2-((S)-tetrahydrofuran-3-yl)phenyl)piperidin-1-yl)-5-oxa-2-azaspiro[3.4]octane or (S)-2-(1,3,4-oxadiazol-2-yl)-7-(4-(2-((R)-tetrahydrofuran-3-yl)phenyl) piperidin-1-yl)-5-oxa-2-azaspiro[3.4]octane

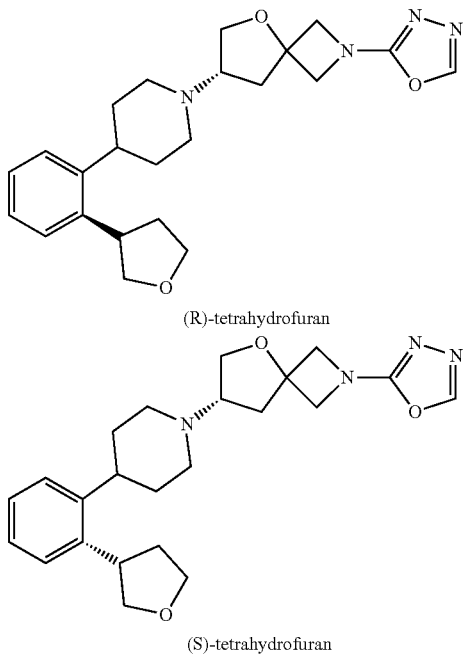

(R)-tetrahydrofuran (S)-tetrahydrofuran

Step 1: tert-butyl (S)-7-(4-(2-(2,5-dihydrofuran-3-yl)phenyl)piperidin-1-yl)-5-oxa-2-azaspiro[3.4]octane-2-carboxylate tert-butyl (S)-7-(4-(2-(((trifluoromethyl)sulfonyl)oxy)phenyl)piperidin-1-yl)-5-oxa-2-azaspiro[3.4]octane-2-carboxylate (Intermediate 9A, 330 mg, 0.634 mmol), 2-(2,5-dihydrofuran-3-yl)-4,4,5,5-tetramethyl-1,3,2-dioxaborolane (124 mg, 0.634 mmol) and potassium phosphate tribasic (404 mg, 1.90 mmol) were dissolved in a mixture of dioxane (1.4 mL), and water (140 μL). Pd(dppf)Cl$_2$·CH$_2$Cl$_2$ (25 mg, 0.032 mmol) was added and the mixture was degassed with nitrogen for 2 minutes, and stirred at 80° C. for 5 hours. The solvent was evaporated under reduced pressure and the residue was diluted with a mixture of DCM, and water. The layers were separated and the organic phase was washed with water, brine, dried with MgSO$_4$, filtered and evaporated under reduced pressure. The residue was purified by FCC (0-40% EtOAc/heptane) to afford the title intermediate (246 mg, 0.558 mmol).

LCMS: Rt: 1.10 min (LCMS Method 2); MS m/z 441.2 [M+H]$^+$.

Step 2: (S)-7-(4-(2-(2,5-dihydrofuran-3-yl)phenyl)piperidin-1-yl)-5-oxa-2-azaspiro[3.4]octane tert-butyl (S)-7-(4-(2-(2,5-dihydrofuran-3-yl)phenyl)piperidin-1-yl)-5-oxa-2-azaspiro[3.4]octane-2-carboxylate (246 mg, 0.558 mmol) was dissolved in DCM (5.5 mL) and cooled to 0° C. and stirred for 10 minutes and then TFA (637 mg, 5.58 mmol) was added and the reaction was stirred for 16 hours at RT. The reaction was then diluted with DCM and washed with 1N NaOH. The DCM layer was dried over sodium sulfate, filtered and concentrated to yield the title intermediate (187 mg, 0.549 mmol) that was used without further purification.

LCMS: Rt: 0.80 min (LCMS Method 2); MS m/z 341.1 [M+H]$^+$.

Step 3: (S)-7-(4-(2-(2,5-dihydrofuran-3-yl)phenyl)piperidin-1-yl)-2-(1,3,4-oxadiazol-2-yl)-5-oxa-2-azaspiro[3.4]octane (S)-7-(4-(2-(2,5-dihydrofuran-3-yl)phenyl)piperidin-1-yl)-5-oxa-2-azaspiro[3.4]octane (187 mg, 0.55 mmol), ethyl 5-bromo-1,3,4-oxadiazole-2-carboxylate (121 mg, 0.55 mmol), and potassium phosphate tribasic (350 mg, 1.65 mmol) were dissolved in a mixture of 2% aqueous TPGS-750-M (1.0 mL), and THF (0.11 mL). The reaction was stirred at room temperature overnight. Next, 4N HCl was added to the adjust pH to 2. The reaction was stirred at room temperature for 3 hours and then basified with 2M LiOH to pH>8. The solution was then extracted with DCM, and the combined organic layers were evaporated under reduced pressure. The residue was purified by FCC (0-7% MeOH/DCM) to afford the title intermediate (38 mg, 0.089 mmol).

LCMS: Rt: 1.85 min (LCMS Method 4); MS m/z 409.7 [M+H]$^+$.

Step 4: (S)-2-(1,3,4-oxadiazol-2-yl)-7-(4-(2-((S)-tetrahydrofuran-3-yl)phenyl)piperidin-1-yl)-5-oxa-2-azaspiro[3.4]octane or (S)-2-(1,3,4-oxadiazol-2-yl)-7-(4-(2-((R)-tetrahydrofuran-3-yl)phenyl)piperidin-1-yl)-5-oxa-2-azaspiro[3.4]octane (S)-7-(4-(2-(2,5-dihydrofuran-3-yl)phenyl)piperidin-1-yl)-2-(1,3,4-oxadiazol-2-yl)-5-oxa-2-azaspiro[3.4]octane (143 mg, 0.35 mmol) and 10% Pd—C (37 mg) were dissolved in MeOH and the reaction was stirred for 16 hours under a balloon of hydrogen. The reaction was then filtered and the crude was purified by preparative HPLC (X-bridge C18 OBD 30×50 mm 5 μm column 25-50% MeCN/H$_2$O (5 mM NH$_4$OH) 75 mL/min). The two diastereomers were then separated by chiral SFC (ChiralPak ID 21×250 mm column, 40% IPA with 10 mM NH$_4$OH, Flow rate: 80 g per minute) to give peak 1 (Example 3A, 32 mg, 0.076 mmol) and peak 2 (Example 3B, 27 mg, 0.064 mmol).

Example 3A

SFC: Rt: 3.99 min (Chiralpak ID 4.6×100 mm 5 μM, 5→55% IPA with 10 mM NH$_4$OH/CO$_2$, 5 mL/min). LCMS: Rt: 1.81 min (LCMS Method 4); MS m/z 411.2 [M+H]$^+$.

$^1$H NMR (DMSO-d$_6$) δ 8.66-8.63 (m, 1H), 7.30-7.20 (m, 2H), 7.19-7.13 (m, 2H), 4.26-4.20 (m, 1H), 4.16-4.10 (m, 2H), 4.05-3.91 (m, 4H), 3.85-3.77 (m, 1H), 3.69-3.59 (m, 2H), 3.58-3.52 (m, 1H), 3.04-2.93 (m, 2H), 2.89-2.75 (m, 2H), 2.44-2.36 (m, 1H), 2.31-2.23 (m, 1H), 2.19-2.04 (m, 3H), 1.95-1.83 (m, 1H), 1.72-1.57 (m, 4H).

Example 3B

SFC: Rt: 4.65 min (Chiralpak ID 4.6×100 mm 5 μM, 5→55% IPA with 10 mM NH$_4$OH/CO$_2$, 5 mL/min). LCMS: Rt: 1.82 min (LCMS Method 4); MS m/z 411.5 [M+H]$^+$.

$^1$H NMR (DMSO-d$_6$) δ 8.64 (s, 1H), 7.31-7.21 (m, 2H), 7.20-7.12 (m, 2H), 4.26-4.20 (m, 1H), 4.16-4.10 (m, 2H), 4.06-3.90 (m, 4H), 3.86-3.77 (m, 1H), 3.69-3.60 (m, 2H), 3.58-3.52 (m, 1H), 3.05-2.92 (m, 2H), 2.90-2.75 (m, 2H), 2.44-2.36 (m, 1H), 2.34-2.22 (m, 1H), 2.19-2.04 (m, 3H), 1.94-1.81 (m, 1H), 1.73-1.59 (m, 4H)

Example 3C: (S)-2-(1,3,4-oxadiazol-2-yl)-7-(4-(2-(tetrahydro-2H-pyran-4-yl)phenyl)piperidin-1-yl)-5-oxa-2-azaspiro[3.4]octane

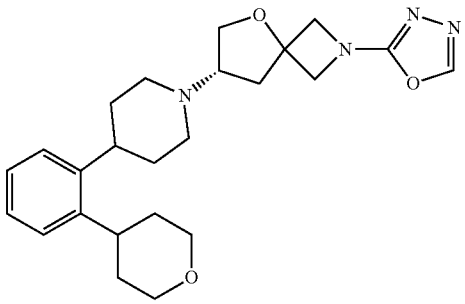 [SMILES: c1ccc(C2CCN([C@@H]3COC4(C3)CN(c3nnco3)C4)CC2)c(C2CCOCC2)c1]

Step 1: tert-butyl (S)-7-(4-(2-(3,6-dihydro-2H-pyran-4-yl)phenyl)piperidin-1-yl)-5-oxa-2-azaspiro[3.4]octane-2-carboxylate tert-butyl (S)-7-(4-(2-(((trifluoromethyl)sulfonyl)oxy)phenyl)piperidin-1-yl)-5-oxa-2-azaspiro[3.4]octane-2-carboxylate (Intermediate 9A, 237 mg, 0.455 mmol), 3,6-dihydro-2Hpyran-4-boronic acid pinacol ester (143 mg, 0.683 mmol), Cs$_2$CO$_3$ (445 mg, 1.366 mmol), and XPhosPd G2 (35.8 mg, 0.046 mmol) were added to a 40 mL vial. Dioxane (5 mL) and water (1 mL) were added and the solution was evacuated and back filled with N$_2$ gas three times. It was then stirred at 80° C. for 4 hr. The reaction was then cooled and extracted with EtOAc. The combined organic layers were dried over magnesium sulfate, filtered and concentrated. The crude was purified by FCC (0-5% MeOH (10% NH$_4$OH)/DCM) to yield the title intermediate (250 mg, 0.455 mmol).

LCMS: Rt: 1.16 min (LCMS Method 2); MS m/z 455.5 [M+H]$^+$.

Step 2: tert-butyl (S)-7-(4-(2-(tetrahydro-2H-pyran-4-yl)phenyl)piperidin-1-yl)-5-oxa-2-azaspiro[3.4]octane-2-carboxylate tert-butyl (S)-7-(4-(2-(3,6-dihydro-2H-pyran-4-yl)phenyl)piperidin-1-yl)-5-oxa-2-azaspiro[3.4]octane-2-carboxylate (250 mg, 0.55 mmol) and 10% Pd—C (117 mg) were dissolved in EtOH (10 mL). The flask was flushed with hydrogen and then the reaction was stirred for 16 hours under a balloon of hydrogen. The solution was filtered and concentrated to yield the title intermediate (250 mg, 0.547 mmol).

LCMS: Rt: 0.77 min (LCMS Method 1); MS m/z 457.5 [M+H]$^+$.

Step 3: (S)-7-(4-(2-(tetrahydro-2H-pyran-4-yl)phenyl)piperidin-1-yl)-5-oxa-2-azaspiro[3.4]octane tert-butyl (S)-7-(4-(2-(tetrahydro-2H-pyran-4-yl)phenyl)piperidin-1-yl)-5-oxa-2-azaspiro[3.4]octane-2-carboxylate (250 mg, 0.547 mmol) was dissolved in DCM (10 mL) and TFA was added (3 mL, 17.6 mmol). The reaction was stirred for 2 hours and then the solvent was concentrated and the residue was taken up in DCM. The DCM solution was washed with sat NaHCO$_3$ and the DCM layer was dried over MgSO$_4$ and concentrated to yield the title intermediate (195 mg, 0.547 mmol).

LCMS: Rt: 0.50 min (LCMS Method 1); MS m/z 357.3 [M+H]$^+$.

Step 4: (S)-2-(1,3,4-oxadiazol-2-yl)-7-(4-(2-(tetrahydro-2H-pyran-4-yl)phenyl)piperidin-1-yl)-5-oxa-2-azaspiro[3.4]octane (S)-7-(4-(2-(tetrahydro-2H-pyran-4-yl)phenyl)piperidin-1-yl)-5-oxa-2-azaspiro[3.4]octane (195 mg, 0.547 mmol), ethyl 5-bromo-1,3,4-oxadiazole-2-carboxylate (157 mg, 0.711 mmol), and K$_3$PO$_4$ (151 mg, 0.711 mmol) were dissolved in a mixture of 2% aqueous TPGS-750-M (6.0 mL), and THF (0.6 mL). The reaction was stirred at room temperature overnight, then a 2M solution of LiOH (2.73 mL, 5.47 mmol) was added, and the reaction was stirred for 2 hours. MeOH and a 4N solution of HCl was added to adjust pH to 2. It was stirred at room temperature for 3 hours, then basified with a 2M solution of LiOH (pH>8), extracted 3 times with DCM, and the combined organic layers were evaporated under reduced pressure. The residue was purified by FCC (0-7% EtOAc/heptane with 1% 7N NH$_4$OH/MeOH), and further by preparative HPLC (XBridge Peptide BEH C18 5 μm 19×150 mm 30-45% MeCN/H$_2$O (5 mM NH$_4$OH) 30 mL/min) to afford the title compound (59 mg, 0.14 mmol).

LCMS: Rt: 1.89 min (LCMS Method 4); MS m/z 425.5 [M+H]$^+$.

$^1$H NMR (400 MHz, CD$_3$OD) δ 8.39 (s, 1H), 7.34-6.98 (m, 4H), 4.38-4.25 (m, 2H), 4.17 (q, J=8.6 Hz, 2H), 4.11-3.98 (m, 3H), 3.79 (dd, J=8.8, 7.3 Hz, 1H), 3.60 (td, J=11.8, 1.9 Hz, 2H), 3.19-3.06 (m, 3H), 2.92 (dd, J=11.7, 3.6 Hz, 2H), 2.56 (dd, J=13.0, 7.5 Hz, 1H), 2.29 (m, 2H), 2.16 (dd, J=13.1, 8.3 Hz, 1H), 1.91-1.69 (m, 6H), 1.67-1.56 (m, 2H).

Example 3D: (S)-7-(4-(5-fluoro-2-(tetrahydro-2H-pyran-4-yl)phenyl)piperidin-1-yl)-2-(1,3,4-oxadiazol-2-yl)-5-oxa-2-azaspiro[3.4]octane

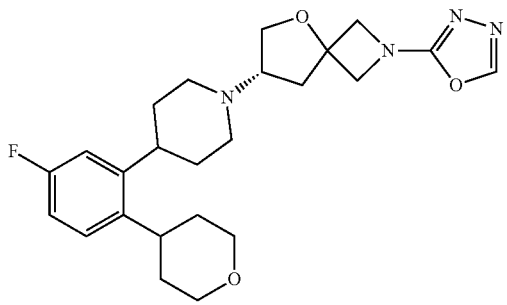 [SMILES: Fc1ccc(C2CCOCC2)c(C2CCN([C@@H]3COC4(C3)CN(c3nnco3)C4)CC2)c1]

Step 1: tert-butyl (S)-7-(4-(2-(3,6-dihydro-2H-pyran-4-yl)-5-fluorophenyl)piperidin-1-yl)-5-oxa-2-azaspiro[3.4]octane-2-carboxylate tert-butyl (S)-7-(4-(5-fluoro-2-(((trifluoromethyl)sulfonyl)oxy)phenyl)piperidin-1-yl)-5-oxa-2-azaspiro[3.4]octane-2-carboxylate (Intermediate 9B, 300 mg, 0.557 mmol), 2-(3,6-dihydro-2H-pyran-4-yl)-4,4,5,5-tetramethyl-1,3,2-dioxaborolane (117 mg, 0.557 mmol), K₃PO₄ (355 mg, 1.671 mmol) and Pd(dppf)Cl2·CH2Cl2 (22.75 mg, 0.028 mmol) were dissolved in dioxane (1.2 mL) and water (0.12 mL). The vial was evacuated and backfilled with nitrogen and this was repeated twice. The reaction was then stirred in a sealed vial at 80° C. for 5 hr. The solvent was concentrated and the residue was taken up in DCM and was washed with water and brine, dried over magnesium sulfate, filtered and concentrated (250 mg, 0.529 mmol).

LCMS: Rt: 1.16 min (LCMS Method 1); MS m/z 473.2 [M+H]⁺.

Step 2: tert-butyl (S)-7-(4-(5-fluoro-2-(tetrahydro-2H-pyran-4-yl)phenyl)piperidin-1-yl)-5-oxa-2-azaspiro[3.4]octane-2-carboxylate tert-butyl (S)-7-(4-(2-(3,6-dihydro-2H-pyran-4-yl)-5-fluorophenyl)piperidin-1-yl)-5-oxa-2-azaspiro[3.4]octane-2-carboxylate (250 mg, 0.529 mmol) and 10% Pd—C (56 mg) were dissolved in MeOH (5.2 mL) and stirred for 16 hours under an atmosphere of hydrogen. The reaction was filtered over a pad of celite and the solvent was removed to yield the title compound (231 mg, 0.487 mmol).

LCMS: Rt: 1.14 min (LCMS Method 2); MS m/z 475.6 [M+H]⁺.

Step 3: (S)-7-(4-(5-fluoro-2-(tetrahydro-2H-pyran-4-yl)phenyl)piperidin-1-yl)-5-oxa-2-azaspiro[3.4]octane tert-butyl (S)-7-(4-(5-fluoro-2-(tetrahydro-2H-pyran-4-yl)phenyl)piperidin-1-yl)-5-oxa-2-azaspiro[3.4]octane-2-carboxylate (231 mg, 0.487 mmol) was dissolved in DCM (4.8 mL) and cooled to 0° C. After incubating for 10 min at 0° C., TFA (0.75 mL, 9.73 mmol) was added and the reaction was warmed to RT and stirred for 16 hours. The solution was concentrated and the residue was dissolved in DCM and washed with 1N NaOH and brine, dried over MgSO₄ filtered and concentrated to yield the title intermediate (111 mg, 0.296 mmol).

LCMS: Rt: 0.53 min (LCMS Method 1); MS m/z 375.1 [M+H]⁺.

Step 4: (S)-7-(4-(5-fluoro-2-(tetrahydro-2H-pyran-4-yl)phenyl)piperidin-1-yl)-2-(1,3,4-oxadiazol-2-yl)-5-oxa-2-azaspiro[3.4]octane (S)-7-(4-(5-fluoro-2-(tetrahydro-2H-pyran-4-yl)phenyl)piperidin-1-yl)-5-oxa-2-azaspiro[3.4]octane (111 mg, 0.296 mmol), ethyl 5-bromo-1,3,4-oxadiazole-2-carboxylate (66 mg, 0.30 mmol), and K₃PO₄ (189 mg, 0.889 mmol) were dissolved in a mixture of 2% aqueous TPGS-750-M (0.53 mL), and THE (0.059 mL). The reaction was treated similarly to Example 1A and the crude was purified by FCC (0-7% MeOH/DCM), and further by preparative HPLC (X-bridge C18 OBD 30×50 mm 5 μm 25-50% MeCN/H₂O (5 mM NH₄OH) 75 mL/min) to afford the title compound (60 mg, 0.13 mmol).

LCMS: Rt: 1.33 min (LCMS Method 4); MS m/z 443.3 [M+H]⁺.

¹H NMR (DMSO-d₆) δ 8.67-8.60 (m, 1H), 7.32-7.23 (m, 1H), 7.06-6.92 (m, 2H), 4.26-4.20 (m, 1H), 4.16-4.10 (m, 2H), 4.06-4.00 (m, 1H), 3.99-3.89 (m, 3H), 3.68-3.59 (m, 1H), 3.53-3.42 (m, 2H), 3.06-2.92 (m, 3H), 2.88-2.74 (m, 2H), 2.46-2.36 (m, 1H), 2.19-2.02 (m, 3H), 1.79-1.49 (m, 8H).

Example 3E: (S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane or (S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane and Example 3F: (S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane or (S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane (S)-tetrahydrofuran (R)-tetrahydrofuran Step 1: tert-butyl (S)-7-(4-(2-(2,5-dihydrofuran-3-yl)-5-fluorophenyl)piperidin-1-yl)-5-oxa-2-azaspiro [3.4]octane-2-carboxylate tert-butyl (S)-7-(4-(5-fluoro-2-(((trifluoromethyl)sulfonyl)oxy)phenyl)piperidin-1-yl)-5-oxa-2-azaspiro[3.4]octane-2-carboxylate (Intermediate 9B, 250 mg, 0.464 mmol), 2-(2,5-dihydrofuran-3-yl)-4,4,5,5-tetramethyl-1,3,2-dioxaborolane (91 mg, 0.464 mmol), and K₃PO₄ (296 mg, 1.393 mmol) were suspended in dioxane (1.0 mL) and water (0.1 mL). Pd(dppf)Cl₂·CH₂Cl₂ (18.95 mg, 0.023 mmol) was added and the vial was evacuated and backfilled with nitrogen. This was repeated twice. The tube was then stirred at 80° C. for 5 hr. The reaction was subsequently concentrated and the residue was dissolved in DCM and washed with water and brine. The organic layer was dried over sodium sulfate and concentrated and the residue was purified by FCC (0-40% EtOAc/heptanes) to yield the title intermediate (207 mg, 0.451 mmol).

LCMS: Rt: 1.16 min (LCMS Method 2); MS m/z 459.3 [M+H]⁺.

Step 2: tert-butyl (7S)-7-(4-(5-fluoro-2-(tetrahydrofuran-3-yl)phenyl)piperidin-1-yl)-5-oxa-2-azaspiro[3.4]octane-2-carboxylate tert-butyl (S)-7-(4-(2-(2,5-dihydrofuran-3-yl)-5-fluorophenyl)piperidin-1-yl)-5-oxa-2-azaspiro[3.4]octane-2-carboxylate (207 mg, 0.451 mmol) and 10% Pd—C (50 mg) were dissolved in MeOH (4.5 mL) and stirred under a balloon of hydrogen for 16 hours. The solution was filtered and washed with MeOH and the filtrate was concentrated to yield the title intermediate (171 mg, 0.371 mmol).
LCMS: Rt: 1.11 min (LCMS Method 2); MS m/z 461.6 [M+H]⁺.

Step 3: (7S)-7-(4-(5-fluoro-2-(tetrahydrofuran-3-yl)phenyl)piperidin-1-yl)-5-oxa-2-azaspiro[3.4]octane tert-butyl (7S)-7-(4-(5-fluoro-2-(tetrahydrofuran-3-yl)phenyl)piperidin-1-yl)-5-oxa-2-azaspiro[3.4]octane-2-carboxylate (171 mg, 0.371 mmol) was dissolved in DCM (3.7 mL) and cooled to 0° C. The reaction was stirred for 10 minutes and then TFA (0.5 mL, 2.94 mmol) was added and the reaction was stirred for 5 hr at 0° C. The reaction was then concentrated and dissolved in DCM and washed with 1N NaOH and brine, dried over sodium sulfate, filtered and concentrated to yield the title intermediate (134 mg, 0.371 mmol).
LCMS: Rt: 0.49 min (LCMS Method 1); MS m/z 361.3 [M+H]⁺.

Step 4: (S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane or (S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane (7S)-7-(4-(5-fluoro-2-(tetrahydrofuran-3-yl)phenyl)piperidin-1-yl)-5-oxa-2-azaspiro[3.4]octane (134 mg, 0.371 mmol), ethyl 5-bromo-1,3,4-oxadiazole-2-carboxylate (90 mg, 0.41 mmol) and K₃PO₄ (260 mg, 1.22 mmol) were dissolved in a mixture of 2% aqueous TPGS-750-M (0.73 mL), and THF (0.082 mL) and the reaction was treated similarly to Example 1A. The crude was purified by FCC (0-7% MeOH/DCM) and further by HPLC (X-bridge C18 OBD 30×50 mm 5 μm 25-50% MeCN/H₂O (5 mM NH₄OH) 75 mL/min) to afford the diastereomeric mixture. The two diastereomers were then separated by SFC (ChiralPak IG 21×250 mm, co-solvent: 35% IPA with 10 mM NH₃, flow rate: 80 g per minute) to give the initial peak Example 3E (18 mg, 0.41 mmol) and the trailing peak Example 3F (17 mg, 0.038 mmol).

Example 3E

SFC: Rt: 3.63 min (Chiralpak IG 4.6×100 mm 5 m, 5→55% IPA with 10 mM NH₄OH/CO₂, 5 mL/min). LCMS: Rt: 1.89 min (LCMS Method 4); MS m/z 429.5 [M+H]⁺.
¹H NMR (DMSO-d₆) δ 8.65 (s, 1H), 7.34-7.28 (m, 1H), 7.06-6.94 (m, 2H), 4.27-4.20 (m, 1H), 4.17-4.10 (m, 2H), 4.06-4.00 (m, 1H), 4.00-3.90 (m, 3H), 3.84-3.75 (m, 1H), 3.68-3.56 (m, 2H), 3.56-3.50 (m, 1H), 3.06-2.91 (m, 2H), 2.90-2.74 (m, 2H), 2.45-2.35 (m, 1H), 2.32-2.23 (m, 1H), 2.20-2.02 (m, 3H), 1.92-1.79 (m, 1H), 1.71-1.57 (m, 4H).

Example 3F

SFC Rt: 3.85 min (Chiralpak IG 4.6×100 mm 5 m, 5→55% IPA with 10 mM NH₄OH/CO₂, 5 mL/min). LCMS: Rt: 1.89 min (LCMS Method 4); MS m/z 429.3 [M+H]⁺.

¹H NMR (DMSO-d₆) δ 8.62 (s, 1H), 7.35-7.27 (m, 1H), 7.07-6.94 (m, 2H), 4.27-4.20 (m, 1H), 4.17-4.10 (m, 2H), 4.06-4.00 (m, 1H), 4.00-3.90 (m, 3H), 3.85-3.75 (m, 1H), 3.69-3.56 (m, 2H), 3.56-3.50 (m, 1H), 3.07-2.90 (m, 2H), 2.90-2.74 (m, 2H), 2.46-2.36 (m, 1H), 2.31-2.23 (m, 1H), 2.20-2.01 (m, 3H), 1.91-1.79 (m, 1H), 1.71-1.59 (m, 4H).

Example 3G: (S)-2-(1,3,4-oxadiazol-2-yl)-7-(4-(2-((tetrahydro-2H-pyran-4-yl)methyl)phenyl)piperidin-1-yl)-5-oxa-2-azaspiro[3.4]octane

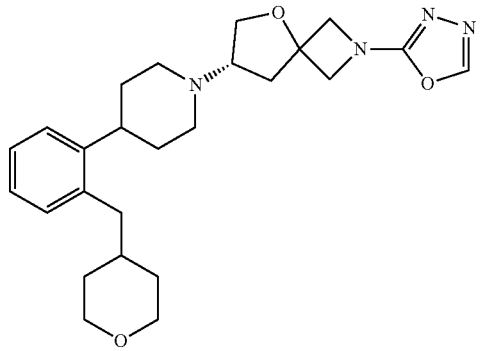 [SMILES: c1ccc(C2CCN([C@@H]3COC4(C3)CN(c3nnco3)C4)CC2)c(CC2CCOCC2)c1]

Step 1: tert-butyl (S)-7-(4-(2-((tetrahydro-2H-pyran-4-yl)methyl)phenyl)piperidin-1-yl)-5-oxa-2-azaspiro[3.4]octane-2-carboxylate tert-butyl (S)-7-(4-(2-((tetrahydro-4H-pyran-4-ylidene)methyl)phenyl)piperidin-1-yl)-5-oxa-2-azaspiro[3.4]octane-2-carboxylate (Intermediate 10D, 80 mg, 0.17 mmol) and Pd(OH)₂/C (24 mg, 0.034 mmol) were dissolved in EtOH (10 mL). The reaction solution was purged with hydrogen gas, stirred under a balloon of hydrogen overnight, filtered through celite pad, and evaporated under reduced pressure. The residue was purified by FCC (0-80% EtOAc/heptane) to afford the title compound (45 mg, 0.083 mmol).
LCMS: Rt: 1.20 min (LCMS Method 2); MS m/z 471.6 m/z [M+H]⁺.

Step 2: (S)-7-(4-(2-((tetrahydro-2H-pyran-4-yl)methyl)phenyl)piperidin-1-yl)-5-oxa-2-azaspiro[3.4]octane tert-butyl (S)-7-(4-(2-((tetrahydro-2H-pyran-4-yl)methyl)phenyl)piperidin-1-yl)-5-oxa-2-azaspiro[3.4]octane-2-carboxylate (45 mg, 0.096 mmol) was dissolved in DCM (1 mL) and TFA (0.5 mL, 2.94 mmol) was added. The reaction was stirred for 2 hours and then the solvent was removed and the residue was dissolved in DCM and washed with 1M NaOH. The DCM layer was concentrated to yield the title intermediate (35 mg, 0.094 mmol).
LCMS: Rt: 0.51 min (LCMS Method 1); MS m/z 371.4 m/z [M+H]⁺.

Step 3: (S)-2-(1,3,4-oxadiazol-2-yl)-7-(4-(2-((tetrahydro-2H-pyran-4-yl)methyl)phenyl)piperidin-1-yl)-5-oxa-2-azaspiro[3.4]octane (S)-7-(4-(2-((tetrahydro-2H-pyran-4-yl)methyl)phenyl)piperidin-1-yl)-5-oxa-2-azaspiro[3.4]octane ethyl 5-bromo-1,3,4-oxadiazole-2-carboxylate (27 mg, 0.12 mmol), and potassium phosphate tribasic (26 mg, 0.12 mmol) were dissolved in a mixture of 2% aqueous TPGS-750-M (0.6 mL), and THF (0.06 mL). The reaction was treated similarly to Example 1A and the crude was purified by preparative HPLC (XBridge Peptide BEH C18 5 μm 19×150 mm 40-55% MeCN/H$_2$O (5 mM NH$_4$OH) 30 mL/min) and by FCC (0-15% MeOH/DCM) to afford the title compound (13 mg, 0.030 mmol).

LCMS: Rt: 2.07 min (LCMS Method 4); MS m/z 439.6 [M+H]$^+$.

$^1$H NMR (400 MHz, CD$_3$OD) δ 8.38 (s, 1H), 7.30-7.22 (m, 1H), 7.19-7.13 (m, 1H), 7.11-7.05 (m, 2H), 4.37-4.26 (m, 2H), 4.18 (t, J=8.1 Hz, 2H), 4.07 (dd, J=8.8, 6.9 Hz, 1H), 3.91 (m, 2H), 3.78 (dd, J=8.8, 7.3 Hz, 1H), 3.35 (dd, J=11.8, 2.0 Hz, 2H), 3.19-3.07 (m, 2H), 3.00-2.77 (m, 2H), 2.58 (m, 3H), 2.38-2.07 (m, 3H), 1.91-1.63 (m, 5H), 1.56 (m, 2H), 1.46-1.09 (m, 2H).

Example 3H: (1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol or (1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol and Example 3I: (1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol or (1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol

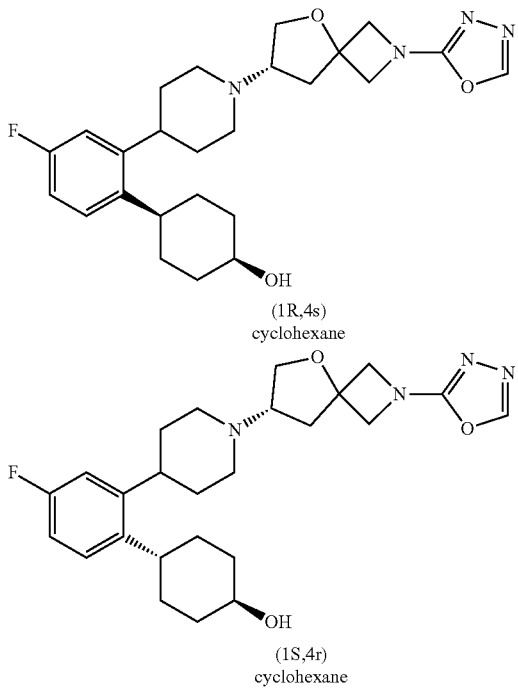

Step 1: tert-butyl (6R)-6-(4-(4'-((tert-butyldimethylsilyl)oxy)-2',3',4',5'-tetrahydro-[1,1'-biphenyl]-2-yl)piperidin-1-yl)-2-azaspiro[3.4]octane-2-carboxylate To a mixture of tert-butyl (R)-6-(4-(2-bromophenyl)piperidin-1-yl)-2-azaspiro[3.4]octane-2-carboxylate (Intermediate 3F, 219 mg, 0.487 mmol), tert-butyldimethyl((4-(4,4,5,5-tetramethyl-1,3,2-dioxaborolan-2-yl)cyclohex-3-en-1-yl)oxy)silane (198 mg, 0.585 mmol), dichloro[1,1'-bis(diphenylphosphino)ferrocene]palladium(II) dichloromethane adduct (17.83 mg, 0.024 mmol) and potassium phosphate (310 mg, 1.462 mmol) was added dioxane (3 mL) and water (0.3 mL). The reaction mixture was stirred at RT for 16 hours and it was then concentrated. The residue was added to water (50 mL) and extracted with EtOAc (×3). The organic extracts were dried over sodium sulfate, filtered and concentrated. The residue was then purified by FCC (0-20% EtOAc (5% 7N NH$_3$ in ammonia)/heptanes). The material was then further purified by FCC (0-5% MeOH/DCM) to yield the title compound (266 mg, 0.441 mmol) as a glassy solid.

LCMS: Rt: 1.78 min (LCMS Method 2); MS m/z 581.0 [M+H]$^+$.

Step 2: tert-butyl (7S)-7-(4-(4-fluoro-4'-hydroxy-2',3',4',5'-tetrahydro-[1,1'-biphenyl]-2-yl)piperidin-1-yl)-5-oxa-2-azaspiro[3.4]octane-2-carboxylate tert-butyl (7S)-7-(4-(4'-((tert-butyldimethylsilyl)oxy)-4-fluoro-2',3',4',5'-tetrahydro-[1,1'-biphenyl]-2-yl)piperidin-1-yl)-5-oxa-2-azaspiro[3.4]octane-2-carboxylate (254 mg, 0.423 mmol) was dissolved in THF (3 mL) and TBAF (1M in THF, 2.114 mL, 2.114 mmol) was added and the reaction was stirred at 40° C. for 16 hours. The reaction was concentrated and the residue was purified by FCC (0-30% EtOAc (8% 7N NH$_3$ in ammonia)/heptanes) to yield the title compound as a yellow oil (200 mg, 0.411 mmol).

LCMS: Rt: 1.11 min (LCMS Method 2); MS m/z 487.6 [M+H]$^+$.

Step 3: tert-butyl (S)-7-(4-(5-fluoro-2-(4-hydroxycyclohexyl)phenyl)piperidin-1-yl)-5-oxa-2-azaspiro[3.4]octane-2-carboxylate tert-butyl (7S)-7-(4-(4-fluoro-4'-hydroxy-2',3',4',5'-tetrahydro-[1,1'-biphenyl]-2-yl)piperidin-1-yl)-5-oxa-2-azaspiro[3.4]octane-2-carboxylate (200 mg, 0.411 mmol) was dissolved in MeOH (1 mL) and Pd—C (4 mg, 0.041 mmol) was added and the reaction was stirred under an atmosphere of hydrogen for 72 hours. The reaction was concentrated and the crude was purified by FCC (0-32% EtOAc (8% 7N NH$_3$ in MeOH)/heptanes) to yield the title compound as a yellow oil (107 mg, 0.197 mmol).

LCMS: Rt: 1.11 min (LCMS Method 2); MS m/z 489.5 [M+H]$^+$.

Step 4: (S)-4-(2-(1-(5-oxa-2-azaspiro[3.4]octan-7-yl)piperidin-4-yl)-4-fluorophenyl)cyclohexan-1-ol To a DCM (750 μL) solution of tert-butyl (S)-7-(4-(5-fluoro-2-(4-hydroxycyclohexyl)phenyl)piperidin-1-yl)-5-oxa-2-azaspiro[3.4]octane-2-carboxylate (107 mg, 0.219 mmol) was added TFA (422 μL, 5.47 mmol). The reaction mixture was let stir at RT for a two hours. The reaction mixture was concentrated, diluted with DCM and washed by 1N NaOH to yield the title compound, which was used without further purification (91 mg, 0.181 mmol).

LCMS: Rt: 0.78 min (LCMS Method 2); MS m/z 389.4 [M+H]+.

Step 5: (1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol or (1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol and Example 3I: (1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol To a THF (1 mL) solution of (S)-4-(2-(1-(5-oxa-2-azaspiro[3.4]octan-7-yl)piperidin-4-yl)-4-fluorophenyl)cyclohexan-1-ol (91 mg, 0.145 mmol) at 0° C. was added ethyl 5-bromo-1,3,4-oxadiazole-2-carboxylate (48.0 mg, 0.174 mmol) and DIEA (0.056 mL, 0.319 mmol). The resulting suspension was stirred at RT for 2 hr, and it was then concentrated and diluted with EtOAc. The crude organic was washed with water and brine. Then the combined organics were dried over MgSO4, filtered and concentrated. The concentrated reaction mixture was diluted in THF (1 mL) and LiOH (36.5 mg, 0.869 mmol) in water (1 mL) was added and the reaction was stirred for 72 hours. 6N HCl (0.241 mL, 1.449 mmol) was then added into the reaction mixture at −5° C. and the solution became clear. It was stirred at RT for 2 hr and then solid Na2CO3 was added until the solution became basic and then the solution was concentrated under vacuum. The residue was diluted with EtOAc and washed with brine and the organic layer was dried over magnesium sulfate and concentrated. The crude was purified by FCC (0-40% EtOAc (10% 7N NH3 in MeOH)/heptanes) to yield a white solid. The two diastereomers were then separated by preparative HPLC (XBridge C18 30×50 mm 10-30% MeCN/H2O (1% formic acid), 75 mL/min). The initial peak was isolated as Example 3H (27.9 mg, 0.055 mmol) as a formate salt and the trailing peak was isolated as Example 3I (1.7 mg, 0.003 mmol) as a formate salt.

Example 3H

LCMS: Rt: 0.97 min (LCMS Method 3); MS m/z 457.5 [M+H]+.
1H NMR (400 MHz, CD3OD) δ 8.40 (s, 1H), 8.32 (d, J=3.6 Hz, 1H), 7.31 (dd, J=8.6, 6.1 Hz, 1H), 6.94 (dd, J=10.9, 2.7 Hz, 1H), 6.89 (td, J=8.5, 2.8 Hz, 1H), 4.41-4.27 (m, 2H), 4.19 (q, J=8.7 Hz, 2H), 4.13-4.03 (m, 2H), 3.94 (m, 1H), 3.45 (dt, J=13.6, 6.0 Hz, 1H), 3.28 (d, J=5.9 Hz, 1H), 3.18-3.09 (m, 1H), 3.03 (p, J=7.8 Hz, 1H), 2.82 (m, 1H), 2.62 (m, 3H), 2.29 (m, 1H), 2.00-1.79 (m, 8H), 1.77-1.62 (m, 2H), 1.53-1.42 (m, 2H).

Example 3I

LCMS: Rt: 1.10 min (LCMS Method 3); MS m/z 457.4 [M+H]+.
1H NMR (400 MHz, CD3OD) δ 8.40 (s, 1H), 8.31 (s, 1H), 7.26 (dd, J=8.6, 6.0 Hz, 1H), 7.00-6.81 (m, 2H), 4.46-4.25 (m, 2H), 4.19 (q, J=8.7 Hz, 2H), 4.15-4.02 (m, 2H), 3.92 (dd, J=9.3, 6.8 Hz, 1H), 3.64 (m, 1H), 3.12 (m, 1H), 3.07-2.94 (m, 1H), 2.91-2.73 (m, 1H), 2.63 (m, 3H), 2.34-2.18 (m, 1H), 2.13-1.98 (m, 2H), 1.97-1.37 (m, 12H).

Example 4A: (S)-7-(4-(5-fluoro-2-(oxetan-3-yloxy)phenyl)piperidin-1-yl)-2-(oxazol-2-yl)-5-oxa-2-azaspiro[3.4]octane

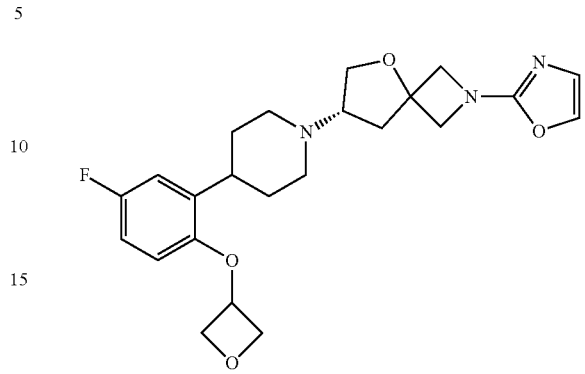

(S)-7-(4-(5-fluoro-2-(oxetan-3-yloxy)phenyl)piperidin-1-yl)-5-oxa-2-azaspiro[3.4]octane (Intermediate 7A, 200 mg, 0.552 mmol), and 2-bromooxazole (98 mg, 0.66 mmol) were dissolved in dioxane (5.5 mL), and the mixture was purged with nitrogen. Pd2(dba)3 (31.7 mg, 0.055 mmol), XantPhos (38 mg, 0.066 mmol), and sodium tert-butoxide (159 mg, 1.66 mmol) were added. The reaction was stirred at 75° C. overnight, filtered with a celite column, rinsed with EtOAc, and concentrated. The residue was purified by FCC (0-10% MeOH (1% NH3)/DCM) to afford the title compound (63 mg, 0.14 mmol) as a light yellow solid.

LCMS: Rt: 1.99 min (LCMS Method 4); MS m/z 430.4 [M+H]+.
1H NMR (400 MHz, CD3OD) δ 7.40 (d, J=1.4 Hz, 1H), 6.96 (dd, J=9.8, 3.2 Hz, 1H), 6.88-6.78 (m, 2H), 6.49 (dd, J=8.8, 4.4 Hz, 1H), 5.25 (m, 1H), 5.05-4.95 (m, 2H), 4.68 (dd, J=7.4, 4.8 Hz, 2H), 4.25-4.16 (m, 2H), 4.13-4.02 (m, 3H), 3.80-3.73 (m, 1H), 3.16-3.03 (m, 3H), 2.91 (d, J=11.5 Hz, 1H), 2.53 (dd, J=13.0, 7.4 Hz, 1H), 2.32-2.19 (m, 2H), 2.13 (dd, J=12.9, 8.4 Hz, 1H), 1.86 (t, J=10.2 Hz, 2H), 1.81-1.64 (m, 2H).

Example 4B: (S)-7-(4-(2-(((R)-1,4-dioxan-2-yl)methoxy)-5-fluorophenyl)piperidin-1-yl)-2-(oxazol-2-yl)-5-oxa-2-azaspiro[3.4]octane

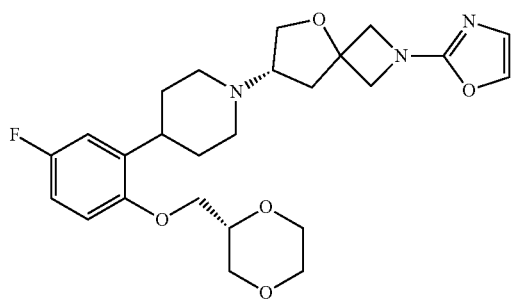 [SMILES: Fc1ccc(OC[C@H]2COCCO2)c(C2CCN([C@@H]3COC4(C3)CN(c3ncco3)C4)CC2)c1]

(S)-7-(4-(2-(((R)-1,4-dioxan-2-yl)methoxy)-5-fluorophenyl)piperidin-1-yl)-5-oxa-2-azaspiro[3.4]octane (Intermediate 7C, 90 mg, 0.22 mmol), and 2-bromooxazole (39 mg, 0.27 mmol) were dissolved in dioxane (2.2 mL), and the mixture was purged with nitrogen. Pd2(dba)3 (12.7 mg, 0.022 mmol), XantPhos (15 mg, 0.027 mmol), and sodium tert-butoxide (64 mg, 0.66 mmol) were added and the reaction was stirred at 75° C. overnight. The reaction was filtered with a celite column, rinsed with EtOAc and concentrated. The residue was purified by FCC (0-10% MeOH (1% NH₃)/DCM) to afford the title compound (32 mg, 0.064 mmol) as a light yellow solid.

LCMS: Rt: 2.12 min (LCMS Method 4); MS m/z 474.4 [M+H]⁺.

$^1$H NMR (400 MHz, CD₃OD) δ 7.40 (d, J=1.2 Hz, 1H), 6.94-6.83 (m, 3H), 6.81 (d, J=1.0 Hz, 1H), 4.26-4.15 (m, 2H), 4.14-4.03 (m, 3H), 4.02-3.87 (m, 4H), 3.87-3.68 (m, 4H), 3.68-3.50 (m, 2H), 3.16-3.06 (m, 2H), 3.06-2.95 (m, 1H), 2.90 (d, J=11.4 Hz, 1H), 2.53 (dd, J=13.0, 7.4 Hz, 1H), 2.23 (m, 2H), 2.12 (dd, J=13.0, 8.5 Hz, 1H), 1.92-1.80 (m, 2H), 1.78-1.57 (m, 2H).

Example 4C: (S)-2-(oxazol-2-yl)-7-(4-(2-(oxetan-3-yloxy)phenyl)piperidin-1-yl)-5-oxa-2-azaspiro[3.4]octane

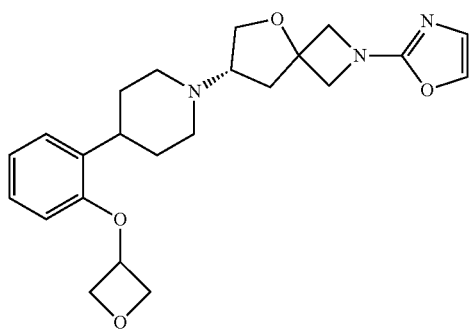 [SMILES: c1ccc(C2CCN([C@@H]3COC4(C3)CN(c3ncco3)C4)CC2)c(OC2COC2)c1]

(S)-7-(4-(2-(oxetan-3-yloxy)phenyl)piperidin-1-yl)-5-oxa-2-azaspiro[3.4]octane (Intermediate 7Q, 130 mg, 0.38 mmol) and 2-bromooxazole (67 mg, 0.45 mmol) were dissolved in dioxane (3.8 mL), and the mixture was purged with nitrogen. Pd₂(dba)₃ (22 mg, 0.038 mmol), XantPhos (26 mg, 0.045 mmol), and sodium tert-butoxide (109 mg, 1.13 mmol) were added and the reaction was stirred at 75° C. overnight. The reaction was filtered over a pad of celite and rinsed with EtOAc and then concentrated. The residue was purified by FCC (0-10% MeOH (1% NH₃)/DCM) to afford the title compound (73 mg, 0.17 mmol) as a light yellow solid.

LCMS: Rt: 1.96 min (LCMS Method 4); MS m/z 412.7 [M+H]⁺.

$^1$H NMR (400 MHz, CD₃OD) δ 7.40 (d, J=1.0 Hz, 1H), 7.22 (dd, J=7.4, 1.8 Hz, 1H), 7.11 (m, 1H), 6.93 (m, 1H), 6.84-6.79 (m, 1H), 6.48 (dd, J=8.3, 1.0 Hz, 1H), 5.27 (m, 1H), 5.06-4.98 (m, 2H), 4.69 (dd, J=7.3, 4.8 Hz, 2H), 4.26-4.16 (m, 2H), 4.14-4.02 (m, 3H), 3.76 (dd, J=8.6, 7.5 Hz, 1H), 3.16-3.00 (m, 3H), 2.90 (m, 1H), 2.53 (dd, J=12.9, 7.4 Hz, 1H), 2.25 (m, 2H), 2.13 (dd, J=12.9, 8.5 Hz, 1H), 1.91-1.71 (m, 4H).

Example 4D: (S)-7-(4-(5-fluoro-2-(((R)-tetrahydrofuran-3-yl)oxy)phenyl)piperidin-1-yl)-2-(oxazol-2-yl)-5-oxa-2-azaspiro[3.4]octane

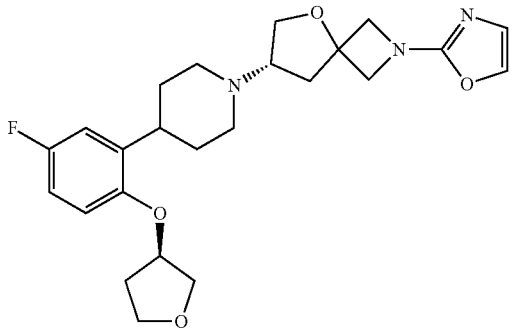 [SMILES: Fc1ccc(O[C@@H]2CCOC2)c(C2CCN([C@@H]3COC4(C3)CN(c3ncco3)C4)CC2)c1]

(S)-7-(4-(5-fluoro-2-(((R)-tetrahydrofuran-3-yl)oxy)phenyl)piperidin-1-yl)-5-oxa-2-azaspiro[3.4]octane (Intermediate 7D, 90 mg, 0.24 mmol) and 2-bromooxazole (42 mg, 0.29 mmol) were dissolved in dioxane (2.4 mL), and the mixture was purged with nitrogen. Pd₂(dba)₃ (14 mg, 0.024 mmol), XantPhos (17 mg, 0.029 mmol), and sodium tert-butoxide (69 mg, 0.72 mmol) were added and the reaction was stirred at 75° C. overnight. The reaction was filtered through a celite column, rinsed with EtOAc and concentrated. The residue was purified by FCC (0-10% MeOH (1% NH₃)/DCM) to afford the title compound (13 mg, 0.029 mmol) as a light yellow solid.

LCMS: Rt: 2.14 min (LCMS Method 4); MS m/z 444.2 [M+H]⁺.

$^1$H NMR (400 MHz, CD₃OD) δ 7.40 (d, J=0.9 Hz, 1H), 6.93 (dd, J=9.8, 2.6 Hz, 1H), 6.90-6.84 (m, 2H), 6.81 (d, J=1.2 Hz, 1H), 5.01 (m, 1H), 4.20 (q, J=8.7 Hz, 2H), 4.13-4.01 (m, 3H), 4.01-3.84 (m, 4H), 3.74 (dd, J=8.7, 7.4 Hz, 1H), 3.08 (m, 2H), 3.03-2.92 (m, 1H), 2.89 (d, J=11.5 Hz, 1H), 2.52 (dd, J=12.9, 7.4 Hz, 1H), 2.30-2.16 (m, 3H), 2.11 (dd, J=13.1, 8.3 Hz, 2H), 1.87-1.74 (m, 2H), 1.67 (m, 2H).

Example 4E: (S)-7-(4-(5-fluoro-2-((tetrahydro-2H-pyran-4-yl)oxy)phenyl)piperidin-1-yl)-2-(oxazol-2-yl)-5-oxa-2-azaspiro[3.4]octane

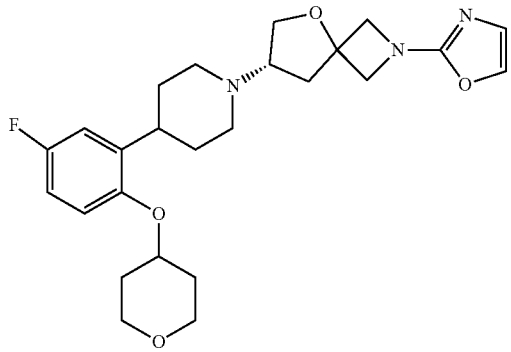 [SMILES: Fc1ccc(OC2CCOCC2)c(C2CCN([C@@H]3COC4(C3)CN(c3ncco3)C4)CC2)c1]

(S)-7-(4-(5-fluoro-2-((tetrahydro-2H-pyran-4-yl)oxy)phenyl)piperidin-1-yl)-5-oxa-2-azaspiro[3.4]octane (Intermediate 7G, 90 mg, 0.23 mmol) and 2-bromooxazole (41 mg, 0.28 mmol) were dissolved in dioxane (2.3 mL), and the mixture was purged with nitrogen. $Pd_2(dba)_3$ (13 mg, 0.023 mmol), XantPhos (16 mg, 0.028 mmol), and sodium tert-butoxide (66 mg, 0.69 mmol) were added and the reaction was stirred at 75° C. overnight. The reaction was filtered through a celite column, rinsed with EtOAc, and concentrated. The residue was purified by FCC (0-10% MeOH (1% $NH_3$)/DCM), and by preparative HPLC (X-Bridge Peptide BEH C18 5 µm 19×150 mm 40-55% $MeCN/H_2O$ (10 mM $NH_4OH$) 75 mL/min) to afford the title compound (12 mg, 0.026 mmol) as a white powder.

LCMS: Rt: 2.22 min (LCMS Method 4); MS m/z 458.7 $[M+H]^+$.

$^1H$ NMR (400 MHz, $CD_3OD$) δ 7.40 (s, 1H), 6.94 (m, 2H), 6.89-6.80 (m, 2H), 4.52 (m, 1H), 4.20 (q, J=8.7 Hz, 2H), 4.14-4.01 (m, 3H), 3.93 (ddd, J=11.6, 6.1, 3.9 Hz, 2H), 3.79-3.71 (m, 1H), 3.60 (ddd, J=11.7, 8.3, 3.3 Hz, 2H), 3.16-2.98 (m, 3H), 2.95-2.85 (m, 1H), 2.53 (dd, J=12.9, 7.4 Hz, 1H), 2.22 (m, 2H), 2.12 (dd, J=12.9, 8.4 Hz, 1H), 2.07-1.96 (m, 2H), 1.83 (m, 2H), 1.71 (m, 4H).

Example 4F: (S)-2-(oxazol-2-yl)-7-(4-(2-(((R)-tetrahydrofuran-3-yl)oxy)phenyl)piperidin-1-yl)-5-oxa-2-azaspiro[3.4]octane

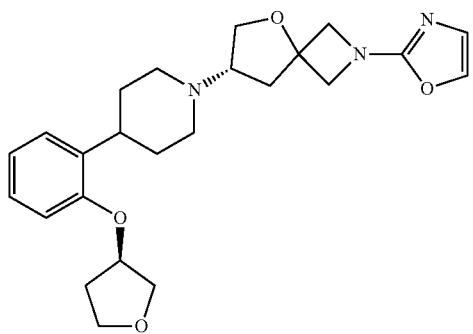 [SMILES: c1ccc(C2CCN([C@@H]3COC4(C3)CN(c3ncco3)C4)CC2)c(O[C@@H]2CCOC2)c1]

(S)-7-(4-(2-(((R)-tetrahydrofuran-3-yl)oxy)phenyl)piperidin-1-yl)-5-oxa-2-azaspiro[3.4]octane (Intermediate 7P, 78 mg, 0.22 mmol) and 2-bromooxazole (39 mg, 0.26 mmol) were dissolved in dioxane (2.2 mL), and the mixture was purged with nitrogen. $Pd_2(dba)_3$ (13 mg, 0.022 mmol), XantPhos (15 mg, 0.026 mmol), and sodium tert-butoxide (63 mg, 0.65 mmol) were added and the reaction was stirred at 75° C. overnight. The reaction was filtered through a celite column, rinsed with EtOAc and concentrated. The residue was purified by FCC (0-10% MeOH (1% $NH_3$)/DCM) to afford the title compound (37 mg, 0.083 mmol) as a light yellow solid.

LCMS: Rt: 2.10 min (LCMS Method 4); MS m/z 426.5 $[M+H]^+$.

$^1H$ NMR (400 MHz, $CD_3OD$) δ 7.40 (d, J=1.0 Hz, 1H), 7.21-7.11 (m, 2H), 6.94-6.86 (m, 2H), 6.81 (d, J=1.2 Hz, 1H), 5.05 (m, 1H), 4.25-4.16 (m, 2H), 4.12-4.02 (m, 3H), 4.00-3.86 (m, 4H), 3.78-3.71 (m, 1H), 3.15-3.04 (m, 2H), 2.98 (m, 1H), 2.92-2.85 (m, 1H), 2.53 (dd, J=12.9, 7.4 Hz, 1H), 2.30-2.18 (m, 3H), 2.12 (ddd, J=13.0, 7.6, 4.8 Hz, 2H), 1.87-1.66 (m, 4H).

Example 4G: (S)-7-(4-(2-((2-oxaspiro[3.3]heptan-6-yl)oxy)-5-fluorophenyl)piperidin-1-yl)-2-(oxazol-2-yl)-5-oxa-2-azaspiro[3.4]octane

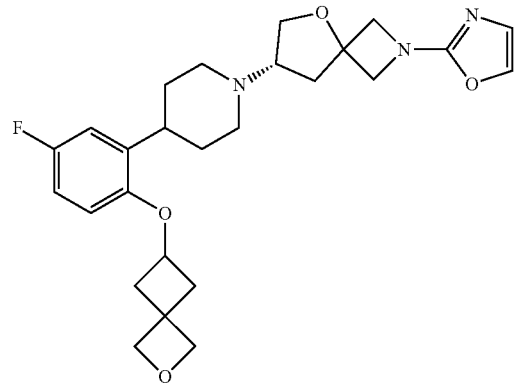 [SMILES: Fc1ccc(OC2CC3(COC3)C2)c(C2CCN([C@@H]3COC4(C3)CN(c3ncco3)C4)CC2)c1]

(S)-7-(4-(2-((2-oxaspiro[3.3]heptan-6-yl)oxy)-5-fluorophenyl)piperidin-1-yl)-5-oxa-2-azaspiro[3.4]octane (Intermediate 7NN, 90 mg, 0.22 mmol) and 2-bromooxazole (40 mg, 0.27 mmol) were dissolved in dioxane (2.2 mL), and the mixture was purged with nitrogen. $Pd_2(dba)_3$ (13 mg, 0.022 mmol), XantPhos (16 mg, 0.028 mmol), and sodium tert-butoxide (65 mg, 0.67 mmol) were added and the reaction was stirred at 75° C. overnight. The reaction was filtered through a celite column, rinsed with EtOAc and concentrated. The residue was purified by preparative HPLC (X-bridge C18 OBD 30×50 mm 5 µm column 25-50% $MeCN/H_2O$ (5 mM $NH_4OH$) 75 mL/min) to afford the title compound (10 mg, 0.021 mmol) as a white powder.

LCMS: Rt: 2.24 min (LCMS Method 4); MS m/z 470.5 $[M+H]^+$.

$^1H$ NMR (400 MHz, $CD_3OD$) δ 7.40 (s, 1H), 6.90 (dd, J=9.8, 3.0 Hz, 1H), 6.87-6.77 (m, 2H), 6.70 (dd, J=9.0, 4.6 Hz, 1H), 4.72 (d, J=30.8 Hz, 4H), 4.53 (p, J=6.7 Hz, 1H), 4.20 (q, J=8.7 Hz, 2H), 4.13-4.01 (m, 3H), 3.75 (dd, J=8.7, 7.4 Hz, 1H), 3.13-3.04 (m, 2H), 2.99-2.85 (m, 2H), 2.85-2.76 (m, 2H), 2.52 (dd, J=13.0, 7.4 Hz, 1H), 2.34-2.26 (m, 2H), 2.21 (m, 2H), 2.11 (dd, J=12.9, 8.5 Hz, 1H), 1.85-1.75 (m, 2H), 1.75-1.61 (m, 2H).

Example 4H: (S)-2-(oxazol-2-yl)-7-(4-(2-(((S)-tetrahydrofuran-3-yl)oxy)phenyl)piperidin-1-yl)-5-oxa-2-azaspiro[3.4]octane

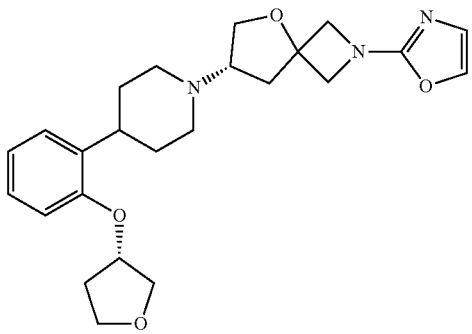 [SMILES: c1ccc(C2CCN([C@@H]3COC4(C3)CN(c3ncco3)C4)CC2)c(O[C@H]2CCOC2)c1]

(S)-7-(4-(2-(((S)-tetrahydrofuran-3-yl)oxy)phenyl)piperidin-1-yl)-5-oxa-2-azaspiro[3.4]octane (Intermediate 7H, 78 mg, 0.22 mmol) and 2-bromooxazole (39 mg, 0.26 mmol) were dissolved in dioxane (2.2 mL), and the mixture was purged with nitrogen. Pd$_2$(dba)$_3$ (12 mg, 0.022 mmol), XantPhos (15 mg, 0.026 mmol), and sodium tert-butoxide (63 mg, 0.65 mmol) were added and the reaction was stirred at 75° C. overnight. The reaction was filtered through a celite column, rinsed with EtOAc and concentrated. The residue was purified twice by FCC (0-10% MeOH (1% NH$_3$)/DCM) to afford the title compound (18 mg, 0.041 mmol) as a light yellow solid.

LCMS: Rt: 2.08 min (LCMS Method 4); MS m/z 426.3 [M+H]$^+$.

$^1$H NMR (400 MHz, CD$_3$OD) δ 7.40 (s, 1H), 7.21-7.12 (m, 2H), 6.94-6.86 (m, 2H), 6.81 (s, 1H), 5.05 (m, 1H), 4.25-4.16 (m, 2H), 4.13-4.03 (m, 3H), 4.00-3.87 (m, 4H), 3.78-3.72 (m, 1H), 3.14-3.06 (m, 2H), 2.98 (m, 1H), 2.89 (d, J=11.4 Hz, 1H), 2.53 (dd, J=13.0, 7.4 Hz, 1H), 2.30-2.17 (m, 3H), 2.12 (ddd, J=13.0, 7.4, 3.8 Hz, 2H), 1.74 (m, 4H).

Example 41: (S)-7-(4-(5-fluoro-2-methoxyphenyl)piperidin-1-yl)-2-(oxazol-2-yl)-5-oxa-2-azaspiro[3.4]octane

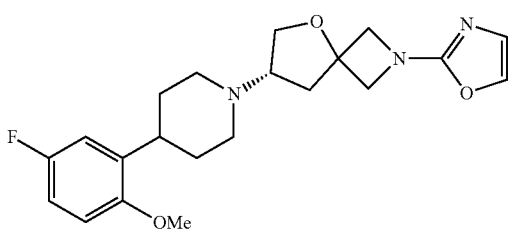 [SMILES: COc1ccc(F)cc1C1CCN([C@@H]2COC3(C2)CN(c2ncco2)C3)CC1]

(S)-7-(4-(5-fluoro-2-methoxyphenyl)piperidin-1-yl)-5-oxa-2-azaspiro[3.4]octane (Intermediate 7DD, 70 mg, 0.22 mmol) and 2-bromooxazole (39 mg, 0.26 mmol) were dissolved in dioxane (2.2 mL), and the mixture was purged with nitrogen. Pd$_2$(dba)$_3$ (12 mg, 0.022 mmol), XantPhos (15 mg, 0.026 mmol), and sodium tert-butoxide (42 mg, 0.44 mmol) were added and the reaction was stirred at 75° C. overnight. The reaction was filtered through a celite column, rinsed with EtOAc, and acetonitrile and then concentrated. The residue was purified by preparative HPLC (X-bridge C18 OBD 30×50 mm 5 μm column 25-50% MeCN/H$_2$O (5 mM NH$_4$OH) 75 mL/min) to afford the title compound (45 mg, 0.11 mmol) as a light yellow solid.

LCMS: Rt: 2.27 min (LCMS Method 4); MS m/z 388.8 [M+H]$^+$.

$^1$H NMR (400 MHz, CD$_3$OD) δ 7.40 (s, 1H), 6.93-6.85 (m, 3H), 6.81 (d, J=1.0 Hz, 1H), 4.20 (q, J=8.7 Hz, 2H), 4.12-4.02 (m, 3H), 3.80 (s, 3H), 3.74 (dd, J=8.7, 7.4 Hz, 1H), 3.14-3.04 (m, 2H), 2.98 (tt, J=12.2, 3.7 Hz, 1H), 2.92-2.84 (m, 1H), 2.52 (dd, J=13.0, 7.4 Hz, 1H), 2.21 (m, 2H), 2.11 (dd, J=13.0, 8.5 Hz, 1H), 1.80 (m, 2H), 1.69 (m, 2H).

Example 4J: (S)-2-(oxazol-2-yl)-7-(4-(2-((tetrahydro-2H-pyran-4-yl)oxy)phenyl)piperidin-1-yl)-5-oxa-2-azaspiro[3.4]octane

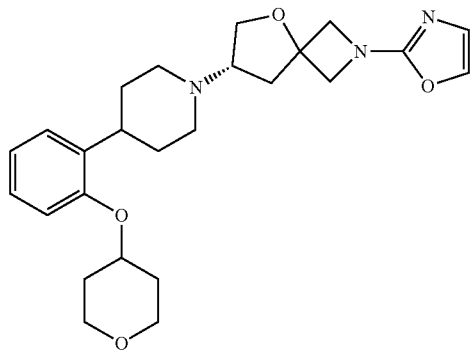 [SMILES: c1ccc(C2CCN([C@@H]3COC4(C3)CN(c3ncco3)C4)CC2)c(OC2CCOCC2)c1]

(S)-7-(4-(2-((tetrahydro-2H-pyran-4-yl)oxy)phenyl)piperidin-1-yl)-5-oxa-2-azaspiro[3.4]octane (Intermediate 7OO, 148 mg, 0.40 mmol) and 2-bromooxazole (71 mg, 0.48 mmol) were dissolved in dioxane (5.0 mL), and the mixture was purged with nitrogen. Pd$_2$(dba)$_3$ (23 mg, 0.040 mmol), XantPhos (28 mg, 0.048 mmol), and sodium tert-butoxide (115 mg, 1.19 mmol) were added and the reaction was stirred at 75° C. overnight. The reaction was filtered through a celite column, rinsed with EtOAc, concentrated. The residue was purified by preparative HPLC (X-bridge C18 OBD 30×50 mm 5 μm column 25-50% MeCN/H$_2$O (5 mM NH$_4$OH) 75 mL/min) to afford the title compound (68 mg, 0.15 mmol) as a light yellow solid.

LCMS: Rt: 1.04 min (LCMS Method 3); MS m/z 440.4 [M+H]$^+$.

$^1$H NMR (400 MHz, CD$_3$OD) δ 7.30 (s, 1H), 7.12-6.99 (m, 2H), 6.90-6.76 (m, 2H), 6.72 (d, J=1.0 Hz, 1H), 4.50 (tt, J=7.6, 3.8 Hz, 1H), 4.11 (q, J=8.7 Hz, 2H), 4.05-3.92 (m, 3H), 3.84 (ddd, J=11.5, 6.2, 3.7 Hz, 2H), 3.70-3.60 (m, 1H), 3.52 (ddd, J=11.4, 8.1, 3.3 Hz, 2H), 3.09-2.87 (m, 3H), 2.80 (m, 1H), 2.44 (dd, J=12.8, 7.4 Hz, 1H), 2.24-1.86 (m, 5H), 1.83-1.55 (m, 6H).

Example 4K: (S)-1-(4-fluoro-2-(1-(2-(oxazol-2-yl)-5-oxa-2-azaspiro[3,4]octan-7-yl)piperidin-4-yl)phenoxy)-2-methylpropan-2-ol

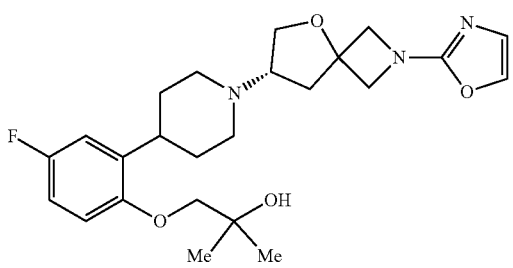 [SMILES: CC(C)(O)COc1ccc(F)cc1C1CCN([C@@H]2COC3(C2)CN(c2ncco2)C3)CC1]

(S)-1-(2-(1-(5-oxa-2-azaspiro[3.4]octan-7-yl)piperidin-4-yl)-4-fluorophenoxy)-2-methylpropan-2-ol (Intermediate 7U, 45 mg, 0.12 mmol) and 2-bromooxazole (21 mg, 0.14 mmol) were dissolved in dioxane (1.2 mL), and the mixture was purged with nitrogen. Pd$_2$(dba)$_3$ (6.8 mg, 0.012 mmol), XantPhos (8.3 mg, 0.014 mmol), and sodium tert-butoxide (23 mg, 0.24 mmol) were added and the reaction was stirred at 75° C. overnight. The reaction was filtered through a celite column, rinsed with EtOAc and acetonitrile and the filtrate was concentrated. The residue was purified by FCC (0-10% MeOH (1% NH$_3$)/DCM) to afford the title compound (25 mg, 0.053 mmol) as a light yellow solid.

LCMS: Rt: 2.09 min (LCMS Method 4); MS m/z 446.6 [M+H]$^+$.

$^1$H NMR (400 MHz, CD$_3$OD) δ 7.40 (s, 1H), 6.95-6.83 (m, 3H), 6.81 (s, 1H), 4.20 (q, J=8.7 Hz, 2H), 4.12-4.03 (m, 3H), 3.75 (s, 3H), 3.14-3.04 (m, 3H), 2.90 (dd, J=11.4, 4.4 Hz, 1H), 2.53 (dd, J=13.0, 7.4 Hz, 1H), 2.24 (m, 2H), 2.11 (dd, J=13.0, 8.5 Hz, 1H), 1.86 (m, 2H), 1.69 (m, 3H), 1.34 (s, 6H).

Example 4L: (S)-7-(4-(5-fluoro-2-(2-methoxyethoxy)phenyl)piperidin-1-yl)-2-(oxazol-2-yl)-5-oxa-2-azaspiro[3.4]octane

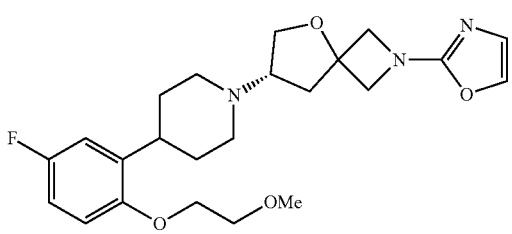 [SMILES: COCCOc1ccc(F)cc1C1CCN([C@@H]2COC3(C2)CN(c2ncco2)C3)CC1]

(S)-7-(4-(5-fluoro-2-(2-methoxyethoxy)phenyl)piperidin-1-yl)-5-oxa-2-azaspiro[3.4]octane (Intermediate 7N, 65 mg, 0.18 mmol) and 2-bromooxazole (32 mg, 0.21 mmol) were dissolved in dioxane (1.8 mL), and the mixture was purged with nitrogen. Pd$_2$(dba)$_3$ (10 mg, 0.018 mmol), XantPhos (12 mg, 0.021 mmol), and sodium tert-butoxide (34 mg, 0.36 mmol) were added and the reaction was stirred at 75° C. overnight. The reaction was filtered through a celite column, rinsed with EtOAc and acetonitrile and the filtrate was concentrated. The residue was purified by FCC (0-7% MeOH/DCM), and by preparative HPLC (X-bridge C18 OBD 30×50 mm 5 μm column 35-60% MeCN/H$_2$O (5 mM NH$_4$OH) 75 mL/min) to afford the title compound (25 mg, 0.057 mmol).

LCMS: Rt: 2.20 min (LCMS Method 4); MS m/z 432.3 [M+H]$^+$.

$^1$H NMR (400 MHz, DMSO-d$_6$) δ 7.57 (s, 1H), 7.03-6.92 (m, 3H), 6.83 (d, J=0.6 Hz, 1H), 4.13 (d, J=8.5 Hz, 1H), 4.09-4.01 (m, 5H), 3.96-3.89 (m, 2H), 3.68-3.63 (m, 2H), 3.62-3.56 (m, 1H), 3.03-2.73 (m, 5H), 2.42-2.34 (m, 1H), 2.11-1.96 (m, 4H), 1.80-1.64 (m, 2H), 1.57 (m, 2H).

Example 4M: (S)-7-(4-(2-((2-oxaspiro[3.3]heptan-6-yl)oxy)phenyl)piperidin-1-yl)-2-(oxazol-2-yl)-5-oxa-2-azaspiro[3.4]octane

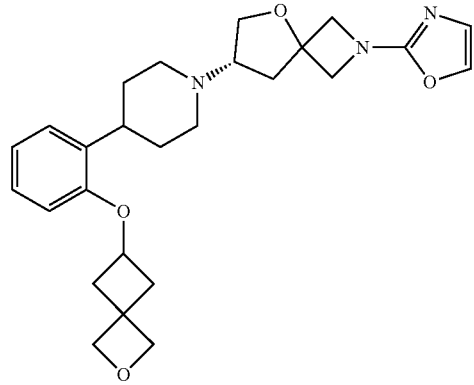 [SMILES: c1ccc(C2CCN([C@@H]3COC4(C3)CN(c3ncco3)C4)CC2)c(OC2CC3(COC3)C2)c1]

(S)-7-(4-(2-((2-oxaspiro[3.3]heptan-6-yl)oxy)phenyl)piperidin-1-yl)-5-oxa-2-azaspiro[3.4]octane (Intermediate 7I1, 110 mg, 0.29 mmol) and 2-bromooxazole (51 mg, 0.34 mmol) were dissolved in dioxane (2.9 mL), and the mixture was purged with nitrogen. Pd$_2$(dba)$_3$ (16 mg, 0.029 mmol), XantPhos (20 mg, 0.034 mmol), and sodium tert-butoxide (82 mg, 0.86 mmol) were added and the reaction was stirred at 75° C. overnight. The reaction was filtered through a celite column, rinsed with EtOAc, and concentrated. The residue was purified by FCC (0-10% MeOH (1% NH$_3$)/DCM), and by preparative HPLC (X-bridge C18 OBD 30×50 mm 5 μm column 25-50% MeCN/H$_2$O (5 mM NH$_4$OH) 75 mL/min) to afford the title compound (9.5 mg, 0.021 mmol).

LCMS: Rt: 2.18 min (LCMS Method 4); MS m/z 452.4 [M+H]$^+$.

$^1$H NMR (400 MHz, CD$_3$OD) δ 7.40 (d, J=1.0 Hz, 1H), 7.19-7.06 (m, 2H), 6.88 (dd, J=8.1, 6.9 Hz, 1H), 6.81 (d, J=1.0 Hz, 1H), 6.72 (d, J=8.2 Hz, 1H), 4.72 (d, J=31.9 Hz, 4H), 4.62-4.52 (m, 1H), 4.21 (q, J=8.8 Hz, 2H), 4.11 (s, 3H), 3.75 (t, J=8.1 Hz, 1H), 3.15-3.04 (m, 2H), 3.02-2.85 (m, 2H), 2.85-2.77 (m, 2H), 2.53 (dd, J=12.9, 7.4 Hz, 1H), 2.37-2.26 (m, 2H), 2.26-2.16 (m, 2H), 2.12 (dd, J=12.9, 8.5 Hz, 1H), 1.76 (m, 4H).

Example 4N: (S)-7-(4-(2-methoxyphenyl)piperidin-1-yl)-2-(oxazol-2-yl)-5-oxa-2-azaspiro[3.4]octane

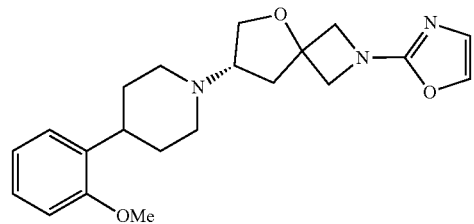 [SMILES: COc1ccccc1C1CCN([C@@H]2COC3(C2)CN(c2ncco2)C3)CC1]

(S)-7-(4-(2-methoxyphenyl)piperidin-1-yl)-5-oxa-2-azaspiro[3.4]octane (Intermediate 7X, 52 mg, 0.17 mmol) and 2-bromooxazole (31 mg, 0.21 mmol) were dissolved in dioxane (1.7 mL), and the mixture was purged with nitrogen. Pd$_2$(dba)$_3$ (9.9 mg, 0.017 mmol), XantPhos (12 mg, 0.021 mmol), and sodium tert-butoxide (31 mg, 0.34 mmol) were added, and the reaction was stirred at 75° C. overnight. The reaction was filtered with a celite column, rinsed with EtOAc and acetonitrile and concentrated. The residue was purified by preparative HPLC (X-bridge C18 OBD 30×50 mm 5 μm column 35-60% MeCN/H₂O (5 mM NH₄OH) 75 mL/min) to afford the title compound (9.4 mg, 0.024 mmol).

LCMS: Rt: 2.19 min (LCMS Method 4); MS m/z 370.3 [M+H]⁺.

$^1$H NMR (400 MHz, CD$_3$OD) δ 7.40 (d, J=1.3 Hz, 1H), 7.21-7.10 (m, 2H), 6.89 (dd, J=14.1, 7.7 Hz, 2H), 6.81 (d, J=1.0 Hz, 1H), 4.32-4.13 (m, 2H), 4.14-4.01 (m, 3H), 3.81 (s, 3H), 3.80-3.70 (m, 1H), 3.08 (t, J=7.7 Hz, 3H), 2.88 (d, J=11.9 Hz, 1H), 2.52 (dd, J=13.0, 7.4 Hz, 1H), 2.27-2.17 (m, 2H), 2.12 (dd, J=13.1, 8.4 Hz, 1H), 1.90-1.66 (m, 4H).

Example 4O: (S)-7-(4-(4,5-difluoro-2-(oxetan-3-ylmethoxy)phenyl)piperidin-1-yl)-2-(oxazol-2-yl)-5-oxa-2-azaspiro[3.4]octane

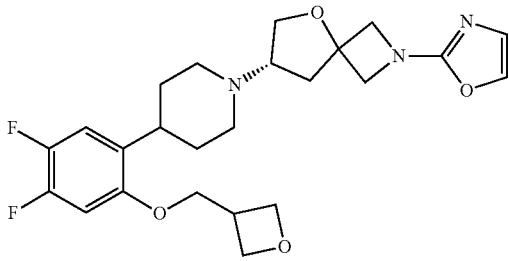 [SMILES: Fc1cc(OCC2COC2)c(C2CCN([C@@H]3COC4(C3)CN(c3ncco3)C4)CC2)cc1F]

(S)-7-(4-(4,5-difluoro-2-(oxetan-3-ylmethoxy)phenyl)piperidin-1-yl)-5-oxa-2-azaspiro[3.4]octane (Intermediate 7JJ, 100 mg, 0.254 mmol) and 2-bromooxazole (45 mg, 0.30 mmol) were dissolved in dioxane (2.5 mL), and the mixture was purged with nitrogen. Pd$_2$(dba)$_3$ (15 mg, 0.025 mmol), XantPhos (18 mg, 0.030 mmol), and sodium tert-butoxide (73 mg, 0.76 mmol) were added, and the reaction was stirred at 75° C. overnight. The reaction was filtered through a celite column, rinsed with EtOAc and concentrated. The residue was purified by FCC (0-10% MeOH (1% NH$_3$)/DCM), and by preparative HPLC (X-bridge C18 OBD 30×50 mm 5 μm column 25-50% MeCN/H₂O (5 mM NH₄OH) 75 mL/min) to afford the title compound (20 mg, 0.041 mmol).

LCMS: Rt: 2.15 min (LCMS Method 4); MS m/z 462.3 [M+H]⁺.

$^1$H NMR (400 MHz, CD$_3$OD) δ 7.40 (d, J=1.3 Hz, 1H), 7.08 (dd, J=11.9, 9.1 Hz, 1H), 6.94 (dd, J=12.6, 6.9 Hz, 1H), 6.81 (s, 1H), 4.93-4.87 (m, 2H), 4.63 (t, J=6.1 Hz, 2H), 4.26-4.11 (m, 4H), 4.11-3.99 (m, 3H), 3.74 (dd, J=8.7, 7.4 Hz, 1H), 3.47 (m, 1H), 3.15-3.04 (m, 2H), 3.04-2.91 (m, 1H), 2.88 (m, 1H), 2.51 (dd, J=12.9, 7.4 Hz, 1H), 2.21 (m, 2H), 2.11 (dd, J=13.0, 8.5 Hz, 1H), 1.82 (m, 2H), 1.66 (m, 2H).

Example 4P: (S)-7-(4-(4,5-difluoro-2-((3-fluorooxetan-3-yl)methoxy)phenyl)piperidin-1-yl)-2-(oxazol-2-yl)-5-oxa-2-azaspiro[3.4]octane

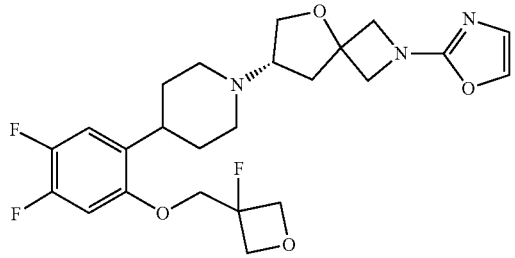 [SMILES: Fc1cc(OCC2(F)COC2)c(C2CCN([C@@H]3COC4(C3)CN(c3ncco3)C4)CC2)cc1F]

(S)-7-(4-(4,5-difluoro-2-((3-fluorooxetan-3-yl)methoxy)phenyl)piperidin-1-yl)-5-oxa-2-azaspiro[3.4]octane (Intermediate 7KK, 100 mg, 0.242 mmol) and 2-bromooxazole (43 mg, 0.29 mmol) were dissolved in dioxane (2.5 mL), and the mixture was purged with nitrogen. Pd$_2$(dba)$_3$ (14 mg, 0.024 mmol), XantPhos (17 mg, 0.029 mmol), and sodium tert-butoxide (70 mg, 0.73 mmol) were added, and the reaction was stirred at 75° C. overnight. The reaction was filtered through a celite column, rinsed with EtOAc, and the filtrate was concentrated. The residue was purified by FCC (0-10% MeOH (1% NH$_3$)/DCM) to afford the title compound (33 mg, 0.069 mmol).

LCMS: Rt: 2.22 min (LCMS Method 4); MS m/z 480.1 [M+H]⁺.

$^1$H NMR (400 MHz, CD$_3$OD) δ 7.40 (d, J=0.9 Hz, 1H), 7.10 (dd, J=11.8, 9.1 Hz, 1H), 7.00 (dd, J=12.3, 6.8 Hz, 1H), 6.83-6.80 (m, 1H), 4.84-4.71 (m, 4H), 4.38 (s, 1H), 4.33 (s, 1H), 4.20 (q, J=8.7 Hz, 2H), 4.14-4.00 (m, 3H), 3.74 (dd, J=8.7, 7.4 Hz, 1H), 3.07 (p, J=7.0 Hz, 2H), 2.99-2.83 (m, 2H), 2.52 (dd, J=12.8, 7.4 Hz, 1H), 2.19 (m, 2H), 2.10 (dd, J=12.9, 8.5 Hz, 1H), 1.82 (m, 2H), 1.65 (m, 2H).

Example 4Q: (S)-7-(4-(4,5-difluoro-2-(oxetan-3-yloxy)phenyl)piperidin-1-yl)-2-(oxazol-2-yl)-5-oxa-2-azaspiro[3.4]octane

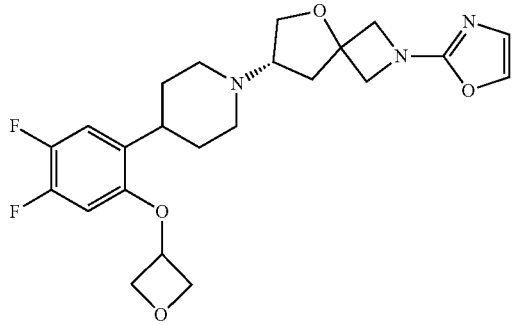 [SMILES: Fc1cc(OC2COC2)c(C2CCN([C@@H]3COC4(C3)CN(c3ncco3)C4)CC2)cc1F]

(S)-7-(4-(4,5-difluoro-2-(oxetan-3-yloxy)phenyl)piperidin-1-yl)-5-oxa-2-azaspiro[3.4]octane (Intermediate 7LL, 140 mg, 0.368 mmol) and 2-bromooxazole (65 mg, 0.44 mmol) were dissolved in dioxane (3.7 mL), and the mixture was purged with nitrogen. Pd$_2$(dba)$_3$ (21 mg, 0.037 mmol), XantPhos (26 mg, 0.044 mmol), and sodium tert-butoxide (106 mg, 1.10 mmol) were added, and the reaction was stirred at 75° C. overnight. The reaction was filtered through a celite column, rinsed with EtOAc, and the filtrate was concentrated. The residue was purified by FCC (0-10% MeOH (1% NH$_3$)/DCM) to afford the title compound (36 mg, 0.076 mmol).

LCMS: Rt: 2.10 min (LCMS Method 4); MS m/z 448.4 [M+H]$^+$.

$^1$H NMR (400 MHz, CD$_3$OD) δ 7.40 (s, 1H), 7.12 (dd, J=11.8, 9.1 Hz, 1H), 6.81 (d, J=0.9 Hz, 1H), 6.52 (dd, J=12.2, 6.8 Hz, 1H), 5.29-5.21 (m, 1H), 5.01 (dd, J=7.4, 5.7 Hz, 2H), 4.67 (dd, J=7.6, 4.9 Hz, 2H), 4.26-4.14 (m, 2H), 4.14-3.99 (m, 3H), 3.75 (dd, J=8.7, 7.4 Hz, 1H), 3.16-3.07 (m, 2H), 3.07-2.94 (m, 1H), 2.90 (dd, J=11.6, 2.6 Hz, 1H), 2.53 (dd, J=13.0, 7.4 Hz, 1H), 2.24 (m, 2H), 2.12 (dd, J=13.0, 8.4 Hz, 1H), 1.91-1.80 (m, 2H), 1.71 (m, 2H).

Example 4R: (S)-2-(oxazol-2-yl)-7-(4-(2-(pyrimidin-5-yl)phenyl)piperidin-1-yl)-5-oxa-2-azaspiro[3.4]octane

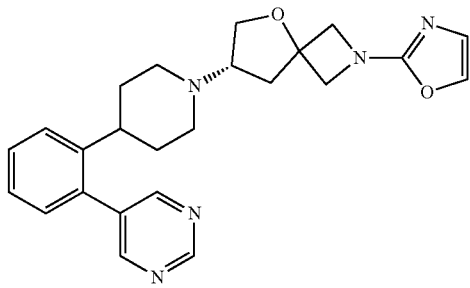 [SMILES: c1ccc(C2CCN([C@@H]3COC4(C3)CN(c3ncco3)C4)CC2)c(-c2cncnc2)c1]

(S)-7-(4-(2-(pyrimidin-5-yl)phenyl)piperidin-1-yl)-5-oxa-2-azaspiro[3.4]octane (Intermediate 7FF, 12 mg, 0.034 mmol) and 2-bromooxazole (15 mg, 0.10 mmol) were dissolved in dioxane (3 mL), and the mixture was purged with nitrogen. Pd$_2$(dba)$_3$ (3.1 mg, 0.0031 mmol), XantPhos (2.4 mg, 0.0041 mmol), and sodium tert-butoxide (19 mg, 0.17 mmol) were added. The reaction was stirred at 75° C. overnight. The reaction was filtered through a silica gel plug, rinsed with EtOAc, and the filtrate was concentrated. The residue was purified by preparative HPLC (X-Bridge Peptide BEH C18 5 μm 19×150 mm 30-45% MeCN/H$_2$O (10 mM NH$_4$OH) 75 mL/min) to afford the title compound (4.0 mg, 0.0094 mmol).

LCMS: Rt: 1.15 min (LCMS Method 4); MS m/z 418.4 [M+H]$^+$.

$^1$H NMR (400 MHz, CD$_3$OD) δ 9.18 (s, 1H), 8.76 (s, 2H), 7.54-7.43 (m, 2H), 7.38 (d, J=1.0 Hz, 1H), 7.36-7.30 (m, 1H), 7.23 (dd, J=7.6, 1.2 Hz, 1H), 6.80 (s, 1H), 4.18 (q, J=8.8 Hz, 2H), 4.11-3.96 (m, 3H), 3.70 (dd, J=8.9, 7.2 Hz, 1H), 3.07-2.91 (m, 2H), 2.87-2.74 (m, 1H), 2.57-2.40 (m, 2H), 2.13-1.65 (m, 7H).

Example 4S: (S)-7-(4-(4-fluoro-2-(oxetan-3-yloxy)phenyl)piperidin-1-yl)-2-(oxazol-2-yl)-5-oxa-2-azaspiro[3.4]octane

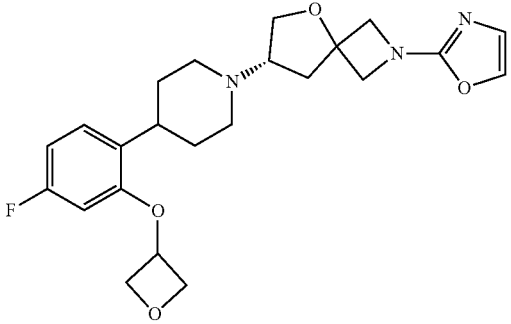 [SMILES: Fc1ccc(C2CCN([C@@H]3COC4(C3)CN(c3ncco3)C4)CC2)c(OC2COC2)c1]

(S)-7-(4-(4-fluoro-2-(oxetan-3-yloxy)phenyl)piperidin-1-yl)-5-oxa-2-azaspiro[3.4]octane (Intermediate 7MM, 100 mg, 0.276 mmol) and 2-bromooxazole (49 mg, 0.33 mmol) were dissolved in dioxane (2.8 mL), and the mixture was purged with nitrogen. Pd$_2$(dba)$_3$ (16 mg, 0.028 mmol), XantPhos (19 mg, 0.033 mmol), and sodium tert-butoxide (80 mg, 0.83 mmol) were added, and the reaction was stirred at 75° C. overnight. The reaction was filtered through a celite pad, rinsed with EtOAc, and the filtrate was concentrated. The residue was purified by FCC (0-10% MeOH (1% NH$_3$)/DCM) to afford the title compound (65 mg, 0.14 mmol) as a light yellow solid.

LCMS: Rt: 2.02 min (LCMS Method 4); MS m/z 430.6 [M+H]$^+$.

$^1$H NMR (400 MHz, CD$_3$OD) δ 7.40 (s, 1H), 7.20 (dd, J=8.5, 6.6 Hz, 1H), 6.82 (d, J=1.0 Hz, 1H), 6.67 (m, 1H), 6.32 (dd, J=10.6, 2.6 Hz, 1H), 5.28 (ddd, J=10.8, 5.9, 4.9 Hz, 1H), 5.12-4.98 (m, 2H), 4.68 (dd, J=7.5, 4.7 Hz, 2H), 4.31-4.13 (m, 2H), 4.13-4.00 (m, 3H), 3.76 (dd, J=8.7, 7.4 Hz, 1H), 3.21-3.07 (m, 2H), 3.07-2.96 (m, 1H), 2.96-2.85 (m, 1H), 2.53 (dd, J=12.9, 7.4 Hz, 1H), 2.25 (m, 2H), 2.13 (dd, J=13.0, 8.4 Hz, 1H), 1.92-1.66 (m, 4H).

Example 4T: 2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol or 2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol and Example 4U: 2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol or 2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol

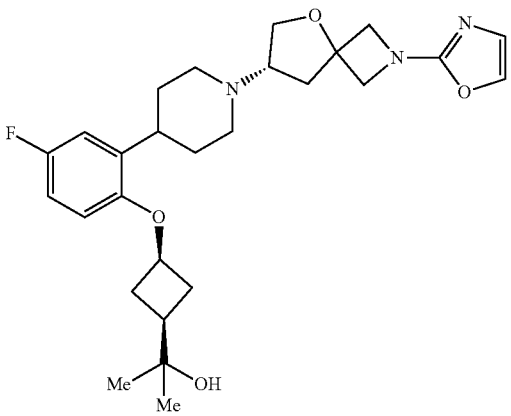

(1R,3s) cyclobutane

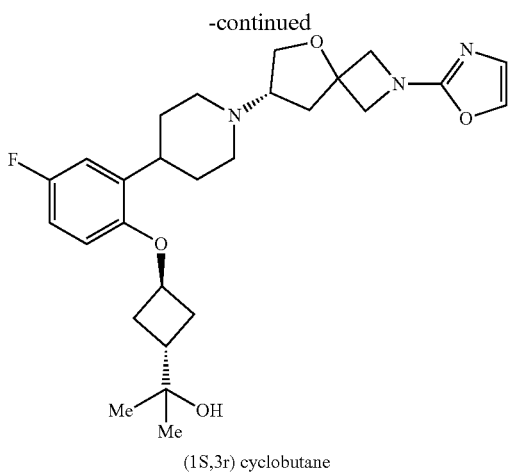

(1S,3r) cyclobutane

Step 1: tert-butyl (S)-7-(4-(5-fluoro-2-(3-(2-hydroxypropan-2-yl)cyclobutoxy)phenyl)piperidin-1-yl)-5-oxa-2-azaspiro[3.4]octane-2-carboxylate tert-butyl (S)-7-(4-(5-fluoro-2-(3-(methoxycarbonyl)cyclobutoxy)phenyl)piperidin-1-yl)-5-oxa-2-azaspiro[3.4]octane-2-carboxylate (Intermediate 6X, 130 mg, 0.251 mmol) was dissolved in THF (2.5 mL), and the solution was cooled to 0° C. Methyl magnesium bromide (0.33 mL, 1.0 mmol, 3M in THF) was added slowly over 5 minutes. The reaction was warmed to room temperature gradually, stirred at room temperature for 6 hours, then cooled to 0° C. and neutralized by addition of a saturated solution of ammonium chloride, stirred for 10 minutes and then diluted with additional amount of saturated solution of ammonium chloride. The aqueous layer was extracted with DCM. The combined organic layers were washed with brine, dried over MgSO$_4$, filtered and concentrated under reduced pressure. The residue was purified by FCC (0-10% MeOH (1% NH$_3$)/DCM) to afford the title intermediate (100 mg, 0.193 mmol).

LCMS: Rt: 2.81 and 2.84 min (LCMS Method 4); MS m/z 519.3 [M+H]$^+$.

Step 2: (S)-2-(3-(2-(1-(5-oxa-2-azaspiro[3.4]octan-7-yl)piperidin-4-yl)-4-fluorophenoxy)cyclobutyl)propan-2-ol tert-butyl (S)-7-(4-(5-fluoro-2-(3-(2-hydroxypropan-2-yl)cyclobutoxy)phenyl)piperidin-1-yl)-5-oxa-2-azaspiro[3.4]octane-2-carboxylate (100 mg, 0.193 mmol) was dissolved in DCM (3 mL) and TFA (0.450 mL, 5.78 mmol) was added. The reaction was stirred for 20 minutes and then the reaction was concentrated and dissolved in DCM and 1N NaOH. The layers were separated and the aq layer was extracted with DCM (3×25 mL) and the combined organic layers were washed with brine (1×10 mL), dried over magnesium sulfate, filtered and concentrated. The material was taken forward to the next step without further purification.

LCMS: Rt: 0.58 and 0.63 min (LCMS Method 1); MS m/z 419.5 [M+H]$^+$.

Step 3: 2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol and 2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol (S)-2-(3-(2-(1-(5-oxa-2-azaspiro[3.4]octan-7-yl)piperidin-4-yl)-4-fluorophenoxy)cyclobutyl)propan-2-ol (70 mg, 0.17 mmol) and 2-bromooxazole (30 mg, 0.20 mmol) were dissolved in dioxane (1.7 mL), and the mixture was purged with nitrogen. Pd$_2$(dba)$_3$ (9.6 mg, 0.017 mmol), XantPhos (12 mg, 0.020 mmol), and sodium tert-butoxide (48 mg, 0.50 mmol) were added, and the reaction was stirred at 75° C. overnight. The reaction was filtered through a celite pad, rinsed with EtOAc and concentrated. The residue was purified by FCC (0-10% MeOH (1% NH$_4$OH)/DCM). The diastereomers were then separated by preparative HPLC (X-Bridge Peptide BEH C18 5 μm 19×150 mm 40-55% MeCN/H$_2$O (10 mM NH$_4$OH) 30 mL/min) to afford peak 1 Example 4T (5.3 mg, 0.0011 mmol) and peak 2 Example 4U (9.5 mg, 0.167 mmol) as white powders.

Peak 1, Example 4T:

LCMS: Rt: 2.33 min (LCMS Method 4); MS m/z 486.7 [M+H]$^+$.

$^1$H NMR (400 MHz, CD$_3$OD) δ 7.40 (s, 1H), 6.90 (dd, J=9.8, 3.2 Hz, 1H), 6.87-6.78 (m, 2H), 6.64 (dd, J=9.0, 4.6 Hz, 1H), 4.68-4.60 (m, 1H), 4.29-4.14 (m, 2H), 4.14-4.02 (m, 3H), 3.83-3.72 (m, 1H), 3.12 (d, J=9.0 Hz, 2H), 3.01 (t, J=12.0 Hz, 1H), 2.91 (d, J=11.0 Hz, 1H), 2.60-2.36 (m, 4H), 2.26 (q, J=10.7 Hz, 2H), 2.14 (m, 3H), 1.85 (s, 2H), 1.70 (m, 2H), 1.16 (s, 6H).

Peak 2, Example 4U:

LCMS: Rt: 2.41 min (LCMS Method 4); MS m/z 486.5 [M+H]$^+$.

$^1$H NMR (400 MHz, CD$_3$OD) δ 7.40 (d, J=0.9 Hz, 1H), 6.89 (dd, J=9.8, 3.0 Hz, 1H), 6.86-6.73 (m, 3H), 4.52-4.42 (m, 1H), 4.26-4.15 (m, 2H), 4.13-4.02 (m, 3H), 3.80-3.71 (m, 1H), 3.10 (q, J=7.0 Hz, 2H), 3.04-2.93 (m, 1H), 2.89 (d, J=11.3 Hz, 1H), 2.53 (dd, J=12.8, 7.4 Hz, 1H), 2.47-2.34 (m, 2H), 2.22 (m, 2H), 2.12 (dd, J=13.0, 8.5 Hz, 1H), 2.08-1.96 (m, 3H), 1.83 (s, 2H), 1.68 (m, 2H), 1.12 (s, 6H).

Example 4V: (S)-2-(oxazol-2-yl)-7-(4-(2-(tetrahydro-2H-pyran-4-yl)phenyl)piperidin-1-yl)-5-oxa-2-azaspiro[3.4]octane

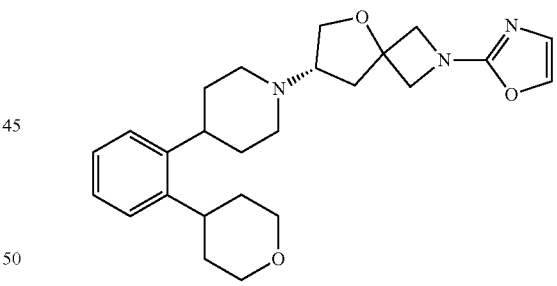

To a stirring solution of (S)-7-(4-(2-(tetrahydro-2H-pyran-4-yl)phenyl)piperidin-1-yl)-5-oxa-2-azaspiro[3.4]octane (Intermediate 7 L, 3.00 g, 8.41 mmol) and 2-iodooxazole (2.051 g, 10.52 mmol) in THF (3.0 mL) was added TPGS-750-M (30 mL) followed by potassium phosphate tribasic (10.72 g, 50.5 mmol). The reaction was stirred at 55° C. for 48 hours and then the reaction was cooled to RT and diluted with water. The mixture was extracted with DCM and the combined organic layers were washed with water dried over magnesium sulfate, filtered and concentrated. The residue was purified by FCC (0-10% MeOH (10% NH$_4$OH)/DCM) to yield the title compound as a light yellow foam (2.1 g, 4.96 mmol).

LCMS: Rt: 2.13 min (LCMS Method 4) MS m/z 424.4 [M+H]$^+$.

¹H NMR (400 MHz, DMSO-d₆) δ 7.57 (s, 1H), 7.23 (dt, J=7.0, 2.5 Hz, 2H), 7.20-7.10 (m, 2H), 6.84 (s, 1H), 4.14 (d, J=8.5 Hz, 1H), 4.04 (d, J=8.4 Hz, 2H), 3.99-3.89 (m, 4H), 3.67-3.58 (m, 2H), 3.48 (m, 2H), 3.10-2.97 (m, 2H), 2.97-2.93 (m, 1H), 2.80 (m, 2H), 2.38 (dd, J=13.0, 7.3 Hz, 1H), 2.21-1.98 (m, 3H), 1.74 (dd, J=12.7, 4.3 Hz, 1H), 1.71-1.58 (m, 5H), 1.54 (dd, J=13.2, 3.4 Hz, 2H).

Example 4W: (S)-7-(4-(5-fluoro-2-(tetrahydro-2H-pyran-4-yl)phenyl)piperidin-1-yl)-2-(oxazol-2-yl)-5-oxa-2-azaspiro[3.4]octane

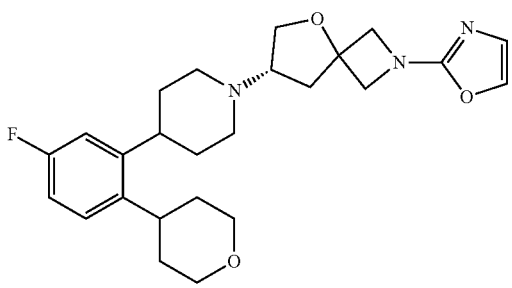 [SMILES: Fc1ccc(C2CCOCC2)c(C2CCN([C@@H]3COC4(C3)CN(c3ncco3)C4)CC2)c1]

(S)-7-(4-(5-fluoro-2-(tetrahydro-2H-pyran-4-yl)phenyl)piperidin-1-yl)-5-oxa-2-azaspiro[3.4]octane (Intermediate 7BB, 90 mg, 0.24 mmol) and 2-iodooxazole (51.5 mg, 0.264 mmol) were dissolved in a mixture of THF (0.3 mL) and TPGS-750-M (9 mL). Potassium phosphate tribasic (306 mg, 1.44 mmol) was added, and the reaction was stirred at 55° C. for 48 hours. The reaction was cooled to room temperature, diluted with water, and extracted with DCM. The combined organics were washed with brine, dried over magnesium sulfate, filtered, and evaporated. The residue was purified by FCC, (0-10% MeOH (1% NH₃)/DCM) to afford the title compound (20 mg, 0.045 mmol).

LCMS: Rt: 2.20 min (LCMS Method 4); MS m/z 442.4 [M+H]⁺.

¹H NMR (400 MHz, CD₃OD) δ 7.31 (d, J=1.3 Hz, 1H), 7.17 (dd, J=8.6, 6.0 Hz, 1H), 6.88 (dd, J=10.8, 2.9 Hz, 1H), 6.80 (td, J=8.4, 2.8 Hz, 1H), 6.72 (d, J=1.3 Hz, 1H), 4.19-4.06 (m, 2H), 4.06-3.88 (m, 5H), 3.67 (dd, J=8.8, 7.3 Hz, 1H), 3.50 (td, J=11.8, 1.9 Hz, 2H), 3.00 (m, 3H), 2.81 (d, J=12.2 Hz, 2H), 2.44 (dd, J=12.9, 7.4 Hz, 1H), 2.25-2.10 (m, 2H), 2.04 (dd, J=12.9, 8.4 Hz, 1H), 1.78-1.59 (m, 6H), 1.58-1.46 (m, 2H).

Example 5A: (S)-7-(4-(5-chloro-2-methoxyphenyl)piperidin-1-yl)-2-(1,2,4-thiadiazol-5-yl)-5-oxa-2-azaspiro[3.4]octane

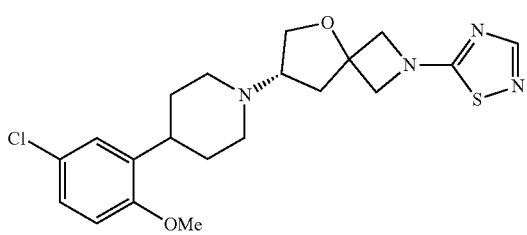 [SMILES: COc1ccc(Cl)cc1C1CCN([C@@H]2COC3(C2)CN(c2ncns2)C3)CC1]

Step 1: tert-butyl (S)-7-(4-(5-chloro-2-methoxyphenyl)piperidin-1-yl)-5-oxa-2-azaspiro[3.4]octane-2-carboxylate (S)-tert-butyl 7-(4-(2-methoxyphenyl)piperidin-1-yl)-5-oxa-2-azaspiro[3.4]octane-2-carboxylate (Intermediate 6C, 109 mg, 0.271 mmol) was dissolved in in DMF (2.7 mL) and under nitrogen CBMG (0.142 g, 0.677 mmol) and HCl (4.0M in Dioxane, 0.237 mL, 0.948 mmol) were added. The reaction was stirred at room temperature for 2 hours and then the solution was diluted with water and EtOAc. The solution was basified with 1N NaOH to pH 13. The aqueous layer was extracted with EtOAc and the combined organics were diluted with heptanes washed with water and dried over magnesium sulfate, filtered and concentrated. The crude material was taken up in DCM, filtered to remove precipitated solids and purified by flash chromatography (0-10% MeOH (10% NH₄OH)/DCM) to yield the title intermediate (18 mg, 0.271 mmol).

LCMS: Rt: 0.82 min (LCMS Method 1); MS m/z 437.4 [M+H]⁺.

Step 2: (S)-7-(4-(5-chloro-2-methoxyphenyl)piperidin-1-yl)-5-oxa-2-azaspiro[3.4]octane (S)-tert-butyl 7-(4-(5-chloro-2-methoxyphenyl)piperidin-1-yl)-5-oxa-2-azaspiro[3.4]octane-2-carboxylate (100 mg, 0.229 mmol) was dissolved in DCM (1.6 mL) and TFA (0.529 mL, 6.87 mmol) was added. The reaction was stirred for 45 minutes and it was then concentrated. The residue was dissolved in MeOH (5 mL), and isoelute Si-Propylsulfonic acid (SCX-2) resin (1.073 g, 0.687 mmol) was added and this was stirred for 1 hour. The resin was filtered and washed with MeOH and then the resin was washed with 7N ammonia in MeOH. The 7N ammonia in MeOH fractions were then concentrated to yield the title intermediate (73 mg, 0.217 mmol).

LCMS: Rt: 0.49 min (LCMS Method 1); MS m/z 337.5 [M+H]⁺.

Step 3: (S)-7-(4-(5-chloro-2-methoxyphenyl)piperidin-1-yl)-2-(1,2,4-thiadiazol-5-yl)-5-oxa-2-azaspiro[3.4]octane (S)-7-(4-(5-chloro-2-methoxyphenyl)piperidin-1-yl)-5-oxa-2-azaspiro[3.4]octane (24 mg, 0.071 mmol) and 5-bromo-1,2,4-thiadiazole (0.018 g, 0.11 mmol) were dissolved in 2-propanol (0.65 mL) and DIPEA (0.02 mL, 0.11 mmol) was added. The reaction was stirred at room temperature under nitrogen for 10 minutes, and then concentrated and purified by preparative HPLC (X-bridge C18 OBD 30×50 mm 5 μm column, 35-60% MeCN/H₂O (5 mM NH₄OH) 75 mL/min) to afford the title compound (19 mg, 0.045 mmol) as a light yellow solid.

LCMS: Rt: 2.47 min (LCMS Method 4); MS m/z 421.3 [M+H]⁺.

¹H NMR (400 MHz, CD₃OD) δ 7.93 (s, 1H), 7.20-7.07 (m, 2H), 6.90 (d, J=8.5 Hz, 1H), 4.36-4.23 (m, 2H), 4.23-4.11 (m, 2H), 4.08 (dd, J=8.8, 6.9 Hz, 1H), 3.84-3.74 (m, 3H), 3.16-3.04 (m, 3H), 3.02-2.83 (m, 2H), 2.55 (dd, J=13.1, 7.5 Hz, 1H), 2.28-2.12 (m, 3H), 1.87-1.61 (m, 4H).

Example 5B: (S)-7-(4-(2-methoxyphenyl)piperidin-1-yl)-2-(1,2,4-thiadiazol-5-yl)-5-oxa-2-azaspiro[3.4]octane

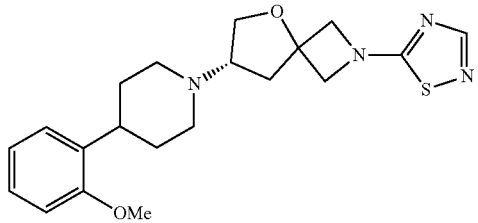 [SMILES: COc1ccccc1C1CCN([C@@H]2COC3(C2)CN(c2ncns2)C3)CC1]

(S)-7-(4-(2-methoxyphenyl)piperidin-1-yl)-5-oxa-2-azaspiro[3.4]octane (Intermediate 7X, 60 mg, 0.20 mmol) and 5-bromo-1,2,4-thiadiazole (0.049 g, 0.30 mmol) were dissolved in 2-propanol (2.0 mL). The reaction was stirred at room temperature overnight under nitrogen, concentrated and purified by FCC (0-10% MeOH (1% NH$_4$OH)/DCM) to afford the title compound (34 mg, 0.086 mmol). LCMS: Rt: 2.20 min (LCMS Method 4); MS m/z 387.3 [M+H]$^+$.

$^1$H NMR (400 MHz, CD$_3$OD) δ 7.93 (s, 1H), 7.15 (td, J=7.1, 1.7 Hz, 2H), 6.96-6.85 (m, 2H), 4.38-4.23 (m, 2H), 4.23-4.03 (m, 3H), 3.81 (s, 4H), 3.17-3.05 (m, 2H), 3.05-2.94 (m, 1H), 2.94-2.84 (m, 1H), 2.56 (dd, J=13.0, 7.5 Hz, 1H), 2.31-2.12 (m, 3H), 1.77 (m, 4H).

Example 5C: (S)-1-(2-1(2-(1-(1,2,4-thiadiazol-5-yl)-5-oxa-2-azaspiro[3.4]octan-7-yl)piperidin-4-yl)-4-fluorophenoxy)-2-methylpropan-2-ol

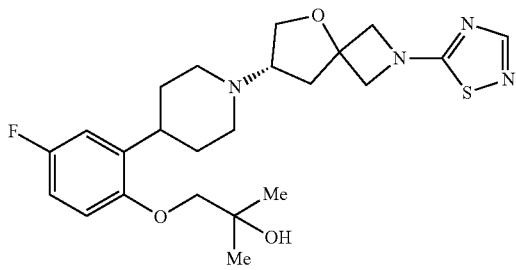 [SMILES: CC(C)(O)COc1ccc(F)cc1C1CCN([C@@H]2COC3(C2)CN(c2ncns2)C3)CC1]

(S)-1-(2-(1-(5-oxa-2-azaspiro[3.4]octan-7-yl)piperidin-4-yl)-4-fluorophenoxy)-2-methylpropan-2-ol (Intermediate 7O, 64 mg, 0.17 mmol) and 5-bromo-1,2,4-thiadiazole (0.042 g, 0.25 mmol) were dissolved in 2-propanol (2.0 mL). The reaction was stirred at room temperature for 2 hours under nitrogen then heated at 40° C. for 3 hours, concentrated and purified by F((0-10% MeOH (1% NH$_4$OH)/DCM) to afford the title compound (40 mg, 0.085 mmol).

LCMS: Rt: 2.06 min (LCMS Method 4) MS m/z 463.4 [M+H]$^+$.

$^1$H NMR (400 MHz, CD$_3$OD) δ 7.93 (s, 1H), 6.96-6.81 (m, 3H), 4.37-4.05 (m, 5H), 3.79 (dd, J=8.8, 7.4 Hz, 1H), 3.75 (s, 2H), 3.17-3.05 (m, 3H), 2.91 (m, 1H), 2.56 (dd, J=13.1, 7.4 Hz, 1H), 2.30-2.12 (m, 3H), 1.86 (m, 2H), 1.69 (m, 2H), 1.34 (s, 6H).

Example 5D: (S)-7-(4-(5-fluoro-2-(2-methoxyethoxy)phenyl)piperidin-1-yl)-2-(1,2,4-thiadiazol-5-yl)-5-oxa-2-azaspiro[3.4]octane

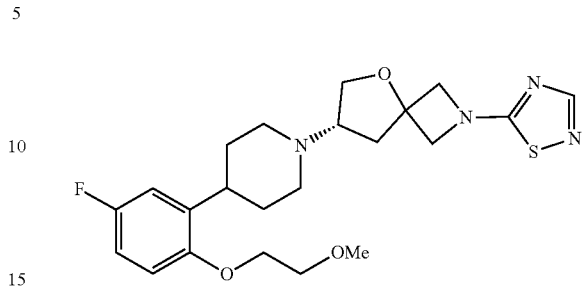

(S)-7-(4-(5-fluoro-2-(2-methoxyethoxy)phenyl)piperidin-1-yl)-5-oxa-2-azaspiro[3.4]octane (Intermediate 7N, 65 mg, 0.18 mmol) and 5-bromo-1,2,4-thiadiazole (0.044 g, 0.27 mmol) were dissolved in THF (1.8 mL). The reaction was stirred at room temperature for 90 minutes under nitrogen, concentrated and purified by FCC (0-7% MeOH/DCM) to afford the title compound (14 mg, 0.031 mmol).

LCMS: Rt: 1.12 min (LCMS Method 3); MS m/z 449.1 [M+H]$^+$.

$^1$H NMR (DMSO-d$_6$) δ 8.02 (s, 1H), 6.92-7.04 (m, 3H), 4.26 (d, J=8.8 Hz, 1H), 4.16 (t, J=7.8 Hz, 2H), 4.03-4.10 (m, 3H), 3.96 (dd, J=8.8, 6.8 Hz, 1H), 3.61-3.69 (m, 3H), 3.33 (s, 3H), 2.93-3.04 (m, 2H), 2.76-2.91 (m, 2H), 2.39-2.44 (m, 1H), 1.99-2.14 (m, 3H), 1.66-1.77 (m, 2H), 1.51-1.64 (m, 2H).

Example 5E: (S)-7-(4-(4-fluoro-2-methoxyphenyl)piperidin-1-yl)-2-(1,2,4-thiadiazol-5-yl)-5-oxa-2-azaspiro[3.4]octane

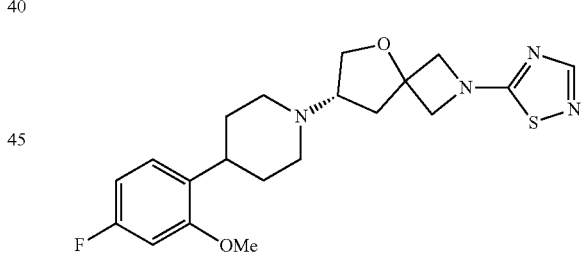

(S)-7-(4-(4-fluoro-2-methoxyphenyl)piperidin-1-yl)-5-oxa-2-azaspiro[3.4]octane (Intermediate 7Y, 85 mg, 0.27 mmol) and 5-bromo-1,2,4-thiadiazole (0.066 g, 0.40 mmol) were dissolved in IPA (3.0 mL). The reaction was stirred at room temperature overnight under nitrogen, concentrated and purified by FCC (0-10% MeOH (1% NH$_4$OH)/DCM) to afford the title compound (59 mg, 0.14 mmol).

LCMS: Rt: 2.29 min (LCMS Method 4); MS m/z 405.3 [M+H]$^+$.

$^1$H NMR (400 MHz, CD$_3$OD) δ 7.93 (s, 1H), 7.14 (dd, J=8.6, 6.6 Hz, 1H), 6.71 (dd, J=11.2, 2.5 Hz, 11H), 6.61 (m, 1H), 4.35-4.23 (m, 2H), 4.23-4.12 (m, 2H), 4.08 (dd, J=8.7, 6.9 Hz, 1H), 3.81 (s, 3H), 3.78 (dd, J=8.8, 7.4 Hz, 1H), 3.13-3.06 (m, 2H), 2.91 (m, 2H), 2.55 (dd, J=13.0, 7.5 Hz, 1H), 2.27-2.13 (m, 3H), 1.84-1.67 (m, 4H)

Example 5F: (S)-7-(4-(2-((5-methyl-1,2,4-oxadiazol-3-yl)methoxy)phenyl)piperidin-1-yl)-2-(1,3,4-thiadiazol-2-yl)-5-oxa-2-azaspiro[3.4]octane

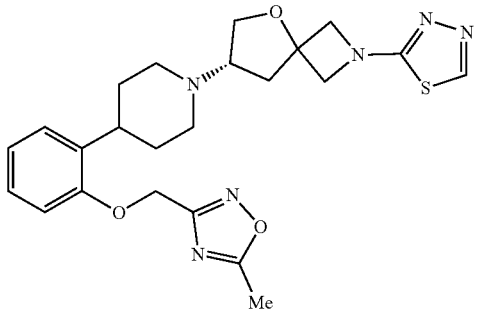 [SMILES: Cc1nc(COc2ccccc2C2CCN([C@@H]3COC4(C3)CN(c3nncs3)C4)CC2)no1]

(S)-7-(4-(2-((5-methyl-1,2,4-oxadiazol-3-yl)methoxy)phenyl)piperidin-1-yl)-5-oxa-2-azaspiro[3.4]octane (Intermediate 7PP, 32 mg, 0.083 mmol), 2-bromo-1,3,4-thiadiazole (14 mg, 0.083 mmol) and potassium phosphate tribasic (18 mg, 0.083 mmol) were dissolved in a mixture of 2% aqueous TPGS-750-M (150 µL), and THF (20 µL). The reaction was stirred at room temperature overnight, then was concentrated under reduced pressure, and purified by FCC (0-5% MeOH/DCM), and further by preparative HPLC (X-bridge C18 OBD 30×50 mm 5 µm 10-30% MeCN/H$_2$O (5 mM NH$_4$OH) 75 mL/min) to afford the title compound (19 mg, 0.040 mmol).

LCMS: Rt: 1.92 min (LCMS Method 4); MS m/z 469.3 [M+H]$^+$.

$^1$H NMR (400 MHz, CD$_3$OD) δ 8.65 (s, 1H), 7.24-7.11 (m, 2H), 7.05 (d, J=7.3 Hz, 1H), 6.96 (m, 1H), 5.19 (s, 2H), 4.32-4.21 (m, 2H), 4.18-4.09 (m, 2H), 4.06 (dd, J=8.6, 7.1 Hz, 1H), 3.81-3.72 (m, 1H), 3.06 (m, 3H), 2.87 (d, J=10.4 Hz, 1H), 2.61 (s, 3H), 2.54 (dd, J=13.0, 7.4 Hz, 1H), 2.27-2.11 (m, 3H), 1.89-1.64 (m, 4H).

Example 5G: (S)-7-(4-(5-fluoro-2-(oxetan-3-yloxy)phenyl)piperidin-1-yl)-2-(1,3,4-thiadiazol-2-yl)-5-oxa-2-azaspiro[3.4]octane

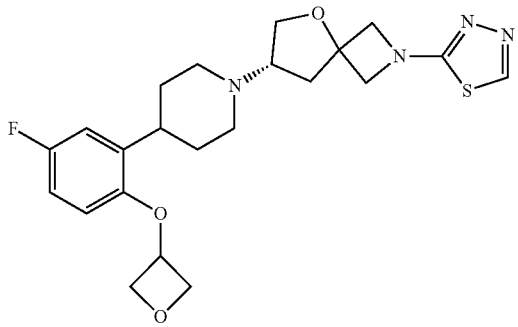 [SMILES: Fc1ccc(OC2COC2)c(C2CCN([C@@H]3COC4(C3)CN(c3nncs3)C4)CC2)c1]

To a solution of (S)-7-(4-(5-fluoro-2-(oxetan-3-yloxy)phenyl)piperidin-1-yl)-5-oxa-2-azaspiro[3.4]octane (Intermediate 7A, 95 mg, 0.26 mmol) in a mixture of 2% aqueous TPGS-750-M (470 µL)/THF (50 µL), was added 2-bromo-1,3,4-thiadiazole (43 mg, 0.26 mmol), followed by potassium phosphate tribasic (56 mg, 0.26 mmol). The mixture was stirred at room temperature overnight, and the crude was then extracted with DCM (3×25 mL) and the organic layers were combined, and evaporated under reduce pressure. The residue was purified by FCC (0-7% MeOH/DCM), and further by preparative HPLC (X-bridge C18 OBD 30×50 mm 5 µm 25-50% MeCN/H$_2$O (5 mM NH$_4$OH) 75 mL/min) to afford the title compound (49 mg, 0.11 mmol).

LCMS: Rt: 1.79 min (LCMS Method 4); MS m/z 447.3 [M+H]$^+$.

$^1$H NMR (400 MHz, DMSO-d$_6$) δ 8.80 (s, 1H), 7.04 (dd, J=9.9, 3.1 Hz, 1H), 6.98-6.87 (m, 1H), 6.56 (dd, J=9.0, 4.6 Hz, 1H), 5.31-5.17 (m, 1H), 4.91 (t, J=6.6 Hz, 2H), 4.52 (dd, J=7.3, 4.9 Hz, 2H), 4.21 (d, J=8.4 Hz, 1H), 4.16-4.05 (m, 2H), 4.03-3.91 (m, 2H), 3.69-3.57 (m, 1H), 3.07-2.74 (m, 4H), 2.42 (dd, J=13.0, 7.3 Hz, 1H), 2.10 (dt, J=13.1, 8.1 Hz, 3H), 1.82-1.68 (m, 2H), 1.61 (m, 2H).

Example 5H: (S)-7-(4-(5-fluoro-2-(((R)-tetrahydrofuran-3-yl)oxy)phenyl)piperidin-1-yl)-2-(1,3,4-thiadiazol-2-yl)-5-oxa-2-azaspiro[3.4]octane

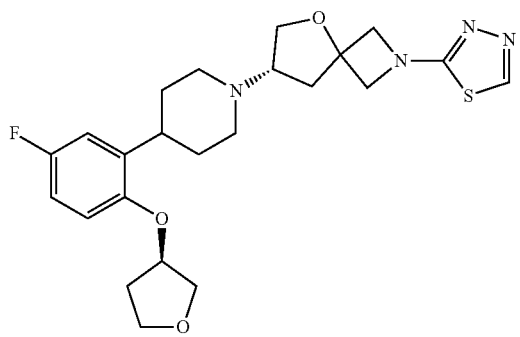 [SMILES: Fc1ccc(O[C@@H]2CCOC2)c(C2CCN([C@@H]3COC4(C3)CN(c3nncs3)C4)CC2)c1]

To a solution of (S)-7-(4-(5-fluoro-2-(((R)-tetrahydrofuran-3-yl)oxy)phenyl)piperidin-1-yl)-5-oxa-2-azaspiro[3.4]octane (Intermediate 7D, 73 mg, 0.19 mmol) in a mixture of 2% aqueous TPGS-750-M (350 µL)/THF (40 µL), was added 2-bromo-1,3,4-thiadiazole (32 mg, 0.19 mmol), followed by potassium phosphate tribasic (41 mg, 0.19 mmol). The reaction was treated similarly to Example 5G and the crude was purified by FCC (0-7% MeOH/DCM), and further by preparative HPLC (X-bridge C18 OBD 30×50 mm 5 µm 25-50% MeCN/H$_2$O (5 mM NH$_4$OH) 75 mL/min) to afford the title compound (31 mg, 0.066 mmol).

LCMS: Rt: 1.98 min (LCMS Method 4); MS m/z 461.1 [M+H]$^+$.

$^1$H NMR (DMSO-d$_6$) δ 8.80 (s, 1H), 7.07-6.91 (m, 3H), 5.01 (br s, 1H), 4.20 (d, J=8.8 Hz, 1H), 4.10 (dd, J=8.1, 5.1 Hz, 2H), 4.04-3.98 (m, 1H), 3.97-3.91 (m, 1H), 3.90-3.71 (m, 4H), 3.63 (t, J=7.6 Hz, 1H), 3.03-2.92 (m, 2H), 2.85-2.75 (m, 2H), 2.41 (dd, J=13.0, 7.1 Hz, 1H), 2.25-2.12 (m, 1H), 2.12-1.91 (m, 4H), 1.74-1.49 (m, 4H).

Example 5I: (S)-7-(4-(5-fluoro-2-(((R)-tetrahydrofuran-3-yl)methoxy)phenyl)piperidin-1-yl)-2-(1,3,4-thiadiazol-2-yl)-5-oxa-2-azaspiro[3.4]octane

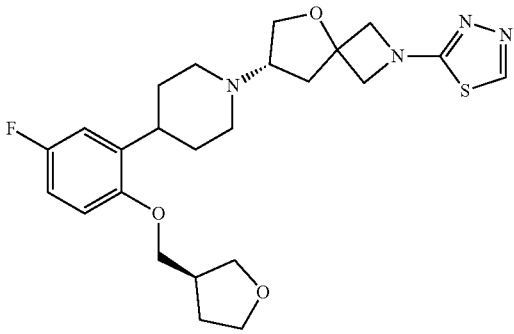 [SMILES: Fc1ccc(OC[C@@H]2CCOC2)c(C2CCN([C@@H]3COC4(C3)CN(c3nncs3)C4)CC2)c1]

To a solution of (S)-7-(4-(5-fluoro-2-(((R)-tetrahydrofuran-3-yl)methoxy)phenyl)piperidin-1-yl)-5-oxa-2-azaspiro[3.4]octane (Intermediate 7QQ, 85 mg, 0.22 mmol) in a mixture of 2% aqueous TPGS-750-M (390 μL)/THF (45 μL), was added 2-bromo-1,3,4-thiadiazole (36 mg, 0.22 mmol), followed by potassium phosphate tribasic (46 mg, 0.22 mmol). The reaction was treated similarly to Example 5G and the crude purified by FCC (0-7% MeOH/DCM), and further by preparative HPLC (X-bridge C18 OBD 30×50 mm 5 μm 25-50% MeCN/H$_2$O (5 mM NH$_4$OH) 75 mL/min) to afford the title compound (36 mg, 0.074 mmol).

LCMS: Rt: 1.16 min (LCMS Method 3); MS m/z 475.2 [M+H]$^+$.

$^1$H NMR (DMSO-d$_6$) δ 8.80 (s, 1H), 7.02-6.93 (m, 3H), 4.20 (d, J=8.8 Hz, 1H), 4.14-4.08 (m, 2H), 4.00 (d, J=8.3 Hz, 1H), 3.98-3.91 (m, 2H), 3.90-3.80 (m, 2H), 3.80-3.73 (m, 1H), 3.72-3.67 (m, 1H), 3.66-3.59 (m, 1H), 3.53 (dd, J=8.3, 5.9 Hz, 1H), 3.03-2.93 (m, 2H), 2.88-2.76 (m, 2H), 2.71-2.61 (m, 1H), 2.42 (dd, J=13.0, 7.1 Hz, 1H), 2.13-1.97 (m, 4H), 1.74-1.64 (m, 3H), 1.63-1.53 (m, 2H).

Example 5J: (S)-7-(4-(5-fluoro-2-((tetrahydro-2H-pyran-4-yl)oxy)phenyl)piperidin-1-yl)-2-(1,3,4-thiadiazol-2-yl)-5-oxa-2-azaspiro[3.4]octane

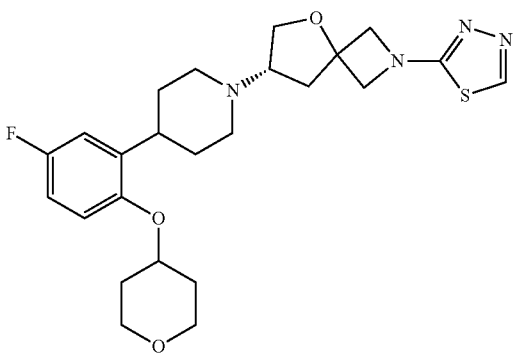 [SMILES: Fc1ccc(OC2CCOCC2)c(C2CCN([C@@H]3COC4(C3)CN(c3nncs3)C4)CC2)c1]

To a solution of (S)-7-(4-(5-fluoro-2-((tetrahydro-2H-pyran-4-yl)oxy)phenyl)piperidin-1-yl)-5-oxa-2-azaspiro[3.4]octane (Intermediate 7G, 60 mg, 0.15 mmol) in a mixture of 2% aqueous TPGS-750-M (280 μL)/THF (30 μL), was added 2-bromo-1,3,4-thiadiazole (25 mg, 0.15 mmol), followed by potassium phosphate tribasic (33 mg, 0.15 mmol). The reaction was treated similarly to Example 5G and the crude was purified by FCC (0-7% MeOH/DCM), and further by preparative HPLC (X-bridge C18 OBD 30×50 mm 5 μm 15-40% MeCN/H$_2$O (5 mM NH$_4$OH) 75 mL/min) to afford the title compound (19 mg, 0.038 mmol).

LCMS: Rt: 2.09 min (LCMS Method 4); MS m/z 475.5 [M+H]$^+$.

$^1$H NMR (DMSO-d$_6$) δ 8.80 (s, 1H), 7.07-6.90 (m, 3H), 4.60-4.48 (m, 1H), 4.20 (d, J=8.3 Hz, 1H), 4.15-4.06 (m, 2H), 4.04-3.90 (m, 2H), 3.86-3.75 (m, 2H), 3.67-3.57 (m, 1H), 3.55-3.45 (m, 2H), 3.05-2.93 (m, 2H), 2.92-2.77 (m, 2H), 2.42 (dd, J=12.7, 7.3 Hz, 1H), 2.14-2.01 (m, 3H), 1.99-1.89 (m, 2H), 1.77-1.64 (m, 2H), 1.64-1.54 (m, 4H).

Example 5K: (S)-7-(4-(2-(((R)-1,4-dioxan-2-yl)methoxy)-5-fluorophenyl)piperidin-1-yl)-2-(1,3,4-thiadiazol-2-yl)-5-oxa-2-azaspiro[3.4]octane

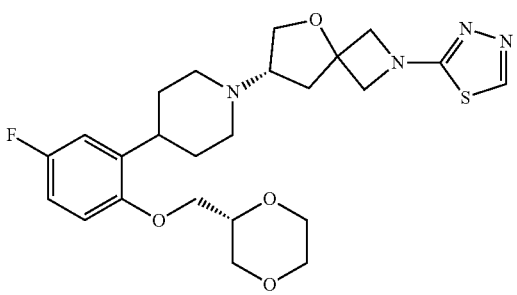

To a solution of (S)-7-(4-(2-(((R)-1,4-dioxan-2-yl)methoxy)-5-fluorophenyl)piperidin-1-yl)-5-oxa-2-azaspiro[3.4]octane (Intermediate 7C, 80 mg, 0.20 mmol) in a mixture of 2% aqueous TPGS-750-M (350 μL)/THF (40 μL), was added 2-bromo-1,3,4-thiadiazole (33 mg, 0.19 mmol), followed by potassium phosphate tribasic (42 mg, 0.19 mmol). The reaction was treated similarly to Example 5G and the crude by FCC (0-7% MeOH/DCM), and further by preparative HPLC (X-bridge C18 OBD 30×50 mm 5 μm 25-50% MeCN/H$_2$O (5 mM NH$_4$OH) 75 mL/min) to afford the title compound (35 mg, 0.070 mmol).

LCMS: Rt: 1.94 min (LCMS Method 4); MS m/z 491.3 [M+H]$^+$.

$^1$H NMR (DMSO-d$_6$) δ 8.80 (s, 1H), 7.02-6.92 (m, 3H), 4.20 (d, J=8.8 Hz, 1H), 4.11 (t, J=7.3 Hz, 2H), 4.03-3.90 (m, 4H), 3.88-3.81 (m, 2H), 3.77 (dd, J=11.2, 2.0 Hz, 1H), 3.72-3.59 (m, 3H), 3.53-3.43 (m, 2H), 3.03-2.95 (m, 2H), 2.88-2.77 (m, 2H), 2.42 (dd, J=12.7, 7.3 Hz, 1H), 2.13-2.02 (m, 3H), 1.75-1.67 (m, 2H), 1.65-1.51 (m, 2H).

Example 5L: (S)-7-(4-(2-(((S)-1,4-dioxan-2-yl)methoxy)-5-fluorophenyl)piperidin-1-yl)-2-(1,3,4-thiadiazol-2-yl)-5-oxa-2-azaspiro[3.4]octane

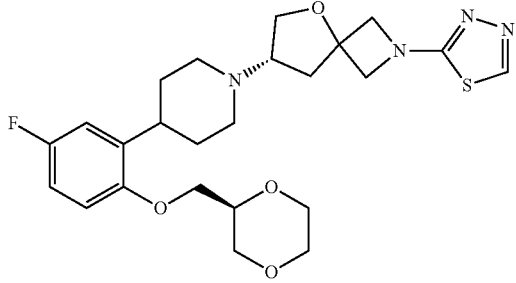 [SMILES: Fc1ccc(OC[C@@H]2COCCO2)c(C2CCN([C@@H]3COC4(C3)CN(c3nncs3)C4)CC2)c1]

To a solution of (S)-7-(4-(2-(((S)-1,4-dioxan-2-yl)methoxy)-5-fluorophenyl)piperidin-1-yl)-5-oxa-2-azaspiro[3.4]octane (Intermediate 7F, 86 mg, 0.21 mmol) in a mixture of 2% aqueous TPGS-750-M (380 µL)/THF (40 µL), was added 2-bromo-1,3,4-thiadiazole (35 mg, 0.21 mmol), followed by potassium phosphate tribasic (45 mg, 0.21 mmol). The reaction was treated similarly to Example 5G and the crude was purified by FCC (0-7% MeOH/DCM), and further by preparative HPLC (X-bridge C18 OBD 30×50 mm 5 µm 25-50% MeCN/H$_2$O (5 mM NH$_4$OH) 75 mL/min) to afford the title compound (41 mg, 0.082 mmol).

LCMS: Rt: 1.95 min (LCMS Method 4); MS m/z 491.5 [M+H]$^+$.

$^1$H NMR (DMSO-d$_6$) δ 8.80 (s, 1H), 7.02-6.92 (m, 3H), 4.20 (d, J=8.8 Hz, 1H), 4.15-4.08 (m, 2H), 4.04-3.89 (m, 4H), 3.88-3.81 (m, 2H), 3.80-3.74 (m, 1H), 3.72-3.59 (m, 3H), 3.53-3.44 (m, 2H), 3.05-2.94 (m, 2H), 2.89-2.76 (m, 2H), 2.46-2.38 (m, 1H), 2.14-2.01 (m, 3H), 1.80-1.49 (m, 4H).

Example 5M: (S)-7-(4-(4,5-difluoro-2-(((R)-tetrahydrofuran-3-yl)oxy)phenyl)piperidin-1-yl)-2-(1,3,4-thiadiazol-2-yl)-5-oxa-2-azaspiro[3.4]octane

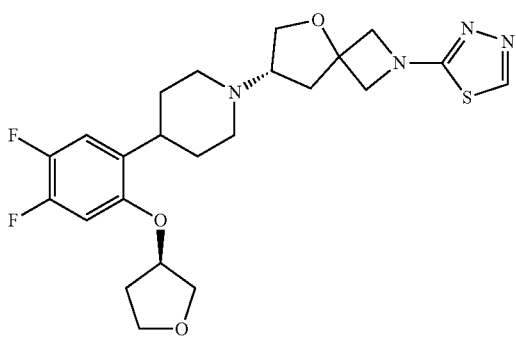 [SMILES: Fc1cc(O[C@@H]2CCOC2)c(C2CCN([C@@H]3COC4(C3)CN(c3nncs3)C4)CC2)cc1F]

To a solution of (S)-7-(4-(4,5-difluoro-2-(((R)-tetrahydrofuran-3-yl)oxy)phenyl)piperidin-1-yl)-5-oxa-2-azaspiro[3.4]octane (Intermediate 7R, 91 mg, 0.23 mmol) in a mixture of 2% aqueous TPGS-750-M (415 µL)/THF (45 µL), was added 2-bromo-1,3,4-thiadiazole (38 mg, 0.23 mmol), followed by potassium phosphate tribasic (49 mg, 0.23 mmol). The reaction was treated similarly to Example 5G and the crude was purified by FCC (0-7% MeOH/DCM), and further by preparative HPLC (X-bridge C18 OBD 30×50 mm 5 µm 25-50% MeCN/H$_2$O (5 mM NH$_4$OH) 75 mL/min) to afford the title compound (29 mg, 0.059 mmol).

LCMS: Rt: 2.09 min (LCMS Method 4); MS m/z 479.1 [M+H]$^+$.

$^1$H NMR (DMSO-d$_6$) δ 8.80 (s, 1H), 7.22 (dd, J=11.7, 9.3 Hz, 1H), 7.12 (dd, J=13.0, 7.1 Hz, 1H), 5.08-5.02 (m, 1H), 4.20 (d, J=8.8 Hz, 1H), 4.13-4.07 (m, 2H), 4.00 (d, J=8.8 Hz, 1H), 3.94 (dd, J=8.3, 6.8 Hz, 1H), 3.90-3.84 (m, 1H), 3.83-3.72 (m, 3H), 3.62 (t, J=7.8 Hz, 1H), 3.02-2.91 (m, 2H), 2.83-2.71 (m, 2H), 2.45-2.37 (m, 1H), 2.26-2.14 (m, 1H), 2.12-1.99 (m, 3H), 1.98-1.91 (m, 1H), 1.71-1.49 (m, 4H).

Example 5N: (S)-7-(4-(5-fluoro-2-(3-methoxy-3-methylbutoxy)phenyl)piperidin-1-yl)-2-(1,3,4-thiadiazol-2-yl)-5-oxa-2-azaspiro[3.4]octane

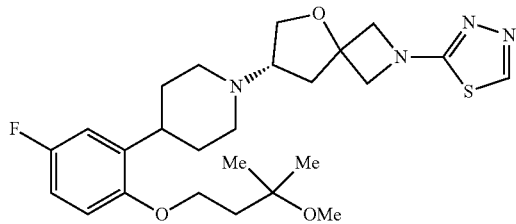 [SMILES: COC(C)(C)CCOc1ccc(F)cc1C1CCN([C@@H]2COC3(C2)CN(c2nncs2)C3)CC1]

To a solution of (S)-7-(4-(5-fluoro-2-(3-methoxy-3-methylbutoxy)phenyl)piperidin-1-yl)-5-oxa-2-azaspiro[3.4]octane (Intermediate 7M, 74 mg, 0.18 mmol) in a mixture of 2% aqueous TPGS-750-M (330 µL)/THF (35 µL), was added 2-bromo-1,3,4-thiadiazole (30 mg, 0.18 mmol), followed by potassium phosphate tribasic (39 mg, 0.18 mmol). The reaction was treated similarly to Example 6B and the crude was purified by FCC (0-7% MeOH/DCM), and further by preparative HPLC (X-bridge C18 OBD 30×50 mm 5 µm 35-60% MeCN/H$_2$O (5 mM NH$_4$OH) 75 mL/min) to afford the title compound (39 mg, 0.076 mmol).

LCMS: Rt: 1.34 min (LCMS Method 3); MS m/z 491.0 [M+H]$^+$.

$^1$H NMR (DMSO-d$_6$) δ 8.82 (s, 1H), 7.02-6.92 (m, 3H), 4.23-4.16 (m, 1H), 4.14-4.06 (m, 2H), 4.03-3.91 (m, 4H), 3.66-3.59 (m, 1H), 3.13-3.09 (m, 3H), 3.02-2.91 (m, 2H), 2.92-2.75 (m, 2H), 2.45-2.37 (m, 1H), 2.12-1.98 (m, 3H), 1.95-1.88 (m, 2H), 1.74-1.49 (m, 4H), 1.20-1.15 (m, 6H).

Example 5O: (S)-7-(4-(5-fluoro-2-(((S)-tetrahydrofuran-3-yl)oxy)phenyl)piperidin-1-yl)-2-(1,3,4-thiadiazol-2-yl)-5-oxa-2-azaspiro[3.4]octane

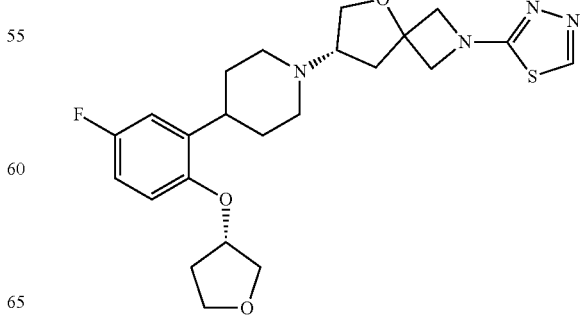

To a solution of (S)-7-(4-(5-fluoro-2-(((S)-tetrahydrofuran-3-yl)oxy)phenyl)piperidin-1-yl)-5-oxa-2-azaspiro[3.4]octane (Intermediate 7H, 89 mg, 0.24 mmol) in a mixture of 2% aqueous TPGS-750-M (425 μL)/THF (50 μL), was added 2-bromo-1,3,4-thiadiazole (39 mg, 0.24 mmol), followed by potassium phosphate tribasic (50 mg, 0.24 mmol). The reaction was treated similarly to Example 5G and the crude was purified by FCC (0-7% MeOH/DCM), and further by preparative HPLC (X-bridge C18 OBD 30×50 mm 5 μm 25-50% MeCN/H₂O (5 mM NH₄OH) 75 mL/min) to afford the title compound (34 mg, 0.072 mmol).

LCMS: Rt: 1.96 min (LCMS Method 4); MS m/z 461.6 [M+H]⁺.

¹H NMR (400 MHz, DMSO-d₆) δ 8.80 (s, 1H), 7.04-6.91 (m, 3H), 5.05-4.98 (m, 1H), 4.26-4.17 (m, 1H), 4.15-4.07 (m, 2H), 4.01 (d, J=8.5 Hz, 1H), 3.95 (dd, J=8.6, 6.7 Hz, 1H), 3.90-3.70 (m, 4H), 3.69-3.57 (m, 1H), 3.05-2.91 (m, 2H), 2.88-2.73 (m, 2H), 2.46-2.37 (m, 1H), 2.25-1.91 (m, 5H), 1.76-1.49 (m, 4H).

Example 5P: (S)-4-(2-(1-(2-(1,3,4-thiadiazol-2-yl)-5-oxa-2-azaspiro[3.4]octan-7-yl)piperidin-4-yl)-4-fluorophenoxy)-2-methylbutan-2-ol

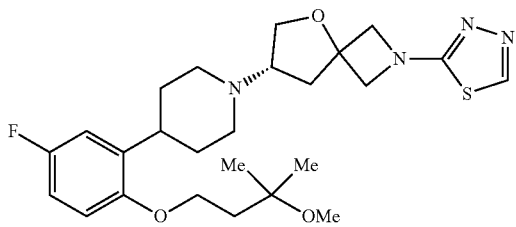 [SMILES: COC(C)(C)CCOc1ccc(F)cc1C1CCN([C@@H]2COC3(C2)CN(c2nncs2)C3)CC1]

To the solution of (S)-4-(2-(1-(5-oxa-2-azaspiro[3.4]octan-7-yl)piperidin-4-yl)-4-fluorophenoxy)-2-methylbutan-2-ol (Intermediate 7O, 143 mg, 0.36 mmol) in a mixture of 2% aqueous TPGS-750-M (655 μL)/THF (70 μL), was added 2-bromo-1,3,4-thiadiazole (60 mg, 0.36 mmol), followed by potassium phosphate tribasic (77 mg, 0.36 mmol). The reaction was treated similarly to Example 5G and the crude was purified by FCC (0-7% MeOH/DCM), and further by preparative HPLC (X-bridge C18 OBD 30×50 mm 5 μm 25-50% MeCN/H₂O (5 mM NH₄OH) 75 mL/min) to afford the title compound (75 mg, 0.15 mmol). LCMS: Rt: 1.91 min (LCMS Method 4); MS m/z 477.1 [M+H]⁺.

¹H NMR (DMSO-d₆) δ 8.80 (s, 1H), 7.02-6.91 (m, 3H), 4.36 (s, 1H), 4.20 (d, J=8.3 Hz, 1H), 4.10 (dd, J=8.3, 4.9 Hz, 2H), 4.07-3.98 (m, 3H), 3.94 (dd, J=8.3, 6.8 Hz, 1H), 3.62 (dd, J=8.3, 7.3 Hz, 1H), 2.97 (quin, J=7.2 Hz, 2H), 2.90-2.75 (m, 2H), 2.41 (dd, J=13.0, 7.1 Hz, 1H), 2.12-1.98 (m, 3H), 1.84 (t, J=6.8 Hz, 2H), 1.74-1.50 (m, 4H), 1.17 (s, 6H).

Example 5Q: (S)-7-(4-(2-(oxetan-3-yloxy)phenyl)piperidin-1-yl)-2-(1,3,4-thiadiazol-2-yl)-5-oxa-2-azaspiro[3.4]octane formate salt

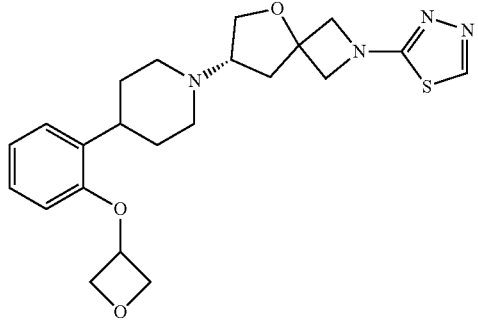 [SMILES: c1ccc(C2CCN([C@@H]3COC4(C3)CN(c3nncs3)C4)CC2)c(OC2COC2)c1]

To a solution of (S)-7-(4-(2-(oxetan-3-yloxy)phenyl)piperidin-1-yl)-5-oxa-2-azaspiro[3.4]octane (Intermediate 7Q, 21 mg, 0.061 mmol) in a mixture of 2% aqueous TPGS-750-M (275 μL)/THF (30 μL), was added 2-bromo-1,3,4-thiadiazole (10 mg, 0.061 mmol), followed by potassium phosphate tribasic (19 mg, 0.061 mmol). The reaction was treated similarly to Example 6B and the crude was purified by preparative HPLC (X-bridge 30×50 mm 5 μm column 30-30% MeCN/H₂O (0.1% formic acid) 75 mL/min) to afford the title compound (2 mg, 0.004 mmol) as a formate salt.

LCMS: Rt: 1.79 min (LCMS Method 4); MS m/z 429.5 [M+H]⁺.

¹H NMR (400 MHz, CD₃OD) δ 8.68 (s, 1H), 8.32 (s, 1H), 7.22 (dd, J=7.5, 1.7 Hz, 1H), 7.15 (td, J=7.8, 1.7 Hz, 1H), 7.01-6.90 (m, 1H), 6.51 (d, J=8.0 Hz, 1H), 5.29 (p, J=5.4 Hz, 1H), 5.07-5.00 (m, 2H), 4.70 (dd, J=7.5, 5.0 Hz, 2H), 4.35 (d, J=8.9 Hz, 1H), 4.28 (d, J=8.9 Hz, 1H), 4.22-4.07 (m, 3H), 3.98 (dd, J=9.6, 6.1 Hz, 1H), 3.68-3.45 (m, 2H), 3.25-3.08 (m, 2H), 2.77-2.60 (m, 3H), 2.33 (dd, J=13.6, 7.4 Hz, 1H), 2.09-1.78 (m, 4H).

Example 5R: (S)-7-(4-(2-methoxyphenyl)piperidin-1-yl)-2-(1,3,4-thiadiazol-2-yl)-5-oxa-2-azaspiro[3.4]octane

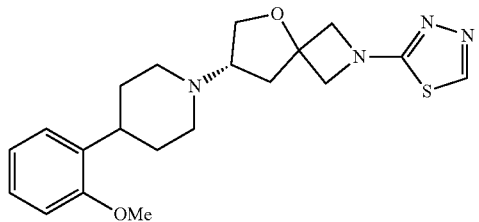 [SMILES: COc1ccccc1C1CCN([C@@H]2COC3(C2)CN(c2nncs2)C3)CC1]

To a solution of (S)-7-(4-(2-methoxyphenyl)piperidin-1-yl)-5-oxa-2-azaspiro[3.4]octane (Intermediate 7X, 87 mg, 0.29 mmol) in a mixture of 2% aqueous TPGS-750-M (520 μL)/THF (60 μL), was added 2-bromo-1,3,4-thiadiazole (48 mg, 0.29 mmol), followed by potassium phosphate tribasic (61 mg, 0.29 mmol). The reaction was treated similarly to Example 5G and the crude was purified by FCC (0-7% MeOH/DCM), and further by preparative HPLC (X-bridge C18 OBD 30×50 mm 5 μm 25-50% MeCN/H$_2$O (5 mM NH$_4$OH) 75 mL/min) to afford the title compound (41 mg, 0.10 mmol).

LCMS: Rt: 2.00 min (LCMS Method 4); MS m/z 387.3 [M+H]$^+$.

$^1$H NMR (DMSO-d$_6$) δ 8.80 (s, 1H), 7.22-7.12 (m, 2H), 7.00-6.84 (m, 2H), 4.21 (d, J=8.8 Hz, 1H), 4.15-4.08 (m, 2H), 4.00 (d, J=8.8 Hz, 1H), 3.94 (dd, J=8.8, 6.8 Hz, 1H), 3.77 (s, 3H), 3.64 (t, J=7.3 Hz, 1H), 3.04-2.91 (m, 2H), 2.91-2.73 (m, 2H), 2.44-2.37 (m, 1H), 2.15-2.00 (m, 3H), 1.74-1.53 (m, 4H).

Example 5S: (S)-7-(4-(5-fluoro-2-(2-methoxyethoxy)phenyl)piperidin-1-yl)-2-(1,3,4-thiadiazol-2-yl)-5-oxa-2-azaspiro[3.4]octane

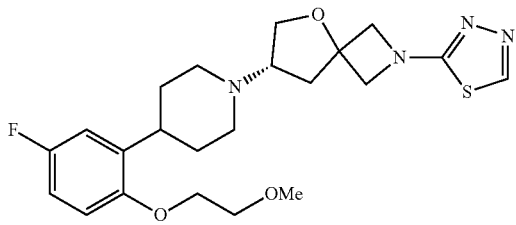 [SMILES: COCCOc1ccc(F)cc1C1CCN([C@@H]2COC3(C2)CN(c2nncs2)C3)CC1]

To a solution of (S)-7-(4-(5-fluoro-2-(2-methoxyethoxy)phenyl)piperidin-1-yl)-5-oxa-2-azaspiro[3.4]octane (Intermediate 7N, 54 mg, 0.15 mmol) in a mixture of 2% aqueous TPGS-750-M (270 μL)/THF (30 μL), was added 2-bromo-1,3,4-thiadiazole (24 mg, 0.15 mmol), followed by potassium phosphate tribasic (31 mg, 0.15 mmol). The reaction was treated similarly to Example 5G and the crude was purified by FCC (0-7% MeOH/DCM), and further by preparative HPLC (X-bridge C18 OBD 30×50 mm 5 μm 25-50% MeCN/H$_2$O (5 mM NH$_4$OH) 75 mL/min) to afford the title compound (24 mg, 0.052 mmol).

LCMS: Rt: 2.03 min (LCMS Method 4); MS m/z 449.3 [M+H]$^+$.

$^1$H NMR (400 MHz, DMSO-d$_6$) δ 8.80 (s, 1H), 7.02-6.90 (m, 3H), 4.20 (d, J=8.3 Hz, 1H), 4.13-4.05 (m, 4H), 4.03-3.98 (m, 1H), 3.95 (dd, J=8.5, 6.6 Hz, 1H), 3.68-3.59 (m, 3H), 3.33 (s, 3H), 3.03-2.93 (m, 2H), 2.92-2.75 (m, 2H), 2.41 (dd, J=12.8, 7.3 Hz, 1H), 2.13-1.99 (m, 3H), 1.77-1.65 (m, 2H), 1.64-1.49 (m, 2H).

Example 5T: (S)-7-(4-(4-fluoro-2-methoxyphenyl)piperidin-1-yl)-2-(1,3,4-thiadiazol-2-yl)-5-oxa-2-azaspiro[3.4]octane

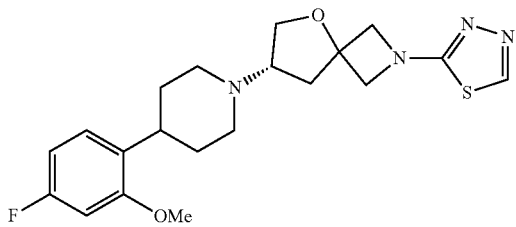

To a solution of (S)-7-(4-(4-fluoro-2-methoxyphenyl)piperidin-1-yl)-5-oxa-2-azaspiro[3.4]octane (Intermediate 7Y, 85 mg, 0.27 mmol) in a mixture of 2% aqueous TPGS-750-M (2.4 mL)/THF (265 μL), was added 2-bromo-1,3,4-thiadiazole (44 mg, 0.27 mmol), followed by potassium phosphate tribasic (56 mg, 0.27 mmol). The reaction was treated similarly to Example 5G and the residue was purified by FCC (0-10% MeOH (1% NH$_4$OH)/DCM), and further by preparative HPLC (X-bridge C18 OBD 30×50 mm 5 μm 25-50% MeCN/H$_2$O (5 mM NH$_4$OH) 75 mL/min) to afford the title compound (26 mg, 0.064 mmol).

LCMS: Rt: 2.10 min (LCMS Method 4); MS m/z 405.5 [M+H]$^+$.

$^1$H NMR (400 MHz, CD$_3$OD) δ 8.66 (s, 1H), 7.14 (dd, J=8.6, 6.6 Hz, 1H), 6.71 (dd, J=11.1, 2.7 Hz, 1H), 6.61 (td, J=8.4, 2.5 Hz, 1H), 4.33-4.20 (m, 2H), 4.20-4.10 (m, 2H), 4.08 (dd, J=8.8, 7.0 Hz, 1H), 3.81 (s, 4H), 3.19-3.06 (m, 2H), 3.02-2.86 (m, 2H), 2.56 (dd, J=13.1, 7.4 Hz, 1H), 2.33-2.12 (m, 3H), 1.86-1.67 (m, 4H).

Example 5U: (S)-1-(2-(1-(2-(1,3,4-thiadiazol-2-yl)-5-oxa-2-azaspiro[3.4]octan-7-yl)piperidin-4-yl)-4-fluorophenoxy)-2-methylpropan-2-ol

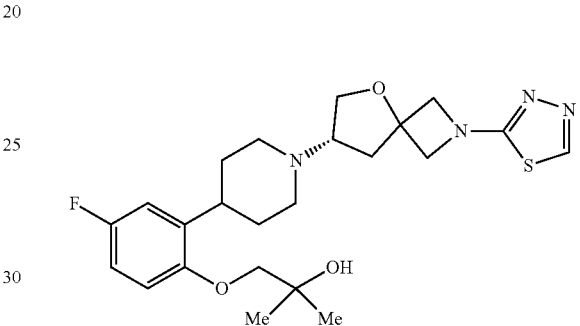

To a solution of (S)-1-(2-(1-(5-oxa-2-azaspiro[3.4]octan-7-yl)piperidin-4-yl)-4-fluorophenoxy)-2-methylpropan-2-ol (Intermediate 7U, 67 mg, 0.18 mmol) in a mixture of 2% aqueous TPGS-750-M (1.6 mL)/THF (160 μL), was added 2-bromo-1,3,4-thiadiazole (29 mg, 0.18 mmol), followed by potassium phosphate tribasic (38 mg, 0.18 mmol). The reaction was treated similarly to Example 5G and the crude was purified by FCC (0-10% MeOH (1% NH$_4$OH)/DCM) to afford the title compound (14 mg, 0.030 mmol).

LCMS: Rt: 1.91 min (LCMS Method 4); MS m/z 463.6 [M+H]$^+$. $^1$H NMR (400 MHz, DMSO-d$_6$) δ 8.80 (s, 1H), 7.04-6.90 (m, 3H), 4.36 (s, 1H), 4.20 (d, J=8.6 Hz, 1H), 4.10 (dd, J=8.4, 5.0 Hz, 2H), 4.08-3.98 (m, 3H), 3.94 (dd, J=8.5, 6.7 Hz, 1H), 3.62 (dd, J=8.5, 7.1 Hz, 1H), 2.97 (p, J=7.4 Hz, 2H), 2.91-2.75 (m, 2H), 2.41 (dd, J=12.9, 7.2 Hz, 1H), 2.15-1.96 (m, 3H), 1.84 (t, J=6.8 Hz, 2H), 1.68 (m, 2H), 1.56 (m, 2H), 1.17 (s, 6H).

Example 5V: (S)-4-(2-(1-(2-(1,3,4-thiadiazol-2-yl)-5-oxa-2-azaspiro[3.4]octan-7-yl)piperidin-4-yl)-5-fluorophenoxy)-2-methylbutan-2-ol

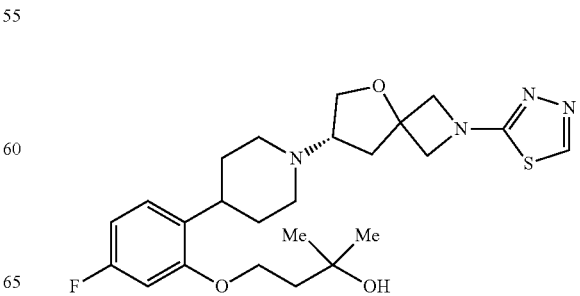

To a solution of (S)-4-(2-(1-(5-oxa-2-azaspiro[3.4]octan-7-yl)piperidin-4-yl)-5-fluorophenoxy)-2-methylbutan-2-ol (Intermediate 7S, 140 mg, 0.36 mmol) in a mixture of 2% aqueous TPGS-750-M (0.64 mL)/THF (70 μL), was added 2-bromo-1,3,4-thiadiazole (59 mg, 0.36 mmol), followed by potassium phosphate tribasic (76 mg, 0.36 mmol). The reaction was treated similarly to Example 5G and the crude was purified by FCC (0-7% MeOH/DCM), and further by preparative HPLC (X-bridge C18 OBD 30×50 mm 5 μm 25-50% MeCN/H$_2$O (5 mM NH$_4$OH) 75 mL/min) to afford title compound (61 mg, 0.13 mmol).

LCMS: Rt: 2.04 min (LCMS Method 4); MS m/z 477.3 [M+H]$^+$.

$^1$H NMR (DMSO-d$_6$) δ 8.80 (s, 1H), 7.15 (dd, J=8.3, 7.3 Hz, 1H), 6.84 (dd, J=11.7, 2.4 Hz, 1H), 6.73-6.58 (m, 1H), 4.20 (d, J=8.3 Hz, 1H), 4.14-4.04 (m, 4H), 4.03-3.98 (m, 1H), 3.98-3.91 (m, 1H), 3.62 (t, J=7.6 Hz, 1H), 3.30-3.27 (m, 1H), 3.30-2.91 (m, 2H), 2.86-2.73 (m, 2H), 2.47-2.37 (m, 1H), 2.13-1.96 (m, 3H), 1.89-1.81 (m, 2H), 1.73-1.50 (m, 4H), 1.21-1.15 (m, 6H).

Example 5W: (S)-7-(4-(2-((2-oxaspiro[3.3]heptan-6-yl)oxy)-5-fluorophenyl)piperidin-1-yl)-2-(1,3,4-thiadiazol-2-yl)-5-oxa-2-azaspiro[3.4]octane

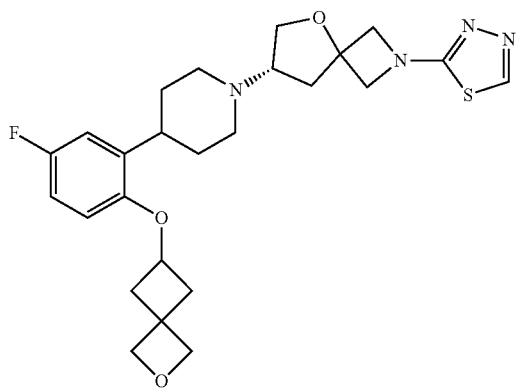

(S)-7-(4-(2-((2-oxaspiro[3.3]heptan-6-yl)oxy)-5-fluorophenyl)piperidin-1-yl)-5-oxa-2-azaspiro[3.4]octane (25 mg, 0.062 mmol) was dissolved in THF (0.62 mL) at −5° C. and 2-bromo-1,3,4-thiadiazole (Intermediate 7NN, 15 mg, 0.086 mmol) was added. The reaction was stirred at room temperature 4 days, then concentrated and diluted with a mixture of EtOAc and water. The layers were separated and the aqueous layer was extracted with EtOAc, and the combined organic layers were dried over magnesium sulfate, filtered and concentrated. The residue was purified by FCC (0-15% MeOH (10% NH$_4$OH)/EtOAc) and by preparative HPLC (X-bridge C18 OBD 30×50 mm 5 μM 25-50% MeCN/H$_2$O (5 mM NH$_4$OH) 75 mL/min) to afford the title compound (6.7 mg, 0.014 mmol).

LCMS: Rt: 2.06 min (LCMS Method 4); MS m/z 487.3.

$^1$H NMR (400 MHz, CD$_3$OD) δ 8.66 (s, 1H), 6.91 (dd, 1H), 6.83 (m, 1H), 6.71 (dd, J=8.9, 4.6 Hz, 1H), 4.75 (s, 2H), 4.68 (s, 2H), 4.53 (p, J=6.6 Hz, 1H), 4.25 (q, 2H), 4.13 (m, 2H), 4.10-4.05 (m, 1H), 3.77 (dd, J=8.7, 7.3 Hz, 1H), 3.13-3.06 (m, 2H), 2.93 (m, 2H), 2.84-2.78 (m, 2H), 2.55 (dd, J=13.0, 7.4 Hz, 1H), 2.29 (m, 2H), 2.24-2.12 (m, 3H), 1.86-1.75 (m, 2H), 1.75-1.60 (m, 2H).

Example 5X: (S)-7-(4-(5-fluoro-2-(((S)-tetrahydrofuran-3-yl)methoxy)phenyl)piperidin-1-yl)-2-(1,3,4-thiadiazol-2-yl)-5-oxa-2-azaspiro[3.4]octane

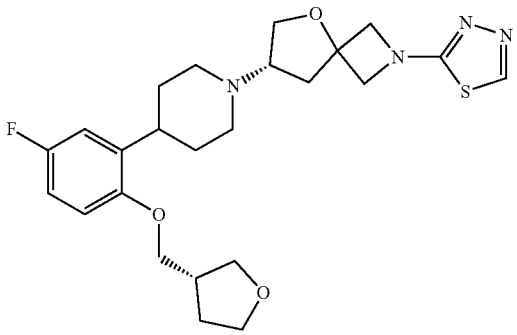 [SMILES: Fc1ccc(OC[C@H]2CCOC2)c(C2CCN([C@@H]3COC4(C3)CN(c3nncs3)C4)CC2)c1]

(S)-7-(4-(5-fluoro-2-(((S)-tetrahydrofuran-3-yl)methoxy)phenyl)piperidin-1-yl)-5-oxa-2-azaspiro[3.4]octane (Intermediate 7J, 74 mg, 0.19 mmol) was dissolved in a mixture of 2% aqueous TPGS-750-M (340 μL)/THF (40 μL), and added 2-bromo-1,3,4-thiadiazole (31 mg, 0.19 mmol) was added followed by potassium phosphate tribasic (40 mg, 0.19 mmol) and the reaction was treated similarly to Example 5G. The residue was purified by FCC (0-7% methanol/dichloromethane), and further by preparative HPLC (X-bridge C18 OBD 30×50 mm 5 μM 25-50% MeCN/H$_2$O (5 mM NH$_4$OH) 75 mL/min) to afford the title compound (32 mg, 0.066 mmol).

LCMS: Rt: 2.12 min (LCMS Method 4); MS m/z 475.1 [M+H]$^+$. $^1$H NMR (DMSO-d$_6$) δ 8.80 (s, 1H), 7.03-6.92 (m, 3H), 4.20 (d, J=8.8 Hz, 1H), 4.13-4.07 (m, 2H), 4.00 (d, J=8.8 Hz, 1H), 3.98-3.91 (m, 2H), 3.90-3.80 (m, 2H), 3.79-3.73 (m, 1H), 3.72-3.66 (m, 1H), 3.66-3.59 (m, 1H), 3.53 (dd, J=8.3, 5.9 Hz, 1H), 3.03-2.93 (m, 2H), 2.88-2.76 (m, 2H), 2.71-2.60 (m, 1H), 2.46-2.38 (m, 1H), 2.12-1.96 (m, 4H), 1.75-1.63 (m, 3H), 1.63-1.51 (m, 2H).

Example 5Y: (S)-1-(2-(1-(2-(1,2-thiadiazol-5-yl)-5-oxa-2-azaspiro[3.4]octan-7-yl)piperidin-4-yl)phenoxy)-2-methylpropan-2-ol

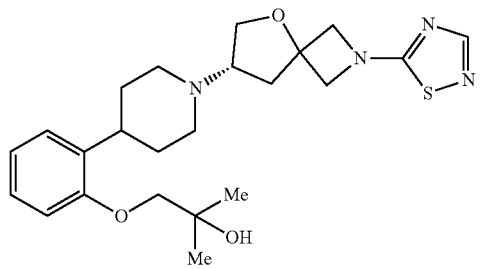 [SMILES: CC(C)(O)COc1ccccc1C1CCN([C@@H]2COC3(C2)CN(c2ncns2)C3)CC1]

(S)-1-(2-(1-(5-oxa-2-azaspiro[3.4]octan-7-yl)piperidin-4-yl)phenoxy)-2-methylpropan-2-ol (110 mg, 0.305 mmol) and 5-bromo-1,2,4-thiadiazole (0.076 g, 0.46 mmol) were dissolved in 2-propanol (3.0 mL). The reaction was stirred at room temperature overnight under nitrogen, concentrated and purified twice by FCC (0-10% MeOH (1% NH$_4$OH)/DCM) to afford the title compound (67 mg, 0.15 mmol).

LCMS: Rt: 2.02 min (LCMS Method 4); MS m/z 445.7 [M+H]$^+$.

¹H NMR (400 MHz, CD₃OD) δ 7.93 (s, 1H), 7.24-7.10 (m, 2H), 6.90 (t, J=7.2 Hz, 2H), 4.36-4.03 (m, 5H), 3.82-3.74 (m, 3H) 3.19-3.04 (m, 3H), 2.91 (m, 1H), 2.56 (dd, J=13.1, 7.4 Hz, 1H), 2.32-2.11 (m, 3H), 1.87 (m, 2H), 1.74 (m, 2H), 1.35 (s, 6H).

Example 6A: (S)-7-(4-(5-fluoro-2-((tetrahydro-2H-pyran-4-yl)oxy)phenyl)piperidin-1-yl)-2-(1,2,4-oxadiazol-3-yl)-5-oxa-2-azaspiro[3.4]octane

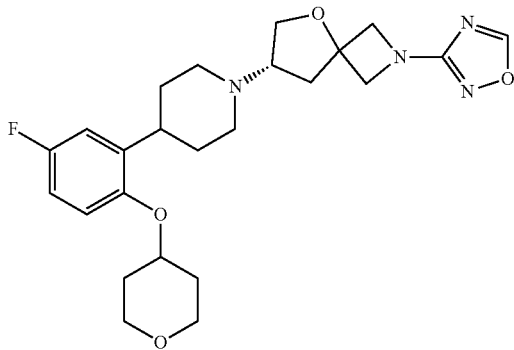 [SMILES: Fc1ccc(OC2CCOCC2)c(C2CCN([C@@H]3COC4(C3)CN(c3ncon3)C4)CC2)c1]

Under nitrogen, (S)-7-(4-(5-fluoro-2-((tetrahydro-2H-pyran-4-yl)oxy)phenyl)piperidin-1-yl)-N-hydroxy-5-oxa-2-azaspiro[3.4]octane-2-carboximidamide (Intermediate 12B, 102 mg, 0.228 mmol) was dissolved in diethyl phenyl orthoformate (2.3 mL) and 4 Å molecular sieves (1 g) were added followed by p-toluenesulfonic acid monohydrate (131 mg, 0.684 mmol). The reaction was stirred at 80° C. under nitrogen overnight then cooled to room temperature, filtered through celite, rinsed with DCM, and then concentrated. The residue was purified by FCC (0-10% MeOH (10% NH₄OH)/EtOAc), then by preparative HPLC (X-bridge C18 OBD 30×50 mm 5 μm column 35-60% MeCN/H₂O (5 mM NH₄OH) 75 mL/min) to afford the title compound (11.5 mg, 0.024 mmol).

LCMS: Rt: 2.24 min (LCMS Method 4); MS m/z 459.4 [M+H]⁺.

¹H NMR (400 MHz, CD₃OD) δ 8.79 (s, 1H), 6.94 (td, J=9.5, 3.9 Hz, 2H), 6.89-6.79 (m, 1H), 4.59-4.46 (m, 1H), 4.21-4.11 (m, 2H), 4.09-3.99 (m, 3H), 3.97-3.90 (m, 2H), 3.75 (t, J=8.1 Hz, 1H), 3.60 (m, 2H), 3.12-2.99 (m, 3H), 2.89 (d, 1H), 2.54 (dd, J=12.8, 7.4 Hz, 1H), 2.28-2.17 (m, 2H), 2.12 (dd, J=13.0, 8.5 Hz, 1H), 2.06-1.98 (m, 2H), 1.90-1.78 (m, 2H), 1.78-1.64 (m, 4H).

Example 6B: (S)-7-(4-(5-fluoro-2-(oxetan-3-yloxy)phenyl)piperidin-1-yl)-2-(1,2,4-oxadiazol-3-yl)-5-oxa-2-azaspiro[3.4]octane

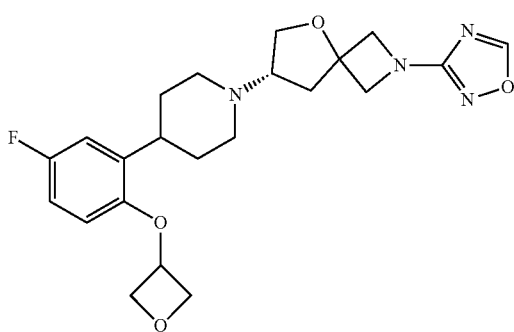 [SMILES: Fc1ccc(OC2COC2)c(C2CCN([C@@H]3COC4(C3)CN(c3ncon3)C4)CC2)c1]

(S)-7-(4-(5-fluoro-2-(oxetan-3-yloxy)phenyl)piperidin-1-yl)-N-hydroxy-5-oxa-2-azaspiro[3.4]octane-2-carboximidamide (Intermediate 12C, 24.5 mg, 0.058 mmol) was dissolved in diethyl phenyl orthoformate (0.8 mL) and 4 Å molecular sieves (0.24 g) were added followed by p-toluenesulfonic acid monohydrate (34 mg, 0.18 mmol). The reaction was stirred at room temperature overnight, then at 50° C. for 5 hours and then at 80° C. for 35 minutes. The reaction was cooled at room temperature, filtered through a pad of celite, rinsed with DCM, and then concentrated. The residue was purified by FCC (0-10% MeOH (10% NH₄OH)/EtOAc), then by preparative HPLC (X-bridge C18 OBD 30×50 mm 5 μm column 25-50% MeCN/H₂O (5 mM NH₄OH) 75 mL/min) to afford the title compound (5.0 mg, 0.012 mmol).

LCMS: Rt: 2.01 min (LCMS Method 4); MS m/z 431.4 [M+H].

¹H NMR (400 MHz, CD₃OD) δ 8.78 (s, 1H), 6.97 (dd, J=9.7, 3.3 Hz, 1H), 6.83 (td, J=8.5, 3.0 Hz, 1H), 6.49 (dd, J=9.0, 4.6 Hz, 1H), 5.24 (m, 1H), 5.05-4.96 (m, 2H), 4.68 (dd, J=7.5, 5.0 Hz, 2H), 4.21-4.12 (m, 2H), 4.09-3.97 (m, 3H), 3.76 (dd, J=8.7, 7.4 Hz, 1H), 3.16-3.00 (m, 3H), 2.91 (m, 1H), 2.54 (dd, J=12.8, 7.4 Hz, 1H), 2.25 (m, 2H), 2.13 (dd, J=12.9, 8.5 Hz, 1H), 1.91-1.83 (m, 2H), 1.80-1.63 (m, 2H).

Example 6C: (S)-7-(4-(2-((2-oxaspiro[3.3]heptan-6-yl)oxy)-5-fluorophenyl)piperidin-1-yl)-2-(1,2,4-oxadiazol-3-yl)-5-oxa-2-azaspiro[3.4]octane

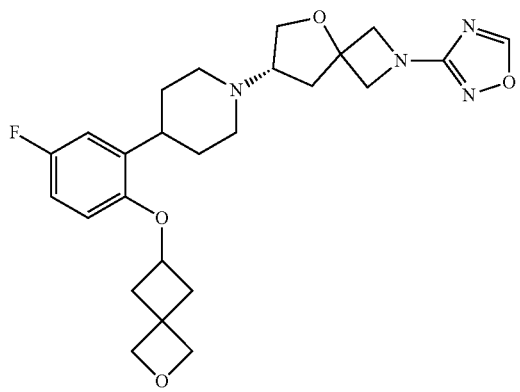 [SMILES: Fc1ccc(OC2CC3(COC3)C2)c(C2CCN([C@@H]3COC4(C3)CN(c3ncon3)C4)CC2)c1]

In a 100 mL round bottom flask, (S)-7-(4-(2-((2-oxaspiro[3.3]heptan-6-yl)oxy)-5-fluorophenyl)piperidin-1-yl)-N-hydroxy-5-oxa-2-azaspiro[3.4]octane-2-carboximidamide (Intermediate 12A, 119.4 mg, 0.259 mmol) was suspended in diethyl phenyl orthoformate (2.6 mL). Next, 4 Å molecular sieves (1 g) were added followed by p-toluenesulfonic acid monohydrate (149 mg, 0.778 mmol). The reaction was stirred at 60° C. under nitrogen for 17 hours and then for 5 hours at 80° C. The reaction was cooled to RT and filtered through a pad of celite and rinsed with DCM, then concentrated. The residue was purified by FCC (0-15% MeOH (10% NH₄OH)/EtOAc) and further by preparative HPLC (X-bridge C18 OBD 30×50 mm 5 μm column 25-50% MeCN/H₂O (5 mM NH₄OH) 75 mL/min) to yield the title compound (29 mg, 0.063 mmol).

LCMS: Rt: 2.16 min (LCMS Method 4); MS m/z 471.3 [M+H]⁺.

¹H NMR (400 MHz, CD₃OD) δ 8.78 (s, 1H), 6.90 (dd, J=9.7, 3.1 Hz, 1H), 6.82 (td, J=8.5, 3.0 Hz, 1H), 6.70 (dd,

J=8.9, 4.5 Hz, 1H), 4.73 (s, 2H), 4.68 (s, 2H), 4.53 (m, 1H), 4.26-4.11 (m, 2H), 4.11-3.97 (m, 3H), 3.75 (dd, J=8.7, 7.4 Hz, 1H), 3.18-3.05 (m, 2H), 2.92 (m, 2H), 2.86-2.76 (m, 2H), 2.53 (dd, J=12.8, 7.4 Hz, 1H), 2.30 (m, 2H), 2.21 (m, 2H), 2.12 (dd, J=12.9, 8.5 Hz, 1H), 1.80 (m, 2H), 1.68 (m, 2H).

Example 7A: (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane

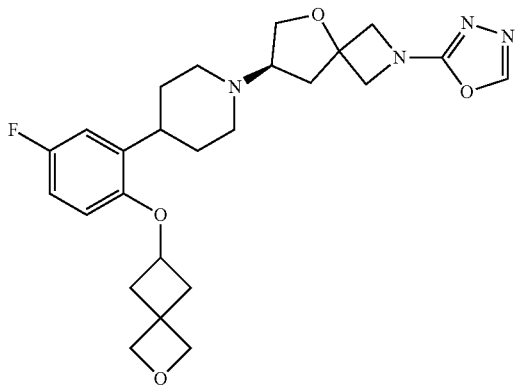 [SMILES: Fc1ccc(OC2CC3(COC3)C2)c(C2CCN([C@H]3COC4(C3)CN(c3nnco3)C4)CC2)c1]

Step 1: tert-butyl 7-(4-(5-fluoro-2-hydroxyphenyl)piperidin-1-yl)-5-oxa-2-azaspiro[3.4]octane-2-carboxylate 4-fluoro-2-(piperidin-4-yl)phenol hydrochloride (see WO 2012/062752 for synthesis, 511 mg, 2.205 mmol) was dissolved in MeOH (15 mL) and tert-butyl 7-oxo-5-oxa-2-azaspiro[3.4]octane-2-carboxylate (526 mg, 2.316 mmol), was added followed by TEA (1.230 mL, 8.82 mmol) and zinc chloride (0.5M in THF, 6.62 mL, 3.31 mmol). The resulting solution was stirred at 50° C. for 2 h. The reaction was then cooled to 0° C. and sodium cyanoborohydride (277 mg, 4.41 mmol) was added and the reaction was stirred for 16 h. The reaction was then concentrated and the residue was dissolved in DCM, washed with water and dried over sodium sulfate, filtered and concentrated. The crude was then purified by FCC (0-8% 7N NH$_3$ in MeOH/32% EtOAc/heptanes) to yield the title compound (950 mg, 2.197 mmol).

LCMS: Rt: 0.99 min (LCMS Method 2); MS m/z 407.3 [M+H]$^+$.

Step 2: tert-butyl 7-(4-(2-(benzyloxy)-5-fluorophenyl)piperidin-1-yl)-5-oxa-2-azaspiro[3.4]octane-2-carboxylate tert-butyl 7-(4-(5-fluoro-2-hydroxyphenyl)piperidin-1-yl)-5-oxa-2-azaspiro[3.4]octane-2-carboxylate was dissolved in MeCN (15 mL) and cesium carbonate (1432 mg, 4.39 mmol) was added followed by benzyl bromide (0.276 mL, 2.307 mmol). The reaction was stirred at RT for 4 h and then the reaction was filtered, washed with DCM and concentrated. The crude was then purified by FCC (0-6% 7N NH$_3$ in MeOH/24% EtOAc/heptanes) to afford the title compound (986 mg, 1.985 mmol).

LCMS: Rt: 1.30 min (LCMS Method 2); MS m/z 497.2 [M+H]$^+$.

Step 3: 7-(4-(2-(benzyloxy)-5-fluorophenyl)piperidin-1-yl)-5-oxa-2-azaspiro[3.4]octane tert-butyl 7-(4-(2-(benzyloxy)-5-fluorophenyl)piperidin-1-yl)-5-oxa-2-azaspiro[3.4]octane-2-carboxylate was dissolved in DCM (3 mL) and TFA (3.01 mL, 39.1 mmol) was added. The reaction was stirred at RT for 2 h and it was then concentrated and diluted with DCM. The organic layer was washed with 1N NaOH, dried over sodium sulfate, filtered and concentrated and used in the next step without further purification (775 mg, 1.955 mmol) LCMS: Rt: 2.32 min (LCMS Method 4); MS m/z 397.8 [M+H]$^+$.

Step 4: 7-(4-(2-(benzyloxy)-5-fluorophenyl)piperidin-1-yl)-2-(1,3,4-oxadiazol-2-yl)-5-oxa-2-azaspiro[3.4]octane 7-(4-(2-(benzyloxy)-5-fluorophenyl)piperidin-1-yl)-5-oxa-2-azaspiro[3.4]octane was dissolved in THF (10 mL) and cooled to 0° C. Ethyl 5-bromo-1,3,4-oxadiazole-2-carboxylate (519 mg, 2.349 mmol) was then added followed by DIPEA (0.82 mL, 4.70 mmol) The reaction was stirred for 2 h and then the reaction was concentrated and diluted with DCM. The organic layer was washed with water and brine, dried over sodium sulfate, filtered and concentrated. The residue was dissolved in THF (8 mL) and LiOH (493 mg, 11.74 mmol) in water (3 mL) was added and the reaction was stirred for 16 h. The reaction was cooled to −5° C. and 6N HCl (3.26 mL, 19.57 mmol) was added and the reaction was stirred for 2 h. Sodium carbonate was added to the reaction until the pH was >12 and the reaction was concentrated. The residue was dissolved in EtOAc and washed with brine and the EtOAc layer was concentrated and the residue was purified by FCC (0-5% MeOH (1% 7N NH$_3$ in MeOH)/DCM) to yield the title compound (706 mg, 1.52 mmol).

LCMS: Rt: 1.10 min (LCMS Method 2); MS m/z 465.4 [M+H]$^+$.

Step 5: 2-(1-(2-(1,3,4-oxadiazol-2-yl)-5-oxa-2-azaspiro[3.4]octan-7-yl)piperidin-4-yl)-4-fluorophenol 7-(4-(2-(benzyloxy)-5-fluorophenyl)piperidin-1-yl)-2-(1,3,4-oxadiazol-2-yl)-5-oxa-2-azaspiro[3.4]octane (706 mg, 1.52 mmol) was dissolved in MeOH (10 mL) and 10% Pd—C (162 mg) was added and the reaction was stirred for 16 h under a balloon of hydrogen. The reaction was filtered and concentrated and the residue was purified by FCC (0-5% MeOH (1% NH$_3$ in MeOH)/DCM) to yield the title compound (385 mg, 1.018 mmol).

LCMS: Rt: 0.74 min (LCMS Method 2); MS m/z 375.3 [M+H]$^+$.

Step 6: (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane To a DMF (4 mL) solution of 2-(1-(2-(1,3,4-oxadiazol-2-yl)-5-oxa-2-azaspiro[3.4]octan-7-yl)piperidin-4-yl)-4-fluorophenol (230 mg, 0.614 mmol), was added 2-oxaspiro[3.3]heptan-6-yl 4-methylbenzenesulfonate (Intermediate 5M, 181 mg, 0.676 mmol) and Cs$_2$CO$_3$ (400 mg, 1.229 mmol). The resulting reaction mixture was stirred at 90° C. for 3 h and then the crude was diluted with EtOAc, washed with water and concentrated. The crude was then purified by FCC (0-5% MeOH (7N NH$_3$ in MeOH)/DCM) and further by FCC (0-10% 7N NH$_3$ in MeOH/40% EtOAc/heptanes) to yield the racemic product (210 mg, 0.437 mmol). Some of this material (156 mg, 0.331 mmol) was then submitted to SFC chromatography to separate the two enantiomers (Lux Cellulose-4 (21×250 mm, 45% MeOH (10 mM NH$_4$OH), 80 g/min) to yield the two enantiomers. Comparison of the SFC retention times of Example 2L (Rt: 3.41 min Lux-Cellulose-4 3×100 mm 3 m, 5→55% MeOH with 10 mM NH$_4$OH/CO$_2$, 2.5 mL/min) demonstrated that the trailing peak from the chiral separation (Rt: 3.43 min Lux-Cellulose-4 3×100 mm 3 m, 5→55% MeOH with 10 mM NH$_4$OH/CO$_2$, 2.5 mL/min) is the same stereochemistry as Example 2L. Based on this data, the initial peak from the chiral separation is the title example (69 mg, 0.144 mmol).

SFC: Rt: 3.17 min; Lux-Cellulose-4 3×100 mm 3 m, 5→55% MeOH with 10 mM NH$_4$OH/CO$_2$, 2.5 mL/min LCMS: Rt: 1.99 min (LCMS Method 4); MS m/z 471.4 [M+H]$^+$.

$^1$H NMR (400 MHz, CD$_3$OD) δ 8.38 (s, 1H), 6.90 (dd, J=9.8, 3.1 Hz, 1H), 6.87-6.79 (m, 1H), 6.71 (dd, J=8.9, 4.5 Hz, 1H), 4.75 (s, 2H), 4.67 (s, 2H), 4.53 (p, J=6.5 Hz, 1H), 4.35-4.24 (m, 2H), 4.17 (q, J=8.6 Hz, 2H), 4.06 (dd, J=8.8, 6.9 Hz, 1H), 3.76 (dd, J=8.8, 7.3 Hz, 1H), 3.15-3.04 (m, 2H), 3.00-2.85 (m, 2H), 2.85-2.76 (m, 2H), 2.54 (dd, J=13.0, 7.4 Hz, 1H), 2.32-2.11 (m, 5H), 1.80 (m, 2H), 1.68 (m, 2H).

2. Biological Activity and Selectivity of Novel Chemical Matter on M1, M2, M3, M4, and M5 Stable Cell Lines The above examples were characterized by measuring the intracellular mobilization of Ca$^{++}$ ions caused by signaling events mediated by the receptor. The Intra-cellular Calcium flux levels were captured by the highly sensitive Ca$^{++}$ indicator, Calcium Assay Kit (BD Biosciences; Catalog Number 640178. The fluorescent activity from all receptors were monitored by the fluorescent imager, FDSS 7000EX (Hamamatsu) over a span of 3 minutes. The change in Calcium flux was readily captured upon activation with the muscarinic orthosteric agonist, Carbachol.

CHRM4 Cell Line Maintenance

CHO-K1 cells stably expressing the human cloned CHRM4 receptor (M4_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% CO$_2$) at 37° C. The cultures were grown to 80-90% confluency in T150 flasks (Corning) and washed with 1×DPBS then lifted with 0.05% Trypsin (Life Technologies). The cells were harvested in growth media then spun (1K rpm, 3 minutes) and cryopreserved using Recovery Cell Culture Freezing Media (Gibco Technologies). Cells were stored in liquid nitrogen and thawed a day before the assay.

CHRM1 Cell Line Maintenance

Cloned human M1 receptor (CHRM1) was stably expressed in HEK293 cells and were grown and maintained in a monolayer culture with DMEM/High Glucose (Life Technologies) supplemented with 10% Fetal Bovine Serum, 1× Pen-Strep, and 0.5 mg/mL Geneticin in a humidified atmosphere (5% CO$_2$) at 37° C. The cultures were grown to 90% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay.

CHRM2 Cell Line Maintenance

CHO-K1 cells stably expressing the human cloned CHRM2 receptor (M2_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% CO$_2$) at 37° C. The cultures were grown to 80-90% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay.

CHRM3 and CHRM5 Cell Line Maintenance

CHO-K1 cells stably expressing the human cloned CHRM3 receptor (M3_CHO cells) were grown and maintained in a monolayer culture with F12/HAM (Life Technologies) supplemented with 10% Fetal Bovine Serum, 1× Pen-Strep, and 0.4 mg/mL Geneticin in a humidified atmosphere (5% CO$_2$) at 37° C. The cultures were grown to 80-90% confluency in T150 flasks (Corning) and washed with 1×DPBS and lifted with 0.05% Trypsin (Life Technologies). The cells were then spun (1K rpm, 3 minutes) and frozen using Recovery Cell Culture Freezing Media (Gibco Technologies). Cells were stored in liquid nitrogen and thawed a day before the assay. A similar procedure was used for cells stably expressing the human cloned CHRM5 receptor (M5_CHO).

CHRM4 Ca$^{++}$ Flux Assay

Prior to the day of the assay, stable M4_CHO cells were thawed and plated on 384 well black walled clear bottom TC treated plates (Greiner Cat #781091) at 12K cells/well using F12/HAM Media supplemented with 10% FBS (Life Technologies) and kept overnight in a humidified atmosphere (5% CO$_2$) at 37° C. The next day, cells were loaded with 20 μL Ca$^{++}$ dye (BD Biosciences) using Loading Buffer (HBSS+Ca/+Mg, 20 mM HEPES, 2.5 mM Probenecid) and placed back in cell incubator for a minimum of 1 hour. After incubation, the dye was replaced with 45 μL Assay Buffer (HBSS−Ca/−Mg, 20 mM HEPES, 2.5 mM Probenecid) supplemented with 20 μM ATP (Sigma Aldrich) and kept at room temperature in the dark for 60 minutes before running on a cell imager. The FDSS 7000EX (Hamamatsu) was used to capture Ca$^{++}$ traces for a span of 3 minutes from cells treated with 11 point dose of compound in triplicate in order to generate dose response curves in agonist mode. All compounds were serially diluted in DMSO then prepared in Assay Buffer for Ca$^{++}$ flux studies. The dose response curves were generated from the average of triplicate wells obtained from each data point and used a non-linear regression of four parameter dose response algorithm. The Percent Activity (PA) was measured to EC$_{100}$ of Carbachol.

CHRM1 Ca$^{++}$ Flux Assay

Prior to the day of the assay, stable HEK293 M1 cells were thawed and plated on 384 well black walled clear bottom TC treated plates (Greiner Cat #781091) at 25K cells/well with DMEM/High Glucose supplemented with 10% FBS (Hyclone) Pen-Strep (Life Technologies) and kept overnight in a humidified atmosphere (5% CO$_2$) at 37° C. The following day, cells were loaded with 20 uL Ca$^{++}$ dye (BD Biosciences) using Loading Buffer (HBSS+Ca/+Mg, 20 mM HEPES) and placed back in cell incubator for a minimum of 1 hour. The dye was replaced with 45 μL Assay Buffer (HBSS−Ca/−Mg, 20 mM HEPES) and kept at room temperature prior to running on cell imager. Compounds were prepared in Assay Buffer and 5 uL was added to the cells. The FDSS 7000EX (Hamamatsu) was used to acquire Ca++ traces for 3 minutes from cells treated with 11 point dose in triplicate in order to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

CHRM2 $Ca^{++}$ Flux Assay

Prior to the day of the assay, stable M2 CHO cells were thawed and plated on Greiner 384 well TC treated plate at a density of 12K cells/well and kept overnight in a humidified atmosphere (5% $CO_2$) at 37° C. The following day, the cells were loaded with $Ca^{++}$ dye (BD Biosciences) using Loading Buffer (HBSS+Ca/+Mg, 20 mM HEPES, 2.5 mM Probenecid) and placed back in cell incubator for a minimum of 1 hour and maximum of 2 hours. After incubation, the dye was replaced with Assay Buffer (HBSS−Ca/−Mg, 20 mM HEPES, 2.5 mM Probenecid) supplemented with 20 µM ATP (Sigma Aldrich) and kept at room temperature for 60 minutes prior before running on cell imager. The FDSS 7000EX (Hamamatsu) was used to acquire $Ca^{++}$ traces from cells in response to compound treatment and the data was used to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

CHRM3 and CHRM5 $Ca^{++}$ Flux Assay

Prior to the day of the assay, stable M3_CHO or M5_CHO cells were thawed and plated on Greiner 384 well black TC treated plates at 12K cells/well in F12/DMEM supplemented with 10% FBS (Hyclone) and kept overnight in a humidified atmosphere (5% $CO_2$) at 37° C. The next day, cells were loaded with $Ca^{++}$ dye (BD Biosciences) using Loading Buffer (HBSS+Ca/+Mg, 20 mM HEPES, 2.5 mM Probenecid) and placed back in cell incubator for a minimum of 1 hour. After incubation, the dye was replaced with Assay Buffer (HBSS−Ca/−Mg, 20 mM HEPES, 2.5 mM Probenecid) and kept at room temperature in the dark before running on cell imager. The FDSS 7000EX (Hamamatsu) was used to acquire $Ca^{++}$ traces from cells treated with 11 point dose response of compounds in triplicate in order to generate dose response curves in agonist mode. All compounds were serially diluted in DMSO then prepared in Assay Buffer for $Ca^{++}$ flux studies. The dose response curves were generated from the average of triplicate wells obtained from each data point and used a non-linear regression of four parameter dose response algorithm. The Percent Activity (PA) was measured to $EC_{100}$ of Carbachol.

If an Example was tested more than once in an assay, then the values below represent the geometric mean of the results from each independent experiment.

TABLE 12

Summary of biological activity

| Example | M1 FDSS EC50 (µM) | M1 FDSS PA % | M2 FDSS EC50 (µM) | M2 FDSS PA % | M3 FDSS EC50 (µM) | M3 FDSS PA % | M4 FDSS EC50 (µM) | M4 FDSS PA % | M5 FDSS EC50 (µM) | M5 FDSS PA % |
|---|---|---|---|---|---|---|---|---|---|---|
| Example 1A | 0.210 | 92 | 0.536 | 32 | >25 | 0 | 0.008 | 82 | >25 | 0 |
| Example 1B | 0.598 | 72 | 0.492 | 39 | >25 | 0 | 0.010 | 84 | >25 | 0 |
| Example 1C | 0.576 | 72 | 0.503 | 29 | >25 | 0 | 0.036 | 78 | >25 | 0 |
| Example 1D | 0.609 | 69 | 0.607 | 50 | >25 | 0 | 0.021 | 80 | >25 | 0 |
| Example 1E | 0.563 | 84 | 0.557 | 32 | >25 | 0 | 0.027 | 78 | >25 | 0 |
| Example 1F | 0.368 | 83 | 0.390 | 31 | >25 | 0 | 0.030 | 78 | >25 | 0 |
| Example 1G | 0.973 | 77 | 1.252 | 35 | >25 | 0 | 0.031 | 84 | >25 | 0 |
| Example 1H | 0.631 | 87 | 0.801 | 30 | >25 | 0 | 0.034 | 77 | >25 | 0 |
| Example 1I | 0.980 | 54 | 0.531 | 32 | >25 | 0 | 0.035 | 69 | >25 | 0 |
| Example 1J | 4.089 | 73 | 0.874 | 35 | >25 | 0 | 0.086 | 79 | >25 | 0 |
| Example 1K | 1.589 | 58 | >25 | 0 | >25 | 0 | 0.097 | 58 | >25 | 0 |
| Example 1L | 1.323 | 75 | >25 | 0 | >25 | 0 | 0.099 | 74 | >25 | 0 |
| Example 1M | 1.366 | 89 | 0.752 | 23 | >25 | 0 | 0.094 | 79 | >25 | 0 |
| Example 1N | 0.376 | 82 | >25 | 0 | >25 | 0 | 0.133 | 63 | >25 | 0 |
| Example 1O | 1.347 | 69 | 0.611 | 36 | >25 | 0 | 0.026 | 89 | >25 | 0 |
| Example 1P | 0.439 | 76 | 1.086 | 51 | >25 | 0 | 0.028 | 94 | >25 | 0 |
| Example 1Q | 0.678 | 81 | 3.808 | 16 | >25 | 0 | 0.052 | 79 | >25 | 0 |
| Example 1R | 0.670 | 76 | 0.359 | 32 | >25 | 0 | 0.041 | 77 | >25 | 0 |

TABLE 12-continued

| | Summary of biological activity | | | | | | | | | |
|---|---|---|---|---|---|---|---|---|---|---|
| Example | M1 FDSS EC50 (μM) | M1 FDSS PA % | M2 FDSS EC50 (μM) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
| Example 1S | 0.634 | 71 | 0.656 | 13 | >25 | 0 | 0.079 | 68 | >25 | 0 |
| Example 1T | 0.640 | 74 | >25 | 0 | >25 | 0 | 0.157 | 45 | >25 | 0 |
| Example 1U | 0.961 | 75 | >25 | 0 | >25 | 0 | 0.090 | 73 | >25 | 0 |
| Example 1V | 0.663 | 76 | 0.598 | 35 | >25 | 0 | 0.035 | 83 | >25 | 0 |
| Example 1W | 0.335 | 94 | 0.527 | 68 | >25 | 0 | 0.012 | 89 | 13.82 | 20 |
| Example 1X | 1.226 | 99 | 2.483 | 25 | >25 | 0 | 0.112 | 84 | >25 | 0 |
| Example 1Y | 0.579 | 107 | 0.874 | 35 | >25 | 0 | 0.112 | 86 | >25 | 0 |
| Example 2A | 0.553 | 103 | 0.520 | 46 | >25 | 0 | 0.024 | 79 | >25 | 0 |
| Example 2B | 1.141 | 91 | 0.416 | 35 | >25 | 0 | 0.025 | 71 | >25 | 0 |
| Example 2C | 1.148 | 75 | 0.321 | 39 | >25 | 0 | 0.094 | 72 | >25 | 0 |
| Example 2D | 0.289 | 72 | 0.446 | 50 | >25 | 0 | 0.020 | 72 | >25 | 0 |
| Example 2E | 0.116 | 112 | 0.081 | 59 | >25 | 0 | 0.001 | 85 | 1.67 | 23 |
| Example 2F | 0.061 | 103 | 0.113 | 67 | >25 | 0 | 0.001 | 90 | 3.65 | 30 |
| Example 2G | 0.289 | 89 | 0.061 | 55 | >25 | 0 | 0.003 | 86 | >25 | 0 |
| Example 2H | 0.542 | 101 | 0.309 | 60 | >25 | 0 | 0.006 | 88 | >25 | 0 |
| Example 2I | 0.098 | 97 | 0.109 | 35 | >25 | 0 | 0.012 | 77 | >25 | 0 |
| Example 2J | 0.411 | 103 | 0.214 | 62 | >25 | 0 | 0.012 | 90 | >25 | 0 |
| Example 2K | 1.364 | 97 | 0.498 | 47 | >25 | 0 | 0.018 | 82 | >25 | 0 |
| Example 2L | 2.221 | 47 | 1.068 | 14 | >25 | 0 | 0.050 | 81 | >25 | 0 |
| Example 2M | 3.573 | 7 | 2.030 | 20 | >25 | 0 | 0.145 | 58 | >25 | 0 |
| Example 2N | 5.093 | 71 | 4.236 | 20 | >25 | 0 | 0.289 | 65 | >25 | 0 |
| Example 2O | 1.117 | 72 | 0.581 | 37 | >25 | 0 | 0.051 | 86 | >25 | 0 |
| Example 2P | 2.078 | 71 | 1.073 | 36 | >25 | 0 | 0.085 | 75 | >25 | 0 |
| Example 2Q | 2.020 | 80 | 1.159 | 26 | >25 | 0 | 0.130 | 81 | >25 | 0 |
| Example 2R | 0.848 | 56 | 0.259 | 42 | >25 | 0 | 0.025 | 76 | >25 | 0 |
| Example 2S | 5.408 | 53 | 2.185 | 29 | >25 | 0 | 0.242 | 68 | >25 | 0 |
| Example 2T | 0.063 | 89 | 0.041 | 44 | >25 | 0 | 0.002 | 89 | 0.73 | 0 |
| Example 2U | 0.223 | 81 | 0.275 | 51 | >25 | 0 | 0.012 | 86 | >25 | 0 |
| Example 2V | 1.648 | 31 | 1.080 | 28 | >25 | 0 | 0.094 | 75 | >25 | 0 |
| Example 2W | 3.441 | 66 | 3.080 | 29 | >25 | 0 | 0.087 | 70 | >25 | 0 |
| Example 2X | 11.29 | 42 | 11.19 | 23 | >25 | 0 | 1.781 | 40 | >25 | 0 |
| Example 2Y | 10.79 | 51 | 3.327 | 35 | >25 | 0 | 0.554 | 76 | 9.46 | 13 |
| Example 2Z | 5.064 | 11 | 0.760 | 24 | >25 | 0 | 0.108 | 51 | >25 | 0 |
| Example 2AA | 6.657 | 30 | 7.976 | 22 | >25 | 0 | 0.210 | 16 | >25 | 0 |
| Example 2BB | 7.000 | 65 | 4.845 | 27 | >25 | 0 | 0.946 | 91 | >25 | 0 |

TABLE 12-continued

Summary of biological activity

| Example | M1 FDSS EC50 (μM) | M1 FDSS PA % | M2 FDSS EC50 (μM) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 2CC | 2.176 | 85 | 2.069 | 37 | >25 | 0 | 0.168 | 79 | >25 | 0 |
| Example 2DD | 1.118 | 67 | 6.757 | 23 | >25 | 0 | 0.155 | 64 | >25 | 0 |
| Example 2EE | 2.343 | 95 | 2.945 | 50 | >25 | 0 | 0.086 | 74 | >25 | 0 |
| Example 2FF | 0.264 | 70 | 0.312 | 28 | >25 | 0 | 0.026 | 66 | >25 | 0 |
| Example 2GG | 2.900 | 64 | >25 | 0 | >25 | 0 | 0.087 | 58 | >25 | 0 |
| Example 2HH | 2.569 | 96 | 6.565 | 25 | >25 | 0 | 0.124 | 85 | >25 | 0 |
| Example 2II | 4.052 | 107 | 4.294 | 23 | >25 | 0 | 0.124 | 81 | >25 | 0 |
| Example 3A | 1.112 | 85 | 1.570 | 35 | >25 | 0 | 0.083 | 91 | >25 | 0 |
| Example 3B | 1.118 | 82 | 1.498 | 31 | >25 | 0 | 0.069 | 86 | >25 | 0 |
| Example 3C | 3.889 | 78 | 4.824 | 34 | >25 | 0 | 0.184 | 85 | >25 | 0 |
| Example 3D | 1.406 | 75 | 1.917 | 48 | >25 | 0 | 0.063 | 84 | >25 | 0 |
| Example 3E | 0.695 | 86 | 0.404 | 60 | >25 | 0 | 0.028 | 86 | >25 | 0 |
| Example 3F | 0.595 | 86 | 0.406 | 49 | >25 | 0 | 0.023 | 80 | >25 | 0 |
| Example 3G | 7.241 | 44 | 3.656 | 16 | >25 | 0 | 0.185 | 82 | >25 | 0 |
| Example 3H | 2.412 | 84 | 2.465 | 30 | 10.70 | 20 | 0.010 | 83.2 | >25 | 0 |
| Example 3I | 3.307 | 76 | 3.857 | 32 | >25 | 0 | 0.038 | 91.2 | >25 | 0 |
| Example 4A | 0.234 | 84 | 0.432 | 21 | >25 | 0 | 0.004 | 80 | >25 | 0 |
| Example 4B | 0.424 | 117 | >25 | 32 | >25 | 0 | 0.004 | 77 | >25 | 0 |
| Example 4C | 0.382 | 79 | 0.433 | 38 | >25 | 0 | 0.007 | 80 | >25 | 0 |
| Example 4D | 0.741 | 95 | >25 | 17 | >25 | 0 | 0.007 | 77 | >25 | 0 |
| Example 4E | 0.979 | 75 | >25 | 0 | >25 | 0 | 0.012 | 81 | >25 | 0 |
| Example 4F | 0.540 | 90 | 3.259 | 17 | >25 | 0 | 0.015 | 80 | >25 | 0 |
| Example 4G | 1.756 | 62 | 13.11 | 58 | >25 | 0 | 0.017 | 68 | >25 | 0 |
| Example 4H | 0.745 | 63 | >25 | 20 | >25 | 0 | 0.017 | 69 | >25 | 0 |
| Example 4I | 0.227 | 82 | >25 | 0 | >25 | 0 | 0.019 | 73 | >25 | 0 |
| Example 4J | 1.668 | 72 | >25 | 0 | >25 | 0 | 0.030 | 82 | >25 | 0 |
| Example 4K | 0.444 | 60 | >25 | 0 | >25 | 0 | 0.025 | 66 | >25 | 0 |
| Example 4L | 0.336 | 66 | >25 | 0 | >25 | 0 | 0.027 | 52 | >25 | 0 |
| Example 4M | 2.806 | 49 | >25 | 0 | >25 | 0 | 0.086 | 82 | >25 | 0 |
| Example 4N | 0.384 | 64 | >25 | 0 | >25 | 0 | 0.093 | 74 | >25 | 0 |
| Example 4O | 0.364 | 63 | 12.68 | 31 | >25 | 0 | 0.007 | 58 | >25 | 0 |
| Example 4P | 0.334 | 89 | 10.47 | 28 | >25 | 0 | 0.005 | 63 | >25 | 0 |
| Example 4Q | 0.294 | 71 | 1.882 | 13 | >25 | 0 | 0.011 | 60 | >25 | 0 |
| Example 4R | 0.128 | 95 | 0.203 | 12 | >25 | 0 | 0.003 | 70 | >25 | 0 |
| Example 4S | 0.624 | 89 | >25 | 31 | >25 | 0 | 0.021 | 74 | >25 | 0 |

TABLE 12-continued

Summary of biological activity

| Example | M1 FDSS EC50 (μM) | M1 FDSS PA % | M2 FDSS EC50 (μM) | M2 FDSS PA % | M3 FDSS EC50 (μM) | M3 FDSS PA % | M4 FDSS EC50 (μM) | M4 FDSS PA % | M5 FDSS EC50 (μM) | M5 FDSS PA % |
|---|---|---|---|---|---|---|---|---|---|---|
| Example 4T | 0.909 | 63 | 17.67 | 43 | >25 | 0 | 0.025 | 63 | >25 | 0 |
| Example 4U | 2.239 | 55 | 15.16 | 38 | >25 | 0 | 0.042 | 62 | >25 | 0 |
| Example 4V | 1.992 | 72 | 10.69 | 14 | >25 | 0 | 0.046 | 82 | >25 | 0 |
| Example 4W | 1.094 | 74 | 5.161 | 21 | >25 | 0 | 0.021 | 75 | >25 | 0 |
| Example 5A | 0.630 | 70 | >25 | 26 | >25 | 0 | 0.074 | 60 | >25 | 0 |
| Example 5B | 1.567 | 22 | >25 | 0 | >25 | 0 | 0.087 | 59 | >25 | 0 |
| Example 5C | 1.601 | 60 | >25 | 0 | >25 | 0 | 0.110 | 66 | >25 | 4 |
| Example 5D | 1.146 | 60 | >25 | 0 | >25 | 0 | 0.128 | 46 | >25 | 0 |
| Example 5E | 2.579 | 29 | >25 | 0 | >25 | 0 | 0.345 | 39 | 13.02 | 0 |
| Example 5F | 0.011 | 106 | 0.073 | 51 | 11.77 | 15 | <0.0004 | 90 | 2.53 | 35 |
| Example 5G | 0.311 | 88 | 0.657 | 35 | >25 | 0 | 0.013 | 76 | >25 | 0 |
| Example 5H | 0.432 | 67 | 0.443 | 40 | >25 | 0 | 0.015 | 99 | >25 | 0 |
| Example 5I | 0.775 | 69 | 0.545 | 43 | >25 | 0 | 0.020 | 71 | >25 | 0 |
| Example 5J | 1.201 | 6 | 4.746 | 46 | >25 | 0 | 0.029 | 92 | >25 | 0 |
| Example 5K | 0.434 | 96 | 0.453 | 32 | >25 | 0 | 0.031 | 87 | 6.64 | 0 |
| Example 5L | 0.370 | 88 | 0.456 | 32 | >25 | 0 | 0.038 | 79 | >25 | 0 |
| Example 5M | 0.786 | 66 | 0.415 | 34 | >25 | 0 | 0.058 | 73 | >25 | 0 |
| Example 5N | 2.969 | 68 | >25 | 38 | >25 | 0 | 0.068 | 61 | 12.45 | 21 |
| Example 5O | 0.789 | 78 | 1.174 | 33 | >25 | 0 | 0.071 | 74 | >25 | 0 |
| Example 5P | 0.413 | 91 | 9.699 | 25 | >25 | 0 | 0.086 | 58 | >25 | 0 |
| Example 5Q | 0.864 | 86 | >25 | 0 | >25 | 0 | 0.092 | 83 | >25 | 0 |
| Example 5R | 0.904 | 52 | 1.236 | 18 | >25 | 0 | 0.096 | 73 | >25 | 0 |
| Example 5S | 0.761 | 87 | 4.598 | 23 | >25 | 0 | 0.197 | 69 | >25 | 0 |
| Example 5T | 1.789 | 57 | 19.99 | 35 | >25 | 0 | 0.208 | 61 | >25 | 0 |
| Example 5U | 2.445 | 75 | 0.483 | 17 | >25 | 0 | 0.238 | 67 | >25 | 0 |
| Example 5V | 0.786 | 79 | >25 | 0 | >25 | 0 | 0.250 | 40 | >25 | 0 |
| Example 5W | 3.591 | 68 | 20.70 | 30 | >25 | 0 | 0.104 | 85 | >25 | 0 |
| Example 5X | 2.343 | 75 | 1.417 | 43 | >25 | 0 | 0.058 | 71 | >25 | 0 |
| Example 5Y | 1.989 | 47 | >25 | 0 | >25 | 0 | 0.109 | 64 | >25 | 0 |
| Example 6A | 0.887 | 53 | 0.623 | 18 | >25 | 0 | 0.012 | 74 | >25 | 0 |
| Example 6B | 0.490 | 88 | 0.390 | 38 | >25 | 0 | 0.008 | 79 | >25 | 0 |
| Example 6C | 2.420 | 65 | 1.505 | 18 | >25 | 0 | 0.044 | 74 | >25 | 0 |
| Example 7A | >25 | 0 | >25 | 0 | >25 | 0 | 1.41 | 42 | >25 | 0 |

Testing Novel Compounds in a Mouse Amphetamine Induced Hyperlocomotion Assay

The aim of these studies is to determine the effect of test compounds on the hyperactivity in mice induced by the stimulant d-amphetamine. Clinically efficacious muscarinic anti-psychotics such as xanomeline are active in this assay and it is therefore considered appropriate as a test for novel M4 agonists. Studies described in this report were performed in a manner approved by the Novartis Institutes for BioMedical Research, Inc. Animal Care and Use Committee. Treatment groups were randomized and counterbalanced by chamber and run. Locomotor activity was assessed in an open-field (40 cm×40 cm) setup. Each chamber is enclosed behind light-blocking curtains and illuminated by an LED light. Mice were acclimated to the room for a minimum of 60 minutes and then administered test article (Vehicle, dose 1, dose 2, dose 3, PO) just prior to being placed in the chamber for the habituation (minutes 1-30) phase. After the habituation phase mice were administered either d-amphetamine (2.0 mg/kg) or Saline (TP), as well as Xanomeline as a positive control (1.0 mg/kg, SC) if they did not previously receive a PO injection of test article. The injection volume for all injections was 10 mL/kg. Measurements were captured via infrared beam breaks by Accuscan hardware and Superflex 5.6 software. Locomotor activity was monitored for an additional 2-hour test phase (minutes 31-150) after amphetamine injections. Animals were returned to their home cage and housing location after the conclusion of the test.

Data Analysis

Figure 2:
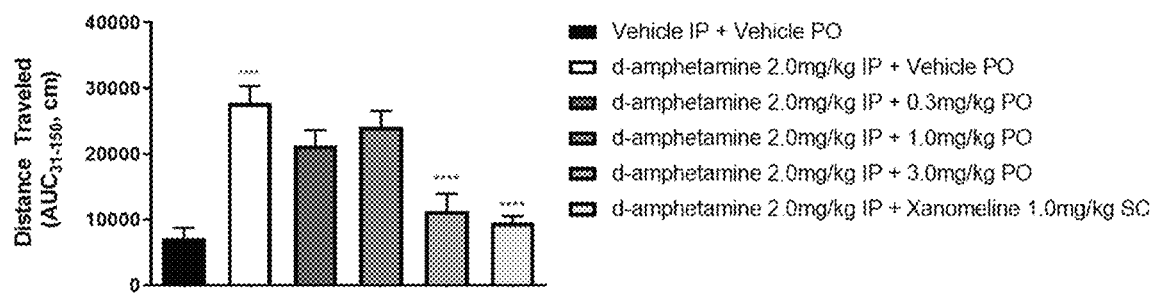
FIG. 2 illustrates the effect of Example 3C and Example 3D on the hyperactivity in mice induced by the stimulant d-amphetamine using a mouse amphetamine induced hyperlocomotion assay.
Figure 2:
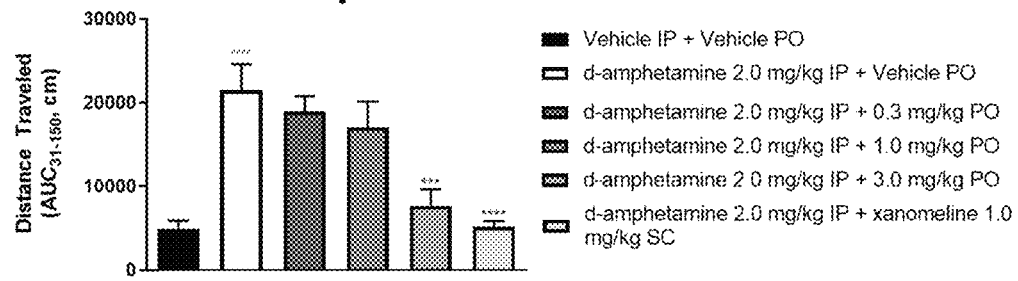

All statistical analyses were performed within Graphpad Prism 7.04. AUC's were calculated by summing the distance traveled during each the 10-minute bins and compared via t-test or one-way ANOVA. A t-test comparing the AUC30-150 of the d-Amphetamine-vehicle injected group to the vehicle-vehicle injected group determined whether d-amphetamine produced an effective stimulation of activity. An ordinary one-way ANOVA was performed to compare each test compound-treated group to the d-Amphetamine-vehicle group using a Dunnett's multiple comparison test. Because d-Amphetamine is primarily active during the first hour of the test phase, these analyses are performed on the first half (minutes 31-90). A p-value of <0.05 was considered statistically significant. Data for Example 1A and Example 2L are shown in FIG. 1. Data for Example 3C and Example 3D are shown in FIG. 2. Data for Example 4A and Example 5G are shown in FIG. 3.

Figure 3:
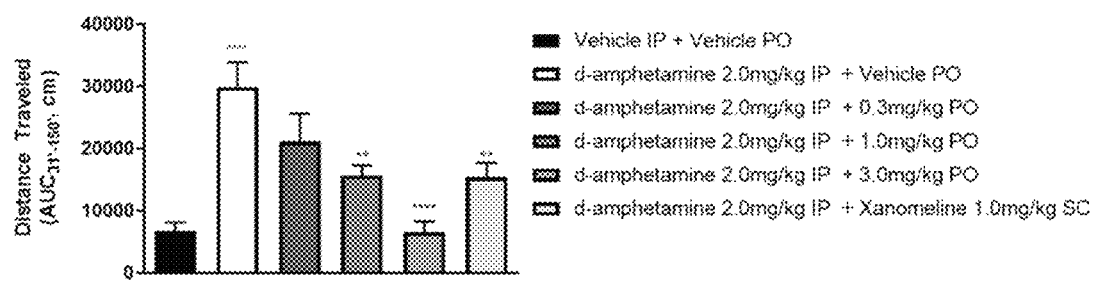
FIG. 3 illustrates the effect of Example 4A and Example 5G on the hyperactivity in mice induced by the stimulant d-amphetamine using a mouse amphetamine induced hyperlocomotion assay.
Figure 3:
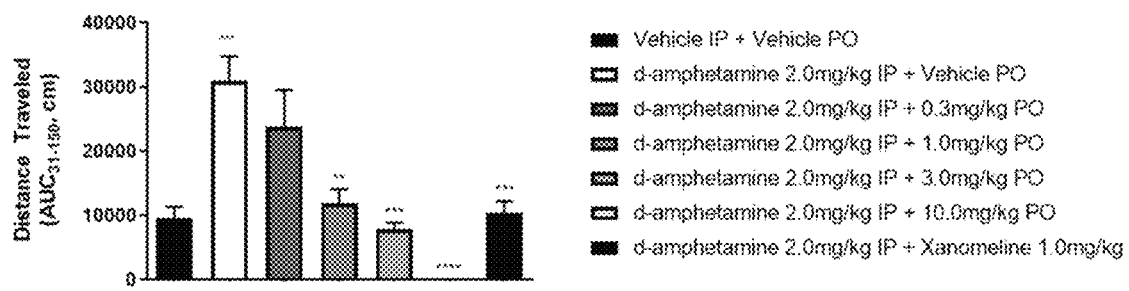

Altogether, the experimental data presented herein indicate that the disclosed compounds are potent and highly selective M4 receptor agonists (see Table 12) and are effective in vivo as indicated by their efficacy in reducing hyperactivity induced by the stimulant d-amphetamine in mice in a dose-dependent manner (see FIG. 1-3).

What is claimed is:

1. A method for the treatment of psychosis associated with Alzheimer's disease, the method comprising administering a therapeutically effective amount of a compound of Formula (I) or a pharmaceutically acceptable salt thereof to a subject in need of treatment thereof, wherein the compound of formula (I) is:

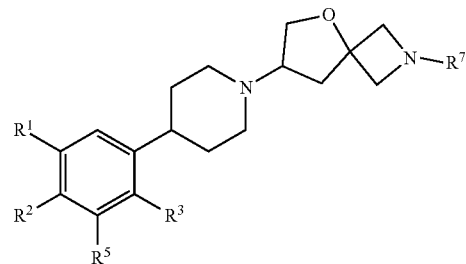

wherein $R^1$ is halogen or hydrogen;

$R^2$ is halogen or hydrogen;

$R^3$ is optionally substituted $C_{1-3}$ alkyl, wherein the alkyl is optionally substituted with one 4- to 6-membered heterocycloalkyl, optionally substituted 5- to 6-membered heteroaryl, wherein the heteroaryl is optionally substituted with one $C_{1-3}$ alkyl, optionally substituted 4- to 6-membered heterocycloalkyl, wherein the heterocycloalkyl is optionally substituted with one —OH, optionally substituted 4- to 6-membered cycloalkyl, wherein the cycloalkyl is optionally substituted with one —OH, or

—$OR^4$;

$R^4$ is optionally substituted $C_{1-5}$ alkyl, wherein the alkyl is optionally substituted with one or two $R^6$, optionally substituted 3- to 9-membered heterocycloalkyl, wherein the heterocycloalkyl is optionally substituted with one or two $R^6$, or optionally substituted 4- to 6-membered cycloalkyl, wherein the cycloalkyl is optionally substituted with one, two, or three $R^6$;

$R^5$ is halogen or hydrogen;

each $R^6$ is independently selected from the group consisting of halogen,

—OH,

—$OCH_3$,

—$C(CH_3)_2OH$,

—$CH_2OH$, cyano, optionally substituted $C_1$-$C_4$ alkyl, wherein the alkyl is optionally substituted with —OH, optionally substituted 4- to 7-membered heterocycloalkyl, wherein the heterocycloalkyl is optionally substituted with one or two substituents independently selected from the group consisting of halogen, —OH, —$OCH_3$, and $C_{1-3}$ alkyl, and optionally substituted 5- to 6-membered heteroaryl, wherein the heteroaryl is optionally substituted with one $C_{1-3}$ alkyl; and $R^7$ is 5-membered heteroaryl.

2. The method of claim 1, wherein the compound of Formula (I) is a compound of Formula (Ia):

(Ia)

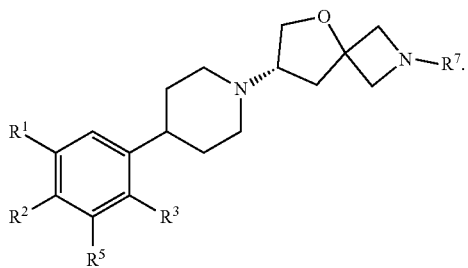

3. The method of claim 1, wherein the compound of Formula (I) is a compound of Formula (Ib)

(Ib)

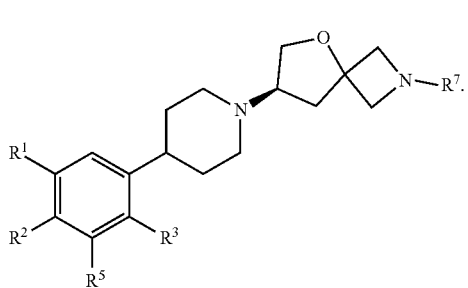

4. The method of claim 1, wherein $R^1$ is selected from the group consisting of H, chloro, and fluoro.

5. The method of claim 1, wherein $R^1$ is fluoro.

6. The method of claim 1, wherein $R^2$ is H or fluoro.

7. The method of claim 1, wherein $R^5$ is H or fluoro.

8. The method of claim 1, wherein $R^1$, $R^2$, and $R^5$ are H.

9. The method of claim 1, wherein $R^2$ and $R^5$ are H.

10. The method of claim 1, wherein $R^3$ is selected from the group consisting of:

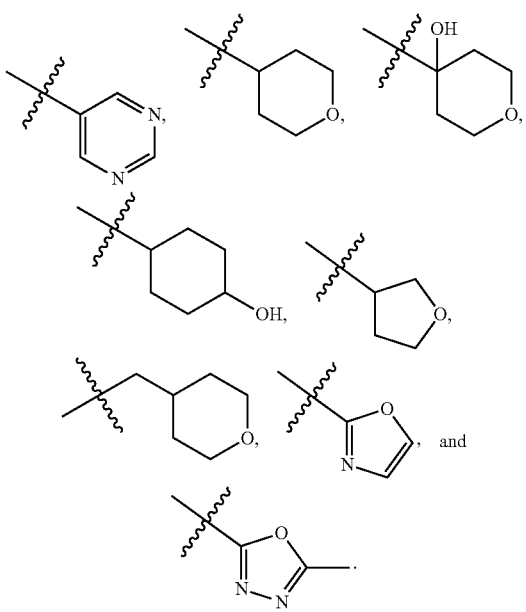

and

11. The method of claim 1, wherein $R^3$ is —$OR^4$.

12. The method of claim 1, wherein $R^4$ is selected from the group consisting of $CH_3$, —$CH_2CH_2C(CH_3)_2OH$, —$CH_2CH_2C(CH_3)_2OCH_3$, —$CH_2CH_2OCH_3$, and —$CH_2C(CH_3)_2OH$.

13. The method of claim 1, wherein $R^4$ is selected from the group consisting of:

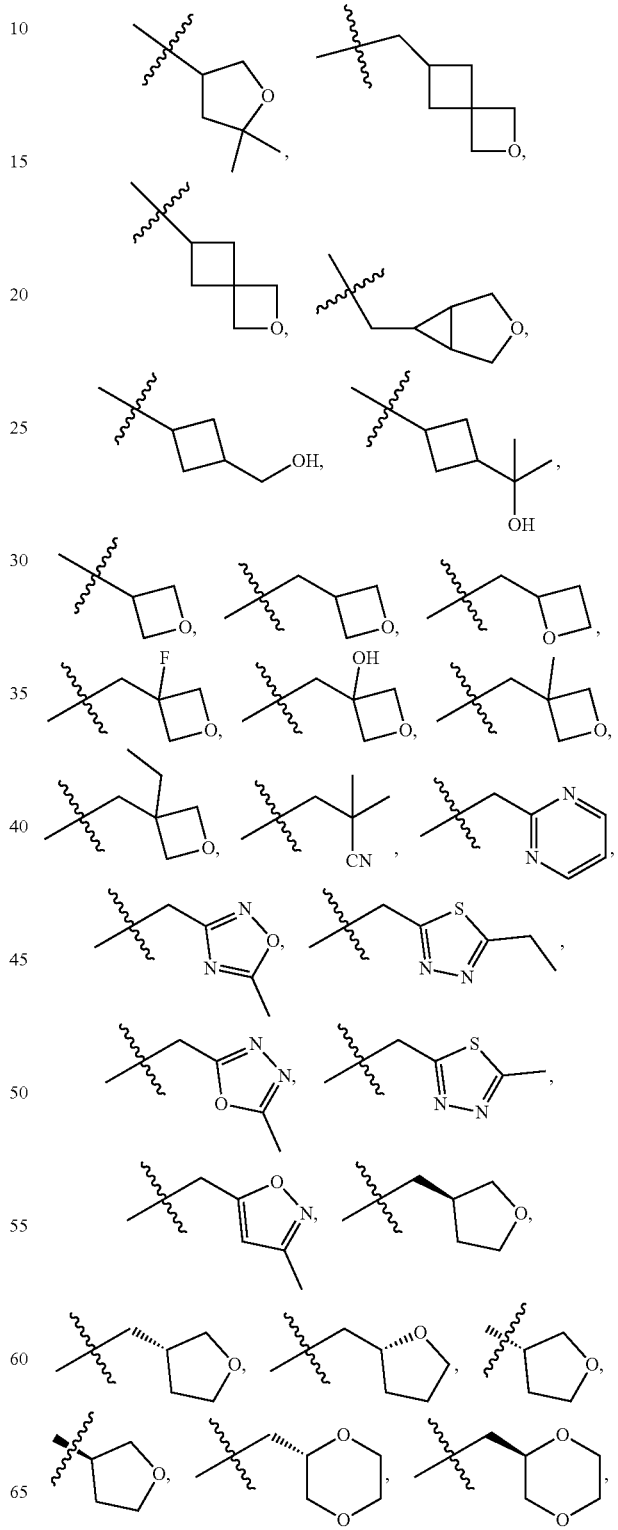

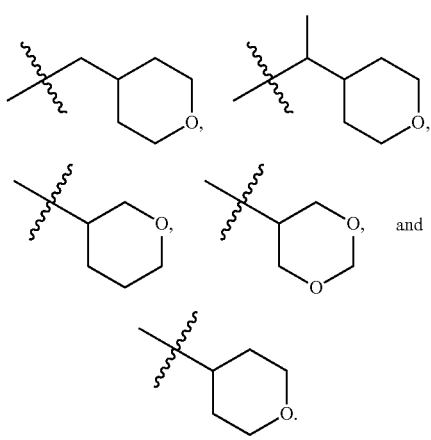

14. The method of claim 1, wherein $R^4$ is $C_1$-$C_5$ alkyl and $R^6$ is independently cyano, —OH, —OCH$_3$,

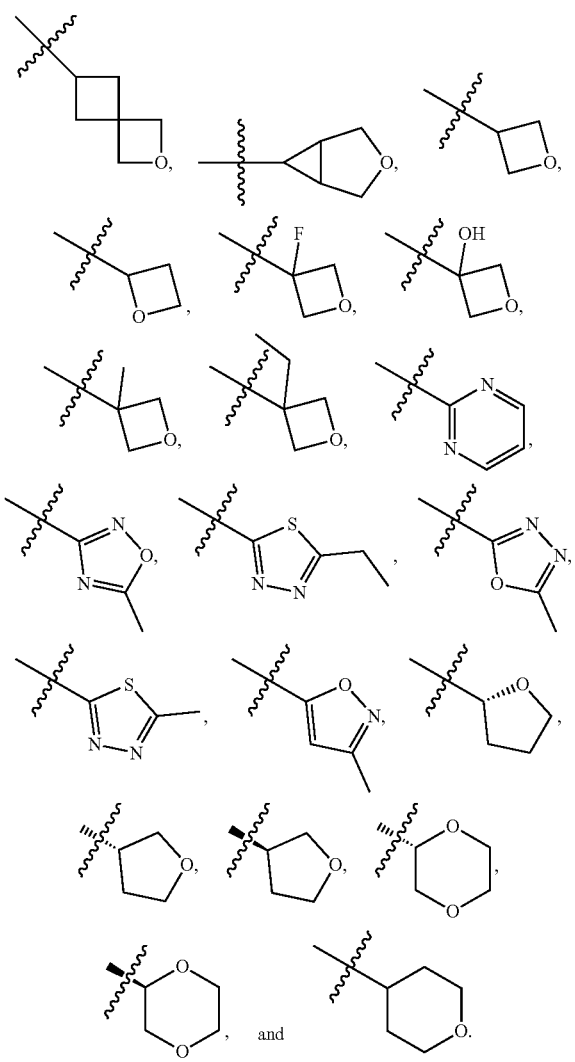

15. The method of claim 3, wherein $R^7$ is selected from the group consisting of:

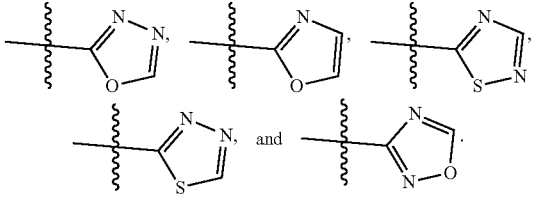

16. A method for the treatment of psychosis associated with Alzheimer's disease, the method comprising administering a therapeutically effective amount of a compound selected from the group consisting of:

(S)-7-(4-(5-fluoro-2-(oxetan-3-yloxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydrofuran-3-yl)methoxy) phenyl)piperidin-1-yl)-2-(1,3,4-oxadiazol-2-yl)-5-oxa-2-azaspiro[3.4]octane;

ethyl 5-((S)-7-(4-(2-(((R)-1,4-dioxan-2-yl)methoxy)-5-fluorophenyl)piperidin-1-yl)-5-oxa-2-azaspiro[3.4]octan-2-yl)-1,3,4-oxadiazole-2-carboxylate;

(S)-7-(4-(5-fluoro-2-(((R)-tetrahydrofuran-3-yl)oxy)phenyl)piperidin-1-yl)-2-(1,3,4-oxadiazol-2-yl)-5-oxa-2-azaspiro[3.4]octane;

(S)-3-(2-(1-(2-(1,3,4-oxadiazol-2-yl)-5-oxa-2-azaspiro[3.4]octan-7-yl)piperidin-4-yl)-4-fluorophenoxy)-2,2-dimethylpropanenitrile;

(S)-7-(4-(2-(((S)-1,4-dioxan-2-yl)methoxy)-5-fluorophenyl)piperidin-1-yl)-2-(1,3,4-oxadiazol-2-yl)-5-oxa-2-azaspiro[3.4]octane;

(S)-7-(4-(5-fluoro-2-((tetrahydro-2H-pyran-4-yl)oxy) phenyl)piperidin-1-yl)-2-(1,3,4-oxadiazol-2-yl)-5-oxa-2-azaspiro[3.4]octane;

(S)-7-(4-(5-fluoro-2-(((S)-tetrahydrofuran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((S)-tetrahydrofuran-3-yl)methoxy) phenyl)piperidin-1-yl)-2-(1,3,4-oxadiazol-2-yl)-5-oxa-2-azaspiro[3.4]octane;

(S)-7-(4-(5-fluoro-2-((tetrahydro-2H-pyran-4-yl) methoxy)phenyl)piperidin-1-yl)-2-(1,3,4-oxadiazol-2-yl)-5-oxa-2-azaspiro[3.4]octane;

(S)-7-(4-(5-fluoro-2-(3-methoxy-3-methylbutoxy)phenyl)piperidin-1-yl)-2-(1,3,4-oxadiazol-2-yl)-5-oxa-2-azaspiro[3.4]octane;

(S)-7-(4-(5-fluoro-2-(2-methoxyethoxy)phenyl)piperidin-1-yl)-2-(1,3,4-oxadiazol-2-yl)-5-oxa-2-azaspiro[3.4]octane;

(S)-7-(4-(2-((1,3-dioxan-5-yl)oxy)-5-fluorophenyl)piperidin-1-yl)-2-(1,3,4-oxadiazol-2-yl)-5-oxa-2-azaspiro[3.4]octane;

(S)-4-(2-(1-(2-(1,3,4-oxadiazol-2-yl)-5-oxa-2-azaspiro[3.4]octan-7-yl)piperidin-4-yl)-4-fluorophenoxy)-2-methylbutan-2-ol;

(S)-2-(1,3,4-oxadiazol-2-yl)-7-(4-(2-(((R)-tetrahydrofuran-3-yl)oxy)phenyl)piperidin-1-yl)-5-oxa-2-azaspiro[3.4]octane;

(S)-2-(1,3,4-oxadiazol-2-yl)-7-(4-(2-(oxetan-3-yloxy) phenyl)piperidin-1-yl)-5-oxa-2-azaspiro[3.4]octane;

(S)-7-(4-(2-methoxyphenyl)piperidin-1-yl)-2-(1,3,4-oxadiazol-2-yl)-5-oxa-2-azaspiro[3.4]octane;

(S)-7-(4-(4,5-difluoro-2-(((R)-tetrahydrofuran-3-yl)oxy) phenyl)piperidin-1-yl)-2-(1,3,4-oxadiazol-2-yl)-5-oxa-2-azaspiro[3.4]octane;

(S)-7-(4-(4-fluoro-2-methoxyphenyl)piperidin-1-yl)-2-(1,3,4-oxadiazol-2-yl)-5-oxa-2-azaspiro[3.4]octane;

(S)-4-(2-(1-(2-(1,3,4-oxadiazol-2-yl)-5-oxa-2-azaspiro[3.4]octan-7-yl)piperidin-4-yl)-5-fluorophenoxy)-2-methylbutan-2-ol;

(S)-1-(2-(1-(2-(1,3,4-oxadiazol-2-yl)-5-oxa-2-azaspiro[3.4]octan-7-yl)piperidin-4-yl)-4-fluorophenoxy)-2-methylpropan-2-ol;

(S)-7-(4-(5-fluoro-2-methoxyphenyl)piperidin-1-yl)-2-(1,3,4-oxadiazol-2-yl)-5-oxa-2-azaspiro[3.4]octane;

(S)-2-(1,3,4-oxadiazol-2-yl)-7-(4-(2-(pyrimidin-5-yl)phenyl)piperidin-1-yl)-5-oxa-2-azaspiro[3.4]octane;

(S)-2-(1,3,4-oxadiazol-2-yl)-7-(4-(2-(oxazol-2-yl)phenyl)piperidin-1-yl)-5-oxa-2-azaspiro[3.4]octane;

(S)-7-(4-(2-(5-methyl-1,3,4-oxadiazol-2-yl)phenyl)piperidin-1-yl)-2-(1,3,4-oxadiazol-2-yl)-5-oxa-2-azaspiro[3.4]octane;

(S)-7-(4-(5-fluoro-2-(oxetan-3-ylmethoxy)phenyl)piperidin-1-yl)-2-(1,3,4-thiadiazol-2-yl)-5-oxa-2-azaspiro[3.4]octane;

(S)-7-(4-(5-fluoro-2-((3-methyloxetan-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;

(S)-7-(4-(5-fluoro-2-((5-methyl-1,3,4-thiadiazol-2-yl)methoxy)phenyl)piperidin-1-yl)-2-(1,3,4-oxadiazol-2-yl)-5-oxa-2-azaspiro[3.4]octane;

(S)-7-(4-(5-fluoro-2-((5-methyl-1,3,4-oxadiazol-2-yl)methoxy)phenyl)piperidin-1-yl)-2-(1,3,4-oxadiazol-2-yl)-5-oxa-2-azaspiro[3.4]octane;

(S)-7-(4-(5-fluoro-2-((3-methylisoxazol-5-yl)methoxy)phenyl)piperidin-1-yl)-2-(1,3,4-oxadiazol-2-yl)-5-oxa-2-azaspiro[3.4]octane;

(S)-7-(4-(5-fluoro-2-(oxetan-3-ylmethoxy)phenyl)piperidin-1-yl)-2-(1,3,4-oxadiazol-2-yl)-5-oxa-2-azaspiro[3.4]octane;

(S)-7-(4-(5-fluoro-2-(pyrimidin-2-ylmethoxy)phenyl)piperidin-1-yl)-2-(1,3,4-oxadiazol-2-yl)-5-oxa-2-azaspiro[3.4]octane;

(S)-7-(4-(5-fluoro-2-((3-fluorooxetan-3-yl)methoxy)phenyl)piperidin-1-yl)-2-(1,3,4-oxadiazol-2-yl)-5-oxa-2-azaspiro[3.4]octane;

(S)-7-(4-(5-fluoro-2-((3-methyloxetan-3-yl)methoxy)phenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane;

(S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane;

(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;

(S)-7-(4-(2-((3-ethyloxetan-3-yl)methoxy)-5-fluorophenyl)piperidin-1-yl)-2-(1,3,4-oxadiazol-2-yl)-5-oxa-2-azaspiro[3.4]octane;

(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)methoxy)-5-fluorophenyl)piperidin-1-yl)-2-(1,3,4-oxadiazol-2-yl)-5-oxa-2-azaspiro[3.4]octane;

(S)-7-(4-(2-((5-ethyl-1,3,4-thiadiazol-2-yl)methoxy)-5-fluorophenyl)piperidin-1-yl)-2-(1,3,4-oxadiazol-2-yl)-5-oxa-2-azaspiro[3.4]octane;

(S)-3-((2-(1-(2-(1,3,4-oxadiazol-2-yl)-5-oxa-2-azaspiro[3.4]octan-7-yl)piperidin-4-yl)-4-fluorophenoxy)methyl)oxetan-3-ol;

2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;

(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;

(7S)-7-(4-(2-((3-oxabicyclo[3.1.0]hexan-6-yl)methoxy)-5-fluorophenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)oxy)-3,5-difluorophenyl)piperidin-1-yl)-2-(1,3,4-oxadiazol-2-yl)-5-oxa-2-azaspiro[3.4]octane;

(S)-7-(4-(3,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;

(S)-7-(4-(3,5-difluoro-2-(((R)-tetrahydrofuran-3-yl)oxy)
phenyl)piperidin-1-yl)-2-(1,3,4-oxadiazol-2-yl)-5-oxa-
2-azaspiro[3.4]octane;
(S)-7-(4-(3,5-difluoro-2-(oxetan-3-ylmethoxy)phenyl)pi-
peridin-1-yl)-2-(1,3,4-oxadiazol-2-yl)-5-oxa-2-
azaspiro[3.4]octane;
(S)-7-(4-(3,5-difluoro-2-(oxetan-3-yloxy)phenyl)piperi-
din-1-yl)-2-(1,3,4-oxadiazol-2-yl)-5-oxa-2-azaspiro
[3.4]octane;
(S)-7-(4-(4,5-difluoro-2-(oxetan-3-yloxy)phenyl)piperi-
din-1-yl)-2-(1,3,4-oxadiazol-2-yl)-5-oxa-2-azaspiro
[3.4]octane;
(S)-7-(4-(4,5-difluoro-2-((tetrahydro-2H-pyran-4-yl)oxy)
phenyl)piperidin-1-yl)-2-(1,3,4-oxadiazol-2-yl)-5-oxa-
2-azaspiro[3.4]octane;
((1S,3r)-3-(2-(1-((S)-2-(1,3,4-oxadiazol-2-yl)-5-oxa-2-
azaspiro[3.4]octan-7-yl)piperidin-4-yl)-4-fluorophe-
noxy)cyclobutyl)methanol;
((1R,3s)-3-(2-(1-((S)-2-(1,3,4-oxadiazol-2-yl)-5-oxa-2-
azaspiro[3.4]octan-7-yl)piperidin-4-yl)-4-fluorophe-
noxy)cyclobutyl)methanol;
((1S,3r)-3-(2-(1-((S)-2-(1,3,4-oxadiazol-2-yl)-5-oxa-2-
azaspiro[3.4]octan-7-yl)piperidin-4-yl)-4-fluorophe-
noxy)cyclobutyl)methanol;
((1R,3s)-3-(2-(1-((S)-2-(1,3,4-oxadiazol-2-yl)-5-oxa-2-
azaspiro[3.4]octan-7-yl)piperidin-4-yl)-4-fluorophe-
noxy)cyclobutyl)methanol;
(S)-2-(1,3,4-oxadiazol-2-yl)-7-(4-(2-((S)-tetrahydro-
furan-3-yl)phenyl)piperidin-1-yl)-5-oxa-2-azaspiro
[3.4]octane;
(S)-2-(1,3,4-oxadiazol-2-yl)-7-(4-(2-((R)-tetrahydro-
furan-3-yl)phenyl)piperidin-1-yl)-5-oxa-2-azaspiro
[3.4]octane;
(S)-2-(1,3,4-oxadiazol-2-yl)-7-(4-(2-((S)-tetrahydro-
furan-3-yl)phenyl)piperidin-1-yl)-5-oxa-2-azaspiro
[3.4]octane;
(S)-2-(1,3,4-oxadiazol-2-yl)-7-(4-(2-((R)-tetrahydro-
furan-3-yl)phenyl)piperidin-1-yl)-5-oxa-2-azaspiro
[3.4]octane;
(S)-2-(1,3,4-oxadiazol-2-yl)-7-(4-(2-(tetrahydro-2H-
pyran-4-yl)phenyl)piperidin-1-yl)-5-oxa-2-azaspiro
[3.4]octane;
(S)-7-(4-(5-fluoro-2-(tetrahydro-2H-pyran-4-yl)phenyl)
piperidin-1-yl)-2-(1,3,4-oxadiazol-2-yl)-5-oxa-2-
azaspiro[3.4]octane;
(S)-7-(4-(5-fluoro-2-((R)-tetrahydrofuran-3-yl)phenyl)pi-
peridin-1-yl)-2-(1,3,4-oxadiazol-2-yl)-5-oxa-2-
azaspiro[3.4]octane;
(S)-7-(4-(5-fluoro-2-((S)-tetrahydrofuran-3-yl)phenyl)pi-
peridin-1-yl)-2-(1,3,4-oxadiazol-2-yl)-5-oxa-2-
azaspiro[3.4]octane;
(S)-7-(4-(5-fluoro-2-((R)-tetrahydrofuran-3-yl)phenyl)pi-
peridin-1-yl)-2-(1,3,4-oxadiazol-2-yl)-5-oxa-2-
azaspiro[3.4]octane;
(S)-7-(4-(5-fluoro-2-((S)-tetrahydrofuran-3-yl)phenyl)pi-
peridin-1-yl)-2-(1,3,4-oxadiazol-2-yl)-5-oxa-2-
azaspiro[3.4]octane;
(S)-2-(1,3,4-oxadiazol-2-yl)-7-(4-(2-((tetrahydro-2H-
pyran-4-yl)methyl)phenyl)piperidin-1-yl)-5-oxa-2-
azaspiro[3.4]octane;
(1R,4s)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1S,4r)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1R,4s)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1S,4r)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1R,4s)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1S,4r)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(1R,4s)-4-(2-(1-((S)-2-(1,3,4-oxadiazol-2-yl)-5-oxa-2-
azaspiro[3.4]octan-7-yl)piperidin-4-yl)-4-fluorophe-
nyl)cyclohexan-1-ol;
(S)-7-(4-(5-fluoro-2-(oxetan-3-yloxy)phenyl)piperidin-1-
yl)-2-(oxazol-2-yl)-5-oxa-2-azaspiro[3.4]octane;
(S)-7-(4-(2-(((R)-1,4-dioxan-2-yl)methoxy)-5-fluorophe-
nyl)piperidin-1-yl)-2-(oxazol-2-yl)-5-oxa-2-azaspiro
[3.4]octane;
(S)-2-(oxazol-2-yl)-7-(4-(2-(oxetan-3-yloxy)phenyl)pip-
eridin-1-yl)-5-oxa-2-azaspiro[3.4]octane;
(S)-7-(4-(5-fluoro-2-(((R)-tetrahydrofuran-3-yl)oxy)phe-
nyl)piperidin-1-yl)-2-(oxazol-2-yl)-5-oxa-2-azaspiro
[3.4]octane;
(S)-7-(4-(5-fluoro-2-((tetrahydro-2H-pyran-4-yl)oxy)
phenyl)piperidin-1-yl)-2-(oxazol-2-yl)-5-oxa-2-
azaspiro[3.4]octane;
(S)-2-(oxazol-2-yl)-7-(4-(2-(((R)-tetrahydrofuran-3-yl)
oxy)phenyl)piperidin-1-yl)-5-oxa-2-azaspiro[3.4]oc-
tane;
(S)-7-(4-(2-((2-oxaspiro[3.3]heptan-6-yl)oxy)-5-fluoro-
phenyl)piperidin-1-yl)-2-(oxazol-2-yl)-5-oxa-2-
azaspiro[3.4]octane;
(S)-2-(oxazol-2-yl)-7-(4-(2-(((S)-tetrahydrofuran-3-yl)
oxy)phenyl)piperidin-1-yl)-5-oxa-2-azaspiro[3.4]oc-
tane;
(S)-7-(4-(5-fluoro-2-methoxyphenyl)piperidin-1-yl)-2-
(oxazol-2-yl)-5-oxa-2-azaspiro[3.4]octane;
(S)-2-(oxazol-2-yl)-7-(4-(2-((tetrahydro-2H-pyran-4-yl)
oxy)phenyl)piperidin-1-yl)-5-oxa-2-azaspiro[3.4]oc-
tane;
(S)-1-(4-fluoro-2-(1-(2-(oxazol-2-yl)-5-oxa-2-azaspiro
[3.4]octan-7-yl)piperidin-4-yl)phenoxy)-2-methylpro-
pan-2-ol;
(S)-7-(4-(5-fluoro-2-(2-methoxyethoxy)phenyl)piperi-
din-1-yl)-2-(oxazol-2-yl)-5-oxa-2-azaspiro[3.4]octane;
(S)-7-(4-(2-((2-oxaspiro[3.3]heptan-6-yl)oxy)phenyl)pi-
peridin-1-yl)-2-(oxazol-2-yl)-5-oxa-2-azaspiro[3.4]oc-
tane;
(S)-7-(4-(2-methoxyphenyl)piperidin-1-yl)-2-(oxazol-2-
yl)-5-oxa-2-azaspiro[3.4]octane;
(S)-7-(4-(4,5-difluoro-2-(oxetan-3-ylmethoxy)phenyl)pi-
peridin-1-yl)-2-(oxazol-2-yl)-5-oxa-2-azaspiro[3.4]oc-
tane;
(S)-7-(4-(4,5-difluoro-2-((3-fluorooxetan-3-yl)methoxy)
phenyl)piperidin-1-yl)-2-(oxazol-2-yl)-5-oxa-2-
azaspiro[3.4]octane;
(S)-7-(4-(4,5-difluoro-2-(oxetan-3-yloxy)phenyl)piperi-
din-1-yl)-2-(oxazol-2-yl)-5-oxa-2-azaspiro[3.4]octane;
(S)-2-(oxazol-2-yl)-7-(4-(2-(pyrimidin-5-yl)phenyl)pip-
eridin-1-yl)-5-oxa-2-azaspiro[3.4]octane;
(S)-7-(4-(4-fluoro-2-(oxetan-3-yloxy)phenyl)piperidin-1-
yl)-2-(oxazol-2-yl)-5-oxa-2-azaspiro[3.4]octane;
2-((1R,3s)-3-(4-fluoro-2-(1-((S)-2-(oxazol-2-yl)-5-oxa-
2-azaspiro[3.4]octan-7-yl)piperidin-4-yl)phenoxy)cy-
clobutyl)propan-2-ol;

2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

(S)-2-(oxazol-2-yl)-7-(4-(2-(tetrahydro-2H-pyran-4-yl)phenyl)piperidin-1-yl)-5-oxa-2-azaspiro[3.4]octane;

(S)-7-(4-(5-fluoro-2-(tetrahydro-2H-pyran-4-yl)phenyl)piperidin-1-yl)-2-(oxazol-2-yl)-5-oxa-2-azaspiro[3.4]octane;

(S)-7-(4-(5-chloro-2-methoxyphenyl)piperidin-1-yl)-2-(1,2,4-thiadiazol-5-yl)-5-oxa-2-azaspiro[3.4]octane;

(S)-7-(4-(2-methoxyphenyl)piperidin-1-yl)-2-(1,2,4-thiadiazol-5-yl)-5-oxa-2-azaspiro[3.4]octane;

(S)-1-(2-(1-(2-(1,2,4-thiadiazol-5-yl)-5-oxa-2-azaspiro[3.4]octan-7-yl)piperidin-4-yl)-4-fluorophenoxy)-2-methylpropan-2-ol;

(S)-7-(4-(5-fluoro-2-(2-methoxyethoxy)phenyl)piperidin-1-yl)-2-(1,2,4-thiadiazol-5-yl)-5-oxa-2-azaspiro[3.4]octane;

(S)-7-(4-(4-fluoro-2-methoxyphenyl)piperidin-1-yl)-2-(1,2,4-thiadiazol-5-yl)-5-oxa-2-azaspiro[3.4]octane;

(S)-7-(4-(2-((5-methyl-1,2,4-oxadiazol-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-(oxetan-3-yloxy)phenyl)piperidin-1-yl)-2-(1,3,4-thiadiazol-2-yl)-5-oxa-2-azaspiro[3.4]octane;

(S)-7-(4-(5-fluoro-2-(((R)-tetrahydrofuran-3-yl)oxy)phenyl)piperidin-1-yl)-2-(1,3,4-thiadiazol-2-yl)-5-oxa-2-azaspiro[3.4]octane;

(S)-7-(4-(5-fluoro-2-(((R)-tetrahydrofuran-3-yl)methoxy)phenyl)piperidin-1-yl)-2-(1,3,4-thiadiazol-2-yl)-5-oxa-2-azaspiro[3.4]octane;

(S)-7-(4-(5-fluoro-2-((tetrahydro-2H-pyran-4-yl)oxy)phenyl)piperidin-1-yl)-2-(1,3,4-thiadiazol-2-yl)-5-oxa-2-azaspiro[3.4]octane;

(S)-7-(4-(2-(((R)-1,4-dioxan-2-yl)methoxy)-5-fluorophenyl)piperidin-1-yl)-2-(1,3,4-thiadiazol-2-yl)-5-oxa-2-azaspiro[3.4]octane;

(S)-7-(4-(2-(((S)-1,4-dioxan-2-yl)methoxy)-5-fluorophenyl)piperidin-1-yl)-2-(1,3,4-thiadiazol-2-yl)-5-oxa-2-azaspiro[3.4]octane;

(S)-7-(4-(4,5-difluoro-2-(((R)-tetrahydrofuran-3-yl)oxy)phenyl)piperidin-1-yl)-2-(1,3,4-thiadiazol-2-yl)-5-oxa-2-azaspiro[3.4]octane;

(S)-7-(4-(5-fluoro-2-(3-methoxy-3-methylbutoxy)phenyl)piperidin-1-yl)-2-(1,3,4-thiadiazol-2-yl)-5-oxa-2-azaspiro[3.4]octane;

(S)-7-(4-(5-fluoro-2-(((S)-tetrahydrofuran-3-yl)oxy)phenyl)piperidin-1-yl)-2-(1,3,4-thiadiazol-2-yl)-5-oxa-2-azaspiro[3.4]octane;

(S)-4-(2-(1-(2-(1,3,4-thiadiazol-2-yl)-5-oxa-2-azaspiro[3.4]octan-7-yl)piperidin-4-yl)-4-fluorophenoxy)-2-methylbutan-2-ol;

(S)-7-(4-(2-(oxetan-3-yloxy)phenyl)piperidin-1-yl)-2-(1,3,4-thiadiazol-2-yl)-5-oxa-2-azaspiro[3.4]octane formate salt;

(S)-7-(4-(2-methoxyphenyl)piperidin-1-yl)-2-(1,3,4-thiadiazol-2-yl)-5-oxa-2-azaspiro[3.4]octane;

(S)-7-(4-(5-fluoro-2-(2-methoxyethoxy)phenyl)piperidin-1-yl)-2-(1,3,4-thiadiazol-2-yl)-5-oxa-2-azaspiro[3.4]octane;

(S)-7-(4-(4-fluoro-2-methoxyphenyl)piperidin-1-yl)-2-(1,3,4-thiadiazol-2-yl)-5-oxa-2-azaspiro[3.4]octane;

(S)-1-(2-(1-(2-(1,3,4-thiadiazol-2-yl)-5-oxa-2-azaspiro[3.4]octan-7-yl)piperidin-4-yl)-4-fluorophenoxy)-2-methylpropan-2-ol;

(S)-4-(2-(1-(2-(1,3,4-thiadiazol-2-yl)-5-oxa-2-azaspiro[3.4]octan-7-yl)piperidin-4-yl)-5-fluorophenoxy)-2-methylbutan-2-ol;

(S)-7-(4-(2-((2-oxaspiro[3.3]heptan-6-yl)oxy)-5-fluorophenyl)piperidin-1-yl)-2-(1,3,4-thiadiazol-2-yl)-5-oxa-2-azaspiro[3.4]octane;

(S)-7-(4-(5-fluoro-2-(((S)-tetrahydrofuran-3-yl)methoxy)phenyl)piperidin-1-yl)-2-(1,3,4-thiadiazol-2-yl)-5-oxa-2-azaspiro[3.4]octane;

(S)-1-(2-(1-(2-(1,2,4-thiadiazol-5-yl)-5-oxa-2-azaspiro[3.4]octan-7-yl)piperidin-4-yl)phenoxy)-2-methylpropan-2-ol;

(S)-7-(4-(5-fluoro-2-((tetrahydro-2H-pyran-4-yl)oxy)phenyl)piperidin-1-yl)-2-(1,2,4-oxadiazol-3-yl)-5-oxa-2-azaspiro[3.4]octane;

(S)-7-(4-(5-fluoro-2-(oxetan-3-yloxy)phenyl)piperidin-1-yl)-2-(1,2,4-oxadiazol-3-yl)-5-oxa-2-azaspiro[3.4]octane;

(S)-7-(4-(2-((2-oxaspiro[3.3]heptan-6-yl)oxy)-5-fluorophenyl)piperidin-1-yl)-2-(1,2,4-oxadiazol-3-yl)-5-oxa-2-azaspiro[3.4]octane; and pharmaceutically acceptable salts thereof.

17. The method of claim 16, wherein the compound is selected from the group consisting of:

(S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

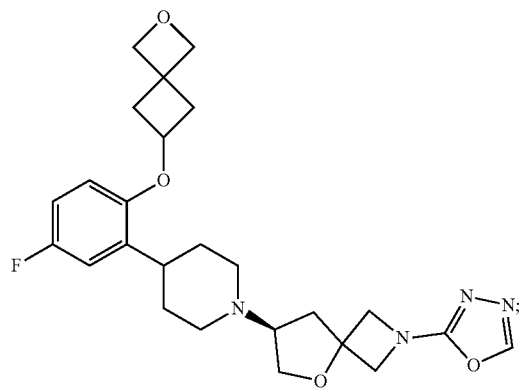 [SMILES: Fc1ccc(OC2CC3(COC3)C2)c(C2CCN([C@@H]3COC4(C3)CN(c3nnco3)C4)CC2)c1]

(R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

(S)-7-(4-(5-fluoro-2-(oxetan-3-yloxy)phenyl)piperidin-1-yl)-2-(1,3,4-oxadiazol-2-yl)-5-oxa-2-azaspiro[3.4]octane, having the following structure:

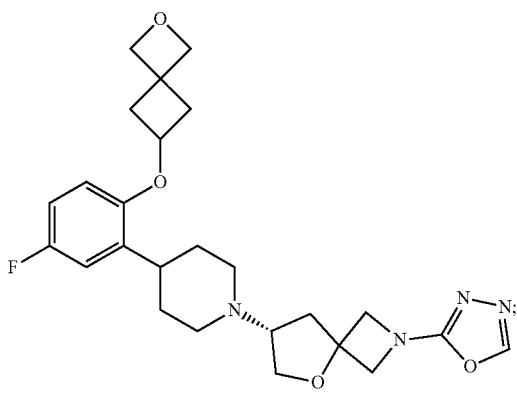 [SMILES: Fc1ccc(OC2CC3(COC3)C2)c(C2CCN([C@H]3COC4(C3)CN(c3nnco3)C4)CC2)c1]

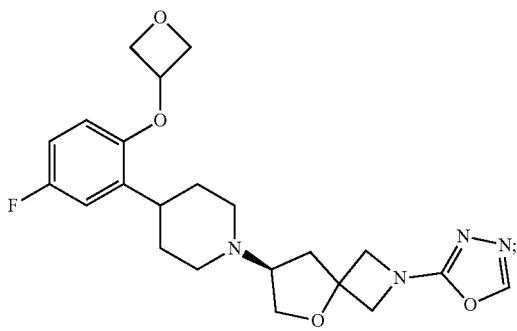 [SMILES: Fc1ccc(OC2COC2)c(C2CCN([C@@H]3COC4(C3)CN(c3nnco3)C4)CC2)c1]

(S)-2-(oxazol-2-yl)-7-(4-(2-(tetrahydro-2H-pyran-4-yl)phenyl)piperidin-1-yl)-5-oxa-2-azaspiro[3.4]octane, having the following structure:

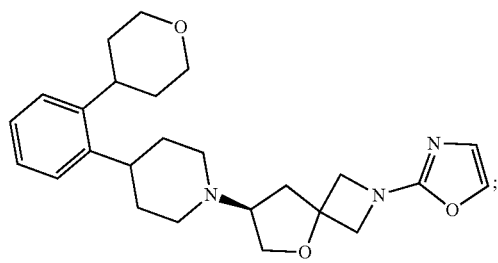 [SMILES: c1ccc(C2CCN([C@@H]3COC4(C3)CN(c3ncco3)C4)CC2)c(C2CCOCC2)c1]

and pharmaceutically acceptable salts thereof.

18. The method of claim 16, wherein the compound is (S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

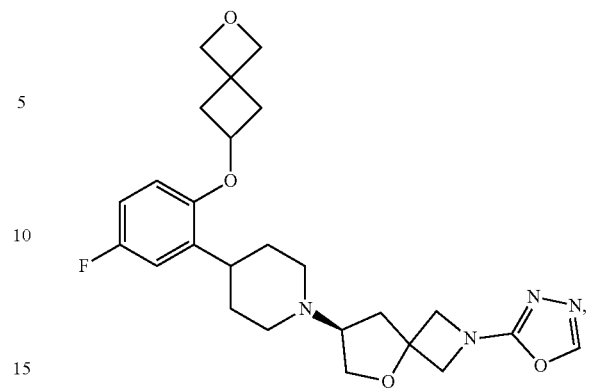

or a pharmaceutically acceptable salt thereof.

19. The method of claim 16, wherein the compound is (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

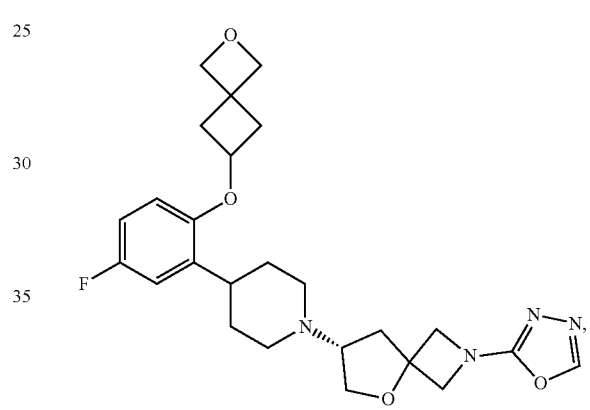

or a pharmaceutically acceptable salt thereof.

20. The method of claim 16, wherein the compound is (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane, having the following structure:

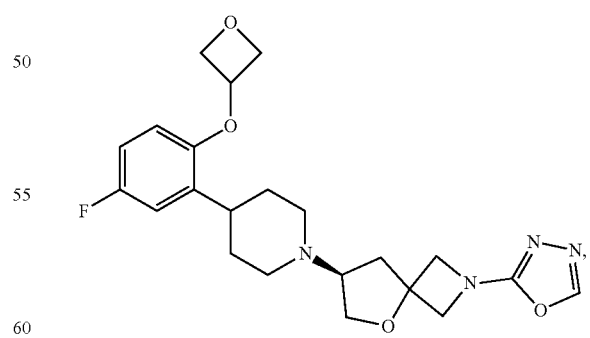

or a pharmaceutically acceptable salt thereof.

21. The method of claim 16, wherein the compound is (S)-2-(oxazol-2-yl)-7-(4-(2-(tetrahydro-2H-pyran-4-yl)phenyl)piperidin-1-yl)-5-oxa-2-azaspiro[3.4]octane, having the following structure:

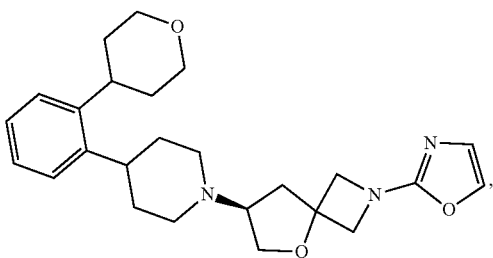 [SMILES: c1ccc(C2CCN([C@@H]3COC4(C3)CN(c3ncco3)C4)CC2)c(C2CCOCC2)c1]

or a pharmaceutically acceptable salt thereof.

22. A method for the treatment of psychosis associated with schizophrenia, a cognitive dysfunction associated with schizophrenia, or a hyperkinetic movement disorder associated with schizophrenia, the method comprising administration of a therapeutically effective amount of a compound of Formula (I) or a pharmaceutically acceptable salt thereof to a subject in need of treatment thereof, wherein the compound of formula (I) is:

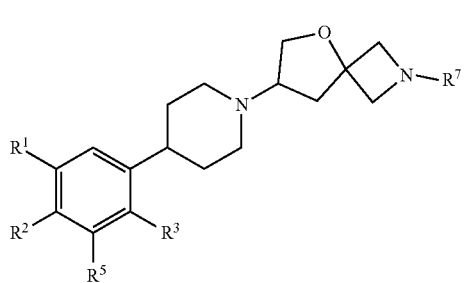

wherein
$R^1$ is halogen or hydrogen;
$R^2$ is halogen or hydrogen;
$R^3$ is
  optionally substituted $C_{1-3}$ alkyl, wherein the alkyl is optionally substituted with one 4- to 6-membered heterocycloalkyl,
  optionally substituted 5- to 6-membered heteroaryl, wherein the heteroaryl is optionally substituted with one $C_{1-3}$ alkyl,
  optionally substituted 4- to 6-membered heterocycloalkyl, wherein the heterocycloalkyl is optionally substituted with one —OH,
  optionally substituted 4- to 6-membered cycloalkyl, wherein the cycloalkyl is optionally substituted with one —OH, or
  —OR$^4$;
$R^4$ is
  optionally substituted $C_{1-5}$ alkyl, wherein the alkyl is optionally substituted with one or two $R^6$,
  optionally substituted 3- to 9-membered heterocycloalkyl, wherein the heterocycloalkyl is optionally substituted with one or two $R^6$, or
  optionally substituted 4- to 6-membered cycloalkyl, wherein the cycloalkyl is optionally substituted with one, two, or three $R^6$;
$R^5$ is halogen or hydrogen;
each $R^6$ is independently selected from the group consisting of
  halogen,
  —OH,
  —OCH$_3$,
  —C(CH$_3$)$_2$OH,
  —CH$_2$OH,
  cyano,
  optionally substituted $C_1$-$C_4$ alkyl, wherein the alkyl is optionally substituted with —OH,
  optionally substituted 4- to 7-membered heterocycloalkyl, wherein the heterocycloalkyl is optionally substituted with one or two substituents independently selected from the group consisting of halogen, —OH, —OCH$_3$, and $C_{1-3}$ alkyl, and
  optionally substituted 5- to 6-membered heteroaryl, wherein the heteroaryl is optionally substituted with one $C_{1-3}$ alkyl; and
$R^7$ is 5-membered heteroaryl.

23. The method of claim 22, wherein the method is for the treatment of psychosis associated with schizophrenia.

24. The method of claim 22, wherein the method is for the treatment of cognitive dysfunction associated with schizophrenia.

25. The method of claim 22, wherein the method is for the treatment of a hyperkinetic movement disorder associated with schizophrenia.

26. A method for the treatment of psychosis associated with schizophrenia, a cognitive dysfunction associated with schizophrenia, or a hyperkinetic movement disorder associated with schizophrenia, the method comprising administration of a therapeutically effective amount of a compound selected from the group consisting of:
  (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane;
  (S)-7-(4-(5-fluoro-2-(((R)-tetrahydrofuran-3-yl)methoxy)phenyl)piperidin-1-yl)-2-(1,3,4-oxadiazol-2-yl)-5-oxa-2-azaspiro[3.4]octane;
  ethyl 5-((S)-7-(4-(2-(((R)-1,4-dioxan-2-yl)methoxy)-5-fluorophenyl)piperidin-1-yl)-5-oxa-2-azaspiro[3.4]octan-2-yl)-1,3,4-oxadiazole-2-carboxylate;
  (S)-7-(4-(5-fluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
  (S)-3-(2-(1-(2-(1,3,4-oxadiazol-2-yl)-5-oxa-2-azaspiro[3.4]octan-7-yl)piperidin-4-yl)-4-fluorophenoxy)-2,2-dimethylpropanenitrile;
  (S)-7-(4-(2-(((S)-1,4-dioxan-2-yl)methoxy)-5-fluorophenyl)piperidin-1-yl)-2-(1,3,4-oxadiazol-2-yl)-5-oxa-2-azaspiro[3.4]octane;
  (S)-7-(4-(5-fluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
  (S)-7-(4-(5-fluoro-2-(((S)-tetrahydrofuran-3-yl)oxy)phenyl)piperidin-1-yl)-2-(1,3,4-oxadiazol-2-yl)-5-oxa-2-azaspiro[3.4]octane;
  (S)-7-(4-(5-fluoro-2-(((S)-tetrahydrofuran-3-yl)methoxy)phenyl)piperidin-1-yl)-2-(1,3,4-oxadiazol-2-yl)-5-oxa-2-azaspiro[3.4]octane;
  (S)-7-(4-(5-fluoro-2-((tetrahydro-2H-pyran-4-yl)methoxy)phenyl)piperidin-1-yl)-2-(1,3,4-oxadiazol-2-yl)-5-oxa-2-azaspiro[3.4]octane;
  (S)-7-(4-(5-fluoro-2-(3-methoxy-3-methylbutoxy)phenyl)piperidin-1-yl)-2-(1,3,4-oxadiazol-2-yl)-5-oxa-2-azaspiro[3.4]octane;
  (S)-7-(4-(5-fluoro-2-(2-methoxyethoxy)phenyl)piperidin-1-yl)-2-(1,3,4-oxadiazol-2-yl)-5-oxa-2-azaspiro[3.4]octane;

(S)-7-(4-(2-((1,3-dioxan-5-yl)oxy)-5-fluorophenyl)piperidin-1-yl)-2-(1,3,4-oxadiazol-2-yl)-5-oxa-2-azaspiro[3.4]octane;
(S)-4-(2-(1-(2-(1,3,4-oxadiazol-2-yl)-5-oxa-2-azaspiro[3.4]octan-7-yl)piperidin-4-yl)-4-fluorophenoxy)-2-methylbutan-2-ol;
(S)-2-(1,3,4-oxadiazol-2-yl)-7-(4-(2-(((R)-tetrahydrofuran-3-yl)oxy)phenyl)piperidin-1-yl)-5-oxa-2-azaspiro[3.4]octane;
(S)-2-(1,3,4-oxadiazol-2-yl)-7-(4-(2-(oxetan-3-yloxy)phenyl)piperidin-1-yl)-5-oxa-2-azaspiro[3.4]octane;
(S)-7-(4-(2-methoxyphenyl)piperidin-1-yl)-2-(1,3,4-oxadiazol-2-yl)-5-oxa-2-azaspiro[3.4]octane;
(S)-7-(4-(4,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
(S)-7-(4-(4-fluoro-2-methoxyphenyl)piperidin-1-yl)-2-(1,3,4-oxadiazol-2-yl)-5-oxa-2-azaspiro[3.4]octane;
(S)-4-(2-(1-(2-(1,3,4-oxadiazol-2-yl)-5-oxa-2-azaspiro[3.4]octan-7-yl)piperidin-4-yl)-5-fluorophenoxy)-2-methylbutan-2-ol;
(S)-1-(2-(1-(2-(1,3,4-oxadiazol-2-yl)-5-oxa-2-azaspiro[3.4]octan-7-yl)piperidin-4-yl)-4-fluorophenoxy)-2-methylpropan-2-ol;
(S)-7-(4-(5-fluoro-2-methoxyphenyl)piperidin-1-yl)-2-(1,3,4-oxadiazol-2-yl)-5-oxa-2-azaspiro[3.4]octane;
(S)-2-(1,3,4-oxadiazol-2-yl)-7-(4-(2-(pyrimidin-5-yl)phenyl)piperidin-1-yl)-5-oxa-2-azaspiro[3.4]octane;
(S)-2-(1,3,4-oxadiazol-2-yl)-7-(4-(2-(oxazol-2-yl)phenyl)piperidin-1-yl)-5-oxa-2-azaspiro[3.4]octane;
(S)-7-(4-(2-(5-methyl-1,3,4-oxadiazol-2-yl)phenyl)piperidin-1-yl)-2-(1,3,4-oxadiazol-2-yl)-5-oxa-2-azaspiro[3.4]octane;
(S)-7-(4-(5-fluoro-2-(oxetan-3-ylmethoxy)phenyl)piperidin-1-yl)-2-(1,3,4-thiadiazol-2-yl)-5-oxa-2-azaspiro[3.4]octane;
(S)-7-(4-(5-fluoro-2-((3-methyloxetan-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((R)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-(((S)-oxetan-2-yl)methoxy)phenyl)piperidin-1-yl)-2-(1,3,4-thiadiazol-2-yl)-5-oxa-2-azaspiro[3.4]octane trifluoroacetate;
(S)-7-(4-(5-fluoro-2-((5-methyl-1,3,4-thiadiazol-2-yl)methoxy)phenyl)piperidin-1-yl)-2-(1,3,4-oxadiazol-2-yl)-5-oxa-2-azaspiro[3.4]octane;
(S)-7-(4-(5-fluoro-2-((5-methyl-1,3,4-oxadiazol-2-yl)methoxy)phenyl)piperidin-1-yl)-2-(1,3,4-oxadiazol-2-yl)-5-oxa-2-azaspiro[3.4]octane;
(S)-7-(4-(5-fluoro-2-((3-methylisoxazol-5-yl)methoxy)phenyl)piperidin-1-yl)-2-(1,3,4-oxadiazol-2-yl)-5-oxa-2-azaspiro[3.4]octane;
(S)-7-(4-(5-fluoro-2-(oxetan-3-ylmethoxy)phenyl)piperidin-1-yl)-2-(1,3,4-oxadiazol-2-yl)-5-oxa-2-azaspiro[3.4]octane;
(S)-7-(4-(5-fluoro-2-(pyrimidin-2-ylmethoxy)phenyl)piperidin-1-yl)-2-(1,3,4-oxadiazol-2-yl)-5-oxa-2-azaspiro[3.4]octane;
(S)-7-(4-(5-fluoro-2-((3-fluorooxetan-3-yl)methoxy)phenyl)piperidin-1-yl)-2-(1,3,4-oxadiazol-2-yl)-5-oxa-2-azaspiro[3.4]octane;
(S)-7-(4-(5-fluoro-2-((3-methyloxetan-3-yl)methoxy)phenyl)piperidin-1-yl)-2-(1,3,4-oxadiazol-2-yl)-5-oxa-2-azaspiro[3.4]octane;
(S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane;
(S)-7-(4-(5-fluoro-2-(((R)-tetrahydrofuran-2-yl)methoxy)phenyl)piperidin-1-yl)-2-(1,3,4-oxadiazol-2-yl)-5-oxa-2-azaspiro[3.4]octane;
(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((R)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-(((S)-5,5-dimethyltetrahydrofuran-3-yl)oxy)-5-fluorophenyl)piperidin-1-yl)-2-(1,3,4-oxadiazol-2-yl)-5-oxa-2-azaspiro[3.4]octane;
(S)-7-(4-(2-((3-ethyloxetan-3-yl)methoxy)-5-fluorophenyl)piperidin-1-yl)-2-(1,3,4-oxadiazol-2-yl)-5-oxa-2-azaspiro[3.4]octane;
(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((S)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(5-fluoro-2-(((R)-tetrahydro-2H-pyran-3-yl)oxy)phenyl)piperidin-1-yl)-2-(1,3,4-oxadiazol-2-yl)-5-oxa-2-azaspiro[3.4]octane;
(S)-7-(4-(2-((2-oxaspiro[3.3]heptan-6-yl)methoxy)-5-fluorophenyl)piperidin-1-yl)-2-(1,3,4-oxadiazol-2-yl)-5-oxa-2-azaspiro[3.4]octane;
(S)-7-(4-(2-((5-ethyl-1,3,4-thiadiazol-2-yl)methoxy)-5-fluorophenyl)piperidin-1-yl)-2-(1,3,4-oxadiazol-2-yl)-5-oxa-2-azaspiro[3.4]octane;
(S)-3-((2-(1-(2-(1,3,4-oxadiazol-2-yl)-5-oxa-2-azaspiro[3.4]octan-7-yl)piperidin-4-yl)-4-fluorophenoxy)methyl)oxetan-3-ol;
2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
2-((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)propan-2-ol;
(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((S)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(S)-7-(4-(5-fluoro-2-((R)-1-(tetrahydro-2H-pyran-4-yl)ethoxy)phenyl)piperidin-1-yl)-2-(1,3,4-oxadiazol-2-yl)-5-oxa-2-azaspiro[3.4]octane;
(7S)-7-(4-(2-((3-oxabicyclo[3.1.0]hexan-6-yl)methoxy)-5-fluorophenyl)piperidin-1-yl)-2-(1,3,4-oxadiazol-2-yl)-5-oxa-2-azaspiro[3.4]octane;

(S)-7-(4-(2-((2-oxaspiro[3.3]heptan-6-yl)oxy)-3,5-difluorophenyl)piperidin-1-yl)-2-(1,3,4-oxadiazol-2-yl)-5-oxa-2-azaspiro[3.4]octane;
(S)-7-(4-(3,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
(S)-7-(4-(3,5-difluoro-2-(((R)-tetrahydrofuran-3-yl)oxy)phenyl)piperidin-1-yl)-2-(1,3,4-oxadiazol-2-yl)-5-oxa-2-azaspiro[3.4]octane;
(S)-7-(4-(3,5-difluoro-2-(oxetan-3-ylmethoxy)phenyl)piperidin-1-yl)-2-(1,3,4-oxadiazol-2-yl)-5-oxa-2-azaspiro[3.4]octane;
(S)-7-(4-(3,5-difluoro-2-(oxetan-3-yloxy)phenyl)piperidin-1-yl)-2-(1,3,4-oxadiazol-2-yl)-5-oxa-2-azaspiro[3.4]octane;
(S)-7-(4-(4,5-difluoro-2-(oxetan-3-yloxy)phenyl)piperidin-1-yl)-2-(1,3,4-oxadiazol-2-yl)-5-oxa-2-azaspiro[3.4]octane;
(S)-7-(4-(4,5-difluoro-2-((tetrahydro-2H-pyran-4-yl)oxy)phenyl)piperidin-1-yl)-2-(1,3,4-oxadiazol-2-yl)-5-oxa-2-azaspiro[3.4]octane;
((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1S,3r)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
((1R,3s)-3-(2-(1-((S)-2-(1,3,4-oxadiazol-2-yl)-5-oxa-2-azaspiro[3.4]octan-7-yl)piperidin-4-yl)-4-fluorophenoxy)cyclobutyl)methanol;
(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((S)-tetrahydrofuran-3-yl)phenyl)piperidin-1-yl)-5-oxa-2-azaspiro[3.4]octane;
(S)-2-(1,3,4-oxadiazol-2-yl)-7-(4-(2-((R)-tetrahydrofuran-3-yl)phenyl)piperidin-1-yl)-5-oxa-2-azaspiro[3.4]octane;
(S)-2-(1,3,4-oxadiazol-2-yl)-7-(4-(2-(tetrahydro-2H-pyran-4-yl)phenyl)piperidin-1-yl)-5-oxa-2-azaspiro[3.4]octane;
(S)-7-(4-(5-fluoro-2-(tetrahydro-2H-pyran-4-yl)phenyl)piperidin-1-yl)-2-(1,3,4-oxadiazol-2-yl)-5-oxa-2-azaspiro[3.4]octane;
(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;
(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;
(S)-7-(4-(5-fluoro-2-((R)-tetrahydrofuran-3-yl)phenyl)piperidin-1-yl)-2-(1,3,4-oxadiazol-2-yl)-5-oxa-2-azaspiro[3.4]octane;
(S)-7-(4-(5-fluoro-2-((S)-tetrahydrofuran-3-yl)phenyl)piperidin-1-yl)-2-(1,3,4-oxadiazol-2-yl)-5-oxa-2-azaspiro[3.4]octane;
(S)-2-(1,3,4-oxadiazol-2-yl)-7-(4-(2-((tetrahydro-2H-pyran-4-yl)methyl)phenyl)piperidin-1-yl)-5-oxa-2-azaspiro[3.4]octane;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1R,4s)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(1S,4r)-4-(2-(1-((S)-2-(1,3,4-oxadiazol-2-yl)-5-oxa-2-azaspiro[3.4]octan-7-yl)piperidin-4-yl)-4-fluorophenyl)cyclohexan-1-ol;
(S)-7-(4-(5-fluoro-2-(oxetan-3-yloxy)phenyl)piperidin-1-yl)-2-(oxazol-2-yl)-5-oxa-2-azaspiro[3.4]octane;
(S)-7-(4-(2-(((R)-1,4-dioxan-2-yl)methoxy)-5-fluorophenyl)piperidin-1-yl)-2-(oxazol-2-yl)-5-oxa-2-azaspiro[3.4]octane;
(S)-2-(oxazol-2-yl)-7-(4-(2-(oxetan-3-yloxy)phenyl)piperidin-1-yl)-5-oxa-2-azaspiro[3.4]octane;
(S)-7-(4-(5-fluoro-2-(((R)-tetrahydrofuran-3-yl)oxy)phenyl)piperidin-1-yl)-2-(oxazol-2-yl)-5-oxa-2-azaspiro[3.4]octane;
(S)-7-(4-(5-fluoro-2-((tetrahydro-2H-pyran-4-yl)oxy)phenyl)piperidin-1-yl)-2-(oxazol-2-yl)-5-oxa-2-azaspiro[3.4]octane;
(S)-2-(oxazol-2-yl)-7-(4-(2-(((R)-tetrahydrofuran-3-yl)oxy)phenyl)piperidin-1-yl)-5-oxa-2-azaspiro[3.4]octane;
(S)-7-(4-(2-((2-oxaspiro[3.3]heptan-6-yl)oxy)-5-fluorophenyl)piperidin-1-yl)-2-(oxazol-2-yl)-5-oxa-2-azaspiro[3.4]octane;
(S)-2-(oxazol-2-yl)-7-(4-(2-(((S)-tetrahydrofuran-3-yl)oxy)phenyl)piperidin-1-yl)-5-oxa-2-azaspiro[3.4]octane;
(S)-7-(4-(5-fluoro-2-methoxyphenyl)piperidin-1-yl)-2-(oxazol-2-yl)-5-oxa-2-azaspiro[3.4]octane;
(S)-2-(oxazol-2-yl)-7-(4-(2-((tetrahydro-2H-pyran-4-yl)oxy)phenyl)piperidin-1-yl)-5-oxa-2-azaspiro[3.4]octane;
(S)-1-(4-fluoro-2-(1-(2-(oxazol-2-yl)-5-oxa-2-azaspiro[3.4]octan-7-yl)piperidin-4-yl)phenoxy)-2-methylpropan-2-ol;
(S)-7-(4-(5-fluoro-2-(2-methoxyethoxy)phenyl)piperidin-1-yl)-2-(oxazol-2-yl)-5-oxa-2-azaspiro[3.4]octane;
(S)-7-(4-(2-((2-oxaspiro[3.3]heptan-6-yl)oxy)phenyl)piperidin-1-yl)-2-(oxazol-2-yl)-5-oxa-2-azaspiro[3.4]octane;
(S)-7-(4-(2-methoxyphenyl)piperidin-1-yl)-2-(oxazol-2-yl)-5-oxa-2-azaspiro[3.4]octane;
(S)-7-(4-(4,5-difluoro-2-(oxetan-3-ylmethoxy)phenyl)piperidin-1-yl)-2-(oxazol-2-yl)-5-oxa-2-azaspiro[3.4]octane;
(S)-7-(4-(4,5-difluoro-2-((3-fluorooxetan-3-yl)methoxy)phenyl)piperidin-1-yl)-2-(oxazol-2-yl)-5-oxa-2-azaspiro[3.4]octane;
(S)-7-(4-(4,5-difluoro-2-(oxetan-3-yloxy)phenyl)piperidin-1-yl)-2-(oxazol-2-yl)-5-oxa-2-azaspiro[3.4]octane;
(S)-2-(oxazol-2-yl)-7-(4-(2-(pyrimidin-5-yl)phenyl)piperidin-1-yl)-5-oxa-2-azaspiro[3.4]octane;
(S)-7-(4-(4-fluoro-2-(oxetan-3-yloxy)phenyl)piperidin-1-yl)-2-(oxazol-2-yl)-5-oxa-2-azaspiro[3.4]octane;
2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;

2-((1R,3s)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
2-((1S,3r)-3-(4-fluoro-2-(1-((S)-2-(oxazol-2-yl)-5-oxa-2-azaspiro[3.4]octan-7-yl)piperidin-4-yl)phenoxy)cyclobutyl)propan-2-ol;
(S)-2-(oxazol-2-yl)-7-(4-(2-(tetrahydro-2H-pyran-4-yl)phenyl)piperidin-1-yl)-5-oxa-2-azaspiro[3.4]octane;
(S)-7-(4-(5-fluoro-2-(tetrahydro-2H-pyran-4-yl)phenyl)piperidin-1-yl)-2-(oxazol-2-yl)-5-oxa-2-azaspiro[3.4]octane;
(S)-7-(4-(5-chloro-2-methoxyphenyl)piperidin-1-yl)-2-(1,2,4-thiadiazol-5-yl)-5-oxa-2-azaspiro[3.4]octane;
(S)-7-(4-(2-methoxyphenyl)piperidin-1-yl)-2-(1,2,4-thiadiazol-5-yl)-5-oxa-2-azaspiro[3.4]octane;
(S)-1-(2-(1-(2-(1,2,4-thiadiazol-5-yl)-5-oxa-2-azaspiro[3.4]octan-7-yl)piperidin-4-yl)-4-fluorophenoxy)-2-methylpropan-2-ol;
(S)-7-(4-(5-fluoro-2-(2-methoxyethoxy)phenyl)piperidin-1-yl)-2-(1,2,4-thiadiazol-5-yl)-5-oxa-2-azaspiro[3.4]octane;
(S)-7-(4-(4-fluoro-2-methoxyphenyl)piperidin-1-yl)-2-(1,2,4-thiadiazol-5-yl)-5-oxa-2-azaspiro[3.4]octane;
(S)-7-(4-(2-((5-methyl-1,2,4-oxadiazol-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-(oxetan-3-yloxy)phenyl)piperidin-1-yl)-2-(1,3,4-thiadiazol-2-yl)-5-oxa-2-azaspiro[3.4]octane;
(S)-7-(4-(5-fluoro-2-(((R)-tetrahydrofuran-3-yl)oxy)phenyl)piperidin-1-yl)-2-(1,3,4-thiadiazol-2-yl)-5-oxa-2-azaspiro[3.4]octane;
(S)-7-(4-(5-fluoro-2-(((R)-tetrahydrofuran-3-yl)methoxy)phenyl)piperidin-1-yl)-2-(1,3,4-thiadiazol-2-yl)-5-oxa-2-azaspiro[3.4]octane;
(S)-7-(4-(5-fluoro-2-((tetrahydro-2H-pyran-4-yl)oxy)phenyl)piperidin-1-yl)-2-(1,3,4-thiadiazol-2-yl)-5-oxa-2-azaspiro[3.4]octane;
(S)-7-(4-(2-(((R)-1,4-dioxan-2-yl)methoxy)-5-fluorophenyl)piperidin-1-yl)-2-(1,3,4-thiadiazol-2-yl)-5-oxa-2-azaspiro[3.4]octane;
(S)-7-(4-(2-(((S)-1,4-dioxan-2-yl)methoxy)-5-fluorophenyl)piperidin-1-yl)-2-(1,3,4-thiadiazol-2-yl)-5-oxa-2-azaspiro[3.4]octane;
(S)-7-(4-(4,5-difluoro-2-(((R)-tetrahydrofuran-3-yl)oxy)phenyl)piperidin-1-yl)-2-(1,3,4-thiadiazol-2-yl)-5-oxa-2-azaspiro[3.4]octane;
(S)-7-(4-(5-fluoro-2-(3-methoxy-3-methylbutoxy)phenyl)piperidin-1-yl)-2-(1,3,4-thiadiazol-2-yl)-5-oxa-2-azaspiro[3.4]octane;
(S)-7-(4-(5-fluoro-2-(((S)-tetrahydrofuran-3-yl)oxy)phenyl)piperidin-1-yl)-2-(1,3,4-thiadiazol-2-yl)-5-oxa-2-azaspiro[3.4]octane;
(S)-4-(2-(1-(2-(1,3,4-thiadiazol-2-yl)-5-oxa-2-azaspiro[3.4]octan-7-yl)piperidin-4-yl)-4-fluorophenoxy)-2-methylbutan-2-ol;
(S)-7-(4-(2-(oxetan-3-yloxy)phenyl)piperidin-1-yl)-2-(1,3,4-thiadiazol-2-yl)-5-oxa-2-azaspiro[3.4]octane formate salt;
(S)-7-(4-(2-methoxyphenyl)piperidin-1-yl)-2-(1,3,4-thiadiazol-2-yl)-5-oxa-2-azaspiro[3.4]octane;
(S)-7-(4-(5-fluoro-2-(2-methoxyethoxy)phenyl)piperidin-1-yl)-2-(1,3,4-thiadiazol-2-yl)-5-oxa-2-azaspiro[3.4]octane;
(S)-7-(4-(4-fluoro-2-methoxyphenyl)piperidin-1-yl)-2-(1,3,4-thiadiazol-2-yl)-5-oxa-2-azaspiro[3.4]octane;
(S)-1-(2-(1-(2-(1,3,4-thiadiazol-2-yl)-5-oxa-2-azaspiro[3.4]octan-7-yl)piperidin-4-yl)-4-fluorophenoxy)-2-methylpropan-2-ol;
(S)-4-(2-(1-(2-(1,3,4-thiadiazol-2-yl)-5-oxa-2-azaspiro[3.4]octan-7-yl)piperidin-4-yl)-5-fluorophenoxy)-2-methylbutan-2-ol;
(S)-7-(4-(2-((2-oxaspiro[3.3]heptan-6-yl)oxy)-5-fluorophenyl)piperidin-1-yl)-2-(1,3,4-thiadiazol-2-yl)-5-oxa-2-azaspiro[3.4]octane;
(S)-7-(4-(5-fluoro-2-(((S)-tetrahydrofuran-3-yl)methoxy)phenyl)piperidin-1-yl)-2-(1,3,4-thiadiazol-2-yl)-5-oxa-2-azaspiro[3.4]octane;
(S)-1-(2-(1-(2-(1,2,4-thiadiazol-5-yl)-5-oxa-2-azaspiro[3.4]octan-7-yl)piperidin-4-yl)phenoxy)-2-methylpropan-2-ol;
(S)-7-(4-(5-fluoro-2-((tetrahydro-2H-pyran-4-yl)oxy)phenyl)piperidin-1-yl)-2-(1,2,4-oxadiazol-3-yl)-5-oxa-2-azaspiro[3.4]octane;
(S)-7-(4-(5-fluoro-2-(oxetan-3-yloxy)phenyl)piperidin-1-yl)-2-(1,2,4-oxadiazol-3-yl)-5-oxa-2-azaspiro[3.4]octane;
(S)-7-(4-(2-((2-oxaspiro[3.3]heptan-6-yl)oxy)-5-fluorophenyl)piperidin-1-yl)-2-(1,2,4-oxadiazol-3-yl)-5-oxa-2-azaspiro[3.4]octane; and
pharmaceutically acceptable salts thereof.

27. The method of claim 26, wherein the compound is (S)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

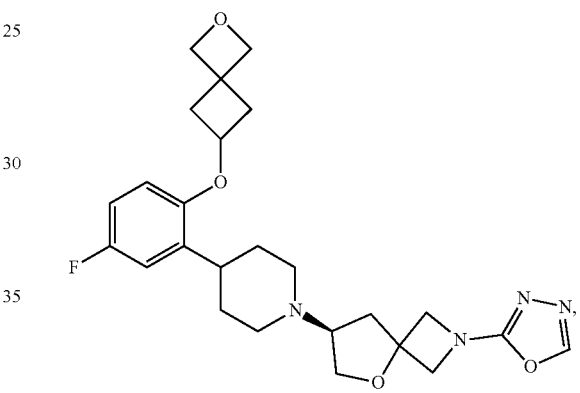

or a pharmaceutically acceptable salt thereof.

28. The method of claim 26, wherein the compound is (R)-7-(4-(2-((2-oxaspiro[3.3]heptan-6-yl)oxy)-5-fluorophenyl)piperidin-1-yl)-2-(1,3,4-oxadiazol-2-yl)-5-oxa-2-azaspiro[3.4]octane, having the following structure:

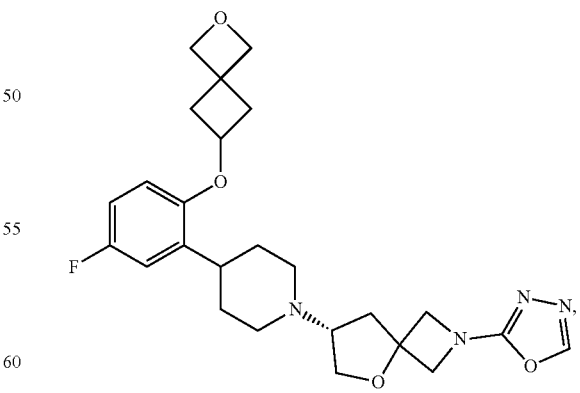

or a pharmaceutically acceptable salt thereof.

29. The method of claim 26, wherein the compound is (S)-7-(4-(5-fluoro-2-(oxetan-3-yloxy)phenyl)piperidin-1-yl)-2-(1,3,4-oxadiazol-2-yl)-5-oxa-2-azaspiro[3.4]octane, having the following structure:

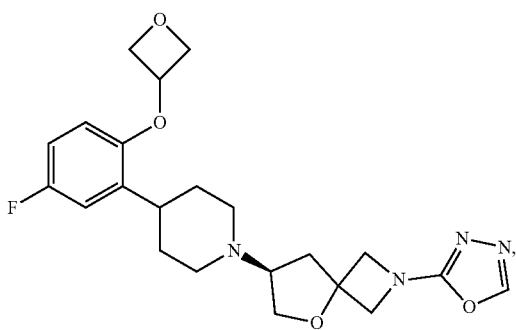 [SMILES: Fc1ccc(OC2COC2)c(C2CCN([C@@H]3COC4(C3)CN(c3nnco3)C4)CC2)c1]
or a pharmaceutically acceptable salt thereof.
30. The method of claim 26, wherein the compound is (S)-2-(oxazol-2-yl)-7-(4-(2-(tetrahydro-2H-pyran-4-yl)phenyl)piperidin-1-yl)-5-oxa-2-azaspiro[3.4]octane, having the following structure:
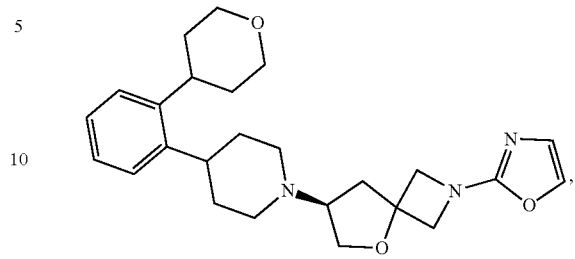
or a pharmaceutically acceptable salt thereof.